(12) United States Patent
Fevig et al.

(10) Patent No.: US 7,572,805 B2
(45) Date of Patent: Aug. 11, 2009

(54) PYRROLO(OXO)ISOQUINOLINES AS 5HT LIGANDS

(75) Inventors: John M. Fevig, Doylestown, PA (US); Jianxin Feng, Levittown, PA (US); Saleem Ahmad, Wall, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 610 days.

(21) Appl. No.: 11/180,268

(22) Filed: Jul. 13, 2005

(65) Prior Publication Data

US 2006/0014777 A1 Jan. 19, 2006

Related U.S. Application Data

(60) Provisional application No. 60/587,682, filed on Jul. 14, 2004.

(51) Int. Cl.
*A61K 31/44* (2006.01)
*C07D 471/00* (2006.01)

(52) U.S. Cl. .......................... 514/292; 546/84
(58) Field of Classification Search .............. 546/84; 514/292
See application file for complete search history.

(56) References Cited

U.S. PATENT DOCUMENTS

2003/0187254 A1 10/2003 Perry et al.

FOREIGN PATENT DOCUMENTS

| WO | WO 99/09025 | 2/1999 |
| WO | WO 03/014121 | 2/2003 |
| WO | WO 2004/065351 | 8/2004 |

OTHER PUBLICATIONS

West, Anthony R., Solid State Chemistry and its Applications, Wiley, New York, 1988, pp. 358 & 365.*
Hcaplus 1981:461933, "The Schmidt reaction on 3a, 4, 5, 6-tetrahydrosuccinimido [3, 4-b] acenapthen-1o-one and its alkylated derivatives", Campaigne et. al., 1981.*
U.S. Appl. No. 11/180,861, filed Jul. 13, 2005, Fevig et al.
Chojnacka-Wójcik, E. et al., "Involvement of 5-HT$_{2C}$ Receptors in the m-CPP-Induced Antinociception in Mice", Pol. J. Pharmacol., vol. 46, pp. 423-428 (1994).
Cryan, J.F. et al., "Antidepressant-Like Behavioral Effects Mediated by 5-Hydroxytryptamine$_{2C}$ Receptors", The Journal of Pharmacology and Experimental Therapeutics, vol. 295, No. 3, pp. 1120-1126 (2000).
Di Matteo, V. et al., "Role of 5-HT$_{2C}$ receptors in the control of central dopamine function", Trends in Pharmacological Sciences, vol. 22, No. 5, pp. 229-232 (2001).
Grottick, A.J. et al., "Activation of 5-HT$_{2C}$ receptors reduces the locomotor and rewarding effects of nicotine", Psychopharmacology, vol. 157, pp. 292-298 (2001).

Grottick, A.J. et al., "Studies to Investigate the Role of 5-HT$_{2C}$ Receptors on Cocaine- and Food-Maintained Behavior", The Journal of Pharmacology and Experimental Therapeutics, vol. 295, No. 3, pp. 1183-1191 (2000).
Hoffman, B.J. et al., "Distribution of serotonin 5-HT$_{1C}$ receptor mRNA in adult rat brain", FEBS Letters, vol. 247, No. 2, pp. 453-462 (1989).
Hoyer, D. et al., "VII. International Union of Pharmacology Classification of Receptors for 5-Hydroxytryptamine (Serotonin)", Pharmacological Reviews, vol. 46, No. 2, pp. 157-203 (1994).
Jones, K. et al., "Intramolecular Reactions Using Amide Links: Aryl Radical Cyclisation of Silylated Acryloylanilides", Tetrahedron Letters, vol. 35, No. 41, pp. 7673-7676 (1994).
Mazzola-Pomietto, P. et al., "Evidence that *m*-chlorophenylpiperazine-induced hyperthermia in rats is mediated by stimulation of 5-HT$_{2C}$ receptors", Psychopharmacology, vol. 123, pp. 333-339 (1996).
Millan, M.J. et al., "5-HT$_{2C}$ receptors mediate penile erections in rats: actions of novel and selective agonists and antagonists", European Journal of Pharmacology, vol. 325, pp. 9-12 (1997).
Nonogaki, K. et al., "Leptin-independent hyperphagia and type 2 diabetes in mice with a mutated serotonin 5-HT$_{2C}$ receptor gene", Nature Medicine, vol. 4, No. 10, pp. 1152-1156 (1998).
Nyerges, M. et al., "A Convenient Synthesis of Pyrrolo[3,4-c]quinolines", Heterocyclic Communications, vol. 9, No. 3, pp. 239-242 (2003).

(Continued)

*Primary Examiner*—Janet L Andres
*Assistant Examiner*—Binta M Robinson
(74) *Attorney, Agent, or Firm*—Terence J. Bogie

(57) ABSTRACT

The present application describes compounds according to Formula I, pharmaceutical compositions, comprising at least one compound according to Formula I and optionally at least one additional therapeutic agent and methods of treating various diseases, conditions and disorders associated with modulation of serotonin receptors such as, for example: metabolic diseases, which includes but is not limited to obesity, diabetes, diabetic complications, atherosclerosis, impaired glucose tolerance and dyslipidemia; central nervous system diseases which includes but is not limited to, anxiety, depression, obsessive compulsive disorder, panic disorder, psychosis, schizophrenia, sleep disorder, sexual disorder and social phobias; cephalic pain; migraine; and gastrointestinal disorders using compounds according to Formula I

I

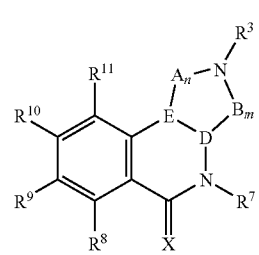

or pharmaceutically acceptable salt forms thereof, wherein A, B, D, E, m, n, $R^3$, $R^7$, $R^8$, $R^9$, $R^{10}$, $R^{11}$ and X are described herein.

7 Claims, No Drawings

OTHER PUBLICATIONS

Rittenhouse, P.A. et al., "Evidence that ACTH Secretion Is Regulated by Serotonin$_{2A/2C}$ (5-HT$_{2A/2C}$) Receptors", The Journal of Pharmacology and Experimental Therapeutics, vol. 271, No. 3, pp. 1647-1655 (1994).

Sharpley, A.L. et al., "Slow Wave Sleep in Humans: Role of 5-HT$_{2A}$ and 5-HT$_{2C}$ Receptors", Neuropharmacology, vol. 33, No. 3/4, pp. 467-471 (1994).

Vickers, S.P. et al., "Comparative effects of continuous infusion of mCPP, Ro 60-0175 and d-fenfluramine on food intake, water intake, body weight and locomotor activity in rats", British Journal of Pharmacology, vol. 130, pp. 1305-1314 (2000).

Vickers, S.P. et al., "Evidence that hypophagia induced by d-fenfluramine and d-norfenfluramine in the rat is mediated by 5-HT$_{2C}$ receptors", Neuropharmacology, vol. 41, pp. 200-209 (2001).

Vickers, S.P. et al., "Reduced satiating effect of d-fenfluramine in serotonin 5-HT$_{2C}$ receptor mutant mice", Psychopharmacology, vol. 143, pp. 309-314 (1999).

Virányi, A. et al., "A Convenient Synthesis of Pyrrolo[3,4-c]quinolines", Synthesis, No. 17, pp. 2655-2660 (2003).

Caplus English Abstract DN 96:104021 Achini Roland, 1981, 64(7), pp. 2203-2218. See RN #80896-99, 80897-00, 80897-01.

* cited by examiner

PYRROLO(OXO)ISOQUINOLINES AS 5HT LIGANDS

RELATED APPLICATIONS

This application claims priority benefit under Title 35 § 119(e) of U.S. Provisional Application No. 60/587,682, filed Jul. 14, 2004, the contents of which are herein incorporated by reference.

BACKGROUND

The neurotransmitter/hormone serotonin (5-hydroxytryptamine, 5-HT) regulates many physiological processes via a group of at least 14 distinct receptors that are organized into 7 subfamilies (Hoyer, D., et al., Pharmacol. Rev., 46, 1994). The $5\text{-}HT_2$ subfamily is composed of the $5\text{-}HT_{2A}$, $5\text{-}HT_{2B}$, and $5\text{-}HT_{2C}$ receptors as determined by gene homology and pharmacological properties. There exists a substantial correlation for the relationship between $5\text{-}HT_2$ receptor modulation and a variety of diseases and therapies. Prior to the early 1990's the $5\text{-}HT_{2C}$ and $5\text{-}HT_{2A}$ receptors were referred to as $5\text{-}HT_{1C}$ and $5\text{-}HT_2$, respectively.

The direct or indirect agonism or antagonism of $5\text{-}HT_2$ receptors, either selectively or non-selectively, has been associated with the treatment of various central nervous system (CNS) disorders including obesity, depression, schizophrenia and bi-polar disorders. In the recent past the contribution of serotonergic activity to the mode of action of anti-obesity drugs has been well documented. Compounds that increase the overall basal tone of serotonin in the CNS have been developed as anorectic drugs. The serotonin releasing agents, such as fenfluramine, function by increasing the amount of serotonin present in the nerve synapse. These breakthrough treatments, however, are not without side effects. Due to the mechanism of action of serotonin releasing agents, they effect the activity of a number of serotonin receptor subtypes in a wide variety of organs including those not associated with the desired mechanism of action. This non-specific modulation of the serotonin family of receptors most likely plays a significant role in the side effect profile. In addition, these compounds or their metabolites often have a high affinity for a number of the serotonin receptors as well as a multitude of other monoamine neurotransmitters and nuisance receptors. Removing some of the receptor cross reactivity would allow for the examination and possible development of potent therapeutic ligands with an improved side effect profile.

The $5\text{-}HT_{2C}$ receptor is a G-protein coupled receptor. It is almost exclusively expressed in the central nervous system including the hypothalamus, hippocampus, amygdala, nucleus of the solitary tract, spinal cord, cortex, olfactory bulb, ventral tegmental area (VTA), nucleus accumbens and choroid plexus (Hoffman, B. and Mezey, E., FEBS Lett., 247, 1989). There is ample evidence to support the role of selective $5\text{-}HT_{2C}$ receptor ligands in a number of disease therapies. $5\text{-}HT_{2C}$ knockout mice develop a late stage obesity syndrome that is not reversed by fenfluramine or other direct acting $5\text{-}HT_{2C}$ agonists such as mCPP (Nonogaki, K., et al., Nature Med., 4, 1998; Vickers, S., et. al., Psychopharmacology, 143, 1999). Administration of selective $5\text{-}HT_{2C}$ agonists to rats causes a reduction in food intake and corresponding reduction in body weight (Vickers, S., et al., Br. J. Pharmacol., 130, 2000) and these responses can be blocked by administration of selective $5\text{-}HT_{2C}$ antagonists (Vicker, S., et al., Neuropharmacol., 41, 2001). $5\text{-}HT_{2C}$ receptor modulation in the hypothalamus can also influence thermoregulation (Mazzola-Pomietto, P., et al., Psychopharmacology, 123, 1996), sleep (Sharpley, A., et al., Neuropharmacology, 33, 1994), sexual behavior and neuroendocrine function (Rittenhouse, P. et al., J. Pharmacol. Exp. Ther., 271, 1994). Activation of $5\text{-}HT_{2C}$ receptors in the VTA modulates the activity of dopaminergic neurons that are involved in aspects of depression (Di Matteo, V. et al., Trends Pharmacol. Sci., 22, 2001) and $5\text{-}HT_{2C}$ receptor agonists such as WAY 161503, RO 60-0175 and RO 60-0332 are active in rodent models of depression (Cryan, J. and Lucki, I., J. Pharmacol. Exp. Ther., 295, 2000). $5\text{-}HT_{2C}$ agonists have been reported to reduce the rewarding effects of nicotine administration in rats (Grottick, A., et al., Psychopharmacology, 157, 2001) and influences rodent responses to cocaine administration (Grottick, A., et al., J. Pharmacol. Exp. Ther., 295, 2000). Modulation of $5\text{-}HT_{2C}$ receptors in the spinal cord can influence pain perception (Chojnacka-Wojcik, E., et al., Pol. J. Pharmacol., 46, 1994). There is also data indicating that the $5\text{-}HT_{2C}$ receptor agonists mCPP and RO 60-0175 mediate penile erections in rats (Millan, M., et al., Eur J. Pharmacol. 325, 1997).

DETAILED DESCRIPTION

The present application describes compounds according to Formula I, pharmaceutical compositions, comprising at least one compound according to Formula I and optionally at least one additional therapeutic agent and methods of treating various diseases, conditions and disorders associated with modulation of serotonin receptors such as, for example: metabolic diseases, which includes but is not limited to obesity, diabetes, diabetic complications, atherosclerosis, impaired glucose tolerance and dyslipidemia; central nervous system diseases which includes but is not limited to, anxiety, depression, obsessive compulsive disorder, panic disorder, psychosis, schizophrenia, sleep disorder, sexual disorder and social phobias; cephalic pain; migraine; and gastrointestinal disorders using compounds according to Formula I

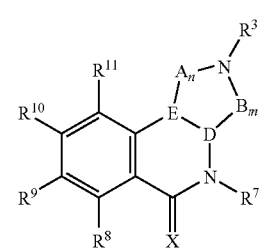

I or pharmaceutically acceptable salt forms thereof, wherein A, B, D, E, m, n, $R^3$, $R^7$, $R^8$, $R^9$, $R^{10}$, $R^{11}$ and X are described herein.

Definitions

The following definitions apply to the terms as used throughout this specification, unless otherwise limited in specific instances.

Unless otherwise indicated, the term "alkyl" as employed herein alone or as part of another group includes both straight and branched chain hydrocarbons, containing 1 to 40 carbons, preferably 1 to 20 carbons, more preferably 1 to 6 carbons, in the normal chain, such as, for example, methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like.

The term "alkylene" as employed herein alone or as part of another group refers to alkyl linking groups above having single bonds for attachment to other groups at two different carbon atoms Unless otherwise indicated, the term "alkenyl" as used herein by itself or as part of another group refers to straight or branched chain radicals of 2 to 20 carbons, preferably 2 to 12 carbons, and more preferably 2 to 6 carbons in the normal chain, which include one or more double bonds in the normal chain, such as, for example, vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like.

The term "alkenylene" and as employed herein alone or as part of another group refers to alkenyl linking groups, having single bonds for attachment at two different carbon atoms.

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one or more triple bonds in the normal chain, such as, for example, 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with one or more functional groups as defined above for alkyl.

The term "alkynylene" as employed herein alone or as part of another group refers to alkynyl linking groups, having single bonds for attachment at two different carbon atoms.

The term "halogen" or "halo" as used herein alone or as part of another group refers to chlorine, bromine, fluorine and iodine.

Unless otherwise indicated, the term "cycloalkyl" as employed herein alone or as part of another group refers to saturated or partially unsaturated (containing 1 or 2 double bonds) cyclic hydrocarbon groups containing 1 to 3 rings, including monocyclic alkyl, bicyclic alkyl and tricyclic alkyl, containing a total of 3 to 20 carbons forming the rings, preferably 4 to 10 carbons, forming the ring such as, for example, cyclopropyl, cyclobutyl, cyclopentyl, cyclohexyl, cycloheptyl, cyclooctyl, cyclodecyl, cyclododecyl, cyclohexenyl,

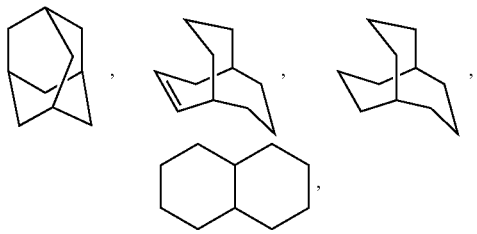

wherein the cycloalkyl may be fused to 1 aromatic ring as described for aryl.

The term "heterocyclyl", as used herein, refers to an unsubstituted or substituted stable 4-, 5-, 6- or 7-membered monocyclic ring system which may be saturated or unsaturated, and which consists of carbon atoms and from one to four heteroatoms selected from N, O, S, SO and/or $SO_2$ group, wherein the nitrogen heteroatoms may optionally be oxidized, and the nitrogen heteroatom may optionally be quaternized. The heterocyclic ring may be attached at any heteroatom or carbon atom which results in the creation of a stable structure such as, for example, piperidinyl, piperazinyl, oxopiperazinyl, oxopiperidinyl and oxadiazolyl.

The term "aryl" as employed herein alone or as part of another group refers to monocyclic and bicyclic aromatic groups containing 6 to 10 carbons in the ring portion such as, for example, phenyl or naphthyl and may optionally include one to three additional rings fused to "aryl" such as, for example, aryl, cycloalkyl, heteroaryl or cycloheteroalkyl rings.

The term "heteroaryl" as used herein refers to a 5-, 6- or 7-membered aromatic heterocyclic ring which contains one or more heteroatoms selected from nitrogen, sulfur, oxygen and/or a SO or $SO_2$ group. Such rings may be fused to another ring such as, for example, cycloalkyl, cycloheteroalkyl, aryl or heteroaryl and include possible N-oxides.

The term "oxy" as used herein as part of another group refers to an oxygen atom serving as a linker between two groups such as, for example, hydroxy, oxyalkyl, alkenyl, alyalkynyl, oxyperfluoroalkyl, oxyaryl, oxyheteroaryl, oxycarboalkyl, oxycarboalkenyl, oxycarboalkynyl, oxycarboaryl, oxycarboheteroaryl, oxycarbocycloalkyl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl and aminocarboxyheteroaryl, The term "carbo" as used herein as part of another group refers to a carbonyl (C═O) group serving as a linker between two groups such as, for example, carboxyalkyl, carboxyalkenyl, carboxyalkynyl, carboxyaryl, carboxyheteroaryl, carboxycycloalkyl, oxycarboalkyl, oxycarboalkenyl, oxycarboalkynyl, oxycarboaryl, oxycarboheteroaryl, oxycarbocycloalkyl, carboaminoalkyl, carboaminoalkenyl, carboaminoakynyl, carboaminoaryl, carboaminocycloalkyl, carboheterocyclyl, carboheteroaryl, carboaminoheterocyclyl, carboaminoheteroaryl, aminocarboalkyl, aminocarboalkenyl, aminocarboalkynyl, aminocarboaryl, aminocarbocycloalkyl, aminocarboheterocyclyl, aminocarboheteroaryl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl, aminocarboxyheteroaryl, aminocarboaminoalkyl, aminocarboaminoalkenyl, aminocarboaminoalkynyl, aminocarboaminoaryl, aminocarboaminocycloalkyl, aminocarboheterocyclyl, aminocarboheteroaryl, aminocarboaminoheterocyclyl and aminocarboaminoheteroaryl.

The term "thio" as used herein as part of another group refers to a sulfur atom serving as a linker between two groups such as, for example, thioalkyl, thioalkenyl, thioalkynyl, thioaryl, thioheteroaryl and thiocycloalkyl.

The term "perfluoro" as used herein as part of another group refers to a group wherein more than one hyrdogen atom attached to one or more carbon atoms in the group has been replaced with a fluorine atom such as, for example, perfluoroalkyl, perfluoroalkenyl, perfluoroalkynyl and oxyperfluoroalkyl.

The term "amino" as used herein alone or as part of another group refers to a nitrogen atom that may be either terminal or a linker between two other groups, wherein the group may be a primary, secondary or tertiary (two hydrogen atoms bonded to the nitrogen atom, one hydrogen atom bonded to the nitrogen atom and no hydrogen atoms bonded to the nitrogen atom, respectively) amine such as, for example, amino, aminoalkyl, aminoalkenyl, aminoalkynyl, aminoaryl, aminoheteroaryl, aminocycloalkyl, alkylamino, alkenylamino, alkynylamino, arylamino, heteroarylamino, cycloalkylamino, carboaminoalkyl, carboaminoalkenyl, carboaminoakynyl, carboaminoaryl, carboaminocycloalkyl, carboheterocyclyl, carboheteroaryl, carboaminoheterocyclyl, carboaminoheteroaryl, aminocarboalkyl, aminocarboalkenyl, aminocarboalkynyl, aminocarboaryl, aminocarbocycloalkyl, aminocarboheterocyclyl, aminocarboheteroaryl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl, aminocarboxyheteroaryl, aminocarboaminoalkyl, aminocarboaminoalkenyl, aminocarboaminoalkynyl, aminocarboaminoaryl, aminocarboaminocycloalkyl, aminocarboheterocyclyl, aminocarboheteroaryl, aminocarboaminoheterocyclyl, aminocarboaminoheteroaryl, sulfoalkyl, sulfoalkenyl, sulfoalkynyl, sulfoaryl, sulfocycloalkyl, sulfoheterocyclyl and sulfoheteroaryl.

The term "nitrile" as used herein refers to a cyano (a carbon atom triple-bonded to a nitrogen atom) group.

The term "sulfinyl" as used herein as part of another group refers to an —SO— group such as, for example, sulfinylalkyl, sulfinylalkenyl, sulfinylalkynyl, sulfinylaryl, sulfinylcycloalkyl, sulfinylheterocyclyl and sulfinylheteroaryl.

The term "sulfonyl" as used herein as part of another group refers to an —SO$_2$— group such as, for example, sulfonylalkyl, sulfonylalkenyl, sulfonylalkynyl, sulfonylaryl, sulfonylcycloalkyl, sulfonylheterocyclyl and sulfonylheteroaryl.

An administration of a therapeutic agent of the application includes administration of a therapeutically effective amount of the agent of the application. The term "therapeutically effective amount" as used herein refers to an amount of a therapeutic agent to treat or prevent a condition treatable by administration of a composition of the application. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

Any compound that can be converted in vivo to provide the bioactive agent (i.e., the compound of formula I) is a prodrug within the scope and spirit of the application.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like.

Various forms of prodrugs are well known in the art and are described in:

a) *The Practice of Medicinal Chemistry*, Camille G. Wermuth et al., Ch 31, (Academic Press, 1996);

b) *Design of Prodrugs*, edited by H. Bundgaard, (Elsevier, 1985); and c) *A Textbook of Drug Design and Development*, P. Krogsgaard-Larson and H. Bundgaard, eds. Ch 5, pgs 113-191 (Harwood Academic Publishers, 1991).

Said references are incorporated herein by reference.

All stereoisomers of the compounds of the instant application are contemplated, either in admixture or in pure or substantially pure form. The compounds of the present application can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic techniques or fractional crystallization.

The pharmaceutically acceptable salts of the compounds of formula I of the application include alkali metal salts such as lithium, sodium or potassium, alkaline earth metal salts such as calcium or magnesium, as well as zinc or aluminum and other cations such as ammonium, choline, diethanolamine, ethylenediamine, t-butylamine, t-octylamine, dehydroabietylamine, as well as pharmaceutically acceptable anions such as chloride, bromide, iodide, tartrate, acetate, methanesulfonate, maleate, succinate, glutarate, stearate and salts of naturally occurring amino acids such as arginine, lysine, alanine and the like, and prodrug esters thereof.

Synthesis

The compounds of the present application can be prepared in a number of ways well known to one skilled in the art of organic synthesis. The compounds of the present application can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The novel compounds of Formula I may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of Formula I falling into a given class may be compatible with some of the reaction conditions required in some of the methods described. Such restrictions to the substituents, which are compatible with the reaction conditions, will be readily apparent to one skilled in the art and alternate methods must be used.

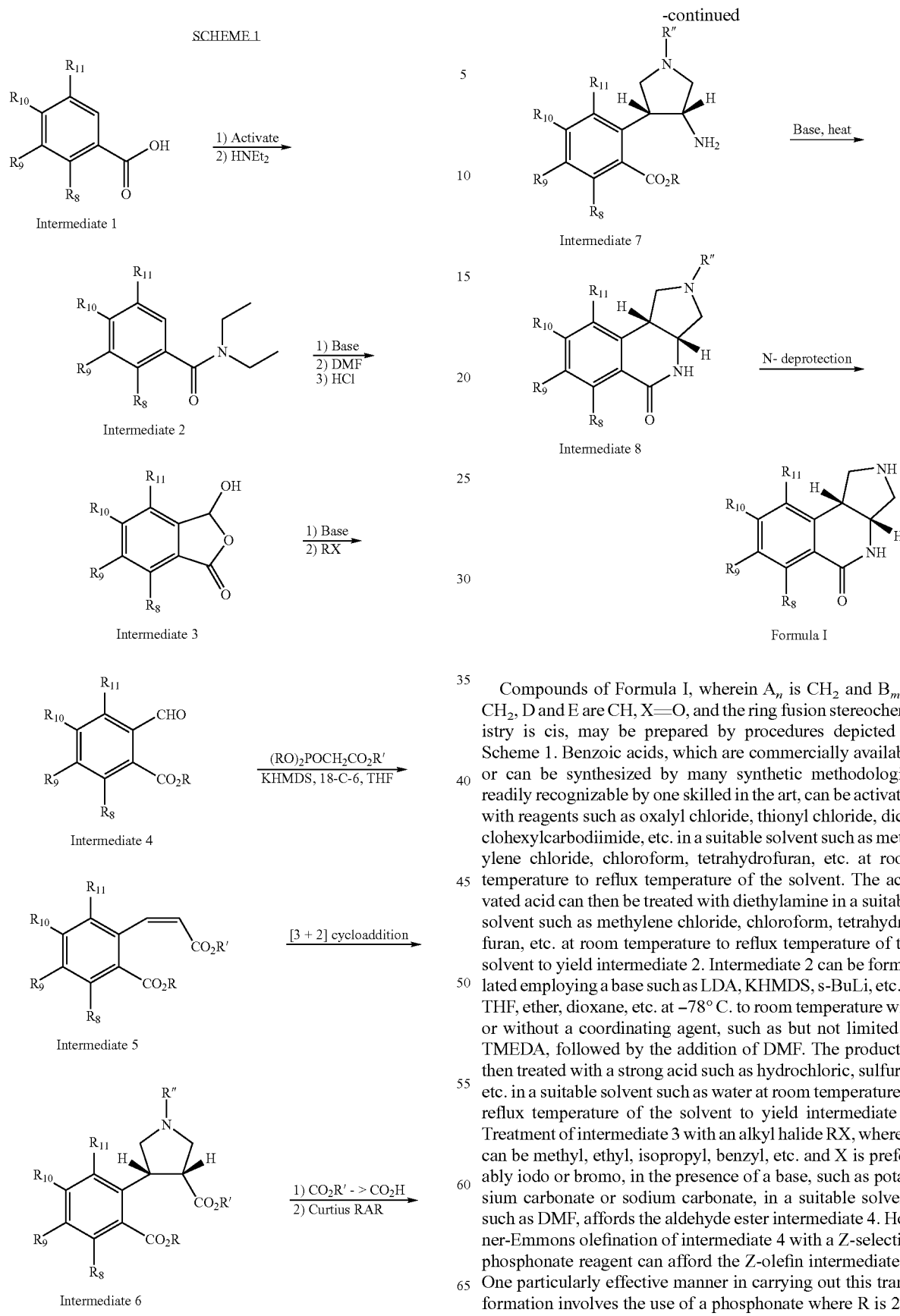

Compounds of Formula I, wherein $A_n$ is $CH_2$ and $B_m$ is $CH_2$, D and E are CH, X=O, and the ring fusion stereochemistry is cis, may be prepared by procedures depicted in Scheme 1. Benzoic acids, which are commercially available or can be synthesized by many synthetic methodologies readily recognizable by one skilled in the art, can be activated with reagents such as oxalyl chloride, thionyl chloride, dicyclohexylcarbodiimide, etc. in a suitable solvent such as methylene chloride, chloroform, tetrahydrofuran, etc. at room temperature to reflux temperature of the solvent. The activated acid can then be treated with diethylamine in a suitable solvent such as methylene chloride, chloroform, tetrahydrofuran, etc. at room temperature to reflux temperature of the solvent to yield intermediate 2. Intermediate 2 can be formylated employing a base such as LDA, KHMDS, s-BuLi, etc. in THF, ether, dioxane, etc. at −78° C. to room temperature with or without a coordinating agent, such as but not limited to TMEDA, followed by the addition of DMF. The product is then treated with a strong acid such as hydrochloric, sulfuric, etc. in a suitable solvent such as water at room temperature to reflux temperature of the solvent to yield intermediate 3. Treatment of intermediate 3 with an alkyl halide RX, where R can be methyl, ethyl, isopropyl, benzyl, etc. and X is preferably iodo or bromo, in the presence of a base, such as potassium carbonate or sodium carbonate, in a suitable solvent, such as DMF, affords the aldehyde ester intermediate 4. Horner-Emmons olefination of intermediate 4 with a Z-selective phosphonate reagent can afford the Z-olefin intermediate 5. One particularly effective manner in carrying out this transformation involves the use of a phosphonate where R is 2,2,2-trifluoroethyl or aryl in the presence of a potassium base, such as KHMDS or $K_2CO_3$, and 18-crown-6, in a solvent such as THF at low temperature (−78° C. to 0° C.) (Still, W. C. et. al.; *Tetrahedron Lett.* 1983, 24 4405; for a review of Z-selective Horner-Emmons reactions, see Jiro, M. *Trends Org. Chem.* 1998, 7, 63). It will be noted that the choice of reagents in preparing intermediates 4 and 5 should be made such that the ester groups R and R' are different from one another, so that one ester can be selectively deprotected over the other. This will be appreciated by those skilled in the art. One preferred strategy is when R is isopropyl and R' is methyl, such that the methyl ester can be selectively hydrolyzed when needed. Intermediates 5 can serve as dipolarophiles in 1,3-dipolar cycloadditions with appropriate azomethine ylides to afford the pyrrolidine intermediate 6 (for reviews of 1,3-dipolar cycloaddition chemistry of azomethine ylides, see 1,3-*Dipolar Cycloaddition Chemistry*, A. Padwa, Ed., Wiley-Interscience, New York, 1984). The required azomethine ylide can be generated in several ways, two preferred methods of which are described. The commercially available tertiary amine N-(methoxymethyl)-N-(trimethylsilylmethyl)benzylamine can be treated with 5-25 mol % TFA in methylene chloride or EtOAc to generate the required azomethine ylide and 1,3-dipolar cycloaddition then occurs at room temperature or reflux temperature to afford intermediate 6. Alternatively, N-benzylglycine can be refluxed with paraformaldehyde in a suitable solvent such as toluene or benzene to generate the azomethine ylide. These methods give intermediate 6 where the pyrrolidine nitrogen is protected with a benzyl group (R"=Bn). The 1,3-dipolar cycloaddition is stereospecific in that the stereochemistry of the olefin is retained and translated into the relative stereochemistry of the pyrrolidine products. Thus, Z-olefins undergo cyclization to produce pyrrolidine intermediates 6 with a cis configuration of the 3,4-substituents on the pyrrolidine ring. The preferred protecting group on the pyrrolidine nitrogen, R", is a carbamate such as BOC or CBZ. Thus, removal of the N-benzyl group of intermediate 6 can be accomplished either by catalytic hydrogenation over Pd/C or Pd(OH)$_2$/C catalyst, or by reaction with α-chloroethyl chloroformate (ACE-Cl) and subsequent refluxing in methanol. The resulting pyrrolidine nitrogen can be protected by a variety of carbamate protecting groups by methods well known to those skilled in the art. A preferred protecting group is BOC, which is readily prepared by reacting the pyrrolidine free amine with di-tert-butyl dicarbonate. Alternatively, and preferably, the N-debenzylation and BOC protection can be accomplished in a single step by performing the catalytic hydrogenation using 10% Pd/C catalyst under 1 atm of hydrogen in the presence of di-tert-butyl dicarbonate. This procedure affords intermediate 6 where R" is BOC. Selective deprotection or hydrolysis of the pyrrolidine ester affords a pyrrolidine acid, for example when R' is methyl and R is isopropyl, treatment of intermediate 6 with lithium hydroxide in aqueous THF readily affords the pyrrolidine acid (intermediate 6, R'=H). The Curtius rearrangement involves conversion of a carboxylic acid into an acyl azide which upon pyrolysis rearranges with loss of $N_2$ to yield an isocyanate, which can in turn be hydrolyzed to a free amine or reacted with an alcohol to afford a carbamate protected amine (for a review, see Banthorpe, in Patai, "The Chemistry of the Azido Group" pp. 397-405, Interscience, New York, 1971). Application of the Curtius rearrangement to the pyrrolidine acid intermediate 6 (R'=H) affords after isocyanate hydrolysis the amine intermediate 7. There are a variety of ways to prepare the requisite acyl azide, such as treatment of the acid with diphenylphosphoryl azide in the presence of a base such as triethylamine. Another preferred method involves preparation of a mixed anhydride, such as by treating the acid with ethyl or isobutyl chloroformate in the presence of a base such as triethylamine, followed by treating the mixed anhydride with sodium azide. Pyrolysis of the acyl azide can be accomplished by refluxing in a solvent such as benzene or toluene. Hydrolysis of the isocyanate with dilute acid, such as 0.1-1.0 N HCl in THF affords the amine intermediate 7. Ring closure of amino ester intermediate 7 to the tricyclic lactam intermediate 8 can be accomplished by heating in a solvent such as methanol or ethanol in the presence of a base such as sodium methoxide or sodium ethoxide. Deprotection of the pyrrolidine nitrogen, such as with HCl or TFA where R"=BOC, affords cis-fused compounds of Formula I, where n=1 and X=O.

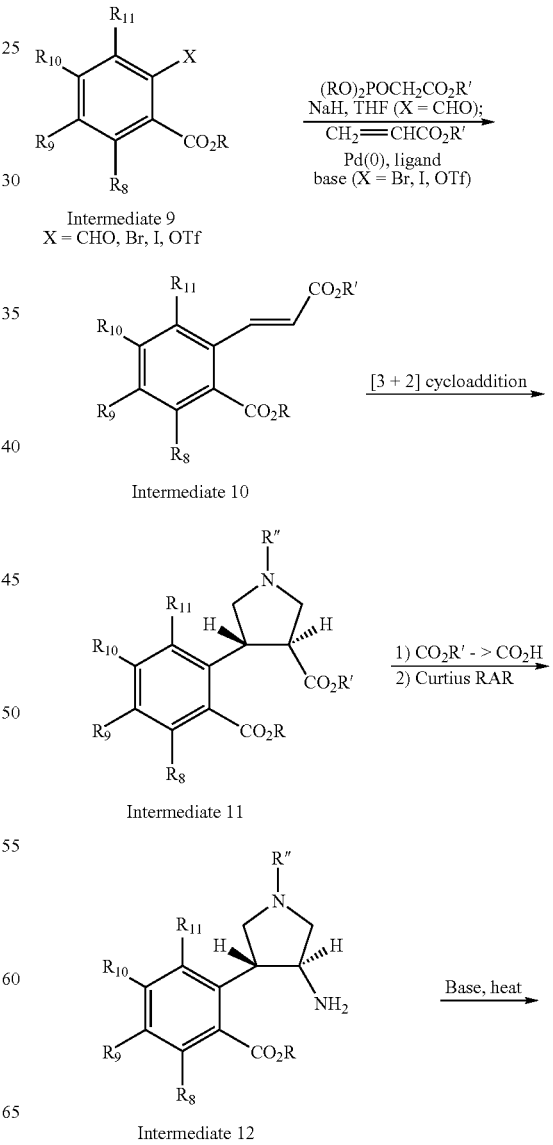

SCHEME 2

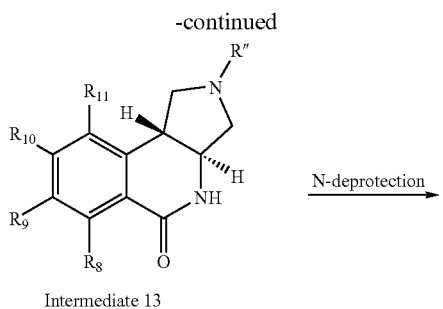

Intermediate 13

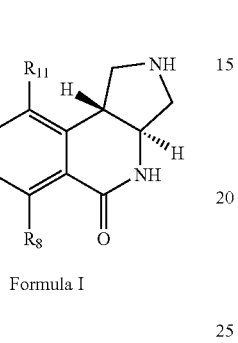

Formula I

Compounds of Formula I, wherein $A_n$ is $CH_2$ and $B_m$ is $CH_2$, D and E are CH, X=O, and the ring fusion stereochemistry is trans, may be prepared by similar procedures as depicted in Scheme 2. Intermediate 9, prepared as shown in Scheme 1 or by other methods known to those skilled in the art, can be subjected to an E-selective Horner-Emmons reaction, which involves treating intermediate 9 (wherein X=CHO) with the sodium salt of an appropriate phosphonate (where R=methyl or ethyl) to afford intermediate 10. Alternatively, intermediate 9, wherein X is Br, I or OTf, can be treated with an appropriate acrylate under a variety of established palladium catalyzed coupling conditions to afford intermediate 10. As in Scheme 1, the reagents should be chosen such that in intermediate 10 the ester groups R and R' are different. A preferred strategy is to use the methyl ester of intermediate 9 while using the benzyl ester of the phosphonate. This affords intermediate 10 where R is methyl and R' is benzyl. Intermediate 10 can undergo [3+2] azomethine ylide cyclization as described in Scheme 1 to afford the pyrrolidine intermediate 11 where R" is benzyl. In this case, the E-olefins undergo cyclization to produce pyrrolidine intermediates 11 with a trans configuration of the 3,4-substituents on the pyrrolidine ring. As in Scheme 1, the preferred protecting group R" on the pyrrolidine nitrogen is a carbamate, especially BOC. This group can be introduced as described in Scheme 1. As in Scheme 1, selective deprotection or hydrolysis of the pyrrolidine ester affords the requisite pyrrolidine acid for the Curtius rearrangement. In the case of intermediate 11 where R' is benzyl, the ester deprotection can occur concomitantly with the N-debenzylation under the conditions of catalytic hydrogenation as described in Scheme 1. The Curtius rearrangement as described previously affords intermediate 12, which can be cyclized and N-deprotected as described in Scheme 1 to afford trans-fused compounds of Formula I, where n=1 and X=O.

SCHEME 3

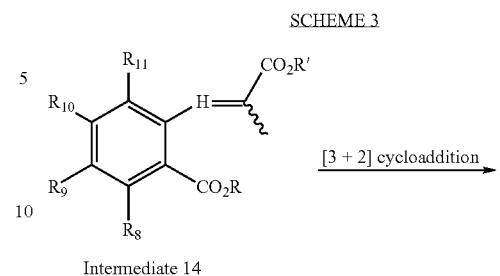

Intermediate 14

[3 + 2] cycloaddition →

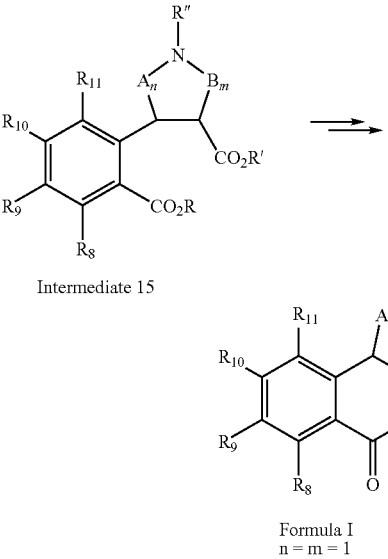

Intermediate 15

Formula I
n = m = 1

It is well known to those skilled in the art that a variety of additional methods can be used to generate substituted azomethine ylides in addition to the methods for the generation of unsubstituted azomethine ylides described in Scheme 1. These methods include, but are not limited to, pyrolysis of appropriately substituted aziridines, desilylation of α-trimethylsilylonium salts, etc. (for references, see *Synthesis*, 1973, 469; *Comprehensive Organic Synthesis*, Vol 4, B. M. Trost and I. Fleming, eds. Pergamon Press, New York, 1991; *Comprehensive Heterocyclic Synthesis*, Vol. 4, A. R. Katritzky and C. W. Rees, eds. Pergamon Press, New York, 1984). Thus, as shown in Scheme 3, additional compounds of Formula I can be prepared by [3+2] cycloaddition of intermediate 14 with an appropriate azomethine ylide to afford intermediate 15, where n and m are 1, and A and B are defined as in Formula I. Conversion of intermediate 15 to final compounds of Formula I follows the procedures described in Schemes 1 and 2.

SCHEME 4

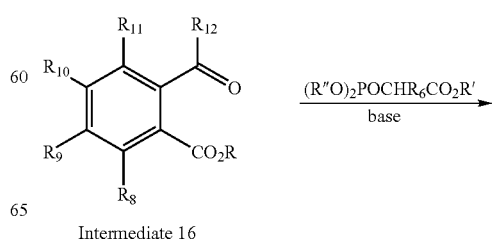

Intermediate 16

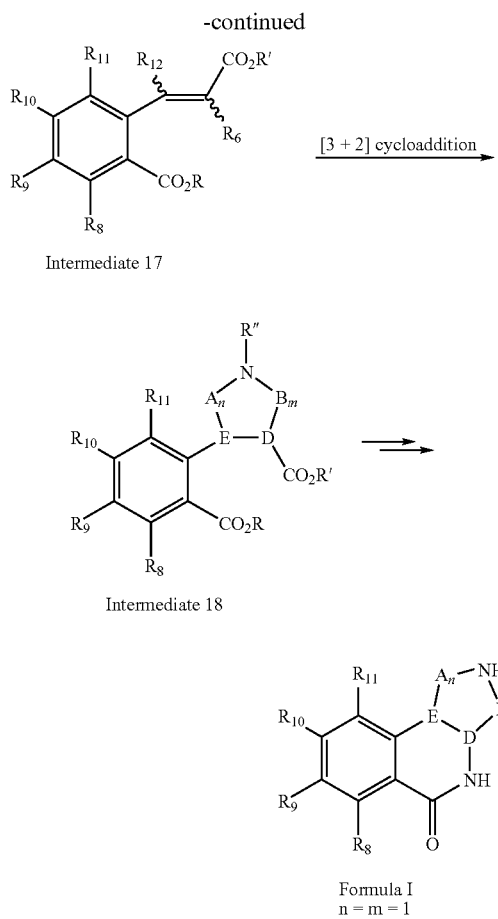
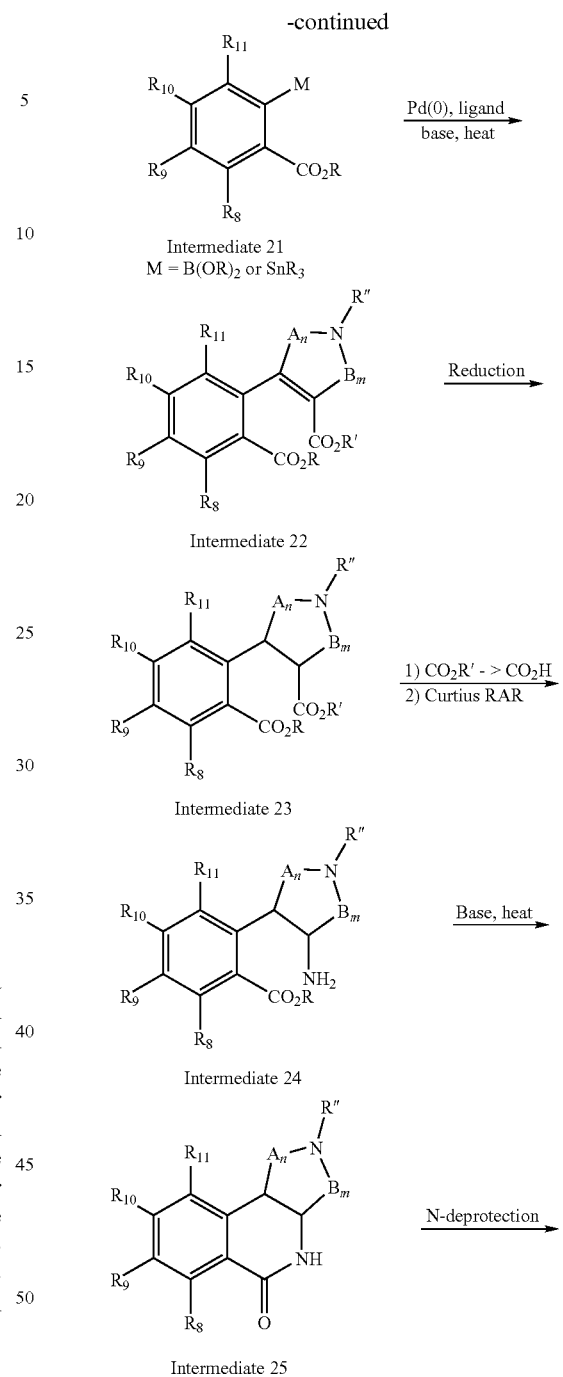

Compounds of Formula I, wherein n and m are 1, and D and E can be other than CH, and X=O, can be prepared as shown in Scheme 4. Readily available ketoester intermediates 16 can be treated with a wide variety of phosphonate reagents in the presence of an appropriate base, such as sodium hydride or KHMDS, to afford the olefin intermediate 17. As described in Schemes 1 and 2, different R″ groups on the phosphonate reagent can give rise to selective production of either the E- or Z-olefin 17. As described previously, intermediately can be treated under a variety of conditions to effect a [3+2] cycloaddition to afford intermediate 18, where n and m are 1. Following procedures described previously, intermediate 18 can be converted to the Final compounds of Formula I.

SCHEME 5

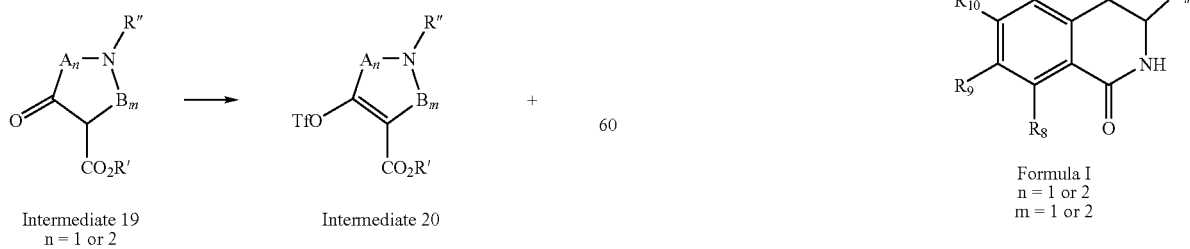

Compounds of Formula I, wherein D and E are CH, and X=O, can also be prepared as described in Scheme 5. A wide variety of cyclic ketoester intermediates 19 are well known in the chemical literature and are readily prepared by procedures known to those skilled in the art. Conversion of 19 to an enol triflate intermediate 20 is readily accomplished with trifluoromethanesulfonic anhydride or N-phenyltrifluoromethanesulfonimide and a base such as sodium hydride. Enol triflates 20 can be coupled with an appropriate, readily available aryl boronic acid or ester, or an aryl stannane reagent, intermediate 21, under a wide variety of palladium-catalyzed cross coupling conditions. For a review and leading references of palladium catalyzed cross coupling reactions, see Miyaura, N., Suzuki, A., *Chem. Rev.*, 1995, 2457; and J. Tsuji, "Palladium Reagents and Catalysts, Innovations in Organic Synthesis", J. Wiley and Sons, New York, 1995. One such procedure entails treatment of intermediate 20 with intermediate 21 in the presence of a catalytic Pd species, such as $Pd(PPh_3)_4$, $Pd(PPh_3)_2Cl_2$, $Pd(OAc)_2$ or $Pd_2(dba)_3$ and a suitable ligand such as $PPh_3$, BINAP, etc., and a base such as NaOtBu, $Ba(OH)_2$ or $Na_2CO_3$ in a suitable solvent such as DMF, toluene, THF, or DME, to afford the intermediate 22. Reduction of intermediate 22 can be carried out to produce both the cis and trans relationship between the ester and aryl groups. Catalytic hydrogenation in the presence of Pd/C catalyst affords the cis intermediates 23. Deprotonation of 23 with a base such as LDA, and allowing equilibration to take place produces a preponderance of the trans intermediates 23. As described in Scheme 1, the reagents to prepare intermediates 23 should be chosen to allow for selective deprotection of the heterocyclic ester ($CO_2R'$). An example of this strategy would be where R' is methyl and R is ethyl, thereby allowing for the selective hydrolysis of the methyl ester with lithium hydroxide. Other strategies for effecting a selective deprotection of R' will be known to those skilled in the art. Curtius rearrangement of the resulting carboxylic acid as described in previous schemes affords intermediates 24. Ring-closure to intermediate 25 and N-deprotection affords compounds of Formula I, wherein n and m are 1 or 2, and X=O.

SCHEME 6

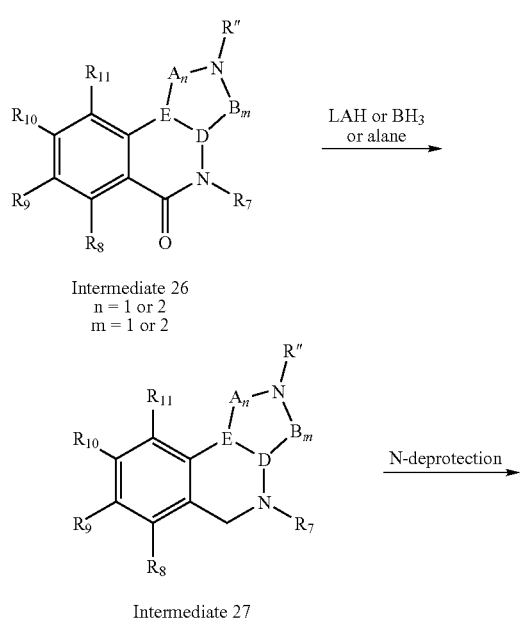

Intermediate 26
n = 1 or 2
m = 1 or 2

LAH or $BH_3$
or alane

N-deprotection

Intermediate 27

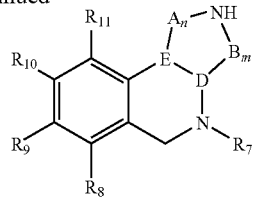

Formula I
n = 1 or 2
m = 1 or 2

Compounds of Formula I, wherein n and m are 1 or 2, and $X=H_2$, are prepared as shown in Scheme 6. Intermediate 26, where R″ is an appropriate protecting group, such as N-benzyl, is treated with a reducing reagent, such as alane, lithium aluminum hydride or borane, in a solvent such as THF or ether, to effect the reduction of the lactam to afford intermediate 27. Standard deprotection of the pyrrolidine nitrogen affords compounds of Formula I wherein n and m are 1 or 2, and $X=H_2$.

SCHEME 7

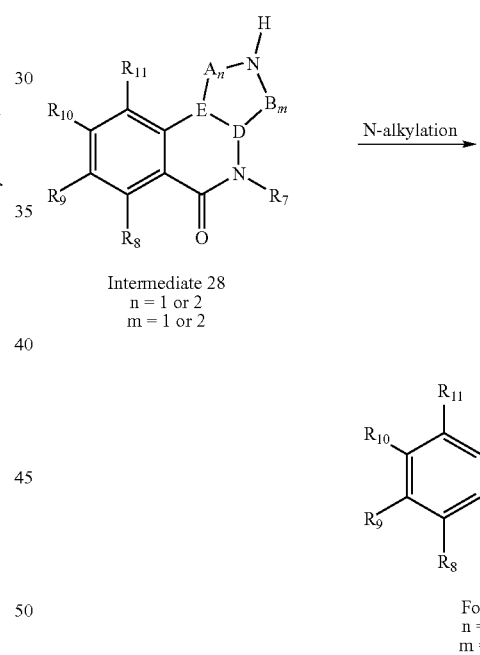

Intermediate 28
n = 1 or 2
m = 1 or 2

N-alkylation

Formula I
n = 1 or 2
m = 1 or 2

Compounds of Formula 1, wherein n and m are 1 or 2, and in which R3 is other than H, are prepared as shown in Scheme 7. These compounds are prepared from intermediate 28 by reductive alkylation with an aldehyde or ketone under conditions known in the art, for example, catalytic hydrogenation with hydrogen in the presence of palladium or platinum or with reducing agents such as sodium triacetoxyborohydride. Alternatively, a similar transformation can be accomplished by treating intermediate 28 with an alkylating agent R3X, where X is a halide (halide=Cl, Br, I), mesylate, tosylate, triflate, etc. in the presence of a base such as triethylamine, pyridine, etc. in acetonitrile, DMF, DMSO, etc. at room temperature to reflux temperature of the solvent to yield compounds of Formula I wherein R3 is not hydrogen.

SCHEME 8

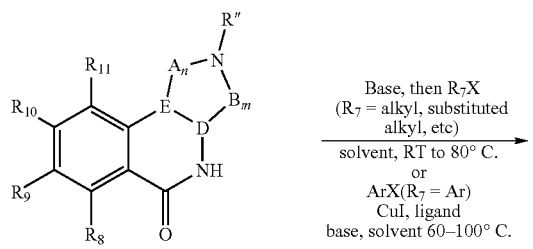

Intermediate 29
n = 1 or 2
m = 1 or 2

Base, then R$_7$X
(R$_7$ = alkyl, substituted alkyl, etc)
solvent, RT to 80° C.
or
ArX(R$_7$ = Ar)
CuI, ligand
base, solvent 60–100° C.

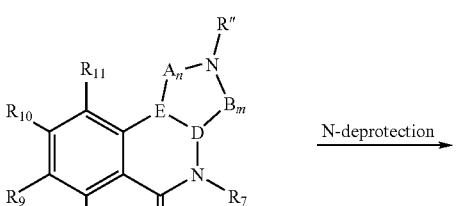

Intermediate 30

N-deprotection

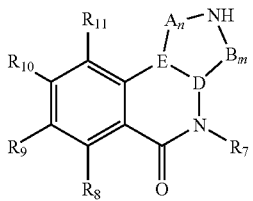

Formula I
n = 1 or 2
m = 1 or 2

Compounds of Formula I, wherein n and m are 1 or 2, and R7 is other than hydrogen, can be prepared as shown in Scheme 8. Treatment of intermediate 29, where R" is an appropriate N-protecting group, such as BOC, under a variety of N-alkylation or N-arylation conditions can afford N-alkyl or N-aryl intermediates 30. For example, for N-alkyl derivatives, treatment of intermediate 29 with a base such as sodium hydride followed by treatment of the resulting anion with a wide variety of alkylating agents, such as but not limited to alkyl halides R7X, where X=Br, I, Cl, OTs, etc., affords intermediate 30. For N-aryl derivatives, treatment of intermediate 29 with an aryl halide under copper or palladium catalysis can afford the intermediate 30. One preferred method uses an appropriate aryl iodide or aryl bromide, CuI and a diamine such as N,N'-dimethylethylenediamine as the catalyst system, and a base such as potassium phosphate in a solvent such as benzene or toluene at reflux temperature to afford the intermediates 30 (Buchwald, S.; et. al. *J. Am. Chem. Soc.* 2002, 124, 7421). N-deprotection of intermediate 30 under appropriate conditions then affords the compounds of Formula I where n and m are 1 or 2, and R7 is a group other than H.

SCHEME 9

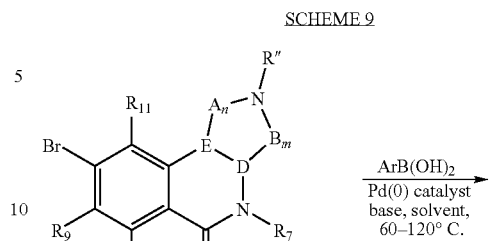

Intermediate 31
n = 1 or 2
m = 1 or 2

ArB(OH)$_2$
Pd(0) catalyst
base, solvent,
60–120° C.

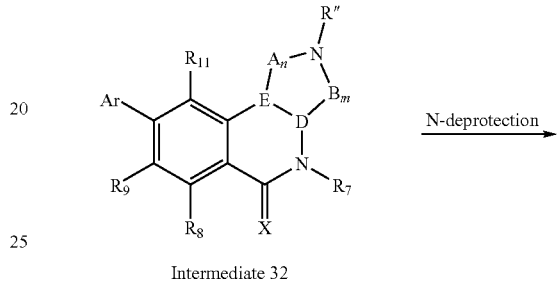

Intermediate 32

N-deprotection

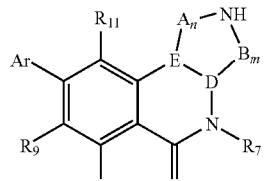

Formula I
n = 1 or 2
m = 1 or 2

Alternatively, compounds of Formula 1 can be further modified by the procedures outlined in Scheme 9. It is understood that the aromatic substitution is shown for only one position on the aromatic ring and that similar transformations may be performed at R8, R9, and R11. Compounds of Formula 1 can be brominated in one of two procedures, the choice of procedures will be readily apparent to one skilled in the art, in which the nitrogen is protected with an amine protecting group (Pg) well familiar to those skilled in the art, and typical examples may be found in Greene, T and Wuts, P. G. M., *Protecting Groups in Organic Synthesis*, John Wiley & Sons, Inc., New York, N.Y., 1991 and references therein, and then treated with N-bromosuccinimide in a suitable solvent such as but not limited to DMF to yield intermediate 31. Alternatively, the compound can be treated with N-bromosuccinimide in a suitable solvent such as sulfuric acid, triflouroacetic acid, etc. and then the amine protected to yield intermediate 31. Intermediate 31 can then be modified to yield compounds of Formula 1 by biaryl couplings, which can be accomplished under Suzuki coupling protocols. For a review and leading references of palladium catalyzed cross coupling reactions, see Miyaura, N., Suzuki, A., *Chem. Rev.*, 1995, 2457. One such procedure entails treatment of intermediate 31 with a functionalized aryl boronic acid in the presence of a catalytic Pd(0) species, such as Pd(PPh$_3$)$_4$, Pd(PPh$_3$)$_2$Cl$_2$, Pd(OAc)$_2$, Pd$_2$(dba)$_3$ and a suitable ligand such as PPh$_3$, AsPh$_3$, etc., or other such Pd(0) catalyst, and a base such as Na$_2$CO$_3$, Ba(OH)$_2$ or Et$_3$N in a suitable solvent such as DMF, toluene, THF, DME or the like, to afford intermediate 32. Removal of the protecting group, R", with the appropriate reagents, well familiar to those skilled in the art, and typical examples may be found in Greene, T and Wuts, P. G. M., *Protecting Groups in Organic Synthesis*, John Wiley & Sons, Inc., New York, N.Y., 1991 and references therein, yields compounds of Formula I.

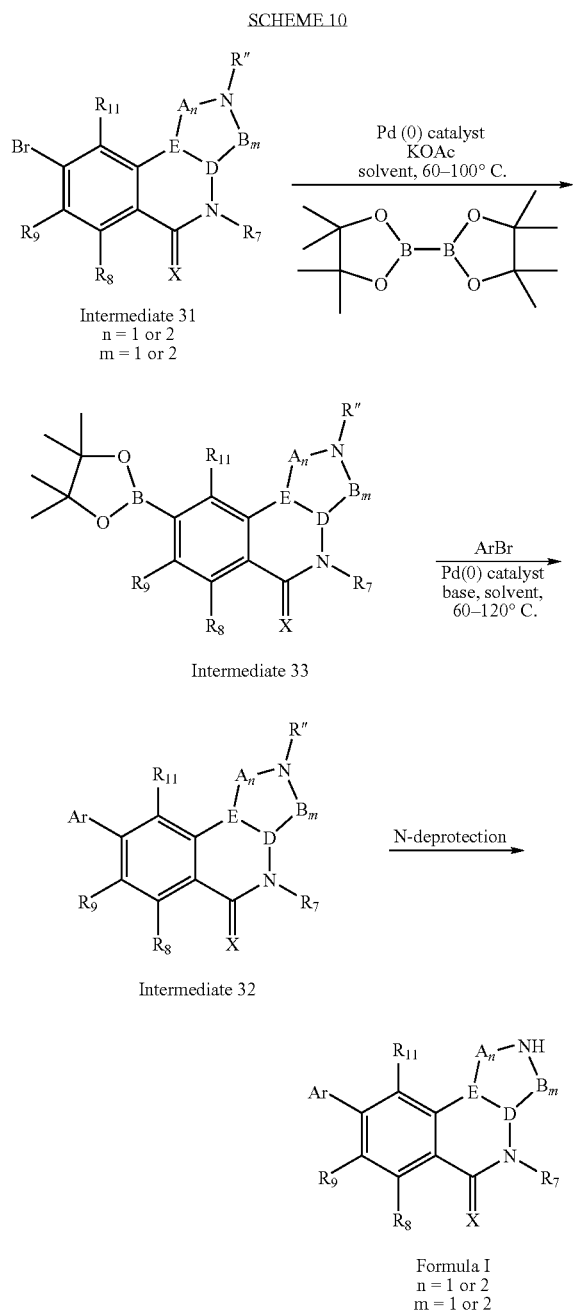

Alternatively formation of the boronic ester from intermediate 31 would allow for greater diversity in the subsequent coupling of this boronic acid with commercially available haloaromatic derivatives in a similar Suzuki coupling strategy as described above to afford compounds of Formula 1. One such procedure is shown in Scheme 10, and it is understood that the aromatic substitution is shown for only one position on the aromatic ring and that similar transformations may be performed at R8, R9, and R11. Treatment of intermediate 31 with a palladium catalyst such as $Pd(PPh_3)_4$ or $Pd(PPh_3)_2Cl_2$ and a suitable base, a preferred one being potassium acetate, in the presence of diboron pinacol ester affords intermediate 33. This boronic ester can undergo Suzuki coupling directly with a wide variety of commercially available aryl bromides under typical Suzuki conditions as described in Scheme 9 to yield intermediate 32, which can be deprotected as described above to afford compounds of Formula 1.

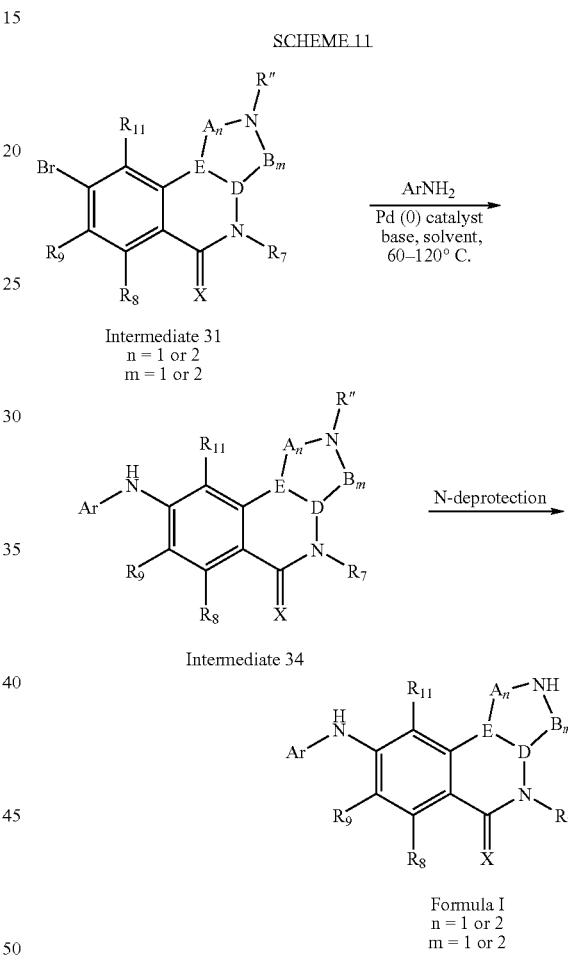

Compounds of Formula I with an arylamino group attached to the aromatic ring can be synthesized by the procedures outlined in Scheme 11, and it is understood that the aromatic substitution is shown for only one position on the aromatic ring and that similar transformations may be performed at R8, R9, R11. Treatment of intermediate 31 with a wide variety of commercially available anilines in the presence of a palladium (0) catalyst, such as $Pd_2(dba)_3$, $Pd(PPh_3)_4$ or $Pd(PPh_3)_2Cl_2$, and a suitable ligand such as BINAP or $PPh_3$, and a base such as NaOtBu in a suitable solvent such as DMF, toluene, THF, etc. to yield intermediate 34, which can be deprotected as described above to afford compounds of Formula 1.

SCHEME 12

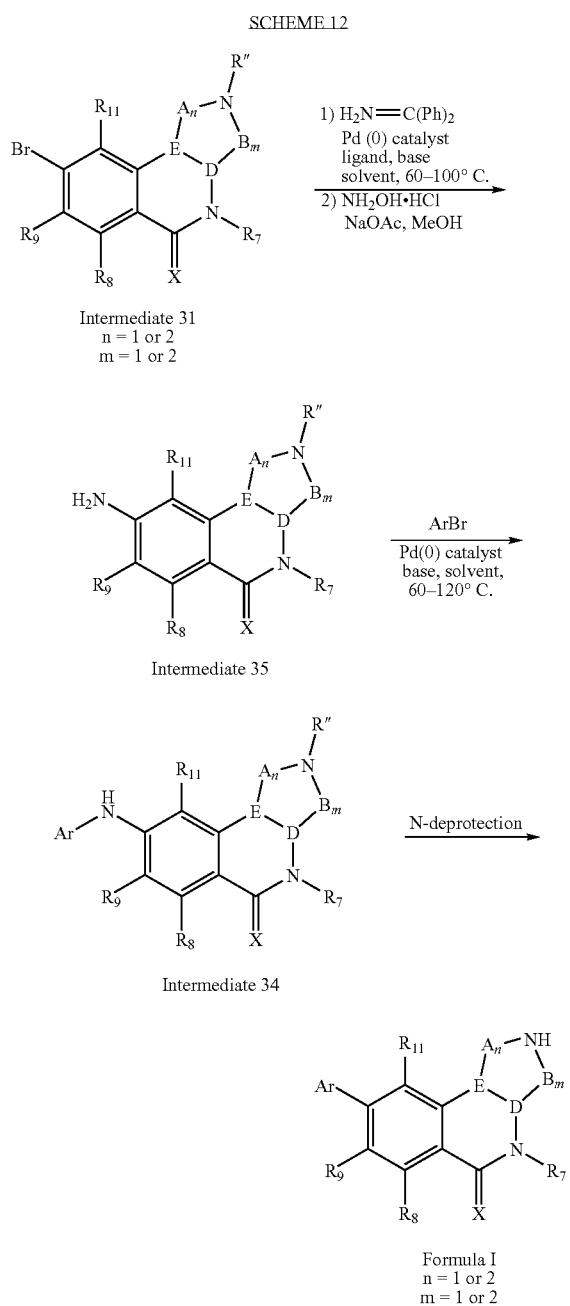

Intermediate 31
n = 1 or 2
m = 1 or 2

Intermediate 35

Intermediate 34

Formula I
n = 1 or 2
m = 1 or 2

Alternatively, compounds of Formula I with an arylamino group attached to the aromatic ring can be synthesized by the procedures outlined in Scheme 12. Treatment of intermediate 31 with benzophenone imine in the presence of a palladium (0) catalyst, such as $Pd_2(dba)_3$, $Pd(PPh_3)_4$ or $Pd(PPh_3)_2Cl_2$, and a suitable ligand such as BINAP or $PPh_3$, and a base such as NaOtBu in a suitable solvent such as DMF, toluene, THF, DME, etc., affords an imine in which nitrogen is attached to the aromatic ring. Hydrolysis of this imine, for example with hydroxylamine and sodium acetate in methanol, affords intermediate 35. This aniline can be treated with a wide variety of commercially available aryl bromides in the presence of a palladium (0) catalyst, such as $Pd_2(dba)_3$, $Pd(PPh_3)_4$ or $Pd(PPh_3)_2Cl_2$, and a suitable ligand such as BINAP or $PPh_3$, and a base such as but not limited to NaOtBu in a suitable solvent such as DMF, toluene, THF, DME, etc. to yield intermediate 34, which can be deprotected as described above to afford compounds of Formula 1.

SCHEME 13

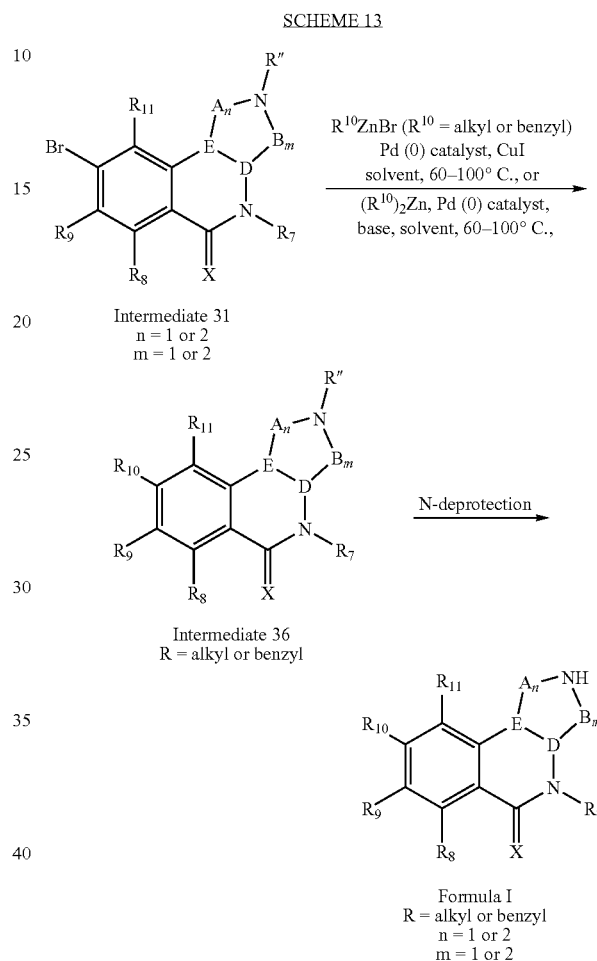

Intermediate 31
n = 1 or 2
m = 1 or 2

Intermediate 36
R = alkyl or benzyl

Formula I
R = alkyl or benzyl
n = 1 or 2
m = 1 or 2

Compounds of Formula I with benzyl or alkyl groups attached to the aromatic group can be prepared as shown in Scheme 13. Treatment of intermediate 31 with an appropriate benzylzinc or alkylzinc reagent, which can be generated from the corresponding benzyl halide, in the presence of a palladium (0) catalyst such as $Pd(PPh_3)_4$, $Pd(PPh_3)_2Cl_2$, or $Pd_2(dba)_3$, and with or without a copper (I) salt, affords intermediate-36 (see Knochel, et al. *Chem. Rev.* 1993, 93, 2117; and Weichert, et al. *Syn. Lett.* 1996, 473). This chemistry can also be extended to include a variety of alkylzinc and cycloalkylzinc reagents, which are available from the corresponding alkyl halides and cycloalkyl halides. Or, intermediate 31 can be treated with an appropriate dialkylzinc reagent, in the presence of a palladium (O) catalyst such as $Pd(PPh_3)_4$, $Pd(PPh_3)_2Cl_2$, or $Pd_2(dba)_3$, and in the presence of a suitable base, such as potassium carbonate, to afford intermediate 36. The above intermediates can be deprotected as described above to afford compounds of Formula 1.

SCHEME 14

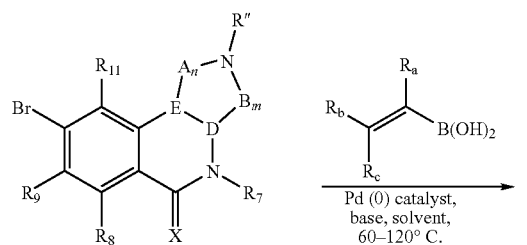

Intermediate 31
n = 1 or 2
m = 1 or 2

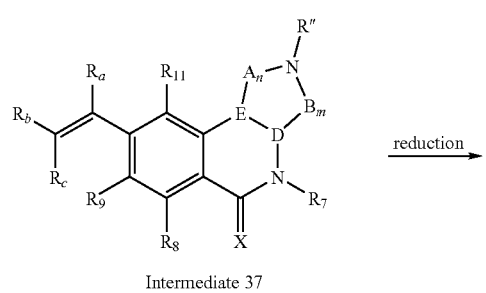

Intermediate 37

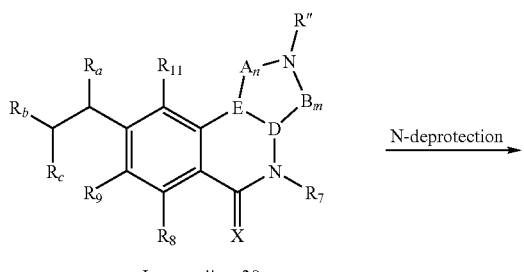

Intermediate 38

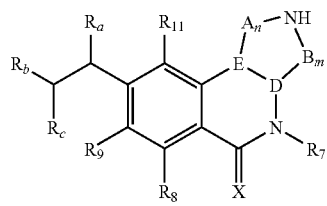

Formula I
n = 1 or 2
m = 1 or 2

Alternatively, compounds of Formula I with alkyl groups attached to the aromatic group can be prepared as shown in Scheme 14. Treatment of intermediate 31 with an appropriate vinyl boronic acid, which are commercially available or can be prepared readily, for example from the corresponding vinyl Grignard reagent, in the presence of a palladium (O) catalyst such as $Pd(PPh_3)_4$, $Pd(PPh_3)_2Cl_2$, or $Pd_2(dba)_3$ and a base such as NaOtBu or $Na_2CO_3$ in a suitable solvent such as DMF, toluene, THF, DME/$H_2O$, etc., affords the vinyl intermediate 37. Reduction of the vinyl group, such as by catalytic hydrogenation over Pd/C catalyst, affords reduced intermediate 38. These intermediates can be deprotected as described above to afford compounds of Formula 1.

SCHEME 15

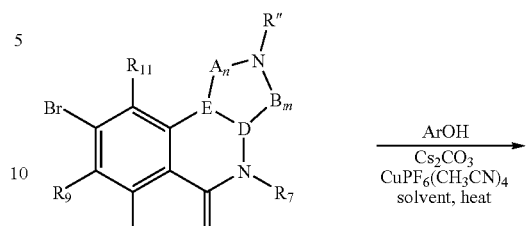

Intermediate 31
n = 1 or 2
m = 1 or 2

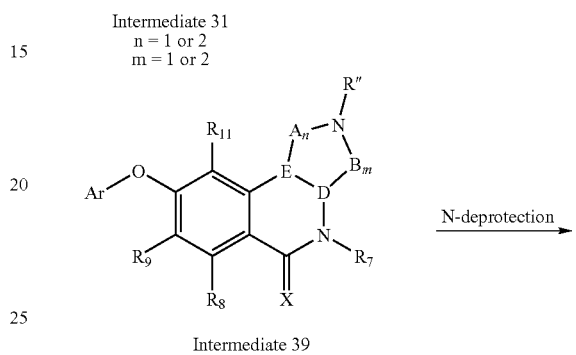

Intermediate 39

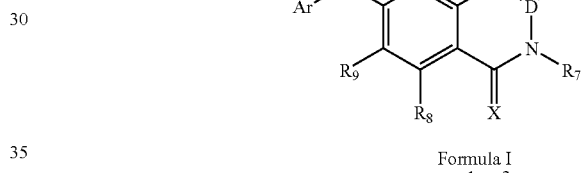

Formula I
n = 1 or 2
m = 1 or 2

Compounds of Formula I with an arylhydroxy group attached to the aromatic ring can be synthesized by the procedures outlined in Scheme 15, and it is understood that the aromatic substitution is shown for only one position on the aromatic ring and that similar transformations may be performed at R8, R9, R11. Intermediate 31 can be treated with various phenols in the presence of a base such as $Cs_2CO_3$, and a copper catalyst, such as $CuPF_6(CH_3CN)_4$, at elevated temperature to yield intermediate 39 (see Sawyer, *Tetrahedron* 2000, 56, 5045). The above intermediates can be deprotected as described above to afford compounds of Formula 1.

In addition, there exists a wide range of procedures and protocols for functionalizing haloaromatics, aryldiazonium and aryltriflate compounds. These procedures are well known by those in the art and described, for example, by Stanforth, *Tetrahedron*, 1998, 263; Buchwald et al., *J. Am. Chem. Soc.*, 1998, 9722; Stille, et al., *J. Am. Chem. Soc.*, 1984, 7500. Among these procedures are biaryl couplings, alkylations, acylations, aminations, and amidations. The power of palladium catalyzed functionalization of aromatic cores has been explored in depth in the last decade. An excellent review of this field can be found in J. Tsuji, "Palladium Reagents and Catalysts, Innovations in Organic Synthesis", J. Wiley and Sons, New York, 1995.

Utilities and Combinations

Utilities

The compounds of the present application are 5HT modulators, and include compounds which are, for example, selective agonists, partial agonists, antagonists or partial antagonists of the $5HT_{2C}$ receptor. Accordingly, the compounds of the present application may be useful for the treatment or prevention of diseases and disorders associated with 5HT receptor activity. Preferably, compounds of the present application possess activity as agonists of the $5HT_{2C}$ receptor, and may be used in the treatment of diseases or disorders associated with the activity of the $5HT_{2C}$ receptor.

Accordingly, the compounds of the present application can be administered to mammals, preferably humans, for the treatment of a variety of conditions and disorders, including, but not limited to metabolic and eating disorders as well as conditions associated with metabolic disorders, (e.g., obesity, diabetes, arteriosclerosis, hypertension, polycystic ovary disease, cardiovascular disease, osteoarthritis, dermatological disorders, impaired glucose hemostatsis, insulin resistance, hypercholesterolemia, hypertriglyceridemia, cholelithiasis and sleep disorders, dislipidemic conditions, bulimia nervosa and compulsive eating disorders); pain; sleep disorders and psychiatric disorders, such as substance abuse, depression, anxiety, psychosis, mania and schizophrenia.

These compounds could also be used for the improvement of cognitive function (e.g., the treatment of dementia, including Alzheimer's disease, short term memory loss and attention deficit disorders); neurodegenerative disorders (e.g., Parkinson's Disease, cerebral apoplexy and craniocerebral trauma) and hypotension (e.g., hemorrhagic and endotoxin-inducd hypotension). These compounds could also be used for treatment of cardiac dysfunction (e.g., associated with valvular disease, myocardial infarction, cardiac hypertrophy or congestive heart failure); and improvement of the overall pulmonary function; transplant rejection; rheumatoid arthritis; osteoarthritis; fibromyalgia; multiple sclerosis; inflammatory bowel disease; lupus; graft vs. host disease; T-cell mediated hypersensitivity disease; psoriasis; asthma; Hashimoto's thyroiditis; Guillain-Barre syndrome; cancer; contact dermatitis; allergic rhinitis; and ischemic or reperfusion injury. These compounds could also be used for treatment of sexual dysfunction and erectogenesis.

Compounds useful in the treatment of appetite or motivational disorders regulate desires to consume sugars, carbohydrates, alcohol or drugs and more generally to regulate the consumption of ingredients with hedonic value. In the present description and in the claims, appetite disorders are understood as meaning: disorders associated with a substance and especially abuse of a substance and/or dependency on a substance, disorders of eating behaviors, especially those liable to cause excess weight, irrespective of its origin, for example: bulimia nervosa, craving for sugars. The present application therefore further relates to the use of a $5HT_{2C}$ receptor agonist for the treatment of bulimia and obesity, including obesity associated with type II diabetes (non-insulin-dependent diabetes), or more generally any disease resulting in the patient becoming overweight. Overweight and obesity, as described herein, is defined by a body mass index ($kg/m^2$) for example, at least 26. It may be due to any cause, whether genetic or environmental, including overeating and bulemia, polycycstic ovary disease, craniopharyngeoma, Prader-Willi Syndrome, Frohlich's Syndrome, Type II diabetes, growth hormone deficiency, Turner's Syndrome and other pathological states characterized by reduced metabolic activity or reduced energy expenditure. As used with reference to the utilities described herein, the term "treating" or "treatment" encompasses prevention, partial alleviation, or cure of the disease or disorder. Further, treatment of obesity is expected to prevent progression of medical covariants of obesity, such as arteriosclerosis, Type II diabetes, polycystic ovary disease, cardiovascular disease, osteoarthritis, dermatological disorders, hypertension, insulin resistance, hypercholesterolemia, hypertriglyceridemia, cholelithiasis and sleep disorders.

Compounds in the present application may also be useful in treating substance abuse disorders, including substance dependence or abuse without physiological dependence. Substances of abuse include alcohol, amphetamines (or amphetamine-like substances), caffeine, *cannabis*, cocaine, hallucinogens, inhalents, nicotine, opioids, phencyclidine (or phencyclidine-like compounds), sedative-hypnotics or benzodiazepines, and other (or unknown) substances and combinations of the above. The terms "substance abuse disorders" also includes drug, nicotine or alcohol withdrawal syndromes and substance-induced anxiety or mood disorder with onset during withdrawal.

Compounds in the present application may be useful in treating memory impairment and cognitive disorders. The condition of memory impairment is manifested by impairment of the ability to learn new information and/or the inability to recall previously learned information. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, attention deficit-hyperactivity disorder, HIV, cardiovascular disease such as ischemia or stroke, and head trauma as well as age-related cognitive decline. Dementias are diseases that include memory loss and additional intellectual impairment separate from memory. $5HT_{2C}$ modulators may also be useful in treating cognitive impairments related to attentional deficits, such as attention deficit-hyperactivity disorders.

Compounds in the present application may also be useful in treating diseases associated with dysfunction of brain dopaminergic systems, such as Parkinson's Disease and substance abuse disorders. Parkinsons's Disease is a neurodenerative movement disorder characterized by bradykinesia and tremor.

Combinations

The present application includes within its scope pharmaceutical compositions comprising, as an active ingredient, a therapeutically effective amount of at least one of the compounds of formula I, alone or in combination with a pharmaceutical carrier or diluent. Optionally, compounds of the present application can be used alone, in combination with other suitable therapeutic agents useful in the treatment of the aforementioned disorders including: anti-obesity agents; anti-diabetic agents, appetite suppressants; cholesterol/lipid-lowering agents, cognition enhancing agents, agents used to treat neurodegeneration, agents used to treat respiratory conditions, agents used to treat bowel disorders, anti-inflammatory agents; anti-anxiety agents; anti-depressants; anti-psychotic agents; sedatives; hypnotics; anti-hypertensive agents; anti-tumor agents and analgesics.

Such other therapeutic agent(s) may be administered prior to, simultaneously with, or following the administration of the $5HT_{2C}$ modulators in accordance with the application.

Examples of suitable anti-obesity agents for use in combination with the compounds of the present application include leptin and leptin-sensitizing agents, melanocortin receptor (MC4R) agonists, agouti-related peptide (AGRP) antagonists, melanin-concentrating hormone receptor (MCHR) antagonists, growth hormone secretagogue receptor (GHSR) antagonists, orexin antagonists, CCK agonists, GLP-1 agonists, NPY1 or NPY5 antagonsits, NPY2 modulators, corticotropin releasing factor agonists, histamine receptor-3 (H3) modulators, aP2 inhibitors, PPAR gamma modulators, PPAR delta modulators, beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a thyroid receptor beta modulator, such as a thyroid receptor ligand as disclosed in WO 97/21993 (U. Cal SF), WO 99/00353 (KaroBio) and GB98/284425 (KaroBio), a lipase inhibitor, such as orlistat or ATL-962 (Alizyme), leptinergics, adiponectin modulating agents, cannabinoid-1 receptor antagonists, such as SR-141716 (Sanofi) or SLV-319 (Solvay), acetyl CoA carboxylase (ACC) inhibitors as disclosed in International patent application WO 03/072197 and monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol, anorectic agents such as topiramate (Johnson & Johnson), axokine (Regeneron).

Examples of suitable anti-diabetic agents for use in combination with the compounds of the present application include: insulin, which may include short- and long-lasting forms as well as oral and inhaled forms, insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, PPAR α/γ dual agonists such as muraglitizar described in Bristol-Myers Squibb U.S. Pat. No. 6,414,002, dipeptidyl peptidase IV (DPP4) inhibitors such as saxagliptin described in Bristol-Myers Squibb U.S. Pat. Nos. 6,395,767 and 6,573,287, SGLT2 inhibitors such as the compounds described in Bristol-Myers Squibb U.S. Pat. Nos. 6,414,126 and 6,515,117, glycogen phosphorylase inhibitors, and/or meglitinides, as well as insulin, and/or glucagon-like peptide-1 (GLP-1), and/or a PTP-1B inhibitor (protein tyrosine phosphatase-1B inhibitor).

The antidiabetic agent may be glucokinase inhibitors, 11 β HSD inhibitors or oral antihyperglycemic agents, which is preferably a biguanide such as metformin or phenformin or salts thereof, preferably metformin HCl. Where the antidiabetic agent is a biguanide, the compounds of the present application will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the beta-cells, with glyburide and glipizide being preferred, which may be administered in the same or in separate oral dosage forms. The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of the present application may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's REZULIN, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of the present application may be employed in combination with anti-hyperlipidemia agents, or agents used to treat arteriosclerosis. An example of an hypolipidemic agent would be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pitavastatin (Nissan/Sankyo's nisvastatin (NK-104) or itavastatin), disclosed in U.S. Pat. No. 5,011,930, Shionogi-Astra/Zeneca rosuvastatin (visastatin (ZD-4522)) disclosed in U.S. Pat. No. 5,260,440, and related statin compounds disclosed in U.S. Pat. No. 5,753,675.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869-1871, including isoprenoid (phosphinyl-methyl)phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1-40 (1996).

In addition, other squalene synthetase inhibitors suitable for use herein include the terpenoid pyrophosphates disclosed by P. Ortiz de Montellano et al, J. Med. Chem., 1977, 20, 243-249, the farnesyl diphosphate analog A and presqualene pyrophosphate (PSQ-PP) analogs as disclosed by Corey and Volante, J. Am. Chem. Soc., 1976, 98, 1291-1293, phosphinylphosphonates reported by McClard, R. W. et al, J.A.C.S., 1987, 109, 5544, cyclopropanes reported by Capson, T. L., PhD dissertation, June, 1987, Dept. Med. Chem. U of Utah, Abstract, Table of Contents, pp 16, 17, 40-43, 48-51, Summary, pyrrolidine derivatives as disclosed by Sasyou, et al, WO 02/083636 and N-aryl-substituted cyclic amine derivatives disclosed by Okada et al, WO 02/076973.

Other hypolipidemic agents suitable for use herein include, but are not limited to, fibric acid derivatives, α PPAR agonists, such as fenofibrate, gemfibrozil, clofibrate, bezafibrate, ciprofibrate, clinofibrate and the like, probucol, and related compounds as disclosed in U.S. Pat. No. 3,674,836, probucol, phenylfibrate and gemfibrozil being preferred, bile acid sequestrants such as cholestyramine, colestipol and DEAE-Sephadex (SECHOLEX, POLICEXIDE) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents.

The other hypolipidemic agent may be an ACAT inhibitor (which also has anti-atherosclerosis activity) such as disclosed in, Drugs of the Future 24, 9-15 (1999), (Avasimibe); "The ACAT inhibitor, Cl-1011 is effective in the prevention and regression of aortic fatty streak area in hamsters", Nicolosi et al, Atherosclerosis (Shannon, Irel). (1998), 137(1), 77-85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16-30; "RP 73163: a bioavailable alkylsulfinyl-diphenylimidazole ACAT inhibitor", Smith, C., et al, Bioorg. Med. Chem. Lett. (1996), 6(1), 47-50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173-98, Publisher: CRC, Boca Raton, Fla.; "ACAT inhibitors: potential anti-atherosclerotic agents", Sliskovic et al, Curr. Med. Chem. (1994), 1(3), 204-25; "Inhibitors of acyl-CoA: cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359-62, or TS-962 (Taisho Pharmaceutical Co. Ltd), as well as F-1394, CS-505, F-12511, HL-004, K-10085 and YIC-C8-434.

The hypolipidemic agent may be an upregulator of LDL receptor activity such as MD-700 (Taisho Pharmaceutical Co. Ltd) and LY295427 (Eli Lilly). The hypolipidemic agent may be a cholesterol absorption inhibitor preferably Schering-Plough's SCH48461 (ezetimibe) as well as those disclosed in Atherosclerosis 115, 45-63 (1995) and J. Med. Chem. 41, 973 (1998).

The other lipid agent or lipid-modulating agent may be a cholesteryl transfer protein inhibitor (CETP) such as Pfizer's Torcetrapib® as well as those disclosed in WO/0038722 and in EP 818448 (Bayer) and EP 992496, and Pharmacia's SC-744 and SC-795, as well as CETi-1 and JTT-705.

The hypolipidemic agent may be an ileal Na+/bile acid cotransporter inhibitor such as disclosed in Drugs of the Future, 24, 425-430 (1999). The ATP citrate lyase inhibitor which may be employed in the combination of the application may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 2000/015201; a beta-lactam cholesterol absorption inhibitor such as disclosed in EP 675714; an HDL upregulator such as an LXR agonist, a PPAR α-agonist and/or an FXR agonist; an LDL catabolism promoter such as disclosed in EP 1022272; a sodium-proton exchange inhibitor such as disclosed in DE 19622222; an LDL-receptor inducer or a steroidal glycoside such as disclosed in U.S. Pat. No. 5,698,527 and GB 2304106; an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B12 and Vitamin E; isoniazid as disclosed in WO 97/35576; a cholesterol absorption inhibitor, an HMG-CoA synthase inhibitor, or a lanosterol demethylase inhibitor as disclosed in WO 97/48701; a PPAR δ agonist for treating dyslipidemia; or a sterol regulating element binding protein-I (SREBP-1) as disclosed in WO 2000/050574, for example, a sphingolipid, such as ceramide, or neutral sphingomyelenase (N-SMase) or fragment thereof, and inhibitors or lipid synthesis enzymes such as, for example, ACC, FAS, DGAT, MGAT, GPAT, AMP kinase, CPT1 and SCD1. Preferred dislipidemic agents are pravastatin, lovastatin, simvastatin, atorvastatin, fluvastatin, pitavastatin, rosuvastatin, fenofibrate and Pfizer's Torcetrapib® as well as niacin and/or cholestagel.

The compounds of the present application may be employed in combination with anti-hypertensive agents. Examples of suitable anti-hypertensive agents for use in combination with the compounds of the present application include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan, candasartan and talmisartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

$5HT_{2C}$ modulators could be useful in treating other diseases associated with obesity, including sleep disorders. Therefore, the compounds described in the present application could be used in combination with therapeutics for treating sleep disorders. Examples of suitable therapies for treatment of sleeping disorders for use in combination with the compounds of the present application include melatonin analogs, melatonin receptor agonists, ML 1 B agonists. GABA A receptor agonists such as barbiturates (e.g., amobarbital, aprobarbital, butabarbital, mephobarbital, pentobarbital, phenobarbital, secobarbital and talbutal), benzodiazepines (e.g., diazepam, lorazepam, oxazepam, alprazolam, chlordiazepoxide, clonazepam, chlorazepate, halazepam and prazepam), also specifically including triazolam (Halcion). Other agents for treating sleep disorders include zolpidem (Ambien) and Neurocrine's indiplon.

$5HT_{2C}$ modulators may reduce or ameliorate substance abuse or addictive disorders. Therefore, combination of $5HT_{2C}$ modulators with agents used to treat addictive disorders may reduce the dose requirement or improve the efficacy of current addictive disorder therapeutics. Examples of agents used to treat substance abuse or addictive disorders are: selective serotonin reuptake inhibitors (SSRI), methadone, buprenorphine, nicotine and bupropion and opiate antagonists.

$5HT_{2C}$ modulators may reduce anxiety or depression; therefore, the compounds described in this application may be used in combination with anti-anxiety agents or antidepressants. Examples of suitable anti-anxiety agents for use in combination with the compounds of the present application include benzodiazepines (e.g., diazepam, lorazepam, oxazepam, alprazolam, chlordiazepoxide, clonazepam, chlorazepate, halazepam and prazepam), $5HT_{1A}$ receptor agonists (e.g., buspirone, flesinoxan, gepirone, ipsapirone and serzone), corticotropin releasing factor (CRF) antagonists and SSRI's.

Examples of suitable classes of anti-depressants for use in combination with the compounds of the present application include norepinephrine reuptake inhibitors (tertiary and secondary amine tricyclics), selective serotonin reuptake inhibitors (SSRIs) (fluoxetine, fluvoxamine, paroxetine, citalopram and sertraline), monoamine oxidase inhibitors (MAOIs) (isocarboxazid, phenelzine, tranylcypromine, selegiline), reversible inhibitors of monoamine oxidase (RIMAs) (moclobemide), serotonin and norepinephrine reuptake inhibitors (SNRIs) (venlafaxine), corticotropin releasing factor (CRF) receptor antagonists (Britsol-Myers Squibb U.S. Pat. Nos. 6,642,230; 6,630,476; 6,589,952; 6,579,876; 6,525,056; 6,521,636; 6,518,271; 6,515,005; 6,448,261; 6,399,609; 6,362,180; and 6,358,950), alpha-adrenoreceptor antagonists, and atypical antidepressants (bupropion, lithium, nefazodone, trazodone and viloxazine).

The combination of a conventional antipsychotic drug with a $5HT_{2C}$ modulator could also enhance symptom reduction in the treatment of psychosis or mania. Further, such a combination could enable rapid symptom reduction, reducing the need for chronic treatment with antipsychotic agents. Such a combination could also reduce the effective antipsychotic dose requirement, resulting in reduced probability of developing the motor dysfunction typical of chronic antipsychotic treatment.

Examples of suitable antipsychotic agents for use in combination with the compounds of the present application include the phenothiazine (chlorpromazine, mesoridazine, thioridazine, acetophenazine, fluphenazine, perphenazine and trifluoperazine), thioxanthine (chlorprothixene, thiothixene), heterocyclic dibenzazepine (clozapine, olanzepine and aripiprazole), butyrophenone (haloperidol), diphenylbutylpiperidine (pimozide) and indolone (molindolone) classes of antipsychotic agents. Other antipsychotic agents with potential therapeutic value in combination with the compounds in the present application include loxapine, sulpiride and risperidone.

Combination of the compounds in the present application with conventional antipsychotic drugs could also provide an enhanced therapeutic effect for the treatment of schizophrenic disorders, as described above for manic disorders. As used here, schizophrenic disorders include paranoid, disorganized, catatonic, undifferentiated and residual schizophrenia, schizophreniform disorder, schizoaffective disorder, delusional disorder, brief psychotic disorder and psychotic disorder not specified. Examples of suitable antipsychotic drugs for combination with the compounds in the present application include the antipsychotics mentioned above, as well as dopamine receptor antagonists, muscarinic receptor agonists, $5HT_{2A}$ receptor antagonists and $5HT_{2A}$/dopamine receptor antagonists or partial agonists (e.g., olanzepine, aripiprazole, risperidone, ziprasidone).

The compounds described in the present application could be used to enhance the effects of cognition-enhancing agents, such as acetylcholinesterase inhibitors (e.g., tacrine the active agent in Cognex®), ADHD agents (e.g. methyl-phenidate, atomoxetine the active agent in Strattera® and histamine 3 antagonists), muscarinic receptor-1 agonists (e.g., milameline), nicotinic agonists, glutamic acid receptor (AMPA and NMDA) modulators such as memantine, and nootropic agents (e.g., piracetam, levetiracetam). Examples of suitable therapies for treatment of Alzheimer's disease and cognitive disorders for use in combination with the compounds of the present application include donepezil, tacrine, revastigraine, 5HT6 receptor antagonists, gamma secretase inhibitors, beta secretase inhibitors, SK channel blockers, Maxi-K blockers, and KCNQs blockers.

The compounds described in the present application could be used to enhance the effects of agents used in the treatment of Parkinson's Disease. Examples of agents used to treat Parkinson's Disease include: levadopa with or without a COMT inhibitor, antiglutamatergic drugs (amantadine, riluzole), alpha-2 adrenergic antagonists such as idazoxan, opiate antagonists, such as naltrexone, other dopamine agonists or transportor modulators, such as ropinirole, or pramipexole or neurotrophic factors such as glial derived neurotrophic factor (GDNF).

The compounds described in the present application could be used in combination with agents used to treat erectile dysfunction. Examples of suitable treatment for erectile dysfunction include sildenafil (Viagra), vardenafil (Levitra) and tadalafil (Cialis). Other compounds that could be used in combination for erectile dysfunction include yohimbine, phentolamine and papaverine.

The compounds described in the present application could be used in combination with suitable anti-inflammatory agents. Examples of suitable anti-inflammatory agents for use in combination with the compounds of the present application include prednisone, dexamethasone, cyclooxygenase inhibitors (i.e., COX-1 and/or COX-2 inhibitors such as NSAIDs, aspirin, indomethacin, ibuprofen, piroxicam, Naproxen®, Celebrex®, Vioxx®, Arcoxia®, and Bextra®), CTLA4-Ig agonists/antagonists, CD40 ligand antagonists, IMPDH inhibitors, such as mycophenolate (CellCept®), integrin antagonists, alpha-4 beta-7 integrin antagonists, cell adhesion inhibitors, interferon gamma antagonists, ICAM-1 inhibitor, tumor necrosis factor (TNF) antagonists (e.g., infliximab, OR1384, including TNF-alpha inhibitors, such as tenidap, anti-TNF antibodies or soluble TNF receptor such as etanercept (Enbrel®), Remicade®, rapamycin (sirolimus or Rapamune) and leflunomide (Arava)), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., Zelnorm® and Maxi-K® openers such as those disclosed in U.S. Pat. No. 6,184,231 B1).

Exemplary of such other therapeutic agents which may be used in combination with $5HT_{2C}$ modulators include the following: cyclosporins (e.g., cyclosporin A), anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), gold compounds, antiproliferative agents such as methotrexate, FK506 (tacrolimus, Prograf), mycophenolate mofetil, cytotoxic drugs such as azathiprine and cyclophosphamide, anticytokines such as antiIL-4 or IL-4 receptor fusion proteins and PDE 4 inhibitors such as Ariflo, and the PTK inhibitors disclosed in the following U.S. patent applications, incorporated herein by reference in their entirety: Ser. No. 09/097,338, filed Jun. 15, 1998; Ser. No. 09/094,797, filed Jun. 15, 1998; Ser. No. 09/173,413, filed Oct. 15, 1998; and Ser. No. 09/262,525, filed Mar. 4, 1999. See also the following documents and references cited therein and incorporated herein by reference: Hollenbaugh, D., Et Al, "Cleavable CD40Ig Fusion Proteins and the Binding to Sgp39", J. Immunol. Methods (Netherlands), 188(1), pp. 1-7 (Dec. 15, 1995); Hollenbaugh, D., et al, "The Human T Cell Antigen Gp39, A Member of the TNF Gene Family, Is a Ligand for the CD40 Receptor: Expression of a Soluble Form of Gp39 with B Cell Co-Stimulatory Activity", EMBO J. (England), 11(12), pp. 4313-4321 (December 1992); and Moreland, L. W. et al., "Treatment of Rheumatoid Arthritis with a Recombinant Human Tumor Necrosis Factor Receptor (P75)-Fc Fusion Protein," New England J. of Medicine, 337(3), pp. 141-147 (1997).

The above other therapeutic agents, when employed in combination with the compounds of the present application, may be used, for example, in those amounts indicated in the Physicians' Desk Reference (PDR) or as otherwise determined by one of ordinary skill in the art.

The compounds of formula I of the application can be administered orally or parenterally, such as subcutaneously or intravenously, as well as by nasal application, transdermally, rectally or sublingually to various mammalian species known to be subject to such maladies, e.g., humans, in an effective amount within the dosage range of about 0.2 to 1000 mg, preferably from about 1 to 100 mg in a regimen of single, two or four divided daily doses.

The compounds of the formula I can be administered for any of the uses described herein by any suitable means, for example, orally, such as in the form of tablets, capsules, granules or powders; sublingually; bucally; parenterally, such as by subcutaneous, intravenous, intramuscular, or intracisternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

Pharmacological Analysis

The pharmacological analysis of each compound for either antagonism or agonism of $5\text{-}HT_{2A}$, $5\text{-}HT_{2B}$ and $5\text{-}HT_{2C}$ receptors consisted of in vitro and in vivo studies. In vitro analyses included $K_i$ determinations at $5\text{-}HT_{2A}$, $5\text{-}HT_{2B}$ and $5\text{-}HT_{2C}$ receptors and an assessment of functional (i.e., agonism or antagonism) activity at each receptor class by IP3 hydrolysis assays. Additional receptor assays were conducted to evaluate receptor specificity of $5\text{-}HT_{2C}$ receptors over monoamine and nuisance receptors (e.g. histamine, dopamine, and muscarinic). A compound is considered active as a $5\text{-}HT_2$ agonist if it has an $EC_{50}$ value or a $K_i$ value of less than about 50 micromolar; preferably less than about 1.0 micromolar; more preferably less than about 0.1 micromolar. Using the assays disclosed herein, compounds of the present application have been shown to have an $EC_{50}$ value of less than about 50 micromolar for $5\text{-}HT_2$ agonism.

In vivo assays assessed compound activity in a variety of behavioral paradigms including acute and chronic feeding models, anxiety and depression models (learned-helplessness, elevated plus maze, Geller-Siefter, conditioned taste aversion, taste reactivity, satiety sequence). In aggregate, these models reflect activity as a $5\text{-}HT_{2C}$ agonist (feeding models, anxiety models, depression models) and provide some indication as to bioavailability, metabolism and pharmacokinetics.

Radioligand binding experiments were conducted on recombinant human $5\text{-}HT_{2A}$, $5\text{-}HT_{2B}$, and $5\text{-}HT_{2C}$ receptors expressed in HEK293E cells. The affinities of compounds of the present application to bind at these receptors is determined by their capacity to compete for $[^{125}I]\text{-}1\text{-}(2,5\text{-}$ dimethoxy-4-iodophenyl)-2-amino-propane (DOI) or [$^3$H]-lysergic acid diethylamide (LSD) binding at the 5-HT$_{2A}$, 5-HT$_{2B}$, or 5-HT$_{2C}$ receptors. General references for binding assays include 1) Lucaites V L, Nelson D L, Wainscott D B, Baez M (1996) Receptor subtype and density determine the coupling repertoire of the 5-HT$_2$ receptor subfamily. Life Sci., 59(13):1081-95. Glennon R A, Seggel M R, Soine W H, Herrick-Davis K, Lyon R A, Titeler M (1988) [125I]-1-(2,5-dimethoxy-4-iodophenyl)-2-amino-propane: an iodinated radioligand that specifically labels the agonist high-affinity state of 5-HT2 serotonin receptors. J. Med. Chem. (1988) 31(1):5-7 and 3 Leonhardt S, Gorospe E, Hoffman B J, Teitler M (1992) Molecular pharmacological differences in the interaction of serotonin with 5-hydroxytryptamine1C and 5-hydroxytryptamine2 receptors. Mol Pharmacol., 42(2):328-35.

The functional properties of compounds (efficacy and potency) were determined in whole cells expressing 5-HT$_{2A}$, 5-HT$_{2B}$, or 5-HT$_{2C}$ receptors by assessing their ability to stimulate or inhibit receptor-mediated phosphoinositol hydrolysis and/or intracellular calcium release. The procedures used are described below.

In Vitro Binding Assays

Stable Expression of 5-HT$_{2A}$, 5-HT$_{2B}$ and 5-HT$_{2C}$ Receptors in HEK293E Cells Stable cell lines were generated by transfecting 293EBNA cells with plasmids containing human 5-HT$_{2A}$, 5-HT$_{2B}$, or 5-HT$_{2C}$ receptor (INI, INV, VNV or VGV RNA-edited isoforms) cDNA using calcium phosphate. These plasmids also contained the cytomegalovirus (CMV) immediate early promoter to drive receptor expression and EBV oriP for their maintenance as an extrachromosomal element, and the hph gene from *E. Coli* to yield hygromycin B resistance (Horlick et al., 1997). Transfected cells were maintained in Dulbecco's Modified Eagle medium (DMEM) containing dialyzed 10% fetal bovine serum at 37° C. in a humid environment (5% CO$_2$) for 10 days. The 5-HT$_{2A}$ cells were adapted to spinner culture for bulk processing whereas it was necessary to maintain the other lines as adherent cultures. On the day of harvest, cells were washed in phosphate-buffered saline (PBS), counted, and stored at −80° C.

Membrane Preparation

On the day of assay, pellets of whole cells (containing approximately 1×10$^8$ cells) expressing the 5-HT$_{2A}$, 5-HT$_{2B}$ or 5-HT$_{2C}$ receptor were thawed on ice and homogenized in 50 mM Tris HCl (pH 7.7) containing 1.0 mM EDTA using a Brinkman Polytron (PT-10, setting 6 for 10 sec). The homogenate was centrifuged at 48,000×g for 10 min and the resulting pellet washed twice by repeated homogenization and centrifugation steps. The final pellet was resuspended in tissue buffer and protein determinations were made by the bichichoninic acid (BCA) assay (Pierce Co., Illinois) using bovine serum albumin as the standard.

Radioligand Binding Assays for the 5-HT$_{2A}$, 5-HT$_{2B}$ and 5-HT$_{2C}$ Receptors Radioligand binding studies were conducted to determine the binding affinities (Ki values) of compounds for the human recombinant 5-HT$_{2A}$, 5-HT$_{2B}$, and 5-HT$_{2C}$ receptors (Fitzgerald et al., 1999). Assays were conducted in disposable polypropylene 96-well plates (Costar Corp., Cambridge, Mass.) and were initiated by the addition of 5-HT$_{2A}$, 5-HT$_{2B}$, or 5-HT$_{2C}$ membrane homogenate in tissue buffer (10-30 (g/well) to assay buffer (50 mM Tris HCl, 0.5 mM EDTA, 10 mM pargyline, 10 mM MgSO$_4$, 0.05% ascorbic acid, pH 7.5) containing [$^{125}$I]DOI for the 5-HT$_{2A}$ and 5-HT$_{2C}$ receptors (0.3-0.5 nM, final) or [$^3$H]LSD (1-2.0 nM, final) for the 5-HT$_{2B}$ receptor, with or without competing drug (i.e, newly synthesized chemical entity). For a typical competition experiment, a fixed concentration of radioligand was competed with duplicate concentrations of ligand (12 concentrations ranging from 10 picomolar to 10 micromolar). The reaction mixtures were incubated to equilibrium for 45 min at 37° C. and terminated by rapid filtration (Packard cell harvester; Perkin-Elmer) over GFB glass-fiber filters that had been pre-soaked in 0.3% polyethyleneimine. Filters were washed in ice-cold 50 mM Tris HCl buffer (pH 7.5) and then counted on a Top Count (Packard).

Phosphoinositide Hydrolysis Studies

The ability of newly synthesized compounds to stimulate phosphoinositide (PI) hydrolysis was monitored in whole cells using a variant (Egan et al., 1998) of a protocol described previously (Berridge et al., 1982). HEK293E cells expressing the human 5-HT$_{2A}$, 5-HT$_{2B}$, or 5-HT$_{2C}$ receptor were lifted with 0.5 mM EDTA and plated at a density of 100,000/well onto poly-D-lysine-coated 24-well plates (Biocoat; Becton Dickinson, Bedford, Mass.) in Dulbecco's modified Eagle's serum (DMEM; Gibco BRL) containing high glucose, 2 mM glutamine, 10% dialyzed fetal calf serum, 250 (g/ml hygromycin B, and 250 (g/ml G418. Following a 24-48 hr period, the growth media was removed and replaced with DMEM without fetal calf serum and inositol (Gibco BRL). The cells were then incubated with DMEM (without serum and inositol) containing a final concentration of 0.5 uCi/well myo-[$^3$H]inositol for 16-18 hr. Following this incubation, the cells were washed with DMEM (without serum or inositol) containing 10 mM LiCl and 10 (M pargyline and then incubated for 30 min with the same media but now containing one of several test compounds. Reactions were terminated by aspirating the media and lysing the cells by freeze-thaw. [$^3$H]phosphoinositides were extracted with chloroform/methanol (1:2 v/v), separated by anion exchange chromatography (Bio-Rad AGI-X8 resin), and counted by liquid scintillation spectroscopy as described previously (Egan et al., 1998).

Calcium Fluorescence Studies

The ability of newly synthesized compounds to stimulate calcium fluorescence was monitored in whole cells using a protocol described previously (Fitzgerlad et al., 1999). HEK293E cells expressing the human 5-HT$_{2C}$, or 5-HT$_{2B}$ receptor were lifted with 0.5 mM EDTA and plated at a density of 50,000/well onto poly-D-lysine-coated 96-well plates (Biocoat; Becton Dickinson, Bedford, Mass.) in Dulbecco's modified Eagle's serum (DMEM; Gibco BRL) containing high glucose, 2 mM glutamine, 10% dialyzed fetal calf serum, 250 μg/ml hygromycin B, and 250 μg/ml G418. Following a 24 hr period, the cell plates are removed from the incubator and an equal volume of Loading Buffer (Hanks BSS with 200 mM HEPES, pH 5.98) containing the calcium dye reagent (Fluo-3) is added to each well (1100 μL per well for 96-well plates and then incubated for 1 hour at 37 C. Following the dye loading of the cells he plates are transferred to the FLIPR. Test compounds are added to the plate as a concentration response curve and the changes in fluorescence units due to calcium influx are monitored for a period of three seconds.

Data Analyses

The equilibrium apparent dissociation constants (Ki's) from the competition experiments were calculated using an iterative nonlinear regression curve-fitting program (Excelfit and TA Activity Base). For the PI hydrolysis and FLIPR experiments, EC50's were calculated using a one-site 'pseudo' Hill model: y=((Rmax−Rmin)/(1+R/EC50)nH))+ Rmax where R= response (GraphPad Prism; San Diego, Calif.). Emax (maximal response) was derived from the fitted curve maxima (net IP stimulation) for each compound. Intrinsic activity (IA) was determined by expressing the Emax of a compound as a percentage of the Emax of 5-HT (IA=1.0).

Efficacy Models to Evaluate Food Consumption and Weight Loss

Acute overnight feeding assay. Compounds are assessed to for their ability to reduce food consumption during the dark cycle, which is the most active period of feeding in the rat. Fischer 344 rats are trained on a fixed ratio three (FR3) response paradigm which requires them to press a bar 3 consecutive times in order to obtain a food pellet. The number of bar presses occurring throughout the dark cycle can be monitored electronically as a measure of food intake by the animal. Rats are dosed orally or intraperitoneally with test compound 30 minutes prior to the onset of the dark cycle. The treated animals are then placed in individual operant boxes for 15 hours (12 hrs of dark cycle and the first three hours of the light cycle). Food intake in compound treated animals is compared to that of vehicle treated animals in order to determine percent reductions in food intake. Simultaneous measurements of water intake and locomotor activity are also measured during the period to assess for potential adverse effects.

Chronic Feeding Assay

Compounds are assessed for their long term impact on food intake and body weight in a three to fourteen week chronic treatment paradigm in Sprague-Dawley rats (starting weight ~450 g). Male Sprague-Dawley rats are pre-handled for one week prior to the onset of dosing during which time they are also assessed for food intake behavior. Rats are then assigned to treatment groups. Rats are dosed with vehicle or compound by oral gavage. The food intake and body weights are cumulatively assessed at the end of each treatment week and compared to vehicle treated animals. In some studies food intake is measured daily in order to assess the impact of reduced food consumption on pair-fed animals. At the end of the study period the animals are assessed for changes in body composition utilizing DEXA and are then sacrificed in order to examine changes in various blood plasma parameters.

REFERENCES

Arnt, J. Acta Pharmacol. et Toxicol. 1982: 51, 321-329.

Berridge M. J., Downes P. C., Hanley M. R. (1982) Lithium amplifies agonist-dependent phosphotidyinositol response in brain and salivary glands. Biochem. J., 206, 587-595.

Costall, B and Naylor, R J. Psychopharmacology. 1975: 43, 69-74.

Egan C. T., Herrick-Davis K., Miller K., Glennon R. A., and Teitler M. (1998) Agonist activity of LSD and lisuride at cloned 5-HT$_{2A}$ and 5-HT$_{2C}$ receptors.

Psychopharmacology, 136, 409-414.

Fitzgerald L W, Conklin D S, Krause C M, Marshall A P, Patterson J P, Tran D P, Iyer G, Kostich W A, Largent B L, Hartig P R (1999) High-affinity agonist binding correlates with efficacy (intrinsic activity) at the human serotonin 5-HT$_{2A}$ and 5-HT$_{2C}$ receptors: evidence favoring the ternary complex and two-state models of agonist action. J. Neurochem., 72, 2127-2134.

Horlick, R. A., Sperle, K., Breth, L. A., Reid, C. C., Shen, E. S., Robbinds, A. K., Cooke, G. M., Largent, B. L. (1997) Rapid Generation of stable cell lines expressing corticotrophin-releasing hormone receptor for drug discovery. Protein Expr. Purif. 9, 301-308.

Dosage and Formulations

The serotonin agonist and serotonin antagonist compounds of this application can be administered as treatment for the control or prevention of central nervous system disorders including obesity, anxiety, depression, psychosis, schizophrenia, sleep and sexual disorders, migraine and other conditions associated with cephalic pain, social phobias, and gastrointestinal disorders such as dysfunction of the gastrointestinal tract motility by any means that produces contact of the active agent with the agent's site of action, i.e., 5-HT2 receptors, in the body of a mammal. It can be administered by any conventional means available for use in conjunction with pharmaceuticals, either as an individual therapeutic agent or in a combination of therapeutic agents. It can be administered alone, but preferably is administered with a pharmaceutical carrier selected on the basis of the chosen route of administration and standard pharmaceutical practice.

The compounds of the present application can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form. Further, they may also be administered by internasal delivery, transdermal delivery and suppository or depot delivery all using dosage forms well known to those of ordinary skill in the pharmaceutical arts.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. By way of general guidance, a daily dosage of active ingredient can be expected to be about 0.001 to about 1000 milligrams per kilogram of body weight, with the preferred dose being about 0.01 to about 100 mg/kg; with the more preferred dose being about 0.01 to about 30 mg/kg. Advantageously, compounds of the present application may be administered in a single daily dose, or the total daily dosage may be administered in divided doses of two, three, or four times daily.

Dosage forms of compositions suitable for administration contain from about 0.5 mg to about 100 mg of active ingredient per unit. In these pharmaceutical compositions the active ingredient will ordinarily be present in an amount of about 0.5-95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in *Remington's Pharmaceutical Sciences*, supra, a standard reference text in this field.

Useful pharmaceutical dosage-forms for administration of the compounds of this application can be illustrated as follows:

Capsules

A large number of unit capsules can be prepared by filling standard two-piece hard gelatin capsules each with 100 mg of powdered active ingredient, 150 mg of lactose, 50 mg of cellulose, and 6 mg magnesium stearic.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A large number of tablets can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly used techniques.

EXAMPLES

Example 1

(±)-cis-6-(Trifluoromethyl)-2,3,3a,4-tetrahydro-1H-pyrrolo[3,4-c]isoquinolin-5(9bH)-one hydrochloride

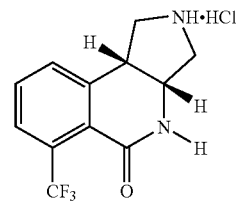

Part A. N,N-Diethyl-2-(trifluoromethyl)benzamide

To a solution of 2-trifluoromethylbenzoic acid (20.0 g, 105 mmol) in 500 mL of methylene chloride was added oxalyl chloride (18.4 mL, 210 mmol) followed by ~8 drops of DMF. The reaction was allowed to stir at ambient temperature for 4 h and then was concentrated in vacuo to a solid. The solid was taken up in 500 mL of methylene chloride and then there was added diethylamine (24 mL, 231 mmol) dropwise as a solution in 50 mL of methylene chloride. The resulting mixture was allowed to stir at ambient temperature for 18 h. The reaction was concentrated in vacuo. The residue was diluted with EtOAc, washed sequentially with 1N HCl, sat'd. aq. NaHCO$_3$ and brine, dried (MgSO$_4$), filtered through a pad of silica gel and concentrated to afford 22 g (85%) of the title compound as an oil. $^1$H NMR (CDCl$_3$): δ 7.68 (d, 1H, J=7.7 Hz), 7.57 (t, 1H, J=7.4 Hz), 7.49 (t, 1H, J=7.7 Hz), 7.32 (d, 1H, J=7.1 Hz), 3.90-3.82 (m, 2H), 3.29-3.22 (m, 2H), 1.23 (t, 3H, J=7.2 Hz), 1.03 (t, 3H, J=7.2 Hz). LRMS (ESI): 246.12 (M+H)+.

Part B. (±)-3-Hydroxy-7-(trifluoromethyl)isobenzofuran-1(3H)-one

To a solution of N,N-diethyl-2-(trifluoromethyl)benzamide (8.0 g, 32.6 mmol) and N,N,N'N'-tetramethylethylenediamine (5.4 mL, 35.9 mmol) in 100 mL of anhydrous THF at −78° C. was added sec-butyllithium (35.9 mL of a 1.0 M solution in hexanes, 35.9 mmol) dropwise over 30 min. The reaction was stirred at −78° C. for 1 h and then there was added DMF (7.6 mL, 97.8 mmol). The reaction was stirred at −78° C. for 1 h and then was quenched with 1N HCl (25 mL). The reaction mixture was concentrated in vacuo. The residue was taken up in 6N HCl (100 mL) and stirred at 100° C. for 18 h. The reaction mixture was allowed to cool, was diluted with water and extracted with EtOAc. The organics were washed with brine, dried (MgSO$_4$) and concentrated to afford 8.5 g of a tan solid. This material was purified by acid-base extraction as follows. The solid was dissolved in 1:1 hexane/EtOAc and extracted twice with sat'd aq NaHCO$_3$/sat'd aq Na$_2$CO$_3$. The organics were discarded. The combined aqueous extracts were acidified with 12 N HCl and extracted with EtOAc. The EtOAc extracts were washed with brine, dried (MgSO$_4$), and concentrated to afford 6.3 g (88%) of the title compound as a pale yellow powder. LRMS (ESI): 219.02 (M+H)+.

Part C. Isopropyl 2-formyl-6-(trifluoromethyl)benzoate

To a solution of (±)-3-hydroxy-7-(trifluoromethyl)isobenzofuran-1(3H)-one (2.2 g, 10.1 mmol) in 20 mL of DMF was added potassium carbonate (2.8 g, 20.2 mmol) followed by 2-iodopropane (1.11 mL, 11.1 mmol). The resulting mixture was allowed to stir at ambient temperature for 18 h. The reaction was diluted with 1N HCl to pH ~4 and extracted with EtOAc. The organics were washed with 1N HCl, sat'd aq NaHCO$_3$ and brine, dried (MgSO$_4$), filtered through a pad of silica gel and concentrated in vacuo to afford 2.3 g (87%) of the title compound which was used without purification. $^1$H NMR (CDCl$_3$): δ 10.08 (s, 1H), 8.12 (d, 1H, J=7.7 Hz), 7.95 (d, 1H, J=8.2 Hz), 7.73 (t, 1H, J=7.7 Hz), 5.44-5.36 (m, 1H), 1.40 (d, 1H, J=6.6 Hz).

Part D. (Z)-isopropyl 2-(3-methoxy-3-oxoprop-1-enyl)-6-(trifluoromethyl)benzoate To a solution of 18-crown-6 (9.1 g, 34.6 mmol) in 100 mL of THF at −78° C. was added bis(2,2,2-trifluoroethyl) (methoxycarbonylmethyl)phosphonate (4.13 g, 12.98 mmol). Potassium bis(trimethylsilyl)amide (19.6 mL of a 15 wt % solution in toluene, 12.98 mmol) was added dropwise over 20 min and the mixture was stirred an additional 1 h at −78° C. Then there was added isopropyl 2-formyl-6-(trifluoromethyl) benzoate (1.5 g, 5.74 mmol) in 10 mL of THF and the resulting cloudy mixture was stirred at −78° C. for 1 h. The reaction was quenched with sat'd aq NH$_4$Cl, diluted with EtOAc, washed with brine, dried (MgSO$_4$), filtered through a pad of silica gel and concentrated in vacuo. The residue was purified by flash chromatography (elution with 6:1 hexane/ethyl acetate) to afford 2.58 g (94%) of the title compound as an oil. $^1$H NMR (CDCl$_3$): δ 7.66-7.62 (m, 2H), 7.51 (t, 1H, J=7.7 Hz), 7.11 (d, 1H, J=12.1 Hz), 6.11 (d, 1H, J=12.1 Hz), 5.26 (septet, 1H), 3.63 (s, 3H), 1.32 (d, 6H, J=6.0 Hz). LRMS (ESI): 339.19 (M+H+Na)+.

Part E. (±)-cis-Methyl 1-benzyl-4-(2-(isopropoxycarbonyl)-3-(trifluoromethyl)phenyl)pyrrolidine-3-carboxylate To a solution of (Z)-isopropyl 2-(3-methoxy-3-oxoprop-1-enyl)-6-(trifluoromethyl)benzoate (2.5 g, 7.9 mmol) in 30 mL of EtOAc was added N-(methoxymethyl)-N-(trimethylsilylmethyl)benzylamine (2.34 g, 9.9 mmol) and trifluoroacetic acid (0.12 mL, 1.6 mmol). The solution was allowed to stir at 65° C. for 4 h. Starting material still remained by TLC analysis and so additional N-(methoxymethyl)-N-(trimethylsilylmethyl)benzylamine (1.0 g, 4.2 mmol) and trifluoroacetic acid (0.05 mL, 0.65 mmol) were added and the reaction was stirred at 65° C. for an additional 3 h. The reaction was allowed to cool and was diluted with EtOAc, washed with sat'd aq NaHCO$_3$ and brine, dried (MgSO$_4$) and concentrated. The residue was purified by flash chromatography (5:1 hexane/EtOAc) to afford 3.3 g (93%) of the title compound as an oil. LRMS (ES)$^+$: 450.35 (M+H)$^+$.

Part F. (±)-cis-1-tert-butyl 3-methyl 4-(2-(isopropoxycarbonyl)-3-(trifluoromethyl)phenyl)pyrrolidine-1,3-dicarboxylate To a solution of (±)-cis-methyl 1-benzyl-4-(2-(isopropoxycarbonyl)-3-(trifluoromethyl)phenyl)pyrrolidine-3-carboxylate (3.3 g, 7.34 mmol) in 100 mL of absolute ethanol was added di-tert-butyl dicarbonate (1.76 g, 8.07 mmol) and 10% Pd/C catalyst (0.66 g, 20 wt %). The resulting mixture was fitted with a three-way stopcock and a hydrogen balloon. The flask was alternatively evacuated (house vacuum) and filled with hydrogen several times and then was allowed to stir under 1 atm of hydrogen for 4 h. The reaction was filtered through a pad of Celite and was concentrated in vacuo. The residue was taken up in EtOAc, washed with 1N HCl, sat'd aq NaHCO$_3$ and brine, dried (MgSO$_4$) and concentrated to afford 3.3 g (98%) of the title compound, which was pure enough to be used without purification. LRMS (ES)$^+$: 482.33 (M+H+Na)$^+$.

Part G. (±)-cis-1-(tert-Butoxycarbonyl)-4-(2-(isopropoxycarbonyl)-3-(trifluoromethyl)phenyl)pyrrolidine-3-carboxylic acid To a solution of (±)-cis-1-tert-butyl 3-methyl 4-(2-(isopropoxycarbonyl)-3-(trifluoromethyl)phenyl)pyrrolidine-1,3-dicarboxylate (0.90 g, 1.96 mmol) in 20 mL of 2:1 THF/H$_2$O was added lithium hydroxide (52 mg, 2.15 mmol). The reaction mixture was allowed to stir at ambient temperature for 2 h. The reaction was partitioned between 1:1 hexane/EtOAc and dilute aq Na$_2$CO$_3$. The organic layer was discarded. The aqueous layer was acidified with 12 N HCl and extracted with EtOAc. The EtOAc layer was washed with brine, dried (MgSO$_4$) and concentrated to afford 0.75 g (86%) of the title compound as a white foam, which was pure enough to be used without purification. LRMS (ES)$^+$: 446 (M+H)$^+$.

Part H. (±)-cis-tert-Butyl 5-oxo-6-(trifluoromethyl)-3,3a,4,5-tetrahydro-1H-pyrrolo[3,4-c]isoquinoline-2 (9bH)-carboxylate To a solution of (±)-cis-1-(tert-butoxycarbonyl)-4-(2-(isopropoxycarbonyl)-3-(trifluoromethyl)phenyl)pyrrolidine-3-carboxylic acid (0.98 g, 2.20 mmol) in 20 mL of THF at 0° C. was added triethylamine (0.34 mL, 2.42 mmol) followed by ethyl chloroformate (0.23 mL, 2.42 mmol). The resulting cloudy mixture was stirred for 30 min at 0° C. Then there was added sodium azide (0.57 g, 8.8 mmol) as a solution in 2 mL of H$_2$O. The resulting clear solution was stirred at 0° C. for 1 h. The reaction mixture was diluted with EtOAc, washed sequentially with 1N HCl, sat'd aq NaHCO$_3$ and brine, dried (MgSO$_4$) and concentrated in vacuo. The residue was dissolved in 20 mL of toluene and stirred at 100° C. for 2 h. The reaction was cooled and concentrated in vacuo to afford 0.90 g (93%) of an intermediate isocyanate. A portion of this isocyanate (700 mg, 1.58 mmol) was dissolved in 30 mL of THF and then there was added 20 mL of 0.1 N HCl and the resulting mixture was stirred at ambient temperature for 3 h. The pH of the solution was adjusted to about pH 9 with sat'd aq. NaHCO$_3$ and sat'd aq. Na$_2$CO$_3$ and then was extracted with EtOAc. The organics were washed with brine, dried (MgSO$_4$) and concentrated in vacuo to afford 610 mg (92%) of an intermediate amine. This amine was taken up in 20 mL of absolute ethanol and then there was added 5 mL of 0.5 M NaOMe in MeOH. The resulting solution was stirred at 80-85° C. for 24 h. The reaction was cooled and concentrated in vacuo. The residue was diluted with EtOAc and water, and the organics were washed with brine, dried (MgSO$_4$) and concentrated in vacuo to afford 460 mg (88%) of the title compound as a solid. Recrystallization from hexane/ethanol afforded 300 mg of pure title compound as a white solid. $^1$H NMR (CDCl$_3$): (some signals doubled due to carbamate rotational isomers) δ 7.79 (d, 1H, J=8.2 Hz), 7.56 (t, 1H, J=7.7 Hz), 7.44 (d, 1H, J=7.7 Hz), 6.35 and 5.76 (singlets, 1H), 4.31-4.28 (m, 1H), 3.95-3.91 and 3.84-3.80 (multiplets, 1H), 3.67-3.36 (overlapping m, 4H), 1.45 and 1.42 (singlets, 9H). LRMS (ESI): 301.13 (M+H—C$_4$H$_8$)+.

Part I. (±)-cis-6-(Trifluoromethyl)-2,3,3a,4-tetrahydro-1H-pyrrolo[3,4-c]isoquinolin-5(9bH)-one, hydrochloride salt To a solution of (±)-cis-tert-butyl 5-oxo-6-(trifluoromethyl)-3,3a,4,5-tetrahydro-1H-pyrrolo[3,4-c]isoquinoline-2(9bH)-carboxylate (50 mg, 0.14 mmol) in 1 mL of 1,4-dioxane was added 4 mL of 4 N HCl in dioxane. The reaction was allowed to stir for 4 h and then was diluted with diethyl ether. A solid slowly settled out of solution. The solvents were decanted and the remaining solid was triturated twice with diethyl ether and dried in vacuo to afford 35 mg (85%) of the title compound of Example 1 as an off-white solid. $^1$H NMR (DMSO-D$_6$): δ 9.8 (broad s, 1H), 9.6 (broad s, 1H), 8.15 (s, 1H), 7.86 (d, 1H, J=7.1 Hz), 7.78-7.70 (m, 2H), 4.40-4.38 (m, 1H), 3.75-3.67 (m, 2H), 3.55-3.52 (m, 1H), 3.45-3.37 (m, 1H), 3.10-3.05 (m, 1H). LRMS (ESI): 257.16 (M+H)+.

Example 2

(±)-cis-4-Methyl-6-(trifluoromethyl)-2,3,3a,4-tetrahydro-1H-pyrrolo[3,4-c]isoquinolin-5(9bH)-one, hydrochloride salt

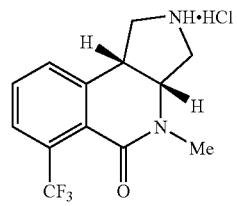

Part A. (±)-cis-tert-Butyl 4-methyl-5-oxo-6-(trifluoromethyl)-3,3a,4,5-tetrahydro-1H-pyrrolo[3,4-c]isoquinoline-2(9bH)-carboxylate To a suspension of NaH (17 mg of 60% in mineral oil, hexane-washed, 0.42 mmol) in 2 mL of THF at ambient temperature was added (±)-cis-tert-butyl 5-oxo-6-(trifluoromethyl)-3,3a,4,5-tetrahydro-1H-pyrrolo[3,4-c]isoquinoline-2(9bH)-carboxylate from Example 1, Part H (75 mg, 0.21 mmol) as a solution in 2 mL of THF. The reaction was stirred for 20 min, at which time gas evolution had ceased and the reaction mixture was homogeneous. Then there was added iodomethane (0.039 mL, 0.63 mmol) and the reaction was allowed to stir at ambient temperature for 1 h. The reaction was quenched with water, diluted with EtOAc and washed with 1N HCl, sat'd aq NaHCO$_3$ and brine, dried (MgSO$_4$) and concentrated in vacuo. The residue was purified by flash chromatography (230-400 mesh silica gel, elution with 2:1 hexane/EtOAc) to afford 30 mg (39%) of the title compound. LRMS (ESI): 315.22 (M+H—C$_4$H$_8$)+.

Part B. (±)-cis-4-Methyl-6-(trifluoromethyl)-2,3,3a,4-tetrahydro-1H-pyrrolo[3,4-c]isoquinolin-5(9bH)-one, hydrochloride salt To a solution of (±)-cis-tert-butyl 4-methyl-5-oxo-6-(trifluoromethyl)-3,3a,4,5-tetrahydro-1H-pyrrolo[3,4-c]isoquinoline-2(9bH)-carboxylate (15 mg, 0.04 mmol) in 3 mL of CH$_2$Cl$_2$ was added 1 mL of trifluoroacetic acid. The reaction was stirred for 1 h at ambient temperature and then was concentrated in vacuo. The residue was taken up in CH$_2$Cl$_2$ and washed with dil. aq. NH$_4$OH, dried (K$_2$CO$_3$), and concentrated. The free base residue was taken up in ether and then there was added 4 N HCl in dioxane (0.10 mL, 0.40 mmol). The reaction was concentrated to dryness and the resulting solid was triturated three times with ether and dried in vacuo to afford 10 mg (83%) of the title compound of Example 2 as an off-white powder. $^1$H NMR (DMSO-D$_6$): δ 9.8 and 9.5 (broad singlets, 2H), 7.86 (d, 1H, J=7.7 Hz), 7.79-7.71 (m, 2H), 4.42-4.40 (m, 1H), 3.94-3.89 (m, 1H), 3.71 (dd, 1H, J=11.5, 8.3 Hz), 3.60-3.48 (m, 2H), 3.22 (dd, 1H, J=11.5, 8.3 Hz), 3.05 (s, 3H). LRMS (ESI): 271.15 (M+H)+.

Example 3

(±)-cis-4-Ethyl-6-(trifluoromethyl)-2,3,3a,4-tetrahydro-1H-pyrrolo[3,4-c]isoquinolin-5(9bH)-one, hydrochloride salt

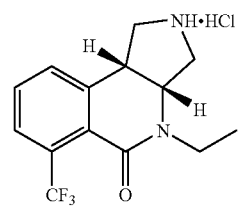

Part A. (±)-cis-tert-Butyl 4-ethyl-5-oxo-6-(trifluoromethyl)-3,3a,4,5-tetrahydro-1H-pyrrolo[3,4-c]isoquinoline-2(9bH)-carboxylate To a suspension of NaH (11 mg of 60% in mineral oil, hexane-washed, 0.28 mmol) in 2 mL of THF at ambient temperature was added (±)-cis-tert-butyl 5-oxo-6-(trifluoromethyl)-3,3a,4,5-tetrahydro-1H-pyrrolo[3,4-c]isoquinoline-2(9bH)-carboxylate from Example 1, Part H (40 mg, 0.11 mmol) as a solution in 2 mL of THF. The reaction was stirred for 20 min, at which time gas evolution had ceased and the reaction mixture was homogeneous. Then there was added iodoethane (0.039 mL, 0.63 mmol) and the reaction was allowed to stir at 45° C. in a sealed vial for 18 h. The reaction was quenched with water, diluted with EtOAc and washed with 1N HCl, sat'd aq NaHCO$_3$ and brine, dried (MgSO$_4$) and concentrated in vacuo. The residue was purified by flash chromatography (230-400 mesh silica gel, elution with 2:1 hexane/EtOAc) to afford 30 mg (71%) of the title compound. LRMS (ESI): 407.22 (M+H+Na)+.

Part B. (±)-cis-4-Ethyl-6-(trifluoromethyl)-2,3,3a,4-tetrahydro-1H-pyrrolo[3,4-c]isoquinolin-5(9bH)-one, hydrochloride salt To a solution of (±)-cis-tert-butyl 4-ethyl-5-oxo-6-(trifluoromethyl)-3,3a,4,5-tetrahydro-1H-pyrrolo[3,4-c]isoquinoline-2(9bH)-carboxylate (26 mg, 0.07 mmol) in 1 mL of ether was added 4 N HCl in dioxane (4 mL of a 4 N solution, 16 mmol). The reaction was stirred for 18 h at ambient temperature and then was concentrated in vacuo to a foam. The residue was triturated three times with ether and dried in vacuo to afford 18 mg (82%) of the title compound of Example 3 as an off-white powder. $^1$H NMR (DMSO-D$_6$): δ 9.65 (broad s, 1H), 9.20 (broad s, 1H), 7.84 (d, 1H, J=7.7 Hz), 7.82 (d, 1H, J=7.1 Hz), 7.75 (t, 1H, J=7.7 Hz), 4.43 (q, 1H, J=6.6 Hz), 3.95 (q, 1H, J=6.1 Hz), 3.74-3.68 (m, 1H), 3.69-3.55 (m, 2H), 3.37 (q, 2H, J=7.0 Hz), 3.12 (dd, 1H, J=11.8, 6.9 Hz), 1.12 (t, 3H, J=6.9 Hz). LRMS (ESI): 285.12 (M+H)+.

Example 4

(±)-cis-4-(Cyclopropylmethyl)-6-(trifluoromethyl)-2,3,3a,4-tetrahydro-1H-pyrrolo[3,4-c]isoquinolin-5(9bH)-one, hydrochloride salt

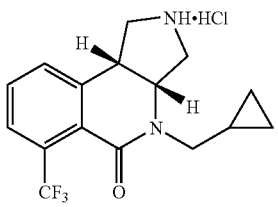

Following the procedures described in Example 3, Parts A and B, except that bromomethylcyclopropane was used instead of iodoethane, (±)-cis-tert-butyl 5-oxo-6-(trifluoromethyl)-3,3a,4,5-tetrahydro-1H-pyrrolo[3,4-c]isoquinoline-2(9bH)-carboxylate from Example 1, Part H was converted into the title compound of Example 4 as an off-white solid. $^1$H NMR (DMSO-D$_6$): δ 9.50 (broad s, 1H), 9.10 (broad s, 1H), 7.87-7.83 (m, 2H), 7.78 (t, 1H, J=7.7 Hz), 4.52 (q, 1H, J=6.6 Hz), 3.99 (q, 1H, J=5.5 Hz), 3.68-3.58 (m, 3H), 3.46 (ABX pattern, 2H), 3.15-3.08 (m, 1H), 1.05-1.00 (m, 1H), 0.53-0.45 (m, 2H), 0.35-0.25 (m, 2H). LRMS (ESI): 311.15 (M+H)+.

Example 5

(±)-cis-4-Benzyl-6-(trifluoromethyl)-2,3,3a,4-tetrahydro-1H-pyrrolo[3,4-c]isoquinolin-5(9bH)-one, hydrochloride salt

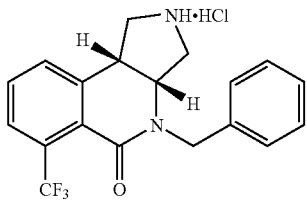

Following the procedures described in Example 3, Parts A and B, except that benzyl bromide was used instead of iodoethane, (±)-cis-tert-butyl 5-oxo-6-(trifluoromethyl)-3,3a,4,5-tetrahydro-1H-pyrrolo[3,4-c]isoquinoline-2(9bH)-carboxylate from Example 1, Part H was converted into the title compound of Example 5 as an off-white solid. $^1$H NMR (DMSO-D$_6$): δ 9.50 (broad s, 1H), 9.15 (broad s, 1H), 7.89 (d, 1H, J=7.5 Hz), 7.84-7.79 (m, 2H), 7.38-7.34 (m, 2H), 7.32-7.28 (m, 3H), 4.82 (ABq, 2H, J$_{AB}$=15.4 Hz, δV$_{AB}$=160 Hz), 4.31 (q, 1H, J=7.1 Hz), 3.96 (q, 1H, J=6.2 Hz), 3.66-3.60 (m, 2H), 3.32-3.25 (m, 1H), 3.08-3.02 (m, 1H). LRMS (ESI): 347.19 (M+H)+.

Example 6

(±)-cis-4-Phenyl-6-(trifluoromethyl)-2,3,3a,4-tetrahydro-1H-pyrrolo[3,4-c]isoquinolin-5(9bH)-one, hydrochloride salt

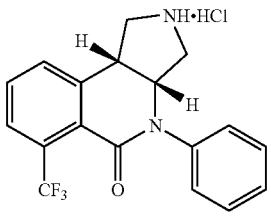

Part A. (±)-cis-tert-Butyl 5-oxo-4-phenyl-6-(trifluoromethyl)-3,3a,4,5-tetrahydro-1H-pyrrolo[3,4-c]isoquinoline-2(9bH)-carboxylate To a solution of (±)-cis-tert-butyl 5-oxo-6-(trifluoromethyl)-3,3a,4,5-tetrahydro-1H-pyrrolo[3,4-c]isoquinoline-2(9bH)-carboxylate from Example 1, Part H (50 mg, 0.14 mmol) in 4 mL of toluene in a screw-cap vial was added copper (I) iodide (2.6 mg, 0.014 mmol) and potassium phosphate (65 mg, 0.31 mmol). The reaction was degassed with a stream of argon for several minutes, and then there was added iodobenzene (17 μL, 0.154 mmol) and N,N'-dimethylethylenediamine (3.0 μL, 0.028 mmol). The reaction was allowed to stir at 90° C. in the sealed vial for 18 h. The reaction was quenched with water, diluted with EtOAc and washed with 1N HCl, sat'd aq NaHCO$_3$ and brine, dried (MgSO$_4$) and concentrated in vacuo. The residue was purified by flash chromatography (230-400 mesh silica gel, elution with 2:1 hexane/EtOAc) to afford 48 mg (80%) of the title compound. LRMS (ESI): 377.23 (M+H—C4H8)+.

Part B. (±)-cis-4-Phenyl-6-(trifluoromethyl)-2,3,3a,4-tetrahydro-1H-pyrrolo[3,4-c]isoquinolin-5(9bH)-one, hydrochloride salt To a solution of (±)-cis-tert-butyl 5-oxo-4-phenyl-6-(trifluoromethyl)-3,3a,4,5-tetrahydro-1H-pyrrolo[3,4-c]isoquinoline-2(9bH)-carboxylate (40 mg, 0.09 mmol) in 1 mL of ether was added 4 N HCl in dioxane (4 mL of a 4 N solution, 16 mmol). The reaction was stirred for 18 h at ambient temperature and then was concentrated in vacuo to a foam. The residue was triturated three times with ether and dried in vacuo to afford 20 mg (59%) of the title compound of Example 6 as an off-white powder. $^1$H NMR (DMSO-D$_6$): δ 9.90 (broad s, 1H), 9.65 (broad s, 1H), 8.00-7.85 (m, 3H), 7.56-7.50 (m, 4H), 7.47-7.42 (m, 1H), 5.03-4.99 (m, 1H), 4.15-4.11 (m, 1H), 3.87-3.80 (m, 1H), 3.62-3.50 (m, 2H), 3.16-3.11 (m, 1H). LRMS (ESI): 333.23 (M+H)+.

Example 7

(3aR,9bR)-6-(Trifluoromethyl)-2,3,3a,4-tetrahydro-1H-pyrrolo[3,4-c]isoquinolin-5(9bH)-one hydrochloride

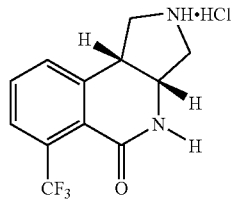

Part A. (Z)-3-(2-(Isopropoxycarbonyl)-3-(trifluoromethyl)phenyl)acrylic acid To a solution of (Z)-isopropyl 2-(3-methoxy-3-oxoprop-1-enyl)-6-(trifluoromethyl)benzoate from Example 1, Part D (1.88 g, 5.94 mmol) in 20 mL of THF and 10 mL of water was added lithium hydroxide (157 mg, 6.53 mmol). The reaction was allowed to stir at ambient temperature for 3 h. The reaction was diluted with sat'd aq NaHCO$_3$ and sat'd aq Na$_2$CO$_3$ to pH 8-9 and extracted with 1:1 hexane/ethyl acetate. The organics were discarded. The aqueous layer was acidified carefully with conc. HCl and extracted with ethyl acetate. The ethyl acetate layer was washed with brine, dried (MgSO$_4$) and concentrated in vacuo to afford 1.65 g (92%) of the title compound as a white solid. $^1$H NMR (CDCl$_3$): δ 7.65 (d, 1H, J=7.7 Hz), 7.60 (d, 1H, J=7.7 Hz), 7.48 (t, 1H, J=7.7 Hz), 7.19 (d, 1H, J=12.1 Hz), 6.09 (d, 1H, J=12.1 Hz), 5.25 (septet, 1H), 1.32 (d, 6H, J=6.1 Hz). LRMS (ESI): 325.19 (M+H+Na)+.

Part B. 2-[(1R,5S,7R)-3-(10,10-Dimethyl-3,3-dioxo-3λ$^6$-thia-4-aza-tricyclo[5.2.1.0$^{1,5}$]dec-4-yl)-3-oxo-propenyl]-6-trifluoromethyl-benzoic acid isopropyl ester To a solution of (Z)-3-(2-(isopropoxycarbonyl)-3-(trifluoromethyl)phenyl)acrylic acid (0.90 g, 2.98 mmol) in 30 mL of THF at 0° C. was added triethylamine (0.46 mL, 3.28 mmol) followed by ethyl chloroformate (0.32 mL, 3.28 mmol). This mixture was stirred at 0° C. for 45 min. In a separate flask, to a suspension of hexane-washed sodium hydride (131 mg of 60% dispersion in mineral oil, 3.28 mmol) in 20 mL of THF was added (1R)-(+)-2,10-camphorsultam (706 mg, 3.28 mmol) as a solution in 5 mL of THF. The mixture was stirred at ambient temperature for 20 min, at which time gas evolution had ceased and a homogeneous solution was obtained. This solution was added to the mixed anhydride solution maintained at 0° C. and the resulting mixture was stirred at 0° C. for 5 min and then was allowed to warm to ambient temperature and was stirred for 1 h. TLC analysis showed the reaction was not complete. In a separate flask an additional portion of the anion of (1R)-(+)-2,10-camphorsultam was prepared as described above (from 130 mg, 0.6 mmol of (1R)-(+)-2,10-camphorsultam and 24 mg of 60% dispersion in mineral oil, 0.6 mmol of sodium hydride). This solution was added to the main reaction mixture and stirring was continued at ambient temperature for 30 min, at which time the reaction was complete. The reaction was quenched with water and diluted with ethyl acetate. The organics were washed with 1N HCl, sat'd aq NaHCO$_3$ and brine, dried (MgSO$_4$) and concentrated in vacuo. The residue was purified by flash chromatography (silica gel, elution with 4:1 hexane/EtOAc) to afford 1.4 g (94%) of the title compound as a foam. LRMS (ESI): 500.2 (M+H)+.

Part C. 2-[1-Benzyl-4-(10,10-dimethyl-3,3-dioxo-3λ$^6$-thia-4-aza-tricyclo[5.2.1.0$^{1,5}$]decane-4-carbonyl)-pyrrolidin-3-yl]-6-trifluoromethyl-benzoic acid isopropyl ester To a solution of 2-[(1R,5S,7R)-3-(10,10-Dimethyl-3,3-dioxo-3λ$^6$-thia-4-aza-tricyclo[5.2.1.0$^{1,5}$]dec-4-yl)-3-oxo-propenyl]-6-trifluoromethyl-benzoic acid isopropyl ester (1.5 g, 3.0 mmol) in 20 mL of CH$_2$Cl$_2$ was added N-(methoxymethyl)-N-trimethylsilylmethyl)benzylamine (1.42 g, 6.0 mmol) and trifluoroacetic acid (0.046 mL, 0.6 mmol). The reaction mixture was stirred at 40° C. for 2 h. Starting material still remained by TLC analysis and so additional N-(methoxymethyl)-N-trimethylsilylmethyl)benzylamine (1.0 g, 4.2 mmol) and trifluoroacetic acid (0.05 mL, 0.65 mmol) were added and the reaction was stirred at 40° C. for an additional 3 h. The reaction was allowed to cool and was diluted with EtOAc, washed with sat'd aq NaHCO$_3$ and brine, dried (MgSO$_4$) and concentrated. The residue was purified by flash chromatography (3:1 hexane/EtOAc) to afford 1.7 g (89%) of the title compound as a single diastereomer. LRMS (ES)+: 633.24 (M+H)+.

Part D. 3-(10,10-Dimethyl-3,3-dioxo-3λ$^6$-thia-4-aza-tricyclo[5.2.1.0$^{1,5}$]decane-4-carbonyl)-4-(2-isopropoxycarbonyl-3-trifluoromethyl-phenyl)-pyrrolidine-1-carboxylic acid tert-butyl ester To a solution of 2-[1-Benzyl-4-(10,10-dimethyl-3,3-dioxo-3λ$^6$-thia-4-aza-tricyclo[5.2.1.0$^{1,5}$]decane-4-carbonyl)-pyrrolidin-3-yl]-6-trifluoromethyl-benzoic acid isopropyl ester (1.75 g, 2.77 mmol) in 50 mL of absolute ethanol was added di-tert-butyl dicarbonate (0.72 g, 3.30 mmol) and 10% Pd/C catalyst (0.35 g, 20 wt %). The resulting mixture was fitted with a three-way stopcock and a hydrogen balloon. The flask was alternatively evacuated (house vacuum) and filled with hydrogen several tines and then was allowed to stir under 1 atm of hydrogen for 4 h. The reaction was filtered through a pad of Celite and was concentrated in vacuo. The residue was taken up in EtOAc, washed with 1N HCl, sat'd aq NaHCO$_3$ and brine, dried (MgSO$_4$) and concentrated. The residue was purified by flash chromatography (silica gel, elution with 5:1 hexane/ethyl acetate) to afford 1.0 g (56%) of the title compound. LRMS (ES)+: 587.28 (M+H—C$_4$H$_8$)+.

Part E. (3R,4R)-1-(tert-butoxycarbonyl)-4-(2-(isopropoxycarbonyl)-3-(trifluoromethyl)phenyl)pyrrolidine-3-carboxylic acid To a solution of 3-(10,10-Dimethyl-3,3-dioxo-3λ$^6$-thia-4-aza-tricyclo[5.2.1.0$^{1,5}$]decane-4-carbonyl)-4-(2-isopropoxycarbonyl-3-trifluoromethyl-phenyl)-pyrrolidine-1-carboxylic acid tert-butyl ester (625 mg, 0.97 mmol)) in 20 mL of 2:1 THF/H$_2$O was added lithium hydroxide (70 mg, 2.91 mmol). The reaction mixture was allowed to stir at ambient temperature for 18 h. The reaction was acidified with 1 N HCl and extracted with EtOAc. The EtOAc layer was washed with brine, dried (MgSO$_4$) and concentrated to afford 0.60 g of a mixture of the title compound and (1R)-(+)-2,10-camphorsultam, which was used without purification. LRMS (ES)+: 446.28 (M+H)+.

Part F. (3aR,9bR)-tert-Butyl 5-oxo-6-(trifluoromethyl)-3,3a,4,5-tetrahydro-1H-pyrrolo[3,4-c]isoquinoline-2(9bH)-carboxylate Following the procedures described in Example 1, Part H, (3R,4R)-1-(tert-butoxycarbonyl)-4-(2-(isopropoxycarbonyl)-3-(trifluoromethyl)phenyl)pyrrolidine-3-carboxylic acid was converted into the title compound. LRMS (ESI): 301.13 (M+H—C$_4$H$_8$)+. Analysis of this material by chiral HPLC (Chiralcel OJ 4.6×250 column, heptane/10% MeOH-EtOH) showed it to be >99% ee (1 peak, retention time 8.0 min). Racemate shows two peaks under identical conditions (retention times 8.0 and 13.8 min).

Part G. (3aR,9bR)-6-(Trifluoromethyl)-2,3,3a,4-tetrahydro-1H-pyrrolo[3,4-c]isoquinolin-5(9bH)-one hydrochloride Following the procedure described in Example 1, Part I, (3aR,9bR)-tert-butyl 5-oxo-6-(trifluoromethyl)-3,3a,4,5-tetrahydro-1H-pyrrolo[3,4-c]isoquinoline-2(9bH)-carboxylate was converted into the title compound of Example 7 as an off-white solid. $^1$H NMR (DMSO-D$_6$): δ 9.8 (broad s, 1H), 9.6 (broad s, 1H), 8.15 (s, 1H), 7.86 (d, 1H, J=7.1 Hz), 7.78-7.70 (m, 2H), 4.40-4.38 (m, 1H), 3.75-3.67 (m, 2H), 3.55-3.52 (m, 1H), 3.45-3.37 (m, 1H), 3.10-3.05 (m, 1H). LRMS (ESI): 257.16 (M+H)+.

Example 8

(3aR,9bR)-4-Methyl-6-(trifluoromethyl)-2,3,3a,4-tetrahydro-1H-pyrrolo[3,4-c]isoquinolin-5(9bH)-one hydrochloride

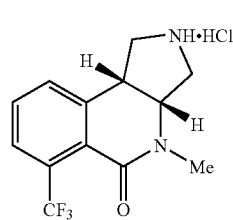

Following the procedures described in Example 2, Parts A and B, (3aR,9bR)-tert-butyl 5-oxo-6-(trifluoromethyl)-3,3a,4,5-tetrahydro-1H-pyrrolo[3,4-c]isoquinoline-2(9bH)-carboxylate from Example 7, Part F, was converted into the title compound of Example 8 as an off-white solid. $^1$H NMR (DMSO-D$_6$): δ 9.8 and 9.5 (broad singlets, 2H), 7.86 (d, 1H, J=7.7 Hz), 7.79-7.71 (m, 2H), 4.42-4.40 (m, 1H), 3.94-3.89 (m, 1H), 3.71 (dd, 1H, J=11.5, 8.3 Hz), 3.60-3.48 (m, 2H), 3.22 (dd, 1H, J=11.5, 8.3 Hz), 3.05 (s, 3H). LRMS (ESI): 271.15 (M+H)+.

Example 9

(3aR,9bR)-4-Benzyl-6-(trifluoromethyl)-2,3,3a,4-tetrahydro-1H-pyrrolo[3,4-c]isoquinolin-5(9bH)-one hydrochloride

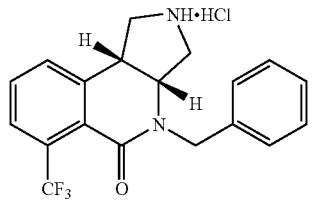

Following the procedures described in Example 3, Parts A and B, except that benzyl bromide was used instead of iodoethane, (3aR,9bR)-tert-butyl 5-oxo-6-(trifluoromethyl)-3,3a,4,5-tetrahydro-1H-pyrrolo[3,4-c]isoquinoline-2(9bH)-carboxylate from Example 7, Part F, was converted into the title compound of Example 9 as an off-white solid. $^1$H NMR (DMSO-D$_6$): δ 9.50 (broad s, 1H), 9.15 (broad s, 1H), 7.89 (d, 1H, J=7.5 Hz), 7.84-7.79 (m, 2H), 7.38-7.34 (m, 2H), 7.32-7.28 (m, 3H), 4.82 (ABq, 2H, J$_{AB}$=15.4 Hz, δV$_{AB}$=160 Hz), 4.31 (q, 1H, J=7.1 Hz), 3.96 (q, 1H, J=6.2 Hz), 3.66-3.60 (m, 2H), 3.32-3.25 (m, 1H), 3.08-3.02 (m, 1H). LRMS (ESI): 347.19 (M+H)+.

Example 10

(±)-trans-6-(Trifluoromethyl)-2,3,3a,4-tetrahydro-1H-pyrrolo[3,4-c]isoquinolin-5(9bH)-one, hydrochloride salt

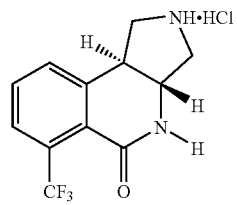

Part A. Methyl 2-formyl-6-(trifluoromethyl)benzoate

To a solution of (±)-3-hydroxy-7-(trifluoromethyl)isobenzofuran-1 (3H)-one, from Example 1, Part B, (3.31 g, 15.2 mmol) in 20 mL of DMF was added potassium carbonate (4.2 g, 30.4 mmol) followed by iodomethane (1.04 mL, 16.7 mmol). The resulting mixture was allowed to stir at ambient temperature for 18 h. The reaction was cooled to 0° C. and carefully acidified with 6N HCl, diluted with water and extracted with EtOAc. The organics were washed with sat'd aq NaHCO$_3$ and brine, dried (MgSO$_4$), filtered through a pad of silica gel and concentrated in vacuo to afford 3.1 g (89%) of the title compound which was used without purification. $^1$H NMR (CDCl$_3$): δ 10.05 (s, 1H), 8.12 (d, 1H, J=7.7 Hz), 7.95 (d, 1H, J=7.7 Hz), 7.76 (t, 1H, J=7.7 Hz), 4.02 (s, 3H).

Part B. (E)-Methyl 2-(3-(benzyloxy)-3-oxoprop-1-enyl)-6-(trifluoromethyl)benzoate To a suspension of hexane-washed sodium hydride (0.42 g of 60% suspension in mineral oil, 10.52 mmol) in 120 mL of THF at 0° C. was added benzyl 2-(dimethoxyphosphoryl) acetate (2.72 g, 10.52 mmol) dropwise in 10 mL of THF. The resulting mixture was stirred 5 min at 0° C. and then was allowed to warm to ambient temperature and stirred for 20 min. To this solution was added methyl 2-formyl-6-(trifluoromethyl)benzoate (2.22 g, 9.56 mmol) dropwise in 10 mL of THF. The resulting solution was stirred at ambient temperature for 1 h. The reaction mixture was quenched with 1N HCl (100 mL) and extracted with ethyl acetate. The organics were washed with sat'd aq $NaHCO_3$ and brine, dried ($MgSO_4$), filtered through a pad of silica gel and concentrated in vacuo to afford 3.4 g (97%) of the title compound which was sufficiently pure to be used without purification. $^1$H NMR ($CDCl_3$): δ 7.79 (d, 1H, J=7.9 Hz), 7.72-7.67 (m, 2H), 7.55 (t, 1H, J=7.9 Hz), 7.38-7.30 (m, 5H), 6.47 (d, 1H, J=15.8 Hz), 5.23 (s, 2H), 3.94 (s, 3H). LRMS (ESI): 387.17 (M+H+Na)+.

Part C. (±)-trans-Benzyl 1-benzyl-4-(2-(methoxycarbonyl)-3-(trifluoromethyl)phenyl)pyrrolidine-3-carboxylate To a solution of (E)-methyl 2-(3-(benzyloxy)-3-oxoprop-1-enyl)-6-(trifluoromethyl)benzoate (5.83 g, 16.0 mmol) in 60 mL of $CH_2Cl_2$ was added N-(methoxymethyl)-N-(trimethylsilylmethyl)benzylamine (4.0 g, 16.8 mmol) and trifluoroacetic acid (0.25 mL, 3.2 mmol). The solution was allowed to stir at ambient temperature for 18 h. Starting material still remained by TLC analysis and so additional N-(methoxymethyl)-N-(trimethylsilylmethyl)benzylamine (0.25 g, 1.05 mmol) and trifluoroacetic acid (0.05 mL, 0.65 mmol) were added and the reaction was stirred at 40° C. for an additional 2 h. The reaction was allowed to cool and was diluted with EtOAc, washed with sat'd aq $NaHCO_3$ and brine, dried ($MgSO_4$) and concentrated. The residue was purified by flash chromatography (4:1 hexane/EtOAc) to afford 7.6 g (95%) of the title compound as an oil. LRMS (ES)$^+$: 498.32 (M+H)$^+$.

Part D. (±)-trans-1-(tert-Butoxycarbonyl)-4-(2-(methoxycarbonyl)-3-(trifluoromethyl)phenyl)pyrrolidine-3-carboxylic acid To a solution of (±)-trans-benzyl 1-benzyl-4-(2-(methoxycarbonyl)-3-(trifluoromethyl)phenyl)pyrrolidine-3-carboxylate (5.7 g, 11.4 mmol) in 200 mL of absolute ethanol was added di-tert-butyl dicarbonate (2.74 g, 12.5 mmol) and 10% Pd/C catalyst (1.14 g, 20 wt %). The resulting mixture was fitted with a three-way stopcock and a hydrogen balloon. The flask was alternatively evacuated (house vacuum) and filled with hydrogen several times and then was allowed to stir under 1 atm of hydrogen for 18 h. The reaction was filtered through a pad of Celite and was concentrated in vacuo. The residue was taken up in EtOAc, washed with 1N HCl and brine, dried ($MgSO_4$) filtered through a pad of Celite and concentrated to afford 4.7 g (98%) of the title compound as a foam, which was pure enough to be used without purification. LRMS (ES)$^+$: 362.07 (M+H—$C_4H_8$)$^+$ and 318.10 (M+H—BOC)$^+$.

Part E. (±)-trans-tert-Butyl 5-oxo-6-(trifluoromethyl)-3,3a,4,5-tetrahydro-1H-pyrrolo[3,4-c]isoquinoline-2(9bH)-carboxylate To a solution of (±)-trans-1-(tert-butoxycarbonyl)-4-(2-(methoxycarbonyl)-3-(trifluoromethyl)phenyl)pyrrolidine-3-carboxylic acid (0.20 g, 0.48 mmol) in 10 mL of THF at 0° C. was added triethylamine (0.081 mL, 0.58 mmol) followed by ethyl chloroformate (0.055 mL, 0.58 mmol). The resulting cloudy mixture was stirred for 30 min at 0° C. Then there was added sodium azide (125 mg, 1.9 mmol) as a solution in 1 mL of $H_2O$. The resulting clear solution was stirred at 0° C. for 1 h. The reaction mixture was diluted with EtOAc, washed sequentially with 1N HCl, sat'd aq $NaHCO_3$ and brine, dried ($MgSO_4$) and concentrated in vacuo. The residue was dissolved in 10 mL of toluene and stirred at 100° C. for 2 h. The reaction was cooled and concentrated in vacuo to afford an intermediate isocyanate. This isocyanate was dissolved in 10 mL of THF and then there was added 10 mL of 0.2 N HCl and the resulting mixture was stirred at ambient temperature for 2 h. The pH of the solution was adjusted to about pH 9 with sat'd aq. $NaHCO_3$ and sat'd aq. $Na_2CO_3$ and then was extracted with EtOAc. The organics were washed with brine, dried ($MgSO_4$) and concentrated in vacuo to afford 160 mg of an intermediate amine. This amine was taken up in 10 mL of methanol and then there was added 2 mL of 0.5 M NaOMe in MeOH. The resulting solution was stirred at 65° C. for 2 h. The reaction was cooled and concentrated in vacuo. The residue was diluted with EtOAc and water, and the organics were washed with brine, dried ($MgSO_4$) and concentrated in vacuo to afford 125 mg (85%) of the title compound as a solid. $^1$H NMR ($CDCl_3$): (some signals doubled due to carbamate rotational isomers) δ 7.82 (d, 1H, J=7.7 Hz), 7.62 and 7.60 (overlapping t, 1H, J=7.7 Hz), 7.30 (d, 1H, J=7.7 Hz), 6.78 and 6.64 (broad singlets, 1H), 4.15 and 4.07 (dd, 1H), 3.95 and 3.88 (dd, 1H), 3.72-3.62 (multiplet, 1H), 3.42-3.25 (overlapping m, 3H), 1.52 and 1.50 (singlets, 9H). LRMS (ESI): 357.14 (M+H)+.

Part F. (±)-trans-6-(Trifluoromethyl)-2,3,3a,4-tetrahydro-1H-pyrrolo[3,4-c]isoquinolin-5(9bH)-one, hydrochloride salt To a solution of (±)-trans-tert-butyl 5-oxo-6-(trifluoromethyl)-3,3a,4,5-tetrahydro-1H-pyrrolo[3,4-c]isoquinoline-2 (9bH)-carboxylate (40 mg, 0.11 mmol) in 5 mL of ether was added 4 mL of 4 N HCl in dioxane. The reaction was allowed to stir for 18 h and then was diluted with diethyl ether. A solid slowly settled out of solution. The solvents were decanted and the remaining solid was triturated twice with diethyl ether and dried in vacuo to afford 25 mg (78%) of the title compound of Example 10 as an off-white solid. $^1$H NMR (DMSO-D6): δ 9.8 (broad s, 1H), 9.6 (broad s, 1H), 9.00 (s, 1H), 7.83 (d, 1H, J=8.2 Hz), 7.73 (t, 1H, J=7.7 Hz), 7.58 (d, 1H, J=7.7 Hz), 3.94-3.90 (m, 1H), 3.67-3.60 (m, 1H), 3.55-3.50 (m, 1H), 3.37-3.32 (m, 1H), 3.20-3.10 (m, 2H). LRMS (ESI): 257.16 (M+H)+.

Example 11

(±)-trans-4-Methyl-6-(trifluoromethyl)-2,3,3a,4-tetrahydro-1H-pyrrolo[3,4-c]isoquinolin-5(9bH)-one hydrochloride

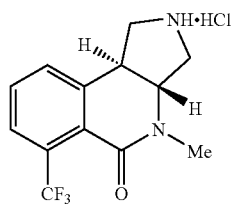

Following the procedures described in Example 3, Parts A and B, except that iodomethane was used instead of iodoethane, (±)-trans-tert-butyl 5-oxo-6-(trifluoromethyl)-3,3a,4,5-tetrahydro-1H-pyrrolo[3,4-c]isoquinoline-2(9bH)-carboxylate from Example 10, Part E was converted into the title compound of Example 11 as an tan powder. $^1$H NMR (DMSO-D$_6$): δ 9.7 and 9.5 (broad singlets, 2H), 7.84 (d, 1H, J=8.3 Hz), 7.74 (t, 1H, J=7.7 Hz), 7.55 (d, 1H, J=7.7 Hz), 4.00-3.95 (m, 1H), 3.89-3.83 (m, 1H), 3.75-3.69 (m, 1H), 3.58-3.52 (m, 1H), 3.40-3.32 (m, 1H), 3.30-3.24 (m, 1H), 3.04 (s, 3H). LRMS (ESI): 271.13 (M+H)+.

Example 12

(±)-trans-4-Benzyl-6-(trifluoromethyl)-2,3,3a,4-tetrahydro-1H-pyrrolo[3,4-c]isoquinolin-5(9bH)-one hydrochloride

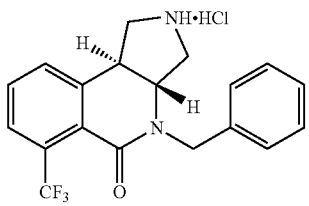

Following the procedures described in Example 3, Parts A and B, except that benzyl bromide was used instead of iodoethane, (±)-trans-tert-butyl 5-oxo-6-(trifluoromethyl)-3,3a,4,5-tetrahydro-1H-pyrrolo[3,4-c]isoquinoline-2(9bH)-carboxylate from Example 10, Part E was converted into the title compound of Example 12 as an off-white powder. $^1$H NMR (DMSO-D$_6$): δ 9.8 and 9.5 (broad singlets, 2H), 7.89 (d, 1H, J=8.3 Hz), 7.77 (t, 1H, J=7.7 Hz), 7.58 (d, 1H, J=7.7 Hz), 7.37-7.24 (m, 5H), 4.81 (ABq, 2H, J$_{AB}$=15.6 Hz, δV$_{AB}$=313 Hz), 4.00-3.92 (m, 1H), 3.85-3.77 (m, 1H), 3.68-3.50 (m, 1H), 3.52-3.45 (m, 1H), 3.30-3.18 (m, 2H). LRMS (ESI): 347.17 (M+H)+.

Example 13

(3aR,9bS)-6-(Trifluoromethyl)-2,3,3a,4-tetrahydro-1H-pyrrolo[3,4-c]isoquinolin-5(9bH)-one hydrochloride

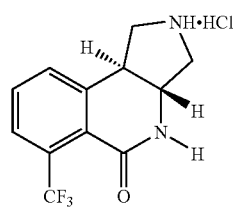

Part A. Separation of (3aR,9bS)-tert-butyl 5-oxo-6-(trifluoromethyl)-3,3a,4,5-tetrahydro-1H-pyrrolo[3,4-c]isoquinoline-2(9bH)-carboxylate and (3aS,9bR)-tert-butyl 5-oxo-6-(trifluoromethyl)-3,3a,4,5-tetrahydro-1H-pyrrolo[3,4-c]isoquinoline-2(9bH)-carboxylate and determination of stereochemistry A 1.4 g sample of racemic (±)-trans-tert-butyl 5-oxo-6-(trifluoromethyl)-3,3a,4,5-tetrahydro-1H-pyrrolo[3,4-c]isoquinoline-2(9bH)-carboxylate from Example 10, Part E, was separated into the two enantiomers by chiral HPLC (Chiralcel OD column, elution with 30% MeOH-EtOH(1:1)/heptane) to afford 0.67 g of (3aR,9bS)-tert-butyl 5-oxo-6-(trifluoromethyl)-3,3a,4,5-tetrahydro-1H-pyrrolo[3,4-c]isoquinoline-2(9bH)-carboxylate as the first eluting compound (>99% ee on chiralcel OD, 4.6×250, 30% MeOH-EtOH(1:1)/heptane, retention time 7.6 min) and 0.66 g of (3aS,9bR)-tert-butyl 5-oxo-6-(trifluoromethyl)-3,3a,4,5-tetrahydro-1H-pyrrolo[3,4-c]isoquinoline-2(9bH)-carboxylate as the second eluting compound (>99% ee on chiralcel OD, 4.6×250, 30% MeOH-EtOH(1:1)/heptane, retention time 13.6 min). A sample of the second eluting peak was deprotected by treating with excess 12N HCl for 30 min and concentrating in vacuo to afford the amine hydrochloride. To confirm the stereochemical assignment, a solution of this salt (25 mg, 0.085 mmol) in THF was treated with triethylamine (0.036 mL, 0.26 mmol) and (1S)-(+)-10-camphorsulfonyl chloride (24 mg, 0.094 mmol). This mixture was allowed to stir at ambient temperature for 2 h. The reaction was quenched with 1N HCl, extracted with EtOAc and the organics washed with sat'd aq NaHCO$_3$ and brine, dried (MgSO$_4$) and concentrated. The residue (35 mg) was placed in a vial with 3 mL of hexane. Methylene chloride was added until a homogeneous solution was obtained. The mixture was allowed to stand with the vial loosely capped for several days, at which time small crystals had settled out of solution. The solvents were decanted and the crystals were washed once with hexane and dried in vacuo to afford the (1S)-(+)-camphorsulfonamide derivative. Single crystal X-ray crystallographic analysis confirmed that the sulfonamide was derived from (3aS,9bR)-tert-butyl 5-oxo-6-(trifluoromethyl)-3,3a,4,5-tetrahydro-1H-pyrrolo[3,4-c]isoquinoline-2(9bH)-carboxylate.

Part B. (3aR,9bS)-6-(Trifluoromethyl)-2,3,3a,4-tetrahydro-1H-pyrrolo[3,4-c]isoquinolin-5(9bH)-one hydrochloride To a solution of the first eluting peak, (3aR,9bS)-tert-butyl 5-oxo-6-(trifluoromethyl)-3,3a,4,5-tetrahydro-1H-pyrrolo

[3,4-c]isoquinoline-2(9bH)-carboxylate (50 mg, 0.14 mmol) in 4 mL of dioxane was added 1 mL of 12 N HCl. The resulting solution was stirred at ambient temperature for 1 h and then was concentrated. The residue was azeotroped with toluene and dried in vacuo to afford a foam. This foam was triturated 3× with ether and dried in vacuo to afford 25 mg (61%) of the title compound of Example 13 as an off-white powder. $^1$H NMR (DMSO-D6): δ 9.8 (broad s, 1H), 9.6 (broad s, 1H), 9.00 (s, 1H), 7.83 (d, 1H, J=8.2 Hz), 7.73 (t, 1H, J=7.7 Hz), 7.58 (d, 1H, J=7.7 Hz), 3.94-3.90 (m, 1H), 3.67-3.60 (m, 1H), 3.55-3.50 (m, 1H), 3.37-3.32 (m, 1H), 3.20-3.10 (m, 2H). LRMS (ESI): 257.16 (M+H)+.

Example 14

(3aS,9bSR)-6-(Trifluoromethyl)-2,3,3a,4-tetrahydro-1H-pyrrolo[3,4-c]isoquinolin-5(9bH)-one hydrochloride

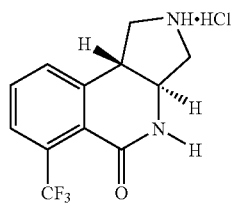

To a solution of the second eluting peak from Example 13, Part A, (3 as,9bR)-tert-butyl 5-oxo-6-(trifluoromethyl)-3,3a,4,5-tetrahydro-1H-pyrrolo[3,4-c]isoquinoline-2(9bH)-carboxylate (100 mg, 0.28 mmol) in 4 mL of dioxane was added 1 mL of 12 N HCl. The resulting solution was stirred at ambient temperature for 1 h and then was concentrated. The residue was azeotroped with toluene and dried in vacuo to afford a foam. This foam was triturated 3× with ether and dried in vacuo to afford 75 mg (91%) of the title compound of Example 14 as an off-white powder. $^1$H NMR (DMSO-D6): δ 9.8 (broad s, 1H), 9.6 (broad s, 1H), 9.00 (s, 1H), 7.83 (d, 1H, J=8.2 Hz), 7.73 (t, 1H, J=7.7 Hz), 7.58 (d, 1H, J=7.7 Hz), 3.94-3.90 (m, 1H), 3.67-3.60 (m, 1H), 3.55-3.50 (m, 1H), 3.37-3.32 (m, 1H), 3.20-3.10 (m, 2H). LRMS (ESI): 257.16 (M+H)+.

Example 15

(3aR,9bS)-4-Methyl-6-(trifluoromethyl)-2,3,3a,4-tetrahydro-1H-pyrrolo[3,4-c]isoquinolin-5(9bH)-one hydrochloride

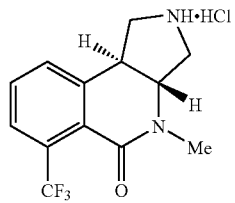

Part A. (3aR,9bS)-tert-Butyl 4-methyl-5-oxo-6-(trifluoromethyl)-3,3a,4,5-tetrahydro-1H-pyrrolo[3,4-c]isoquinoline-2(9bH)-carboxylate To a suspension of NaH (8.5 mg of 60% in mineral oil, hexane-washed, 0.21 mmol) in 2 mL of THF at ambient temperature was added (3aR,9bS)-tert-butyl 5-oxo-6-(trifluoromethyl)-3,3a,4,5-tetrahydro-1H-pyrrolo[3,4-c]isoquinoline-2(9bH)-carboxylate from Example 13, Part A (50 mg, 0.14 mmol) as a solution in 2 mL of THF. The reaction was stirred for 20 min, at which time gas evolution had ceased and the reaction mixture was homogeneous. Then there was added iodomethane (0.022 mL, 0.35 mmol) and the reaction was allowed to stir at ambient temperature for 18 h. The reaction was quenched with water, diluted with EtOAc and washed with 1N HCl, sat'd aq NaHCO$_3$ and brine, dried (MgSO$_4$) and concentrated in vacuo. The residue was purified by flash chromatography (230-400 mesh silica gel, elution with 3:1 hexane/EtOAc) to afford 40 mg (77%) of the title compound. LRMS (ESI): 371.12 (M+H)+.

Part B. (3aR,9bS)-4-Methyl-6-(trifluoromethyl)-2,3,3a,4-tetrahydro-1H-pyrrolo[3,4-c]isoquinolin-5(9bH)-one hydrochloride To a solution of (3aR,9bS)-tert-butyl 4-methyl-5-oxo-6-(trifluoromethyl)-3,3a,4,5-tetrahydro-1H-pyrrolo[3,4-c]isoquinoline-2(9bH)-carboxylate (35 mg, 0.09 mmol) in 4 mL of dioxane was added 1 mL of 12 N HCl. The resulting solution was stirred at ambient temperature for 1 h and then was concentrated. The residue was azeotroped with toluene and dried in vacuo to afford a foam. This foam was triturated 3× with ether and dried in vacuo to afford 22 mg (78%) of the title compound of Example 15 as a white powder. $^1$H NMR (DMSO-D$_6$): δ 9.7 and 9.5 (broad singlets, 2H), 7.84 (d, 1H, J=8.3 Hz), 7.74 (t, 1H, J=7.7 Hz), 7.55 (d, 1H, J=7.7 Hz), 4.00-3.95 (m, 1H), 3.89-3.83 (m, 1H), 3.75-3.69 (m, 1H), 3.58-3.52 (m, 1H), 3.40-3.32 (m, 1H), 3.30-3.24 (m, 1H), 3.04 (s, 3H). LRMS (ESI): 271.08 (M+H)+.

Example 16

(3aS,9bR)-4-Methyl-6-(trifluoromethyl)-2,3,3a,4-tetrahydro-1H-pyrrolo[3,4-c]isoquinolin-5(9bH)-one hydrochloride

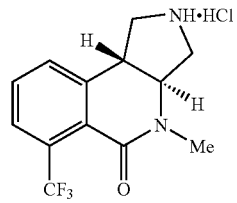

Part A. (3aS,9bR)-tert-Butyl 4-methyl-5-oxo-6-(trifluoromethyl)-3,3a,4,5-tetrahydro-1H-pyrrolo[3,4-c]isoquinoline-2(9bH)-carboxylate To a suspension of NaH (9 mg of 60% in mineral oil, hexane-washed, 0.22 mmol) in 2 mL of THF at ambient temperature was added (3aS,9bR)-tert-butyl 5-oxo-6-(trifluoromethyl)-3,3a,4,5-tetrahydro-1H-pyrrolo[3,4-c]isoquinoline-2(9bH)-carboxylate from Example 13, Part A (52 mg, 0.145 mmol) as a solution in 2 mL of THF. The reaction was stirred for 20 min, at which time gas evolution had ceased and the reaction mixture was homogeneous. Then there was added iodomethane (0.023 mL, 0.36 mmol) and the reaction was allowed to stir at ambient temperature for 18 h. The reaction was quenched with water, diluted with EtOAc and washed with 1N HCl, sat'd aq NaHCO$_3$ and brine, dried (MgSO$_4$) and concentrated in vacuo. The residue was purified by flash chromatography (230-400 mesh silica gel, elution with 3:1 hexane/EtOAc) to afford 40 mg (74%) of the title compound. LRMS (ESI): 371.12 (M+H)+.

Part B. (3aS,9bR)-4-Methyl-6-(trifluoromethyl)-2,3,3a,4-tetrahydro-1H-pyrrolo[3,4-c]isoquinolin-5(9bH)-one hydrochloride To a solution of (3aS,9bR)-tert-butyl 4-methyl-5-oxo-6-(trifluoromethyl)-3,3a,4,5-tetrahydro-1H-pyrrolo[3,4-c]isoquinoline-2(9bH)-carboxylate (40 mg, 0.11 mmol) in 4 mL of dioxane was added 1 mL of 12 N HCl. The resulting solution was stirred at ambient temperature for 1 h and then was concentrated. The residue was azeotroped with toluene and dried in vacuo to afford a foam. This foam was triturated 3× with ether and dried in vacuo to afford 28 mg (82%) of the title compound of Example 16 as a pale yellow powder. $^1$H NMR (DMSO-D$_6$): δ 9.7 and 9.5 (broad singlets, 2H), 7.84 (d, 1H, J=8.3 Hz), 7.74 (t, 1H, J=7.7 Hz), 7.55 (d, 1H, J=7.7 Hz), 4.00-3.95 (m, 1H), 3.89-3.83 (m, 1H), 3.75-3.69 (m, 1H), 3.58-3.52 (m, 1H), 3.40-3.32 (m, 1H), 3.30-3.24 (m, 1H), 3.04 (s, 3H). LRMS (ESI): 271.04 (M+H)+.

Example 17

(3aR,9bS)-4-Benzyl-6-(trifluoromethyl)-2,3,3a,4-tetrahydro-H-pyrrolo[3,4-c]isoquinolin-5(9bH)-one hydrochloride

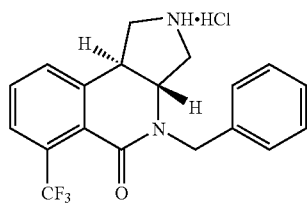

Following the procedures described in Example 15, Parts A and B, except that benzyl bromide was used instead of iodomethane, (3aR,9bS)-tert-butyl 5-oxo-6-(trifluoromethyl)-3,3a,4,5-tetrahydro-1H-pyrrolo[3,4-c]isoquinoline-2(9bH)-carboxylate from Example 13, Part A was converted into the title compound of Example 17 as a pale yellow powder. $^1$H NMR (DMSO-D$_6$): δ 9.8 and 9.5 (broad singlets, 2H), 7.89 (d, 1H, J=8.3 Hz), 7.77 (t, 1H, J=7.7 Hz), 7.58 (d, 1H, J=7.7 Hz), 7.37-7.24 (m, 5H), 4.81 (ABq, 2H, J$_{AB}$=15.6 Hz, δV$_{AB}$=313 Hz), 4.00-3.92 (m, 1H), 3.85-3.77 (m, 1H), 3.68-3.50 (m, 1H), 3.52-3.45 (m, 1H), 3.30-3.18 (m, 2H). LRMS (ESI): 347.10 (M+H)+.

Example 18

Methyl 2-((3aR,9bS)-5-oxo-6-(trifluoromethyl)-1,2,3,3a-tetrahydro-5H-pyrrolo[3,4-c]isoquinolin-4(9bH)-yl)acetate hydrochloride

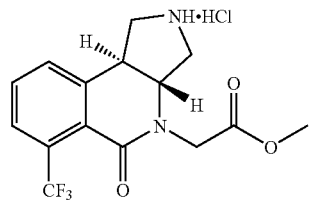

Part A. (3aR,9bS)-tert-Butyl 4-(2-methoxy-2-oxoethyl)-5-oxo-6-(trifluoromethyl)-3,3a,4,5-tetrahydro-1H-pyrrolo[3,4-c]isoquinoline-2(9bH)-carboxylate To a suspension of sodium hydride (17 mg of 60% dispersion in mineral oil, hexane-washed, 0.42 mmol) in 2 mL of THF was added (3aR,9bS)-tert-butyl 5-oxo-6-(trifluoromethyl)-3,3a,4,5-tetrahydro-1H-pyrrolo[3,4-c]isoquinoline-2(9bH)-carboxylate from Example 13, Part A (101 mg, 0.28 mmol) in 2 mL of THF. The resulting mixture was stirred at ambient temperature for 30 min, at which time gas evolution has ceased. Then there was added methyl bromoacetate (0.053 mL, 0.56 mmol) and the resulting mixture was stirred at ambient temperature for 1 h. The reaction was quenched with 10 mL of 1 N HCl and extracted with ethyl acetate. The organics were washed with sat'd aq NaHCO$_3$ and brine, dried (MgSO$_4$), filtered through a pad of silica gel and concentrated in vacuo to afford 120 mg (99%) of the title compound which was sufficiently pure to be used without purification. LRMS (ESI): 429.22 (M+H)+.

Part B. Methyl 2-((3aR,9bS)-5-oxo-6-(trifluoromethyl)-1,2,3,3a-tetrahydro-5H-pyrrolo[3,4-c]isoquinolin-4(9bH)-yl)acetate hydrochloride To a solution of (3aR,9bS)-tert-butyl 4-(2-methoxy-2-oxoethyl)-5-oxo-6-(trifluoromethyl)-3,3a,4,5-tetrahydro-1H-pyrrolo[3,4-c]isoquinoline-2(9bH)-carboxylate (20 mg, 0.05 mmol) in 4 mL of CH$_2$Cl$_2$ was added 1 mL of trifluoroacetic acid. The reaction was stirred for 1 h at ambient temperature and then was concentrated in vacuo. The residue was taken up in CH$_2$Cl$_2$ and washed with dil. aq. NH$_4$OH, dried (K$_2$CO$_3$), and concentrated. The free base residue was taken up in ether and then there was added 4 N HCl in dioxane (0.10 mL, 0.40 mmol). The reaction was concentrated to dryness and the resulting solid was triturated three times with ether and dried in vacuo to afford 12 mg (70%) of the title compound of Example 18 as an off-white powder. $^1$H NMR (DMSO-D$_6$): δ 9.8 (broad s, 1H), 9.7 (broad s, 1H), 7.87 (d, 1H, J=7.9 Hz), 7.78 (t, 1H, J=7.9 Hz), 7.60 (d, 1H, J=7.5 Hz), 4.31 (ABq, 2H, J$_{AB}$=7.8 Hz), 4.05-3.95 (m, 2H), 3.75-3.68 (m, 1H), 3.67 (s, 3H), 3.62-3.54 (m, 1H), 3.33-3.22 (m, 2H). LRMS (ESI): 329.16 (M+H)+.

Example 19

N-Methyl-2-((3aR,9bS)-5-oxo-6-(trifluoromethyl)-1,2,3,3a-tetrahydro-5H-pyrrolo[3,4-c]isoquinolin-4(9bH)-yl)acetamide hydrochloride

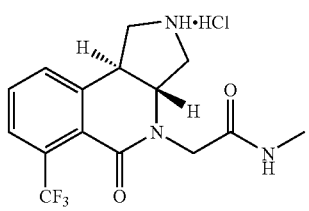

Part A. 2-((3aR,9bS)-2-(tert-Butoxycarbonyl)-5-oxo-6-(trifluoromethyl)-1,2,3,3a-tetrahydro-5H-pyrrolo[3,4-c]isoquinolin-4(9bH)-yl)acetic acid To a solution of (3aR,9bS)-tert-butyl 4-(2-methoxy-2-oxoethyl)-5-oxo-6-(trifluoromethyl)-3,3a,4,5-tetrahydro-1H-pyrrolo[3,4-c]isoquinoline-2(9bH)-carboxylate from Example 18, Part A (105 mg, 0.25 mmol) in 4 mL of THF and 2 mL of water was added lithium hydroxide (12 mg, 0.49 mmol). The resulting mixture was allowed to stir at ambient temperature for 2 h. The reaction was quenched with 10 mL of 1N HCl and extracted with ethyl acetate. The organics were washed with brine, dried (MgSO$_4$) and concentrated in vacuo to afford 100 mg (98%) of the title compound. LRMS (ESI): 415.20 (M+H)+.

Part B. (3aR,9bS)-tert-Butyl 4-(2-(methylamino)-2-oxoethyl)-5-oxo-6-(trifluoromethyl)-3,3a,4,5-tetrahydro-1H-pyrrolo[3,4-c]isoquinoline-2(9bH)-carboxylate To a solution of 2-((3aR,9bS)-2-(tert-butoxycarbonyl)-5-oxo-6-(trifluoromethyl)-1,2,3,3a-tetrahydro-5H-pyrrolo[3,4-c]isoquinolin-4(9bH)-yl)acetic acid (40 mg, 0.1 mmol) in 4 mL of THF at 0° C. was added triethylamine (0.017 mL, 0.12 mmol) and ethyl chloroformate (0.012 mL, 0.12 mmol). The reaction was allowed to stir for 30 min at 0° C. and then there was added methylamine (0.1 mL of a 2.0M solution in THF, 0.2 mmol). The resulting mixture was stirred for 1 h at 0° C. and then was quenched with 10 mL of 1N HCl. The mixture was extracted with ethyl acetate and the organics were washed with sat'd aq NaHCO$_3$ and brine, dried (MgSO$_4$), filtered through a pad of silica gel and concentrated in vacuo to afford 30 mg (70%) of the title compound which was sufficiently pure to be used without purification. LRMS (ESI): 428.24 (M+H)+.

Part C. N-Methyl-2-((3aR,9bS)-5-oxo-6-(trifluoromethyl)-1,2,3,3a-tetrahydro-5H-pyrrolo[3,4-c]isoquinolin-4(9bH)-yl)acetamide hydrochloride To a solution of (3aR,9bS)-tert-butyl 4-(2-(methylamino)-2-oxoethyl)-5-oxo-6-(trifluoromethyl)-3,3a,4,5-tetrahydro-1H-pyrrolo[3,4-c]isoquinoline-2(9bH)-carboxylate (30 mg, 0.07 mmol) in 4 mL of 1,4-dioxane was added 1 mL of 12N HCl. The resulting solution was stirred at ambient temperature for 1 h and then was concentrated. The residue was azeotroped with toluene and dried in vacuo to afford a foam. This foam was triturated 3× with ether and dried in vacuo to afford 20 mg (80%) of the title compound of Example 19 as a pale yellow powder. $^1$H NMR (DMSO-D$_6$): δ 9.73 and 9.61 (broad singlets, 2H), 8.08 (m, 1H), 7.86 (d, 1H, J=8.3 Hz), 7.76 (t, 1H, J=7.7 Hz), 7.58 (d, 1H, J=7.2 Hz), 4.12 (s, 2H), 4.02-3.95 (m, 2H), 3.70-3.60 (m, 2H), 3.35-3.25 (m, 2H), 2.60 (d, 3H, J=5.0 Hz). LRMS (ESI): 328.17 (M+H)+.

Example 20

(3aR,9bS)-4-(2-Hydroxyethyl)-6-(trifluoromethyl)-2,3,3a,4-tetrahydro-1H-pyrrolo[3,4-c]isoquinolin-5(9bH)-one hydrochloride

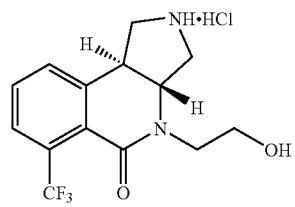

Part A. (3aR,9bS)-tert-Butyl 4-(2-hydroxyethyl)-5-oxo-6-(trifluoromethyl)-3,3a,4,5-tetrahydro-1H-pyrrolo[3,4-c]isoquinoline-2(9bH)-carboxylate To a solution of 2-((3aR,9bS)-2-(tert-butoxycarbonyl)-5-oxo-6-(trifluoromethyl)-1,2,3,3a-tetrahydro-5H-pyrrolo[3,4-c]isoquinolin-4(9bH)-yl)acetic acid from Example 19, Part A (70 mg, 0.17 mmol) in 4 mL of THF at 0° C. was added triethylamine (0.028 mL, 0.20 mmol) and ethyl chloroformate (0.019 mL, 0.20 mmol). The reaction was allowed to stir for 30 min at 0° C. and then there was added sodium borohydride (19 mg, 0.51 mmol) in a minimal amount of water. The resulting mixture was stirred for 1 h at 0° C. and then was quenched with 10 mL of 1N HCl. The mixture was extracted with ethyl acetate and the organics were washed with sat'd aq NaHCO$_3$ and brine, dried (MgSO$_4$), filtered through a pad of silica gel and concentrated in vacuo to afford 60 mg (88%) of the title compound which was sufficiently pure to be used without purification. LRMS (ESI): 401.21 (M+H)+.

Part B. (3aR,9bS)-4-(2-Hydroxyethyl)-6-(trifluoromethyl)-2,3,3a,4-tetrahydro-1H-pyrrolo[3,4-c]isoquinolin-5(9bH)-one hydrochloride Following the procedure described in Example 19, Part C, (3aR,9bS)-tert-butyl 4-(2-hydroxyethyl)-5-oxo-6-(trifluoromethyl)-3,3a,4,5-tetrahydro-1H-pyrrolo[3,4-c]isoquinoline-2(9bH)-carboxylate was converted into the title compound of Example 20 as an off-white powder. $^1$H NMR (DMSO-D$_6$): δ 9.60 (broad singlet, 2H), 7.85 (d, 1H, J=7.7 Hz), 7.74 (t, H, J=7.7 Hz), 7.56 (d, H, J=7.7 Hz), 4.98 (t, 1H, J=5.5 Hz), 3.98 (dd, 1H, J=11.0, 7.7 Hz), 3.97-3.90 (m, 1H), 3.76-3.68 (m, 2H), 3.60-3.50 (m, 1H), 3.55-3.43 (m, 3H), 3.30-3.22 (m, 2H). LRMS (ESI): 301.13 (M+H)+.

Example 21

(3aR,9bS)-4-(2-Methoxyethyl)-6-(trifluoromethyl)-2,3,3a,4-tetrahydro-1H-pyrrolo[3,4-c]isoquinolin-5(9bH)-one hydrochloride

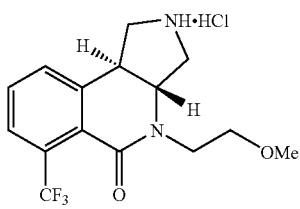

Part A. (3aR,9bS)-tert-Butyl 4-(2-methoxyethyl)-5-oxo-6-(trifluoromethyl)-3,3a,4,5-tetrahydro-1H-pyrrolo[3,4-c]isoquinoline-2(9bH)-carboxylate To a suspension of sodium hydride (8 mg of 60% dispersion in mineral oil, hexane-washed, 0.20 mmol) in 2 mL of THF was added (3aR,9bS)-tert-butyl 4-(2-hydroxyethyl)-5-oxo-6-(trifluoromethyl)-3,3a,4,5-tetrahydro-1H-pyrrolo[3,4-c]isoquinoline-2(9bH)-carboxylate from Example 20, Part A (40 mg, 0.10 mmol) in 2 mL THF. The reaction was stirred for 20 min, at which time gas evolution had ceased. Then there was added iodomethane (0.125 mL of a 2M solution in tert-butyl methyl ether, 0.25 mmol) and the reaction was allowed to stir at ambient temperature for 18 h. TLC analysis showed that starting material remained. Additional sodium hydride (8 mg of 60% dispersion in mineral oil, 0.20 mmol) and iodomethane (0.125 mL of a 2M solution in tert-butyl methyl ether, 0.25 mmol) were added and the reaction was allowed to stir at 40° C. for 2 h. The reaction was quenched with 10 mL of 1N HCl and extracted with EtOAc. The organics were washed with sat'd aq NaHCO$_3$ and brine, dried (MgSO$_4$) and concentrated in vacuo. The residue was purified by flash chromatography (230-400 mesh silica gel, elution with 4:1 hexane/EtOAc) to afford 15 mg (37%) of the title compound. $^1$H NMR (CDCl$_3$): δ 7.79 (d, 1H, J=7.7 Hz), 7.57-7.52 (m, 2H), 7.25-7.22 (m, 1H), 4.15-4.10 (m, 1H), 4.08-3.98 (m, 2H), 3.82-3.77 (m, 1H), 3.61-3.54 (m, 2H), 3.50-3.27 (overlapping m, 4H), 3.31 and 3.28 (singlets, 3H), 1.50 (s, 9H).

Part B. (3aR,9bS)-4-(2-Methoxyethyl)-6-(trifluoromethyl)-2,3,3a,4-tetrahydro-1H-pyrrolo[3,4-c]isoquinolin-5(9bH)-one hydrochloride Following the procedure described in Example 19, Part C, (3aR,9bS)-tert-butyl 4-(2-methoxyethyl)-5-oxo-6-(trifluoromethyl)-3,3a,4,5-tetrahydro-1H-pyrrolo[3,4-c]isoquinoline-2(9bH)-carboxylate was converted into the title compound of Example 21 as an off-white powder. $^1$H NMR (DMSO-D$_6$): δ 9.90 (broad s, 1H), 9.66 (broad s, 1H), 7.84 (d, 1H, J=7.7 Hz), 7.74 (t, 1H, J=7.7 Hz), 7.57 (d, 1H, J=7.7 Hz), 4.02-3.96 (m, 1H), 3.92-3.82 (m, 2H), 3.70-3.63 (m, 1H), 3.52-3.32 (overlapping m, 5H), 3.31-3.25 (m, 1H), 3.23 (s, 3H). LRMS (ESI): 315.15 (M+H)+.

Example 22

(3aR,9bS)-4-(Pyridin-2-ylmethyl)-6-(trifluoromethyl)-2,3,3a,4-tetrahydro-1H-pyrrolo[3,4-c]isoquinolin-5(9bH)-one dihydrochloride

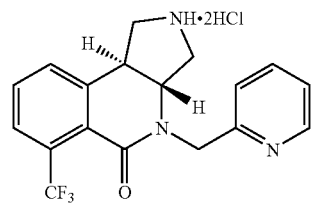

Following the procedures described in Example 15, Parts A and B, except that 2-(bromomethyl)pyridine was used instead of iodomethane, (3aR,9bS)-tert-butyl 5-oxo-6-(trifluoromethyl)-3,3a,4,5-tetrahydro-1H-pyrrolo[3,4-c]isoquinoline-2(9bH)-carboxylate from Example 13, Part A was converted into the title compound of Example 22 as a pale yellow powder. LRMS (ESI): 348.18 (M+H)+.

Example 23

(3aR,9bS)-6-Chloro-8-propyl-2,3,3a,4-tetrahydro-1H-pyrrolo[3,4-c]isoquinolin-5(9bH)-one hydrochloride

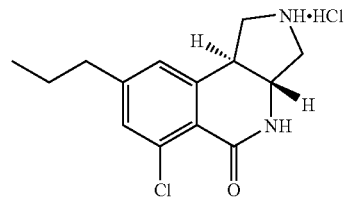

Part A. 4-Bromo-2-chloro-N,N-diethylbenzamide

Following the procedure described in Example 1, Part A, 4-bromo-2-chlorobenzoic acid was converted into the title compound as a solid. $^1$H NMR (CDCl$_3$): δ 7.56 (d, 1H, J=1.6 Hz), 7.42 (dd, 1H, J=1.6, 8.2 Hz), 7.14 (d, 1H, J=8.2 Hz), 3.80-3.70 (m, 1H), 3.38-3.30 (m, 1H), 3.18-3.05 (m, 2H), 1.24 (t, 3H, J=7.1 Hz), 1.03 (t, 3H, J=7.1 Hz). LRMS (ESI): 290/292/294 (M+H)+.

Part B. 2-Chloro-N,N-diethyl-4-propylbenzamide

To a solution of trimethyl borate (18.7 g, 180 mmol) in 60 mL of THF at 0° C. was added 1-propenylmagnesium bromide (120 mL of a 0.5 M solution in THF, 60 mmol) dropwise via addition funnel over 30 minutes. After addition was complete the reaction was allowed to stir at ambient temperature for 2 h. The reaction was cooled to 0° C. and then there was added 1N HCl (80 mL) via addition funnel over 15 minutes. The reaction was allowed to stir with warming to ambient temperature for 20 min and then most of the THF was removed by rotary evaporation. The remainder was diluted with EtOAc and the organics were washed with brine, dried (Na$_2$SO$_4$) and concentrated to afford 4.0 g (77%) of (E)-prop- 1-enylboronic acid as a yellow solid. This material was used immediately without characterization in the following reaction.

A solution of 4-bromo-2-chloro-N,N-diethylbenzamide from Part A, (3.7 g, 12.7 mmol) in 40 mL of 1,2-dimethoxyethane was degassed with a stream of argon. There was added tetrakis(triphenylphosphine)palladium(0) (0.29 g, 0.25 mmol) and the reaction was stirred for 5 min. Then there was added (E)-prop-1-enylboronic acid (3.3 g, 38 mmol), potassium carbonate (1.76 g, 12.7 mmol) and 10 mL of water. The reaction mixture was again degassed with a stream of argon and then stirred at 100° C. for 3 h. The reaction was allowed to cool and was diluted with brine (50 mL) and extracted with EtOAc. The organics were washed with brine, dried (MgSO$_4$) and concentrated to afford ~5 g of a crude intermediate olefin, (E)-2-chloro-N,N-diethyl-4-(prop-1-enyl)benzamide, which was used without purification.

To the crude (E)-2-chloro-N,N-diethyl-4-(prop-1-enyl) benzamide in 100 mL of absolute ethanol was added 10% Pd/C catalyst (1 g). The mixture was stirred under 1 atm of hydrogen, maintained by a balloon, for 18 h. Starting material still remained and so additional 10% Pd/C (0.5 g) was added and the reaction was charged with a fresh hydrogen balloon and stirred and additional 24 h. The reaction mixture was filtered through a pad of Celite and concentrated. The residue was purified by flash chromatography (230-400 mesh silica gel, elution with 8:1 to 6:1 hexane/EtOAc) to afford 2.15 g (67%) of the title compound. $^1$H NMR (CDCl$_3$): δ 7.12 (d, 1H, J=1.1 Hz), 7.09 (d, 1H, J=7.7 Hz), 7.02 (dd, 1H, J=1.6, 7.7 Hz), 3.75-3.68 (m, 1H), 3.32-3.25 (m, 1H), 3.11-3.06 (m, 2H), 2.50 (t, 2H, J=7.7 Hz), 1.60-1.52 (m, 2H), 1.19 (t, 3H, J=7.1 Hz), 0.99 (t, 3H, J=7.1 Hz), 0.87 (t, 3H, J=7.4 Hz). LRMS (ESI): 254.10/256.10 (M+H)+.

Part C. (±)-7-Chloro-3-hydroxy-5-propylisobenzofuran-1(3H)-one

To a solution of 2-chloro-N,N-diethyl-4-propylbenzamide (1.82 g, 7.17 mmol) and N,N,N'N'-tetramethylethylenediamine (1.2 mL, 7.9 mmol) in 100 mL of anhydrous THF at −78° C. was added sec-butyllithium (7.9 mL of a 1.0 M solution in hexanes, 7.9 mmol). The reaction was stirred at −78° C. for 30 min and then there was added DMF (7.6 mL, 97.8 mmol). The reaction was stirred at −78° C. for 30 min and then was quenched with 1N HCl (10 mL). The reaction mixture was concentrated in vacuo. The residue was taken up in 6N HCl (40 mL) and stirred at 100° C. for 18 h. The reaction mixture was allowed to cool, was diluted with water and extracted with EtOAc. The organics were washed with brine, dried (MgSO$_4$) and concentrated to afford a solid. This material was purified by acid-base extraction as follows. The solid was dissolved in 1:1 hexane/EtOAc and extracted twice with sat'd aq NaHCO$_3$/sat'd aq Na$_2$CO$_3$. The organics were discarded. The combined aqueous extracts were acidified with 12 N HCl and extracted with EtOAc. The EtOAc extracts were washed with brine, dried (MgSO$_4$), and concentrated to afford 0.66 g (41%) of the title compound as a tan powder. $^1$H NMR (CDCl$_3$): δ 7.25 (s, 1H), 6.55 (s, 1H), 4.85 (broad s, 1H), 2.68 (t, 2H, J=7.7 Hz), 1.72-1.63 (m, 2H), 0.95 (t, 3H, J=7.4 Hz).

Part D. Ethyl 2-chloro-6-formyl-4-propylbenzoate

To a solution of (±)-7-chloro-3-hydroxy-5-propylisobenzofuran-1 (3H)-one (0.66 g, 2.91 mmol) in 10 mL of DMF was added potassium carbonate (0.80 g, 5.82 mmol) followed by iodoethane (0.26 mL, 3.20 mmol). The resulting mixture was allowed to stir at ambient temperature for 18 h. The reaction was cooled to 0° C. and carefully acidified with 6N HCl, diluted with water and extracted with EtOAc. The organics were washed with sat'd aq NaHCO$_3$ and brine, dried (MgSO$_4$), filtered through a pad of silica gel and concentrated in vacuo to afford 0.69 g (93%) of the title compound which was used without purification. $^1$H NMR (CDCl$_3$): δ 9.88 (s, 1H), 7.52 (d, 1H, J=1.4 Hz), 7.40 (d, 1H, J=1.6 Hz), 4.42 (q, 2H, J=7.1 Hz), 2.60 (t, 2H, J=7.7 Hz), 1.64-1.55 (m, 2H), 1.34 (t, 3H, J=7.1 Hz), 0.89 (t, 3H, J=7.1 Hz).

Part E. (E)-Ethyl 2-chloro-6-(3-methoxy-3-oxoprop-1-enyl)-4-propylbenzoate

To a suspension of hexane-washed sodium hydride (0.14 g of 60% suspension in mineral oil, 3.45 mmol) in 20 mL of THF was added trimethyl phosphonoacetate (0.56 mL, 3.45 mmol). The resulting mixture was stirred for 30 min at ambient temperature, at which time a white slurry was obtained. To this slurry was added ethyl 2-chloro-6-formyl-4-propylbenzoate (0.80 g, 3.14 mmol) dropwise in 5 mL of THF. The resulting solution was stirred at ambient temperature for 1 h, at which time the mixture had become homogeneous. The reaction mixture was quenched with water and extracted with ethyl acetate. The organics were washed sequentially with 1N HCl, sat'd aq NaHCO$_3$ and brine, dried (MgSO$_4$), filtered through a pad of silica gel and concentrated in vacuo to afford 0.92 g (95%) of the title compound which was sufficiently pure to be used without purification. $^1$H NMR (CDCl$_3$): δ 7.58 (d, 1H, J=15.9 Hz), 7.25 (s, 1H), 7.18 (s, 1H), 6.33 (d, 1H, J=15.9 Hz), 4.40 (q, 2H, J=7.2 Hz), 3.73 (s, 3H), 2.52 (t, 2H, J=7.5 Hz), 1.60-1.52 (m, 2H), 1.35 (t, 3H, J=7.1 Hz), 0.88 (t, 3H, J=7.4 Hz). LRMS (ESI): 333.1 (M+H+Na)+.

Part F. (±)-trans-Methyl 1-benzyl-4-(3-chloro-2-(ethoxycarbonyl)-5-propylphenyl)pyrrolidine-3-carboxylate To a solution of (E)-ethyl 2-chloro-6-(3-methoxy-3-oxoprop-1-enyl)-4-propylbenzoate (0.92 g, 2.96 mmol) in 20 mL of CH$_2$Cl$_2$ was added N-(methoxymethyl)-N-(trimethylsilylmethyl)benzylamine (0.77 g, 3.25 mmol) and trifluoroacetic acid (0.045 mL, 0.6 mmol). The solution was allowed to stir at 40° C. for 2 h. Starting material still remained by TLC analysis and so additional N-(methoxymethyl)-N-(trimethylsilylmethyl)benzylamine (0.1 g, 0.4 mmol) and trifluoroacetic acid (2 drops) were added and the reaction was stirred at 40° C. for an additional 30 min and then at ambient temperature for 18 h. The reaction was quenched with sat'd aq NaHCO$_3$ and extracted with EtOAc. The organics were washed with brine, dried (Na$_2$SO$_4$) and concentrated. The residue was purified by flash chromatography (230-400 mesh silica gel, 6:1 hexane/EtOAc) to afford 1.17 g (90%) of the title compound as an oil. LRMS (ES)+: 444.25/446.24 (M+H)+.

Part G. (±)-trans-1-tert-Butyl 3-methyl 4-(3-chloro-2-(ethoxycarbonyl)-5-propylphenyl)pyrrolidine-1,3-dicarboxylate To a solution of (±)-trans-methyl 1-benzyl-4-(3-chloro-2-(ethoxycarbonyl)-5-propylphenyl)pyrrolidine-3-carboxylate (0.97 g, 2.18 mmol) in 20 mL of toluene was added 1-chloroethyl chloroformate (0.47 mL, 4.37 mmol). The reaction was stirred at 100° C. for 3 h. Starting material still remained so an additional portion of 1-chloroethyl chloroformate (0.2 mL, 1.8 mmol) was added and stirring was continued at 100°

C. for 1 h. The reaction was allowed to cool and was diluted with ethyl acetate. The organics were washed with sat'd aq NaHCO₃ and brine, dried (Na₂SO₄) and concentrated. The residue was taken up in methanol (20 mL) and stirred at 65° C. for 1 h. The reaction was allowed to cool and was concentrated in vacuo. The residue was taken up in 10 mL of methylene chloride and then there was added triethylamine (0.67 mL, 4.8 mmol) and di-tert-butyl dicarbonate (0.52 g, 2.4 mmol). The reaction was stirred at ambient temperature for 1 h. The methylene chloride was removed in vacuo and the residue was taken up in EtOAc. The organics were washed with 1N HCl, sat'd aq NaHCO₃ and brine, dried (MgSO₄) and concentrated. The residue was purified by flash chromatography (230-400 mesh silica gel, elution with 8:1 hexane/EtOAc) to afford 0.78 g (79%) of the title compound. LRMS (ES)⁺: 354.18/356.16 (M+H—BOC)⁺.

Part H. (±)-trans-1-(tert-Butoxycarbonyl)-4-(3-chloro-2-(ethoxycarbonyl)-5-propylphenyl)pyrrolidine-3-carboxylic acid To a solution of (±)-trans-1-tert-butyl 3-methyl 4-(3-chloro-2-(ethoxycarbonyl)-5-propylphenyl)pyrrolidine-1,3-dicarboxylate (0.78 g, 1.72 mmol) in 20 mL of THF and 10 mL of water was added lithium hydroxide (0.051 g, 2.15 mmol). The reaction was stirred at ambient temperature for 3 h and then was acidified with 1N HCl. The reaction mixture was extracted with EtOAc and the organics were washed with brine, dried (MgSO₄) and concentrated to afford 0.75 g (98%) of the title compound as a white foam. LRMS (ES)⁺: 340.17/342.16 (M+H—BOC)⁺.

Part I. (±)-trans-tert-Butyl 6-chloro-5-oxo-8-propyl-3,3a,4,5-tetrahydro-1H-pyrrolo[3,4-c]isoquinoline-2 (9bH)-carboxylate Following the procedures described in Example 10, Part E, (±)-trans-1-(tert-butoxycarbonyl)-4-(3-chloro-2-(ethoxycarbonyl)-5-propylphenyl)pyrrolidine-3-carboxylic acid (0.75 g, 1.70 mmol) was converted into 0.55 g (89%) of the title compound as a racemate, which was sufficiently pure to be used for the chiral separation of the two enantiomers. LRMS (ES)⁺: 365.19/367.16 (M+H)⁺.

Part J. Chiral separation of (3aR,9bS)-tert-Butyl 6-chloro-5-oxo-8-propyl-3,3a,4,5-tetrahydro-1H-pyrrolo[3,4-c]isoquinoline-2(9bH)-carboxylate and (3aS,9bR)-tert-butyl 6-chloro-5-oxo-8-propyl-3,3a,4, 5-tetrahydro-1H-pyrrolo[3,4-c]isoquinoline-2(9bH)-carboxylate A 0.55 g sample of racemic (±)-trans-tert-butyl 6-chloro-5-oxo-8-propyl-3,3a,4,5-tetrahydro-1H-pyrrolo[3,4-c]isoquinoline-2(9bH)-carboxylate was separated into the two enantiomers by chiral HPLC (Chiralcel OD column, elution with 30% MeOH-EtOH(1:1)/heptane) to afford 0.24 g of (3aR,9bS)-tert-butyl 6-chloro-5-oxo-8-propyl-3,3a,4,5-tetrahydro-1H-pyrrolo[3,4-c]isoquinoline-2(9bH)-carboxylate as the first eluting compound (>99% ee on chiralcel OD, 4.6×250, 30% MeOH-EtOH(1:1)/heptane, retention time 6.7 min) and 0.22 g of (3aS,9bR)-tert-butyl 6-chloro-5-oxo-8-propyl-3,3a,4,5-tetrahydro-1H-pyrrolo[3,4-c]isoquinoline-2 (9bH)-carboxylate as the second eluting compound (>99% ee on chiralcel OD, 4.6×250, 30% MeOH-EtOH(1:1)/heptane, retention time 14.4 min). Data for first eluting peak: ¹H NMR (CDCl₃): (some signals doubled due to carbamate rotational isomers) δ 7.24 (s, 1H), 6.75 and 6.74 (s, 1H), 6.44 and 6.38 (s, 1H), 4.06 and 3.99 (dd, 1H), 3.90 and 3.84 (dd, 1H), 3.63-3.57 (m, 1H), 3.35 (app q, 1H), 3.26 (app t, 1H, J=9.9 Hz), 3.23-3.17 (m, 1H), 2.60-2.54 (m, 2H), 1.67-1.60 (m, 2H), 1.49 and 1.47 (s, 9H), 0.96-0.91 (m, 3H). LRMS (ESI): 365.19/367.17 (M+H)+.). Data for second eluting peak: ¹H NMR (CDCl₃): (some signals doubled due to carbamate rotational isomers) δ 7.24 (s, 1H), 6.75 and 6.74 (s, 1H), 6.48 and 6.40 (s, 1H), 4.06 and 3.99 (dd, 1H), 3.90 and 3.84 (dd, 1H), 3.63-3.57 (m, 1H), 3.35 (app q, 1H), 3.26 (app t, 1H, J=9.9 Hz), 3.23-3.17 (m, 1H), 2.60-2.54 (m, 2H), 1.67-1.60 (m, 2H), 1.49 and 1.47 (s, 9H), 0.96-0.91 (m, 3H). LRMS (ESI): 365.18/367.17 (M+H)+.

Part K. (3aR,9bS)-6-Chloro-8-propyl-2,3,3a,4-tetrahydro-1H-pyrrolo[3,4-c]isoquinolin-5(9bH)-one hydrochloride To a solution of (3aR,9bS)-tert-butyl 6-chloro-5-oxo-8-propyl-3,3a,4,5-tetrahydro-1H-pyrrolo[3,4-c]isoquinoline-2 (9bH)-carboxylate, the first eluting peak from Part J above, (39 mg, 0.107 mmol) in 4 mL of diethyl ether was added 1 mL of 12 N HCl. The resulting mixture was stirred for 30 min at ambient temperature and then was concentrated and dried in vacuo. The resulting white solid was triturated once with 10:1 diethyl ether/ethanol and twice with diethyl ether and dried in vacuo to afford 25 mg (78%) of the title compound of Example 23 as a white solid. ¹H NMR (DMSO-D₆): δ 9.58 (broad s, 2H), 8.72 (s, 1H), 7.32 (s, 1H), 7.06 (s, 1H), 3.87 (dd, 1H, J=7.0, 10.5 Hz), 3.62-3.55 (m, 1H), 3.47 (dd, 1H, J=7.0, 10.5 Hz), 3.30-3.20 (m, 1H), 3.18-3.11 (m, 1H), 3.10-3.04 (m, 1H), 2.58 (t, 2H, J=7.7 Hz), 1.65-1.55 (m, 2H), 0.89 (t, 3H, J=7.3 Hz). LRMS (ESI): 265.08/267.05 (M+H)+.

Example 24

(3aR,9bS)-6-Chloro-4-methyl-8-propyl-2,3,3a,4-tetrahydro-1H-pyrrolo[3,4-c]isoquinolin-5(9bH)-one hydrochloride

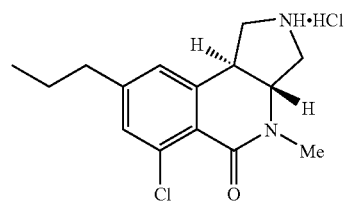

Part A. (3aR,9bS)-tert-Butyl 6-chloro-4-methyl-5-oxo-8-propyl-3,3a,4,5-tetrahydro-1H-pyrrolo[3,4-c] isoquinoline-2(9bH)-carboxylate Following the procedure described in Example 15, Part A, (3aR,9bS)-tert-butyl 6-chloro-5-oxo-8-propyl-3,3a,4,5-tetrahydro-1H-pyrrolo[3,4-c]isoquinoline-2(9bH)-carboxylate, the first eluting compound from Example 23, Part J, was converted into the title compound. LRMS (ESI): 379.17/381.15 (M+H)+.

Part B. (3aR,9bS)-6-Chloro-4-methyl-8-propyl-2,3, 3a,4-tetrahydro-1H-pyrrolo[3,4-c]isoquinolin-5 (9bH)-one hydrochloride Following the procedure described in Example 23, Part K, (3aR,9bS)-tert-butyl 6-chloro-4-methyl-5-oxo-8-propyl-3, 3a,4,5-tetrahydro-1H-pyrrolo[3,4-c]isoquinoline-2(9bH)-carboxylate was converted into the title compound of Example 24 as an off-white solid. ¹H NMR (DMSO-D₆): δ 9.77 (broad s, 2H), 7.33 (s, 1H), 7.05 (s, 1H), 3.93 (dd, 1H, J=7.7, 10.8 Hz), 3.80-3.65 (overlapping m, 2H), 3.48-3.20 (overlapping m, 3H), 2.99 (s, 3H), 2.58 (t, 2H, J=7.7 Hz), 1.65-1.55 (m, 2H), 0.89 (t, 3H, J=7.3 Hz). LRMS (ESI): 279.09/281.08 (M+H)+.

Example 25

(3aS,9bR)-6-Chloro-8-propyl-2,3,3a,4-tetrahydro-H-pyrrolo[3,4-c]isoquinolin-5(9bH)-one hydrochloride

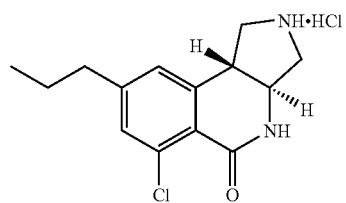

Following the procedure described in Example 23, Part K, (3aS,9bR)-tert-butyl 6-chloro-5-oxo-8-propyl-3,3a,4,5-tetrahydro-1H-pyrrolo[3,4-c]isoquinoline-2(9bH)-carboxylate, the second eluting compound from Example 23, Part J, was converted to the title compound of Example 25 as an off-white solid. ¹H NMR (DMSO-D₆): δ 9.84 (broad s, 1H), 9.67 (broad s, 1H), 8.72 (s, 1H), 7.31 (s, 1H), 7.06 (s, 1H), 3.91-3.83 (m, 1H), 3.62-3.55 (m, 1H), 3.50-3.43 (m, 1H), 3.30-3.20 (m, 1H), 3.18-3.04 (overlapping m, 2H), 2.57 (t, 2H, J=7.7 Hz), 1.65-1.55 (m, 2H), 0.88 (t, 3H, J=7.5 Hz). LRMS (ESI): 265.08/267.05 (M+H)+.

Example 26

(3aS,9bR)-6-Chloro-4-methyl-8-propyl-2,3,3a,4-tetrahydro-1H-pyrrolo[3,4-c]isoquinolin-5(9bH)-one hydrochloride

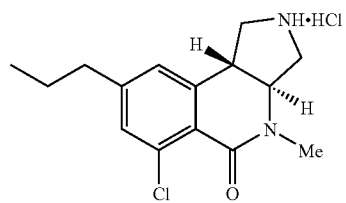

Following the procedures described in Example 24, Parts A and B, (3aS,9bR)-tert-butyl 6-chloro-5-oxo-8-propyl-3,3a,4,5-tetrahydro-1H-pyrrolo[3,4-c]isoquinoline-2(9bH)-carboxylate, the second eluting compound from Example 23, Part J, was converted to the title compound of Example 26 as an off-white solid. ¹H NMR (DMSO-D₆): δ 9.77 (broad s, 2H), 7.33 (s, 1H), 7.05 (s, 1H), 3.96-3.90 (m, 1H), 3.80-3.65 (overlapping m, 2H), 3.48-3.20 (overlapping m, 3H), 2.99 (s, 3H), 2.58 (t, 2H, J=7.7 Hz), 1.65-1.55 (m, 2H), 0.89 (t, 3H, J=7.3 Hz). LRMS (ESI): 279.09/281.07 (M+H)+.

Example 27

(3aR,9bS)-6-Chloro-2,3,3a,4-tetrahydro-1H-pyrrolo[3,4-c]isoquinolin-5(9bH)-one hydrochloride

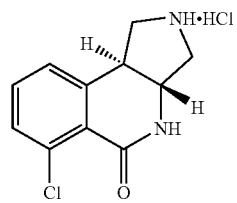

Part A. (±)-trans-tert-Butyl 6-chloro-5-oxo-3,3a,4,5-tetrahydro-1H-pyrrolo[3,4-c]isoquinoline-2(9bH)-carboxylate Following the procedures described in Example 23, Parts C-I, 2-chloro-N,N-diethylbenzamide was converted into the title compound as a racemate. LRMS (ESI): 323.15/325.13 (M+H)+.

Part B. Chiral separation of (3aR,9bS)-tert-Butyl 6-chloro-5-oxo-3,3a,4,5-tetrahydro-1H-pyrrolo[3,4-c]isoquinoline-2(9bH)-carboxylate and (3aS,9bR)-tert-butyl 6-chloro-5-oxo-3,3a,4,5-tetrahydro-1H-pyrrolo[3,4-c]isoquinoline-2(9bH)-carboxylate A 0.45 g sample of racemic (±)-trans-tert-butyl 6-chloro-5-oxo-3,3a,4,5-tetrahydro-1H-pyrrolo[3,4-c]isoquinoline-2 (9bH)-carboxylate was separated into the two enantiomers by chiral HPLC (Chiralcel OD column, elution with 30% iPrOH/heptane) to afford 0.17 g of (3aR,9bS)-tert-butyl 6-chloro-5-oxo-3,3a,4,5-tetrahydro-1H-pyrrolo[3,4-c]isoquinoline-2 (9bH)-carboxylate as the first eluting compound (>99% ee on chiralcel OD, 4.6×250, 30% iPrOH/heptane, retention time 9.85 min) and 0.14 g of (3aS,9bR)-tert-butyl 6-chloro-5-oxo-3,3a,4,5-tetrahydro-1H-pyrrolo[3,4-c]isoquinoline-2(9bH)-carboxylate as the second eluting compound (>99% ee on chiralcel OD, 4.6×250, 30% iPrOH/heptane, retention time 16.9 min).

Part C. (3aR,9bS)-6-Chloro-2,3,3a,4-tetrahydro-1H-pyrrolo[3,4-c]isoquinolin-5(9bH)-one hydrochloride Following the procedure described in Example 23, Part K, (3aR,9bS)-tert-butyl 6-chloro-5-oxo-3,3a,4,5-tetrahydro-1H-pyrrolo[3,4-c]isoquinoline-2(9bH)-carboxylate, the first eluting compound from Part B above, was converted into the title compound of Example 27 as an off-white solid. ¹H NMR (DMSO-D₆): δ 10.03 (broad s, 1H), 9.80 (broad s, 1H), 8.87 (s, 1H), 7.55-7.45 (m, 2H), 7.22 (d, 1H), 3.92-3.84 (m, 1H), 3.63-3.53 (m, 1H), 3.50-3.42 (m, 1H), 3.32-3.22 (m, 1H), 3.20-3.05 (overlapping m, 2H). LRMS (ESI): 223.07/225.05 (M+H)+.

Example 28

(3aS,9bR)-6-Chloro-2,3,3a,4-tetrahydro-1H-pyrrolo[3,4-c]isoquinolin-5(9bH)-one hydrochloride

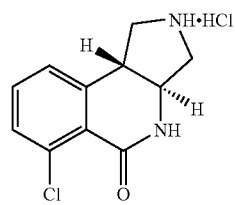

Following the procedure described in Example 23, Part K, (3aS,9bR)-tert-butyl 6-chloro-5-oxo-3,3a,4,5-tetrahydro-1H-pyrrolo[3,4-c]isoquinoline-2(9bH)-carboxylate, the second eluting compound from Example 27, Part B, was converted into the title compound of Example 28 as an off-white solid. $^1$H NMR (DMSO-D$_6$): δ 10.00 (broad s, 1H), 9.77 (broad s, 1H), 8.86 (s, 1H), 7.55-7.45 (m, 2H), 7.22 (d, 1H), 3.92-3.84 (m, 1H), 3.63-3.53 (m, 1H), 3.50-3.42 (m, 1H), 3.32-3.22 (m, 1H), 3.20-3.05 (overlapping m, 2H). LRMS (ESI): 223.06/225.08 (M+H)+.

Examples 29 and 30

(3aR,9bS)-6-Chloro-8-ethyl-2,3,3a,4-tetrahydro-1H-pyrrolo[3,4-c]isoquinolin-5(9bH)-one hydrochloride (Example 29) and (3aS,9bR)-6-Chloro-8-ethyl-2,3,3a,4-tetrahydro-1H-pyrrolo[3,4-c]isoquinolin-5(9bH)-one hydrochloride (Example 30)

Example 29
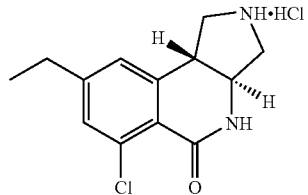

Example 30
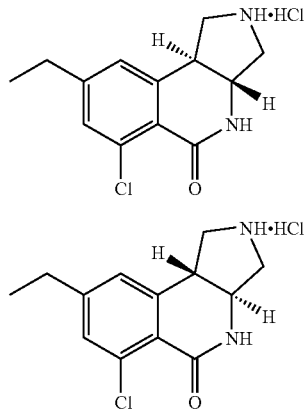

Following the procedures described in Example 23, Parts A-K, except that in Part B vinylboronic acid was used instead of (E)-prop-1-enylboronic acid, 4-bromo-2-chlorobenzoic acid was converted into the title compounds of Example 29 (first eluting N-BOC intermediate) and Example 30 (second eluting N-BOC intermediate) as off-white solids. Data for Example 29: $^1$H NMR (CD$_3$OD): 7.35 (s, 1H), 7.03 (s, 1H), 4.07-4.02 (m, 1H), 3.74-3.67 (m, 2H), 3.42-3.35 (m, 2H), 3.30-3.25 (m, 1H), 2.69 (q, 2H), 1.25 (t, 3H). LRMS (ESI): 251.12/253.10 (M+H)+. Data for Example 30: $^1$H NMR (CD$_3$OD): 7.35 (s, 1H), 7.03 (s, 1H), 4.07-4.02 (m, 1H), 3.74-3.67 (m, 2H), 3.42-3.35 (m, 2H), 3.30-3.25 (m, 1H), 2.69 (q, 2H), 1.25 (t, 3H). LRMS (ESI): 251.12/253.11 (M+H)+.

Example 31

(3aR,9bS)-6-Chloro-8-ethyl-4-methyl-2,3,3a,4-tetrahydro-1H-pyrrolo[3,4-c]isoquinolin-5(9bH)-one hydrochloride

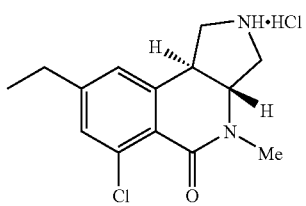

Following the procedures described in Example 24, Parts A and B, (3aR,9bS)-tert-butyl 6-chloro-8-ethyl-5-oxo-3,3a,4,5-tetrahydro-1H-pyrrolo[3,4-c]isoquinoline-2(9bH)-carboxylate, an intermediate in the preparation of Example 29 (the first eluting peak from the chiral separation of the enantiomers, as described in Example 23 Part J), was converted to the title compound of Example 31 as an off-white solid. LRMS (ESI): 279.09/281.07 (M+H)+.

Example 32

(3aR,9bS)-2,3,3a,4-Tetrahydro-1H-pyrrolo[3,4-c]isoquinolin-5(9bH)-one hydrochloride

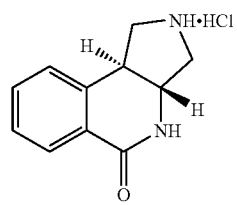

To a solution of (3aR,9bS)-tert-butyl 6-chloro-5-oxo-3,3a,4,5-tetrahydro-1H-pyrrolo[3,4-c]isoquinoline-2(9bH)-carboxylate, the first eluting compound from Example 27, Part B (10 mg) in methanol was added 2 drops of acetic acid and 2 mg of 10% Pd/C catalyst. The mixture was shaken under 70 psi of hydrogen on a Parr shaker for 3 h. The mixture was filtered through a pad of Celite and concentrated in vacuo. The residue was taken up in 2 mL of methanol and then there was added 1 mL of 12 N HCl. The reaction was stirred at ambient temperature for 10 min and then was concentrated in vacuo at 60° C. to afford 7 mg of the title compound of Example 32 as an off-white solid. $^1$H NMR (CD$_3$OD): 7.92 (d, 1H), 7.51 (app t, 1H), 7.39 (app t, 1H), 7.18 (d, 1H), 4.02-3.95 (m, 1H), 3.76-3.70 (m, 1H), 3.66-3.61 (m, 1H), 3.58-3.52 (m, 1H), 3.41-3.30 (overlapping m, 2H). LRMS (ESI): 189 (M+H)+.

Example 33

(3aR,9bS)-4-Methyl-2,3,3a,4-tetrahydro-1H-pyrrolo[3,4-c]isoquinolin-5(9bH)-one hydrochloride

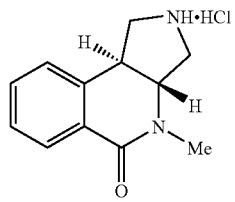

Part A. (E)-Ethyl 2-(3-(benzyloxy)-3-oxoprop-1-enyl)benzoate

To a solution of ethyl 2-bromobenzoate (1.15 g, 5.0 mmol) in 20 mL of DMF was added benzyl acrylate (1.22 g, 7.5 mmol) and triethylamine (1.39 mL, 10.0 mmol). The mixture was degassed and then there was added [1,1'-bis(diphenylphoshino)ferrocene]dichloropalladium (II), complex with dichloromethane (12.2 mg, 0.015 mol). The reaction mixture was stirred at 90° C. for 18 h. The reaction mixture was allowed to cool and was diluted with EtOAc. The organics were washed with water and brine, dried ($MgSO_4$) and concentrated to an oil. The residue was purified (ISCO, elution with 0-15% EtOAc/hexane) to give 1.44 g (92%) of the title compound. $^1$H NMR ($CDCl_3$): δ 8.51 (d, 1H), 7.96 (d, 1H), 7.57 (d, 1H), 7.50 (t, 1H), 7.45-7.22 (overlapping m, 6H), 6.35 (d, 1H), 5.26 (s, 2H), 4.38 (q, 2H), 1.37 (t, 3H). LRMS (ESI): 311.2 (M+H)+.

Part B. (±)-trans-Benzyl 1-benzyl-4-(2-(ethoxycarbonyl)phenyl)pyrrolidine-3-carboxylate To a solution of (E)-ethyl 2-(3-(benzyloxy)-3-oxoprop-1-enyl)benzoate (1.44 g, 4.64 mmol) in 20 mL of $CH_2Cl_2$ was added N-(methoxymethyl)-N-(trimethylsilylmethyl)benzylamine (1.78 mL, 6.96 mmol) and trifluoroacetic acid (0.072 mL, 0.93 mmol). The solution was allowed to stir at ambient temperature for 18 h. Starting material still remained by TLC analysis and so additional N-(methoxymethyl)-N-(trimethylsilylmethyl)benzylamine (0.5 g, 2.1 mmol) and trifluoroacetic acid (2 drops) were added and the reaction was stirred at ambient temperature for 1 h. The reaction was evaporated and purified by ISCO (elution with 0-30% EtOAc/hexane) to afford 1.97 g (95%) of the title compound as an oil. LRMS (ES)+: 444.3 (M+H)+.

Part C. (±)-trans-1-(tert-Butoxycarbonyl)-4-(2-(ethoxycarbonyl)phenyl)pyrrolidine-3-carboxylic acid To a solution of (±)-trans-benzyl 1-benzyl-4-(2-(ethoxycarbonyl)phenyl)pyrrolidine-3-carboxylate (1.97 g, 4.44 mmol) in 20 mL of methanol was added di-tert-butyl dicarbonate (1.06 g, 4.88 mmol) and 10% Pd/C catalyst (0.2 g, 10 wt %). The resulting mixture was fitted with a three-way stopcock and a hydrogen balloon. The flask was alternatively evacuated (house vacuum) and filled with hydrogen several times and then was allowed to stir under 1 atm of hydrogen for 18 h. The reaction was filtered through a pad of Celite and was concentrated in vacuo. The residue was purified (ISCO, elution with 0-50% EtOAc/hexane) to give 1.45 g (90%) of the title compound. LRMS (ES)+: 364.3 (M+H)+ and 264.2 (M+H—BOC)+.

Part D. (±)-trans-tert-Butyl 5-oxo-3,3a,4,5-tetrahydro-1H-pyrrolo[3,4-c]isoquinoline-2(9bH)-carboxylate Following the procedures described in Example 10, Part E, (±)-trans-1-(tert-butoxycarbonyl)-4-(2-(ethoxycarbonyl)phenyl)pyrrolidine-3-carboxylic acid was converted into the title compound as a racemate, which was sufficiently pure to be used for the chiral separation of the two enantiomers. LRMS (ES)+: 189.1 (M+H)+.

Part E. Chiral separation of (3aR,9bS)-tert-Butyl 5-oxo-3,3a,4,5-tetrahydro-1H-pyrrolo[3,4-c]isoquinoline-2(9bH)-carboxylate and (3aS,9bR)-tert-Butyl 5-oxo-3,3a,4,5-tetrahydro-1H-pyrrolo[3,4-c]isoquinoline-2(9bH)-carboxylate A sample of racemic (±)-trans-tert-butyl 5-oxo-3,3a,4,5-tetrahydro-1H-pyrrolo[3,4-c]isoquinoline-2(9bH)-carboxylate was separated into the two enantiomers by chiral HPLC (Chiralcel OD column, elution with 30% iPrOH/heptane) to afford (3aR,9bS)-tert-butyl 5-oxo-3,3a,4,5-tetrahydro-1H-pyrrolo[3,4-c]isoquinoline-2(9bH)-carboxylate as the first eluting compound (>99% ee on chiralcel OD, 4.6×250, 30% iPrOH/heptane, retention time 8.1 min) and (3aS,9bR)-tert-butyl 5-oxo-3,3a,4,5-tetrahydro-1H-pyrrolo[3,4-c]isoquinoline-2(9bH)-carboxylate as the second eluting compound (>99% ee on chiralcel OD, 4.6×250, 30% iPrOH/heptane, retention time 19.7 min).

Part F. (3aR,9bS)-4-Methyl-2,3,3a,4-tetrahydro-1H-pyrrolo[3,4-c]isoquinolin-5(9bH)-one hydrochloride Following the procedures described in Example 24, Parts A and B, (3aR,9bS)-tert-butyl 5-oxo-3,3a,4,5-tetrahydro-1H-pyrrolo[3,4-c]isoquinoline-2(9bH)-carboxylate, the first eluting compound from Example 33, Part E, was converted to the title compound of Example 33 as an off-white solid. $^1$H NMR (DMSO-$D_6$): δ 10.00 (broad s, 1H), 9.87 (broad s, 1H), 7.89 (d, 1H), 7.56 (t, 1H), 7.44 (t, 1H), 7.27 (d, 1H), 3.98-3.92 (m, 1H), 3.82-3.75 (m, 1H), 3.72-3.66 (m, 1H), 3.52-3.42 (m, 1H), 3.38-3.22 (overlapping m, 2H), 3.00 (s, 3H). LRMS (ESI): 203.1 (M+H)+.

Example 34

(3aR,9bS)-4-Ethyl-2,3,3a,4-tetrahydro-1H-pyrrolo[3,4-c]isoquinolin-5(9bH)-one hydrochloride

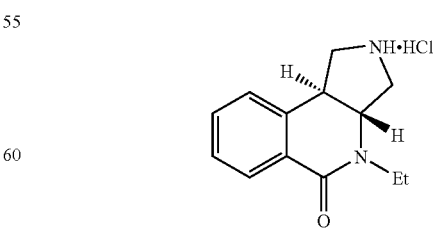

Following the procedures described in Example 24, Parts A and B, except that iodoethane was used instead of iodomethane, (3aR,9bS)-tert-butyl 5-oxo-3,3a,4,5-tetrahydro-1H-pyrrolo[3,4-c]isoquinoline-2(9bH)-carboxylate, the first eluting compound from Example 33, Part E, was converted to the title compound of Example 34 as an off-white solid. ¹H NMR (DMSO-D₆): δ 9.91 (broad s, 1H), 9.70 (broad s, 1H), 7.90 (d, 1H), 7.56 (t, 1H), 7.45 (t, 1H), 7.27 (d, 1H), 4.00-3.93 (m, 1H), 3.89-3.77 (overlapping m, 2H), 3.75-3.69 (m, 1H), 3.50-3.45 (m, 1H), 3.35-3.23 (overlapping m, 2H), 3.21-3.14 (m, 1H), 1.08 (t, 3H). LRMS (ESI): 217.2 (M+H)+.

Example 35

(3aS,9bR)-2,3,3a,4-Tetrahydro-1H-pyrrolo[3,4-c]isoquinolin-5(9bH)-one hydrochloride

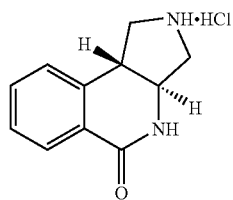

Following the procedure described in Example 24, Part B, (3aS,9bR)-tert-butyl 5-oxo-3,3a,4,5-tetrahydro-1H-pyrrolo[3,4-c]isoquinoline-2(9bH)-carboxylate, the second eluting compound from Example 33, Part E, was converted into the title compound of Example 35 as an off-white solid. LRMS (ESI): 189.1 (M+H)+.

Example 36

(3aR,9bS)-4-Benzyl-2,3,3a,4-tetrahydro-1H-pyrrolo[3,4-c]isoquinolin-5(9bH)-one hydrochloride

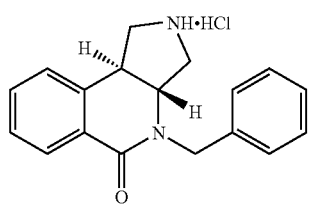

Following the procedures described in Example 24, Parts A and B, except that benzyl bromide was used instead of iodomethane, (3aR,9bS)-tert-butyl 5-oxo-3,3a,4,5-tetrahydro-1H-pyrrolo[3,4-c]isoquinoline-2(9bH)-carboxylate, the first eluting compound from Example 33, Part E, was converted to the title compound of Example 36 as an off-white solid. LRMS (ESI): 279.2 (M+H)+.

Example 37

(3aR,9bS)-6-Chloro-8-methyl-2,3,3a,4-tetrahydro-1H-pyrrolo[3,4-c]isoquinolin-5(9bH)-one hydrochloride

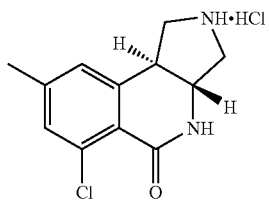

Part A. 2-Chloro-N,N-diethyl-4-methylbenzamide

To a solution of 4-bromo-2-chloro-N,N-diethylbenzamide from Example 23, Part A (3.10 g, 10.67 mmol) in 50 mL of DMF was added potassium carbonate (3.68 g, 26.7 mmol) and dimethyl zinc (8.0 mL of a 2.0 M solution in toluene, 16.0 mmol). The solution was degassed with a stream of argon and then there was added [1,1'-bis(diphenylphosphino)ferrocene]dichloropalladium (II) complex with dichloromethane (1:1) (175 mg, 0.21 mmol). The reaction mixture was allowed to stir at 90° C. for 18 h. The reaction mixture was allowed to cool and was diluted with ethyl acetate. The organics were washed with water and brine, dried (MgSO₄) and concentrated. The residue was purified (ISCO, elution with 0-50% EtOAc/hexane, 30 min) to afford 2.15 g (90%) of the title compound as a colorless oil. LRMS (ESI): 226.2/228.2 (M+H)+.

Part B. (±)-trans-tert-Butyl 6-chloro-5-oxo-8-methyl-3,3a,4,5-tetrahydro-1H-pyrrolo[3,4-c]isoquinoline-2(9bH)-carboxylate Following the procedures described in Example 23, Parts C-I, 2-chloro-N,N-diethyl-4-methylbenzamide was converted into the title compound as a racemate. ¹H NMR (CD₃OD): δ 7.28 (s, 1H), 6.95 (d, 1H), 4.10-4.00 (m, 1H), 3.85-3.80 (m, 1H), 3.60-3.50 (m, 1H), 3.37-3.30 (m, 1H), 3.28-3.18 (m, 2H), 2.37 (s, 3H), 1.50 and 1.48 (s, 9H).

Part C. Chiral separation of (3aR,9bS)-tert-Butyl 6-chloro-5-oxo-8-methyl-3,3a,4,5-tetrahydro-1H-pyrrolo[3,4-c]isoquinoline-2(9bH)-carboxylate and (3aS,9bR)-tert-butyl 6-chloro-5-oxo-8-methyl-3,3a,4,5-tetrahydro-1H-pyrrolo[3,4-c]isoquinoline-2(9bH)-carboxylate A 0.25 g sample of racemic (±)-trans-tert-butyl 6-chloro-5-oxo-8-methyl-3,3a,4,5-tetrahydro-1H-pyrrolo[3,4-c]isoquinoline-2(9bH)-carboxylate was separated into the two enantiomers by chiral HPLC (Chiralcel OD column, elution with 25% isopropanol/heptane) to afford 0.074 g of (3aR,9bS)-tert-butyl 6-chloro-5-oxo-8-methyl-3,3a,4,5-tetrahydro-1H-pyrrolo[3,4-c]isoquinoline-2(9bH)-carboxylate as the first eluting compound (>99% ee on chiralcel OD, 4.6× 250, 30% isopropanol/heptane, retention time 8.7 min) and 0.070 g of (3aS,9bR)-tert-butyl 6-chloro-5-oxo-8-methyl-3,3a,4,5-tetrahydro-1H-pyrrolo[3,4-c]isoquinoline-2(9bH)-carboxylate as the second eluting compound (>99% ee on chiralcel OD, 4.6×250, 30% isopropanol/heptane, retention time 16.0 min).

Part D. (3aR,9bS)-6-Chloro-8-methyl-2,3,3a,4-tetrahydro-1H-pyrrolo[3,4-c]isoquinolin-5(9bH)-one hydrochloride Following the procedure described in Example 23, Part K, (3aR,9bS)-tert-butyl 6-chloro-5-oxo-8-methyl-3,3a,4,5-tetrahydro-1H-pyrrolo[3,4-c]isoquinoline-2(9bH)-carboxylate, the first eluting compound from Part C above, was converted into the title compound of Example 37 as an off-white solid. ¹H NMR (CD₃OD): δ 7.26 (s, 1H), 6.93 (s, 1H), 4.06-4.02 (m, 1H), 3.73-3.67 (m, 2H), 3.40-3.34 (m, 2H), 3.30-3.25 (m, 1H), 2.39 (s, 3H). LRMS (ESI): 237.1/239.1 (M+H)+.

Example 38

(3aS,9bR)-6-Chloro-8-methyl-2,3,3a,4-tetrahydro-1H-pyrrolo[3,4-c]isoquinolin-5(9bH)-one hydrochloride

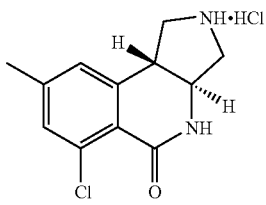

Following the procedure described in Example 23, Part K, (3aS,9bR)-tert-butyl 6-chloro-5-oxo-8-methyl-3,3a,4,5-tetrahydro-1H-pyrrolo[3,4-c]isoquinoline-2(9bH)-carboxylate, the second eluting compound from Example 37, Part C, was converted into the title compound of Example 38 as an off-white solid. ¹H NMR (DMSO-D₆): δ 9.55 (broad s, 1H), 9.41 (broad s, 1H), 8.67 (s, 1H), 7.29 (s, 1H), 7.02 (s, 1H), 3.85-3.80 (m, 1H), 3.66-3.61 (m, 1H), 3.58-3.52 (m, 1H), 3.30-3.25 (m, 1H), 3.15-3.10 (m, 1H), 3.07-3.02 (m, 1H), 2.30 (s, 3H). LRMS (ESI): 237.1/239.1 (M+H)+.

Example 39

(3aR,9bS)-6-Chloro-4,8-dimethyl-2,3,3a,4-tetrahydro-1H-pyrrolo[3,4-c]isoquinolin-5(9bH)-one hydrochloride

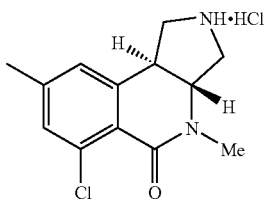

Following the procedures described in Example 24, Parts A and B, (3aR,9bS)-tert-butyl 6-chloro-5-oxo-8-methyl-3,3a,4,5-tetrahydro-1H-pyrrolo[3,4-c]isoquinoline-2(9bH)-carboxylate, an intermediate in the preparation of Example 37 (the first eluting peak from the chiral separation of the enantiomers, as described in Example 37, Part C), was converted to the title compound of Example 39 as an off-white solid. ¹H NMR (CD₃OD): δ 7.34 (s, 1H), 7.00 (s, 1H), 4.07-4.01 (m, 1H), 3.89-3.80 (m, 2H), 3.55-3.48 (m, 2H), 3.44-3.39 (m, 1H), 3.07 (s, 3H), 2.33 (s, 3H). LRMS (ESI): 251.1/253.1 (M+H)+.

Example 40

(3aR,9bS)-8-Ethyl-2,3,3a,4-tetrahydro-1H-pyrrolo[3,4-c]isoquinolin-5(9bH)-one hydrochloride

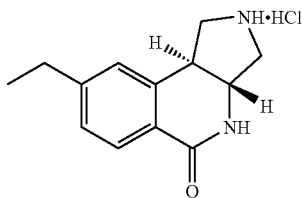

To a solution of (3aR,9bS)-6-chloro-8-ethyl-2,3,3a,4-tetrahydro-1H-pyrrolo[3,4-c]isoquinolin-5(9bH)-one hydrochloride (the title compound of Example 29) (36 mg, 0.12 mmol) in 5 mL of methanol was added 10% Pd/C catalyst (2.5 mg). The mixture was stirred at room temperature under 1 atm of hydrogen maintained by a balloon for 3 h. The reaction mixture was filtered through a pad of Celite and concentrated in vacuo. The resulting solid was triturated with ether and dried in vacuo to afford 25 mg (80%) of the title compound of Example 40 as an off-white solid. ¹H NMR (CD₃OD): δ 7.91 (d, 1H, J=8.3 Hz), 7.32 (d, 1H, J=7.7 Hz), 7.10 (s, 1H), 4.10-4.03 (m, 1H), 3.80-3.68 (m, 2H), 3.47-3.39 (m, 2H), 3.30-3.25 (m, 1H), 2.72 (q, 2H, J=7.5 Hz), 1.25 (t, 3H, J=7.7 Hz). LRMS (ESI): 217.2 (M+H)+.

Example 41

(3aR,9bS)-6-Chloro-4,8-diethyl-2,3,3a,4-tetrahydro-1H-pyrrolo[3,4-c]isoquinolin-5(9bH)-one hydrochloride

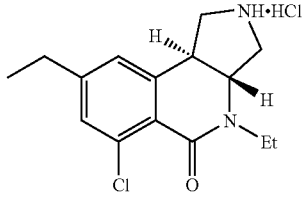

Following the procedures described in Example 24, Parts A and B, except that iodoethane was used instead of iodomethane, (3aR,9bS)-tert-butyl 6-chloro-5-oxo-8-ethyl-3,3a,4,5-tetrahydro-1H-pyrrolo[3,4-c]isoquinoline-2(9bH)-carboxylate, the first eluting compound from the OD column separation of N-BOC intermediate enantiomers in Example 29 and 30 (the first eluting compound gave Example 29), was converted to the title compound of Example 41 as an off-white solid. ¹H NMR (CD₃OD): δ 7.28 (s, 1H), 7.22 (s, 1H), 4.43-4.37 (m, 1H), 3.88-3.81 (m, 1H), 3.73-3.68 (m, 1H), 3.69 (q, 2H), 3.63 (dd, 1H, J=7.8, 12.3 Hz), 3.45-3.38 (m, 1H), 3.26-3.20 (m, 1H), 2.61 (q, 2H, J=7.5 Hz), 1.17 (t, 3H, J=7.7 Hz), 1.14 (t, 3H, J=7.5 Hz). LRMS (ESI): 279.2/281.2 (M+H)+.

Example 42

(3aR,9bS)-6-Chloro-8-ethyl-4-propyl-2,3,3a,4-tetrahydro-1H-pyrrolo[3,4-c]isoquinolin-5(9bH)-one hydrochloride

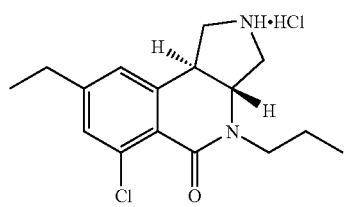

Following the procedures described in Example 24, Parts A and B, except that iodopropane was used instead of iodomethane, (3aR,9bS)-tert-butyl 6-chloro-5-oxo-8-ethyl-3,3a,4,5-tetrahydro-1H-pyrrolo[3,4-c]isoquinoline-2(9bH)-carboxylate, the first eluting compound from the OD column separation of N-BOC intermediate enantiomers in Example 29 and 30 (the first eluting compound gave Example 29), was converted to the title compound of Example 42 as an off-white solid. $^1$H NMR (CD$_3$OD): δ 7.37 (s, 1H), 7.32 (s, 1H), 4.48 (q, 1H, J=6.8 Hz), 3.98-3.92 (m, 1H), 3.80-3.69 (overlapping m, 4H), 3.41-3.35 (m, 1H), 3.35-3.30 (m, 1H), 2.71 (q, 2H, J=7.5 Hz), 1.72-1.60 (m, 2H), 1.27 (t, 3H, J=7.7 Hz), 0.96 (t, 3H, J=7.4 Hz). LRMS (ESI): 293.2/295.2 (M+H)+.

Example 43

(3aR,9bS)-4-Benzyl-6-chloro-8-ethyl-2,3,3a,4-tetrahydro-1H-pyrrolo[3,4-c]isoquinolin-5(9bH)-one hydrochloride

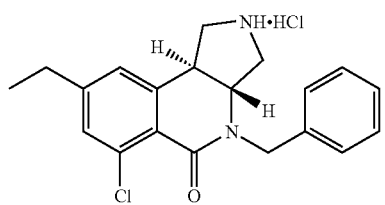

Following the procedures described in Example 24, Parts A and B, except that benzyl bromide was used instead of iodomethane, (3aR,9bS)-tert-butyl 6-chloro-5-oxo-8-ethyl-3,3a,4,5-tetrahydro-1H-pyrrolo[3,4-c]isoquinoline-2(9bH)-carboxylate, the first eluting compound from the OD column separation of N-BOC intermediate enantiomers in Example 29 and 30 (the first eluting compound gave Example 29), was converted to the title compound of Example 43 as an off-white solid. $^1$H NMR (CD$_3$OD): δ 7.40 (s, 1H), 7.38-7.24 (m, 5H), 7.01 (s, 1H), 5.09 and 4.67 (ABq, 2H, J$_{AB}$=15.7 Hz), 4.04 (dd, 1H, J=7.4, 11.3 Hz), 3.88-3.81 (m, 1H), 3.65-3.55 (m, 2H), 3.40-3.32 (m, 2H), 2.70 (q, 2H, J=7.5 Hz), 1.25 (t, 3H, J=7.7 Hz). LRMS (ESI): 341.3/343.3 (M+H)+.

Example 44

(3aR,9bS)-8-Ethyl-6-phenyl-2,3,3a,4-tetrahydro-1H-pyrrolo[3,4-c]isoquinolin-5(9bH)-one hydrochloride

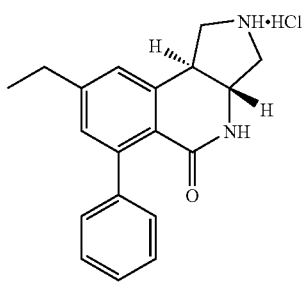

Part A. (3aR,9bS)-tert-Butyl 8-ethyl-5-oxo-6-phenyl-3,3a,4,5-tetrahydro-1H-pyrrolo[3,4-c]isoquinoline-2 (9bH)-carboxylate To a solution of (3aR,9bS)-tert-butyl 6-chloro-5-oxo-8-ethyl-3,3a,4,5-tetrahydro-1H-pyrrolo[3,4-c]isoquinoline-2 (9bH)-carboxylate, the first eluting compound from the OD column separation of N-BOC intermediate enantiomers in Example 29 and 30 (the first eluting compound gave Example 29), (45 mg, 0.13 mmol) in 5 mL of DMF was added phenylboronic acid (29 mg, 0.26 mmol) and potassium carbonate (45 mg, 0.33 mmol). The solution was degassed with a stream of argon and then there was added POPd (Combiphos) (3.5 mg, 0.007 mmol). The reaction mixture was allowed to stir at 120° C. for 18 h. The reaction mixture was allowed to cool and was diluted with ethyl acetate. The organics were washed with water and brine, dried (MgSO$_4$) and concentrated. The residue was purified (ISCO, elution with 0-50% EtOAc/hexane, 30 min) to afford 19 mg (40%) of the title compound as an oil.

Part B. (3aR,9bS)-8-Ethyl-6-phenyl-2,3,3a,4-tetrahydro-1H-pyrrolo[3,4-c]isoquinolin-5(9bH)-one hydrochloride To (3aR,9bS)-tert-Butyl 8-ethyl-5-oxo-6-phenyl-3,3a,4,5-tetrahydro-1H-pyrrolo[3,4-c]isoquinoline-2(9bH)-carboxylate (19 mg, 0.05 mmol) in ether (1 mL) was added 12 N HCl (0.5 mL). The mixture was stirred vigorously for 5 min and then concentrated in vacuo. The residue was purified by prep HPLC and desired fractions were basified with NH$_4$OH, extracted with ethyl acetate, dried (MgSO$_4$) and concentrated. The residual free base was taken up in ether and then there was added 4N HCl (0.05 mL of a solution in dioxane, 0.2 mmol). The mixture was concentrated in vacuo and the solid was triturated with ether and dried in vacuo to afford 7 mg (44%) of the title compound of Example 44 as an off-white solid. $^1$H NMR (CD$_3$OD): δ 7.35-7.22 (m, 5H), 7.14 (s, 1H), 7.08 (s, 1H), 4.12-4.07 (m, 1H), 3.89-3.82 (m, 1H), 3.74-3.69 (m, 1H), 3.45-3.37 (m, 2H), 3.30-3.24 (m, 1H), 2.73 (q, 2H, J=7.6 Hz), 1.27 (t, 3H, J=7.5 Hz). LRMS (ESI): 293.2 (M+H)+.

Example 45

(3aR,9bS)-8-Ethyl-6-(trifluoromethyl)-2,3,3a,4-tetrahydro-1H-pyrrolo[3,4-c]isoquinolin-5(9bH)-one hydrochloride

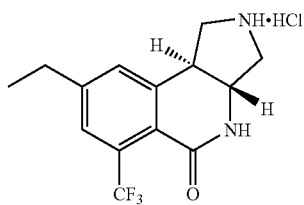

Part A. 4-Chloro-2-(trifluoromethyl)benzoic acid

To a solution of 4-chloro-2-iodobenzotrifluoride (24.4 g, 79.6 mmol) in 400 mL of THF at −78° C. was added n-butyllithium (60 mL of a 1.6 M solution in hexanes, 95.5 mmol) dropwise via an addition funnel over 20 min. The mixture was allowed to stir at −78° C. for 10 min, and then $CO_2$ (g) was allowed to pass through the solution for about 20 min. The solution was allowed to warm to ambient temperature, and then was recooled to 0° C. and quenched carefully with water (gas evolution). Most of the THF was removed and the mixture was diluted with ethyl acetate. The organics were washed with 1N HCl and brine, dried ($MgSO_4$) and concentrated in vacuo to afford 18.1 g of crude carboxylic acid.

Part B. 4-Chloro-N,N-diethyl-2-(trifluoromethyl)benzamide

To a solution of 4-chloro-2-(trifluoromethyl)benzoic acid (18.1 g, 80 mmol) in 500 mL of methylene chloride was added oxalyl chloride (60 mL of a 2.0 M solution in methylene chloride, 120 mmol) followed by N,N-dimethylformamide (0.2 mL). The reaction was allowed to stir at ambient temperature for 18 h. The volatiles were removed in vacuo to afford the crude acid chloride intermediate. The residue was taken up in 500 mL of methylene chloride and then there was added diethylamine (16.5 mL, 160 mmol). The resulting solution was allowed to stir at ambient temperature for 2 h, and then the mixture was concentrated to an oil. The residue was purified (ISCO, 0-30% EtOAc/hexane, 45 min) to afford 11.4 g (51%) of the title compound as a pale yellow oil.

Part C. N,N,4-Triethyl-2-(trifluoromethyl)benzamide

To a solution of 4-chloro-N,N-diethyl-2-(trifluoromethyl) benzamide (5.04 g, 18 mmol) in 100 mL of N,N-dimethylformamide was added potassium carbonate (6.2 g, 45 mmol) and diethylzinc (29.5 mL of a 1.1 M solution in toluene, 32.4 mmol). The mixture was degassed and then there was added POPd (Combiphos) (0.27 g, 0.54 mmol). The resulting solution was heated at 120° C. in a sealed tube for 18 h. The mixture was allowed to cool and was diluted with water and extracted with ethyl acetate. The organics were washed with water and brine, dried ($MgSO_4$) and concnentrated in vacuo. The residue was purified (ISCO, elution with 0-25% EtOAc/ hexane) to afford 3.7 g (75%) of the title compound as an oil. LRMS (ESI): 274.2 (M+H)+.

Part D. (±)-5-Ethyl-3-hydroxy-7-(trifluoromethyl) isobenzofuran-1(3H)-one

To a solution of N,N,4-triethyl-2-(trifluoromethyl)benzamide (3.7 g, 13.6 mmol) and N,N,N'N'-tetramethylethylenediamine (4.1 mL, 27.2 mmol) in 100 mL of anhydrous THF at −78° C. was added sec-butyllithium (19.4 mL of a 1.4 M solution in THF, 27.2 mmol) dropwise over 30 min. The reaction was stirred at −78° C. for 1 h and then there was added DMF (3.0 mL). The reaction was stirred at −78° C. for 30 min and then was quenched with 1N HCl (25 mL). The reaction mixture was concentrated in vacuo and the residue purified (ISCO, elution with 0-30% EtOAc/hexane, 30 min) to afford 2.85 g of an intermediate aldehyde as a solid. The aldehyde was taken up in 6N HCl (80 mL) and stirred at 100° C. for 18 h. The reaction mixture was allowed to cool, was diluted with water and extracted with EtOAc. The organics were washed with brine, dried ($MgSO_4$) and concentrated to an oil. This material was purified (ISCO, elution with 0-30% EtOAC/hexane, 30 min) to afford 1.97 g (59%) of the title compound as an oil. $^1H$ NMR ($CDCl_3$): δ 7.69 (s, 1H), 7.66 (s, 1H), 6.62 (s, 1H), 5.05 (broad s, 1H), 2.87 (q, 2H), 1.33 (t, 3H).

Part E. Ethyl 4-ethyl-2-formyl-6-(trifluoromethyl)benzoate

To a solution of (±)-5-ethyl-3-hydroxy-7-(trifluoromethyl) isobenzofuran-1 (3H)-one (1.97 g, 8.0 mmol) in 20 mL of DMF was added potassium carbonate (4.42 g, 32.0 mmol) followed by iodoethane (1.92 mL, 24.0 mmol). The resulting mixture was allowed to stir at ambient temperature for 1 h. The reaction was diluted with 1N HCl to pH ~4 and extracted with EtOAc. The organics were washed with 1N HCl, sat'd aq $NaHCO_3$ and brine, dried ($MgSO_4$), and concentrated in vacuo. The residue was purified by flash chromatography (elution with 10% EtOAc/hexane) to afford 1.8 g (83%) of the title compound. $^1H$ NMR ($CDCl_3$): δ 10.05 (s, 1H), 7.92 (s, 1H), 7.73 (s, 1H), 4.47 (q, 2H), 2.80 (q, 2H), 1.38 (t, 3H), 1.29 (t, 3H).

Part F. (E)-Ethyl 4-ethyl-2-(3-methoxy-3-oxoprop-1-enyl)-6-(trifluoromethyl)benzoate To a solution of trimethyl phosphonoacetate (1.60 mL, 9.90 mmol) in 100 mL of THF was added sodium hydride (0.24 g of 60% dispersion in mineral oil, 9.90 mmol) portionwise. The mixture was stirred at ambient temperature for 30 min and then ethyl 4-ethyl-2-formyl-6-(trifluoromethyl)benzoate (1.81 g, 6.60 mmol) as a solution in THF. The reaction mixture was allowed to stir at ambient temperature for 30 min and then was diluted with water. The mixture was extracted with ethyl acetate, washed with brine, dried ($MgSO_4$) and concentrated in vacuo. The residue was purified by flash chromatography (elution with 15% EtOAc/hexane) to afford 2.1 g (96%) of the title compound as an off-white solid. $^1H$ NMR ($CDCl_3$): δ 7.72 (d, 1H, J=15.9 Hz), 7.62 (s, 1H), 7.53 (s, 1H), 6.44 (d, 1H, J=15.9 Hz), 4.45 (q, 2H, J=7.2 Hz), 3.81 (s, 3H), 2.75 (q, 2H, J=7.6 Hz), 1.40 (t, 3H, J=7.2 Hz), 1.28 (t, 3H, J=7.4 Hz).

Part G. (±)-trans-tert-Butyl 8-ethyl-5-oxo-6-(trifluoromethyl)-3,3a,4,5-tetrahydro-1H-pyrrolo[3,4-c] isoquinoline-2(9bH)-carboxylate Following the procedures described in Example 1, Parts E-H, (E)-ethyl 4-ethyl-2-(3-methoxy-3-oxoprop-1-enyl)-6-

(trifluoromethyl)benzoate was converted into the title compound as a racemic mixture. LRMS (ESI): 385.3 (M+H)+.

Part H. Chiral separation of (3aR,9bS)-tert-butyl 8-ethyl-5-oxo-6-(trifluoromethyl)-3,3a,4,5-tetrahydro-1H-pyrrolo[3,4-c]isoquinoline-2(9bH)-carboxylate and (3aS,9bR)-tert-butyl 8-ethyl-5-oxo-6-(trifluoromethyl)-3,3a,4,5-tetrahydro-1H-pyrrolo[3,4-c]isoquinoline-2(9bH)-carboxylate A 1.1 g sample of racemic (±)-trans-tert-butyl 8-ethyl-5-oxo-6-(trifluoromethyl)-3,3a,4,5-tetrahydro-1H-pyrrolo[3,4-c]isoquinoline-2(9bH)-carboxylate was separated into the two enantiomers by chiral HPLC (Chiralcel OD column, elution with 10% isopropanol/heptane) to afford 0.31 g of (3aR,9bS)-tert-butyl 8-ethyl-5-oxo-6-(trifluoromethyl)-3,3a,4,5-tetrahydro-1H-pyrrolo[3,4-c]isoquinoline-2(9bH)-carboxylate as the first eluting compound (>99% ee on chiralcel OD, 4.6×250, 30% isopropanol/heptane, retention time 6.3 min) and 0.30 g of (3aS,9bR)-tert-butyl 8-ethyl-5-oxo-6-(trifluoromethyl)-3,3a,4,5-tetrahydro-1H-pyrrolo[3,4-c]isoquinoline-2(9bH)-carboxylate as the second eluting compound (>99% ee on chiralcel OD, 4.6×250, 30% isopropanol/heptane, retention time 9.6 min).

Part I. (3aR,9bS)-8-Ethyl-6-(trifluoromethyl)-2,3,3a,4-tetrahydro-1H-pyrrolo[3,4-c]isoquinolin-5(9bH)-one hydrochloride To a solution of (3aR,9bS)-tert-butyl 8-ethyl-5-oxo-6-(trifluoromethyl)-3,3a,4,5-tetrahydro-1H-pyrrolo[3,4-c]isoquinoline-2(9bH)-carboxylate, the first eluting peak from Part H above, (55 mg, 0.14 mmol) in 2 mL of diethyl ether was added 1 mL of 12 N HCl. The resulting mixture was stirred vigorously for 5 min at ambient temperature and then was concentrated and dried in vacuo. The resulting white solid was triturated twice with diethyl ether and dried in vacuo to afford 40 mg (88%) of the title compound of Example 45 as a white solid. $^1$H NMR (DMSO-D$_6$): δ 9.83 (broad s, 1H), 9.64 (broad s, 1H), 8.89 (s, 1H), 7.66 (s, 1H), 7.43 (s, 1H), 3.95-3.90 (m, 1H), 3.63-3.58 (m, 1H), 3.51-3.45 (m, 1H), 3.34-3.28 (m, 1H), 3.21-3.10 (m, 2H), 2.73 (q, 2H, J=7.7 Hz), 1.21 (t, 3H, J=7.7 Hz). LRMS (ESI): 285.2 (M+H)+.

Example 46

(3aS,9bR)-8-Ethyl-6-(trifluoromethyl)-2,3,3a,4-tetrahydro-1H-pyrrolo[3,4-c]isoquinolin-5(9bH)-one hydrochloride

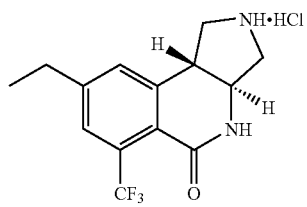

To a solution of (3aS,9bR)-tert-butyl 8-ethyl-5-oxo-6-(trifluoromethyl)-3,3a,4,5-tetrahydro-1H-pyrrolo[3,4-c]isoquinoline-2(9bH)-carboxylate, the second eluting peak from Example 45, Part H (63 mg, 0.16 mmol) in 2 mL of diethyl ether was added 1 mL of 12 N HCl. The resulting mixture was stirred vigorously for 5 min at ambient temperature and then was concentrated and dried in vacuo. The resulting white solid was triturated twice with diethyl ether and dried in vacuo to afford 45 mg (86%) of the title compound of Example 46 as a white solid. $^1$H NMR (DMSO-D$_6$): δ 9.83 (broad s, 1H), 9.64 (broad s, 1H), 8.89 (s, 1H), 7.66 (s, 1H), 7.43 (s, 1H), 3.95-3.90 (m, 1H), 3.63-3.58 (m, 1H), 3.51-3.45 (m, 1H), 3.34-3.28 (m, 1H), 3.21-3.10 (m, 2H), 2.73 (q, 2H, J=7.7 Hz), 1.21 (t, 3H, J=7.7 Hz). LRMS (ESI): 285.2 (M+H)+.

Example 47

(3aR,9bS)-8-Ethyl-6-fluoro-2,3,3a,4-tetrahydro-1H-pyrrolo[3,4-c]isoquinolin-5(9bH)-one hydrochloride

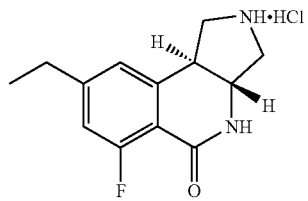

Part A. 4-Bromo-N,N-diethyl-2-fluorobenzamide

Following the procedure described in Example 45, Part B, 4-bromo-2-fluorobenzoic acid was converted into the title compound as an oil. LRMS (ESI): 274.1/276.1 (M+H)+.

Part B. N,N,4-Triethyl-2-fluorobenzamide

To a solution of 4-bromo-N,N-diethyl-2-fluorobenzamide (5.12 g, 18.9 mmol) in 100 mL of DMF was added potassium carbonate (6.45 g, 46.7 mmol) and diethylzinc (25.5 mL of a 1.1 M solution in toluene, 28.02 mmol). The solution was degassed with a stream of argon and then there was added [1,1'-bis(diphenylphosphino)ferrocene]dichloropalladium (II) complex with dichloromethane (1:1) (305 mg, 0.37 mmol). The reaction mixture was allowed to stir at 80° C. for 3 h. The reaction mixture was allowed to cool and was diluted with ethyl acetate. The organics were washed with water and brine, dried (MgSO$_4$) and concentrated. The residue was purified (ISCO, elution with 0-40% EtOAc/hexane, 40 min) to afford 3.70 g (88%) of the title compound as a colorless oil. LRMS (ESI): 224.2 (M+H)+.

Part C. (±)-trans-tert-Butyl 8-ethyl-6-fluoro-5-oxo-3,3a,4,5-tetrahydro-1H-pyrrolo[3,4-c]isoquinoline-2 (9bH)-carboxylate Following the procedures described in Example 45, Parts D-G, N,N,4-triethyl-2-fluorobenzamide was converted into the title compound as a racemic mixture. LRMS (ESI): 335.3 (M+H)+.

Part D. Chiral separation of (3aR,9bS)-tert-butyl 8-ethyl-6-fluoro-5-oxo-3,3a,4,5-tetrahydro-1H-pyrrolo[3,4-c]isoquinoline-2(9bH)-carboxylate and (3 as,9bR)-tert-butyl 8-ethyl-6-fluoro-5-oxo-3,3a,4,5-tetrahydro-1H-pyrrolo[3,4-c]isoquinoline-2(9bH)-carboxylate A 2.0 g sample of racemic (±)-trans-tert-butyl 8-ethyl-6-fluoro-5-oxo-3,3a,4,5-tetrahydro-1H-pyrrolo[3,4-c]isoquinoline-2(9bH)-carboxylate was separated into the two enantiomers by chiral HPLC (Chiralcel OD column, elution with 15-60% isopropanol/heptane) to afford 0.72 g of (3aR, 9bS)-tert-butyl 8-ethyl-6-fluoro-5-oxo-3,3a,4,5-tetrahydro-1H-pyrrolo[3,4-c]isoquinoline-2(9bH)-carboxylate as the first eluting compound (>99% ee on chiralcel OD, 4.6×250, 30% isopropanol/heptane, retention time 9.9 min) and 0.70 g of (3aS,9bR)-tert-butyl 8-ethyl-6-fluoro-5-oxo-3,3a,4,5-tetrahydro-1H-pyrrolo[3,4-c]isoquinoline-2(9bH)-carboxylate as the second eluting compound (>99% ee on chiralcel OD, 4.6×250, 30% isopropanol/heptane, retention time 15.9 min).

Part E. (3aR,9bS)-8-Ethyl-6-fluoro-2,3,3a,4-tetrahydro-1H-pyrrolo[3,4-c]isoquinolin-5(9bH)-one hydrochloride To a solution of (3aR,9bS)-tert-butyl 8-ethyl-6-fluoro-5-oxo-3,3a,4,5-tetrahydro-1H-pyrrolo[3,4-c]isoquinoline-2(9bH)-carboxylate, the first eluting peak from Part D above, (80 mg, 0.24 mmol) in 2 mL of diethyl ether was added 1 mL of 12 N HCl. The resulting mixture was stirred vigorously for 5 min at ambient temperature and then was concentrated and dried in vacuo. The resulting white solid was triturated twice with diethyl ether and dried in vacuo to afford 55 mg (84%) of the title compound of Example 47 as a white solid. $^1$H NMR (DMSO-D$_6$): δ 10.12 (broad s, 1H), 10.00 (broad s, 1H), 8.64 (s, 1H), 7.09 (d, 1H), 6.96 (s, 1H), 3.88-3.82 (m, 1H), 3.61-3.55 (m, 1H), 3.48-3.43 (m, 1H), 3.26-3.20 (m, 1H), 3.18-3.12 (m, 1H), 3.09-3.02 (m, 1H), 2.63 (q, 2H, J=7.7 Hz), 1.18 (t, 3H, J=7.7 Hz). LRMS (ESI): 235.2 (M+H)+.

Example 48

(3aS,9bR)-8-Ethyl-6-fluoro-2,3,3a,4-tetrahydro-1H-pyrrolo[3,4-c]isoquinolin-5(9bH)-one hydrochloride

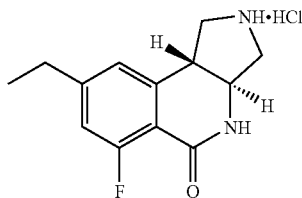

To a solution of (3aS,9bR)-tert-butyl 8-ethyl-6-fluoro-5-oxo-3,3a,4,5-tetrahydro-1H-pyrrolo[3,4-c]isoquinoline-2(9bH)-carboxylate, the second eluting peak from Example 47, Part D, (60 mg, 0.18 mmol) in 2 mL of diethyl ether was added 1 mL of 12 N HCl. The resulting mixture was stirred vigorously for 5 min at ambient temperature and then was concentrated and dried in vacuo. The resulting white solid was triturated twice with diethyl ether and dried in vacuo to afford 35 mg (71%) of the title compound of Example 48 as a white solid. $^1$H NMR (DMSO-D$_6$): δ 10.12 (broad s, 1H), 10.00 (broad s, 1H), 8.64 (s, 1H), 7.09 (d, 1H), 6.96 (s, 1H), 3.88-3.82 (m, 1H), 3.61-3.55 (m, 1H), 3.48-3.43 (m, 1H), 3.26-3.20 (m, 1H), 3.18-3.12 (m, 1H), 3.09-3.02 (m, 1H), 2.63 (q, 2H, J=7.7 Hz), 1.18 (t, 3H, J=7.7 Hz). LRMS (ESI): 235.2 (M+H)+.

Example 49

(3aR,9bS)-8-Ethyl-4-methyl-6-(trifluoromethyl)-2,3,3a,4-tetrahydro-1H-pyrrolo[3,4-c]isoquinolin-5(9bH)-one hydrochloride

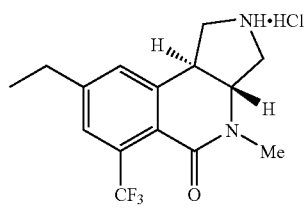

Following the procedures described in Example 15, Part A and Example 45, Part I, (3aR,9bS)-tert-butyl 8-ethyl-5-oxo-6-(trifluoromethyl)-3,3a,4,5-tetrahydro-1H-pyrrolo[3,4-c]isoquinoline-2(9bH)-carboxylate, the first eluting compound from Example 45, Part H, was converted into the title compound of Example 49 as a white solid. $^1$H NMR (CD$_3$OD): δ 7.70 (s, 1H), 7.33 (s, 1H), 4.13 (dd, 1H, J=7.4, 11.3 Hz), 3.97-3.90 (m, 1H), 3.89-3.84 (m, 1H), 3.64-3.58 (m, 1H), 3.56-3.50 (m, 1H), 3.48-3.43 (m, 1H), 3.13 (s, 3H), 2.79 (q, 2H, J=7.7 Hz), 1.28 (t, 3H, J=7.7 Hz). LRMS (ESI): 299.2 (M+H)+.

Example 50

(3aR,9bS)-8-Ethyl-6-fluoro-4-methyl-2,3,3a,4-tetrahydro-1H-pyrrolo[3,4-c]isoquinolin-5(9bH)-one hydrochloride

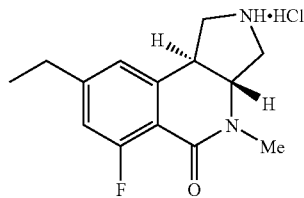

Following the procedures described in Example 15, Part A and Example 45, Part I, (3aR,9bS)-tert-butyl 8-ethyl-6-fluoro-5-oxo-3,3a,4,5-tetrahydro-1H-pyrrolo[3,4-c]isoquinoline-2(9bH)-carboxylate, the first eluting compound from Example 47, Part D, was converted into the title compound of Example 50 as an off-white solid. $^1$H NMR (DMSO-D$_6$): δ 9.87 (broad s, 2H), 7.10 (d, 1H), 6.93 (s, 1H), 3.95-3.88 (m, 1H), 3.75-3.65 (overlapping m, 2H), 3.47-3.40 (m, 1H), 3.32-3.21 (overlapping m, 2H), 2.96 (s, 3H), 2.63 (q, 2H, J=7.7 Hz), 1.18 (t, 3H, J=7.5 Hz). LRMS (ESI): 249.1 (M+H)+.

Example 51

(3aR,9bS)-8-Ethyl-6-methoxy-2,3,3a,4-tetrahydro-1H-pyrrolo[3,4-c]isoquinolin-5(9bH)-one hydrochloride

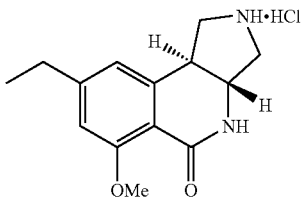

Part A. (±)-trans-tert-Butyl 8-ethyl-6-methoxy-5-oxo-3,3a,4,5-tetrahydro-1H-pyrrolo[3,4-c]isoquinoline-2(9bH)-carboxylate Following the procedures described in Example 45, Parts D-G, N,N,4-triethyl-2-methoxybenzamide was converted into the title compound as a racemic mixture. $^1$H NMR (CDCl$_3$) (some signals doubled due to carbamate rotational isomers): δ 6.79 (s, 1H), 6.58 and 6.41 (s, 1H), 6.48 (d, 1H, J=7.1 Hz), 4.08-4.02 and 4.00-3.95 (m, 1H), 3.94 (s, 3H), 3.92-3.88 and 3.86-3.81 (m, 1H), 3.63-3.55 (m, 1H), 3.40-3.32 (m, 1H), 3.26 (t, 1H), 3.21-3.14 (m, 1H), 6.44 (d, 1H, J=15.9 Hz), 4.45 (q, 2H, J=7.2 Hz), 3.81 (s, 3H), 2.67 (q, 2H), 1.51 and 1.48 (s, 9H), 1.27 and 1.25 (t, 3H). LRMS (ESI): 347.2 (M+H)+.

Part B. Chiral separation of (3aR,9bS)-tert-butyl 8-ethyl-6-methoxy-5-oxo-3,3a,4,5-tetrahydro-1H-pyrrolo[3,4-c]isoquinoline-2(9bH)-carboxylate and (3aS,9bR)-tert-butyl 8-ethyl-6-methoxy-5-oxo-3,3a,4,5-tetrahydro-1H-pyrrolo[3,4-c]isoquinoline-2(9bH)-carboxylate A 4.1 g sample of racemic (±)-trans-tert-butyl 8-ethyl-6-methoxy-5-oxo-3,3a,4,5-tetrahydro-1H-pyrrolo[3,4-c]isoquinoline-2(9bH)-carboxylate was separated into the two enantiomers by chiral HPLC (Chiralcel OD column, elution with 15% isopropanol/heptane) to afford 1.23 g of (3aR,9bS)-tert-butyl 8-ethyl-6-methoxy-5-oxo-3,3a,4,5-tetrahydro-1H-pyrrolo[3,4-c]isoquinoline-2(9bH)-carboxylate as the first eluting compound (>99% ee on chiralcel OD, 4.6×250, 30% isopropanol/heptane, retention time 10.4 min) and 1.05 g of (3aS,9bR)-tert-butyl 8-ethyl-6-methoxy-5-oxo-3,3a,4,5-tetrahydro-1H-pyrrolo[3,4-c]isoquinoline-2(9bH)-carboxylate as the second eluting compound (>99% ee on chiralcel OD, 4.6×250, 30% isopropanol/heptane, retention time 14.0 min).

Part C. (3aR,9bS)-8-Ethyl-6-methoxy-2,3,3a,4-tetrahydro-1H-pyrrolo[3,4-c]isoquinolin-5(9bH)-one hydrochloride Following the procedure described in Example 45, Part I, (3aR,9bS)-tert-butyl 8-ethyl-6-methoxy-5-oxo-3,3a,4,5-tetrahydro-1H-pyrrolo[3,4-c]isoquinoline-2(9bH)-carboxylate, the first eluting compound from Part B above, was converted into the title compound of Example 51 as a white solid. $^1$H NMR (CD$_3$OD): δ 6.98 (s, 1H), 6.64 (s, 1H), 4.05-4.00 (m, 1H), 3.87 (s, 3H), 3.72-3.65 (m, 2H), 3.38-3.32 (m, 2H), 3.28-3.23 (m, 1H), 2.69 (q, 2H, J=7.7 Hz), 1.26 (t, 3H, J=7.5 Hz). LRMS (ESI): 247.2 (M+H)+.

Example 52

(3aS,9bR)-8-Ethyl-6-methoxy-2,3,3a,4-tetrahydro-1H-pyrrolo[3,4-c]isoquinolin-5(9bH)-one hydrochloride

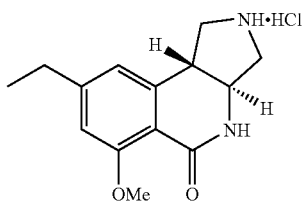

Following the procedure described in Example 45, Part I, (3aS,9bR)-tert-butyl 8-ethyl-6-methoxy-5-oxo-3,3a,4,5-tetrahydro-1H-pyrrolo[3,4-c]isoquinoline-2(9bH)-carboxylate, the second eluting compound from Example 51, Part B, was converted into the title compound of Example 52 as a white solid. $^1$H NMR (CD$_3$OD): δ 6.98 (s, 1H), 6.64 (s, 1H), 4.05-4.00 (m, 1H), 3.87 (s, 3H), 3.72-3.65 (m, 2H), 3.38-3.32 (m, 2H), 3.28-3.23 (m, 1H), 2.69 (q, 2H, J=7.7 Hz), 1.26 (t, 3H, J=7.5 Hz). LRMS (ESI): 247.3 (M+H)+.

Example 53

(3aR,9bS)-8-Ethyl-6-methoxy-4-methyl-2,3,3a,4-tetrahydro-1H-pyrrolo[3,4-c]isoquinolin-5(9bH)-one hydrochloride

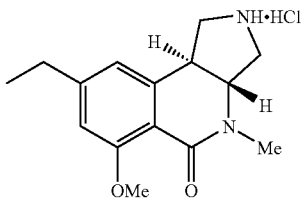

Following the procedures described in Example 15, Part A and Example 45, Part I, (3aR,9bS)-tert-butyl 8-ethyl-6-methoxy-5-oxo-3,3a,4,5-tetrahydro-1H-pyrrolo[3,4-c]isoquinoline-2(9bH)-carboxylate, the first eluting compound from Example 51, Part B, was converted into the title compound of Example 53 as an off-white solid. $^1$H NMR (DMSO-D$_6$): δ 9.72 (broad s, 2H), 6.92 (s, 1H), 6.61 (s, 1H), 3.91-3.86 (m, 1H), 3.77 (s, 3H), 3.69-3.61 (m, 2H), 3.38-3.25 (m, 2H), 3.25-3.18 (m, 2H), 2.93 (s, 3H), 2.62 (q, 2H, J=7.6 Hz), 1.20 (t, 3H, J=7.5 Hz). LRMS (ESI): 261.2 (M+H)+.

Example 54

(3aR,9bS)-6-Chloro-9-methyl-2,3,3a,4-tetrahydro-1H-pyrrolo[3,4-c]isoquinolin-5(9bH)-one hydrochloride

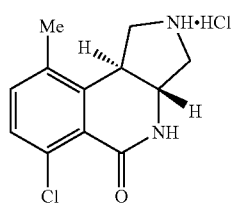

Part A. (±)-trans-tert-Butyl 6-chloro-9-methyl-5-oxo-3,3a,4,5-tetrahydro-1H-pyrrolo[3,4-c]isoquinoline-2(9bH)-carboxylate Following the procedures described in Example 45, Parts D-G, 2-chloro-N,N-diethyl-5-methylbenzamide was converted into the title compound as a racemic mixture. $^1$H NMR (CDCl$_3$) (some signals doubled due to carbamate rotational isomers): δ 7.32 (d, 1H, J=8.2 Hz), 7.17 (d, 1H, J=8.2 Hz), 6.99 and 6.84 (s, 1H), 4.35-4.30 and 4.22-4.18 (m, 1H), 4.05-4.00 and 3.72-3.65 (m, 1H), 3.92-3.87 and 3.85-3.80 (m, 1H), 3.48-3.42 (m, 1H), 3.32-3.22 (m, 2H), 2.33 (s, 3H), 1.50 and 1.49 (s, 9H).

Part B. Chiral separation of (3aR,9bS)-tert-Butyl 6-chloro-9-methyl-5-oxo-3,3a,4,5-tetrahydro-1H-pyrrolo[3,4-c]isoquinoline-2(9bH)-carboxylate and (3aS,9bR)-tert-Butyl 6-chloro-9-methyl-5-oxo-3,3a, 4,5-tetrahydro-1H-pyrrolo[3,4-c]isoquinoline-2(9bH)-carboxylate A 90 mg sample of racemic (±)-trans-tert-butyl 6-chloro-9-methyl-5-oxo-3,3a,4,5-tetrahydro-1H-pyrrolo[3,4-c]isoquinoline-2(9bH)-carboxylate was separated into the two enantiomers by chiral HPLC (Chiralcel AD column, elution with 15% isopropanol/heptane) to afford 29 mg of (3aR,9bS)-tert-butyl 6-chloro-9-methyl-5-oxo-3,3a,4,5-tetrahydro-1H-pyrrolo[3,4-c]isoquinoline-2(9bH)-carboxylate as the second eluting compound (>99% ee on chiralcel OD, 4.6×250, 30% isopropanol/heptane, retention time 12.6 min) and 31 mg of (3aS,9bR)-tert-butyl 6-chloro-9-methyl-5-oxo-3,3a,4,5-tetrahydro-1H-pyrrolo[3,4-c]isoquinoline-2(9bH)-carboxylate as the first eluting compound (>99% ee on chiralcel OD, 4.6×250, 30% isopropanol/heptane, retention time 10.0 min).

Part C. (3aR,9bS)-6-Chloro-9-methyl-2,3,3a,4-tetrahydro-1H-pyrrolo[3,4-c]isoquinolin-5(9bH)-one hydrochloride Following the procedure described in Example 45, Part I, (3aR,9bS)-tert-butyl 6-chloro-9-methyl-5-oxo-3,3a,4,5-tetrahydro-1H-pyrrolo[3,4-c]isoquinoline-2(9bH)-carboxylate, the second eluting compound from Part B above, was converted into the title compound of Example 54 as a white solid. $^1$H NMR (DMSO-D$_6$): δ 9.77 (broad s, 1H), 9.63 (broad s, 1H), 8.89 (s, 1H), 7.37 (d, 1H, J=8.2 Hz), 7.32 (d, 1H, J=8.2 Hz), 4.02-3.96 (m, 1H), 3.65-3.60 (m, 1H), 3.47-3.41 (m, 1H), 3.35-3.27 (m, 2H), 3.10-3.02 (m, 1H), 2.26 (s, 3H). LRMS (ESI): 237.2/239.2 (M+H)+.

Example 55

(3aS,9bR)-6-Chloro-9-methyl-2,3,3a,4-tetrahydro-1H-pyrrolo[3,4-c]isoquinolin-5(9bH)-one hydrochloride

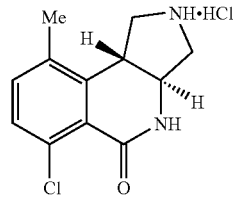

Following the procedure described in Example 45, Part I, (3aS,9bR)-tert-butyl 6-chloro-9-methyl-5-oxo-3,3a,4,5-tetrahydro-1H-pyrrolo[3,4-c]isoquinoline-2(9bH)-carboxylate, the first eluting compound from Example 54, Part B, was converted into the title compound of Example 55 as a white solid. $^1$H NMR (DMSO-D$_6$): δ 9.77 (broad s, 1H), 9.63 (broad s, 1H), 8.89 (s, 1H), 7.37 (d, 1H, J=8.2 Hz), 7.32 (d, 1H, J=8.2 Hz), 4.02-3.96 (m, 1H), 3.65-3.60 (m, 1H), 3.47-3.41 (m, 1H), 3.35-3.27 (m, 2H), 3.10-3.02 (m, 1H), 2.26 (s, 3H). LRMS (ESI): 237.2/239.2 (M+H)+.

Example 56

(3aR,9bS)-6-Chloro-9-ethyl-2,3,3a,4-tetrahydro-1H-pyrrolo[3,4-c]isoquinolin-5(9bH)-one hydrochloride

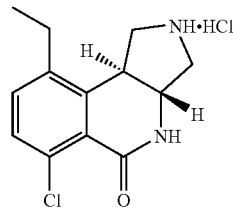

Part A. (±)-trans-tert-Butyl 6-chloro-9-ethyl-5-oxo-3,3a,4,5-tetrahydro-1H-pyrrolo[3,4-c]isoquinoline-2(9bH)-carboxylate Following the procedures described in Example 45, Parts D-G, 2-chloro-N,N,5-triethylbenzamide was converted into the title compound as a racemic mixture. LRMS (ESI): 351.1/353.1 (M+H)+.

Part B. Chiral separation of (3aR,9bS)-tert-Butyl 6-chloro-9-ethyl-5-oxo-3,3a,4,5-tetrahydro-1H-pyrrolo[3,4-c]isoquinoline-2(9bH)-carboxylate and (3aS,9bR)-tert-Butyl 6-chloro-9-ethyl-5-oxo-3,3a,4, 5-tetrahydro-1H-pyrrolo[3,4-c]isoquinoline-2(9bH)-carboxylate A 910 mg sample of racemic (±)-trans-tert-butyl 6-chloro-9-ethyl-5-oxo-3,3a,4,5-tetrahydro-1H-pyrrolo[3,4-c]isoquinoline-2(9bH)-carboxylate was separated into the two enantiomers by chiral HPLC (Chiralcel OD column, elution with 20% isopropanol/heptane) to afford 200 mg of (3aR,9bS)-tert-butyl 6-chloro-9-ethyl-5-oxo-3,3a,4,5-tetrahydro-1H-pyrrolo[3,4-c]isoquinoline-2(9bH)-carboxylate as the first eluting compound (>99% ee on chiralcel OD, 4.6×250, 50% isopropanol/heptane, retention time 6.1 min) and 220 mg of (3aS,9bR)-tert-butyl 6-chloro-9-ethyl-5-oxo-3,3a,4,5-tetrahydro-1H-pyrrolo[3,4-c]isoquinoline-2(9bH)-carboxylate as the second eluting compound (>99% ee on chiralcel OD, 4.6×250, 50% isopropanol/heptane, retention time 13.7 min).

Part C. (3aR,9bS)-6-Chloro-9-ethyl-2,3,3a,4-tetrahydro-1H-pyrrolo[3,4-c]isoquinolin-5(9bH)-one hydrochloride Following the procedure described in Example 45, Part I, (3aR,9bS)-tert-butyl 6-chloro-9-ethyl-5-oxo-3,3a,4,5-tetrahydro-1H-pyrrolo[3,4-c]isoquinoline-2(9bH)-carboxylate, the first eluting compound from Part B above, was converted into the title compound of Example 56 as a white solid. $^1$H NMR (DMSO-D$_6$): δ 9.77 (broad s, 1H), 9.61 (broad s, 1H), 8.84 (s, 1H), 7.32 (d, 1H, J=8.2 Hz), 7.27 (d, 1H, J=8.2 Hz), 3.93-3.86 (m, 1H), 3.60-3.53 (m, 1H), 3.33-3.20 (m, 3H), 3.04-2.96 (m, 1H), 2.47 (q, 2H, J=7.5 Hz), 1.05 (t, 3H, J=7.5 Hz). LRMS (ESI): 251.1/253.1 (M+H)+.

Example 57

(3aS,9bR)-6-Chloro-9-ethyl-2,3,3a,4-tetrahydro-1H-pyrrolo[3,4-c]isoquinolin-5(9bH)-one hydrochloride

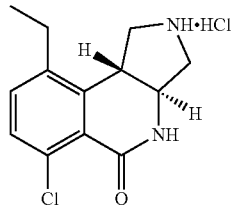

Following the procedure described in Example 45, Part I, (3aS,9bR)-tert-butyl 6-chloro-9-ethyl-5-oxo-3,3a,4,5-tetrahydro-1H-pyrrolo[3,4-c]isoquinoline-2(9bH)-carboxylate, the second eluting compound from Example 56, Part B, was converted into the title compound of Example 57 as a white solid. $^1$H NMR (DMSO-D$_6$): δ 9.77 (broad s, 1H), 9.61 (broad s, 1H), 8.84 (s, 1H), 7.32 (d, 1H, J=8.2 Hz), 7.27 (d, 1H, J=8.2 Hz), 3.93-3.86 (m, 1H), 3.60-3.53 (m, 1H), 3.33-3.20 (m, 3H), 3.04-2.96 (m, 1H), 2.47 (q, 2H, J=7.5 Hz), 1.05 (t, 3H, J=7.5 Hz). LRMS (ESI): 251.1/253.1 (M+H)+.

Example 58

(3aR,9bS)-6-Chloro-9-ethyl-4-methyl-2,3,3a,4-tetrahydro-1H-pyrrolo[3,4-c]isoquinolin-5(9bH)-one hydrochloride

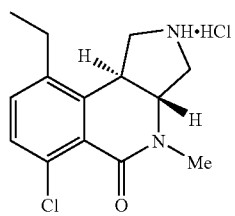

Following the procedures described in Example 15, Part A and Example 45, Part I, (3aR,9bS)-tert-butyl 6-chloro-9-ethyl-5-oxo-3,3a,4,5-tetrahydro-1H-pyrrolo[3,4-c]isoquinoline-2(9bH)-carboxylate, the first eluting compound from Example 56, Part B, was converted into the title compound of Example 58 as an pale yellow solid. $^1$H NMR (DMSO-D$_6$): δ 9.84 (broad s, 1H), 9.79 (broad s, 1H), 7.33 (d, 1H, J=8.2 Hz), 7.26 (d, 1H, J=8.2 Hz), 3.98-3.92 (m, 1H), 3.78-3.71 (m, 1H), 3.62-3.48 (m, 2H), 3.35-3.20 (m, 2H), 2.93 (s, 3H), 2.47 (q, 2H, J=7.4 Hz), 1.05 (t, 3H, J=7.5 Hz). LRMS (ESI): 265.1/267.1 (M+H)+.

Example 59

(3aR,9bS)-6,7-Dichloro-2,3,3a,4-tetrahydro-1H-pyrrolo[3,4-c]isoquinolin-5(9bH)-one hydrochloride

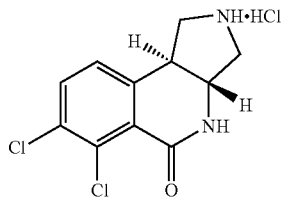

Part A. (±)-trans-tert-Butyl 6,7-dichloro-5-oxo-3,3a,4,5-tetrahydro-1H-pyrrolo[3,4-c]isoquinoline-2(9bH)-carboxylate Following the procedures described in Example 45, Parts D-G, 2,3-dichloro-N,N-diethylbenzamide was converted into the title compound as a racemic mixture. LRMS (ESI): 357.1/359.1 (M+H)+.

Part B. Chiral separation of (3aR,9bS)-tert-Butyl 6,7-dichloro-5-oxo-3,3a,4,5-tetrahydro-1H-pyrrolo[3,4-c]isoquinoline-2(9bH)-carboxylate and (3aS,9bR)-tert-Butyl 6,7-dichloro-5-oxo-3,3a,4,5-tetrahydro-1H-pyrrolo[3,4-c]isoquinoline-2(9bH)-carboxylate A 945 mg sample of racemic (±)-trans-tert-butyl 6,7-dichloro-5-oxo-3,3a,4,5-tetrahydro-1H-pyrrolo[3,4-c]isoquinoline-2(9bH)-carboxylate was separated into the two enantiomers by chiral HPLC (Chiralcel OD column, elution with 30-90% isopropanol/heptane) to afford 206 mg of (3aR,9bS)-tert-butyl 6,7-dichloro-5-oxo-3,3a,4,5-tetrahydro-1H-pyrrolo[3,4-c]isoquinoline-2(9bH)-carboxylate as the first eluting compound (>99% ee on chiralcel OD, 4.6×250, 50% isopropanol/heptane, retention time 9.7 min) and 212 mg of (3aS,9bR)-tert-butyl 6,7-dichloro-5-oxo-3,3a,4,5-tetrahydro-1H-pyrrolo[3,4-c]isoquinoline-2(9bH)-carboxylate as the second eluting compound (>99% ee on chiralcel OD, 4.6×250, 50% isopropanol/heptane, retention time 15.3 min).

Part C. (3aR,9bS)-6,7-Dichloro-2,3,3a,4-tetrahydro-1H-pyrrolo[3,4-c]isoquinolin-5(9bH)-one hydrochloride Following the procedure described in Example 45, Part I, (3aR,9bS)-tert-butyl 6,7-dichloro-5-oxo-3,3a,4,5-tetrahydro-1H-pyrrolo[3,4-c]isoquinoline-2(9bH)-carboxylate, the first eluting compound from Part B above, was converted into the title compound of Example 59 as a white solid. $^1$H NMR (DMSO-D$_6$): δ 10.19 (broad s, 1H), 9.95 (broad s, 1H), 9.26 (s, 1H), 8.08 (d, 1H, J=8.2 Hz), 7.53 (d, 1H, J=8.2 Hz), 4.20-4.12 (m, 1H), 3.90-3.70 (m, 2H), 3.57-3.47 (m, 1H), 3.43-3.31 (m, 2H). LRMS (ESI): 257.0/259.0 (M+H)+.

Example 60

(3aS,9bR)-6,7-Dichloro-2,3,3a,4-tetrahydro-1H-pyrrolo[3,4-c]isoquinolin-5(9bH)-one hydrochloride

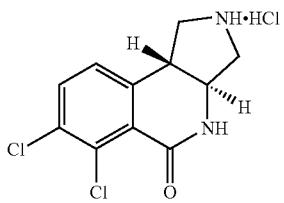

Following the procedure described in Example 45, Part I, (3aS,9bR)-tert-butyl 6,7-dichloro-5-oxo-3,3a,4,5-tetrahydro-1H-pyrrolo[3,4-c]isoquinoline-2(9bH)-carboxylate, the second eluting compound from Example 59, Part B, was converted into the title compound of Example 60 as a white solid. $^1$H NMR (DMSO-D$_6$): δ 10.19 (broad s, 1H), 9.95 (broad s, 1H), 9.26 (s, 1H), 8.08 (d, 1H, J=8.2 Hz), 7.53 (d, 1H, J=8.2 Hz), 4.20-4.12 (m, 1H), 3.90-3.70 (m, 2H), 3.57-3.47 (m, 1H), 3.43-3.31 (m, 2H). LRMS (ESI): 257.0/259.0 (M+H)+.

Example 61

(3aR,9bS)-6,7-Dichloro-4-methyl-2,3,3a,4-tetrahydro-1H-pyrrolo[3,4-c]isoquinolin-5(9bH)-one hydrochloride

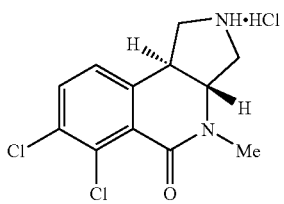

Following the procedures described in Example 15, Part A and Example 45, Part I, (3aR,9bS)-tert-butyl 6,7-dichloro-5-oxo-3,3a,4,5-tetrahydro-1H-pyrrolo[3,4-c]isoquinoline-2(9bH)-carboxylate, the first eluting compound from Example 59, Part B, was converted into the title compound of Example 61 as an pale yellow solid. $^1$H NMR (DMSO-D$_6$): δ 10.00 (broad s, 1H), 9.87 (broad s, 1H), 7.82 (d, 1H, J=8.2 Hz), 7.26 (d, 1H, J=8.2 Hz), 3.96-3.90 (m, 1H), 3.85-3.78 (m, 1H), 3.72-3.67 (m, 1H), 3.48-3.41 (m, 1H), 3.38-3.32 (m, 1H), 3.27-3.20 (m, 1H), 3.02 (s, 3H). LRMS (ESI): 271.1/273.1 (M+H)+.

Example 62

(3aR,9bS)-6-Chloro-8-ethyl-2-methyl-2,3,3a,4-tetrahydro-1H-pyrrolo[3,4-c]isoquinolin-5(9bH)-one hydrochloride

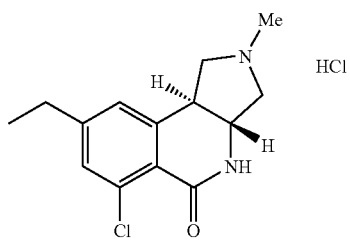

To a solution of (3aR,9bS)-6-chloro-8-ethyl-2,3,3a,4-tetrahydro-1H-pyrrolo[3,4-c]isoquinolin-5(9bH)-one hydrochloride (Example 29) (20 mg, 0.07 mmol) in 2 mL of methanol was added formaldehyde (0.017 mL of 37% aqueous solution, 0.21 mmol) followed by sodium borohydride (14 mg, 0.35 mmol) portionwise. The reaction mixture was stirred at ambient temperature for 1 h. The reaction was concentrated and the residue was purified (ISCO, elution with 0-15% methanol/methylene chloride) to afford the free base. To the free base in 1 mL of ether was added two drops 12 N HCl. The mixture was concentrated in vacuo, triturated with ether, and dried in vacuo to afford 15 mg (71%) of the title compound of Example 62 as an off-white solid. $^1$H NMR (CD$_3$OD): 7.35 (s, 1H), 7.00 and 6.97 (s, 1H), 4.07-4.02 (m, 1H), 3.91-3.85 (m, 1H), 3.74-3.69 (m, 1H), 3.61-3.55 (m, 1H), 3.45-3.28 (m, 2H), 3.14 and 3.08 (s, 3H), 2.69 (q, 2H), 1.25 (t, 3H). LRMS (ESI): 265.2/267.2 (M+H)+.

Example 63

(3aR,9bS)-6-Chloro-8-ethyl-2,4-dimethyl-2,3,3a,4-tetrahydro-1H-pyrrolo[3,4-c]isoquinolin-5(9bH)-one hydrochloride

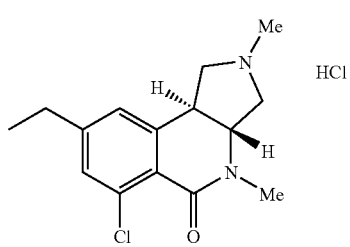

Following the procedure described in Example 62, (3aR,9bS)-6-chloro-8-ethyl-4-methyl-2,3,3a,4-tetrahydro-1H-pyrrolo[3,4-c]isoquinolin-5(9bH)-one hydrochloride (Example 31) was converted into the title compound of Example 63 as a white solid. $^1$H NMR (CD$_3$OD): 7.35 (s, 1H), 6.97-6.94 (m, 1H), 4.20-4.15 (m, 1H), 3.97-3.85 (m, 3H), 3.50-3.35 (m, 2H), 3.16 (s, 3H), 3.09 (s, 3H), 2.68 (q, 2H), 1.24 (t, 3H). LRMS (ESI): 279.2/281.2 (M+H)+.

Example 64

(3aR,9bS)-6-Chloro-8-ethyl-2-isopropyl-2,3,3a,4-tetrahydro-1H-pyrrolo[3,4-c]isoquinolin-5(9bH)-one hydrochloride

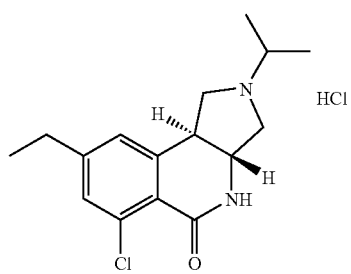

To a solution of (3aR,9bS)-6-chloro-8-ethyl-2,3,3a,4-tetrahydro-1H-pyrrolo[3,4-c]isoquinolin-5(9bH)-one hydrochloride (Example 29) (19 mg, 0.066 mmol) in 2 mL of methanol was added acetone (0.015 mL, 0.20 mmol) followed by sodium borohydride (13 mg, 0.33 mmol) portionwise. The reaction mixture was stirred at ambient temperature for 18 h. The reaction was concentrated and the residue was purified (ISCO, elution with 0-15% methanol/methylene chloride) to afford the free base. To the free base in 1 mL of ether was added 4N HCl in dioxane (0.05 mL). The mixture was concentrated in vacuo, triturated with ether, and dried in vacuo to afford 13 mg (60%) of the title compound of Example 64 as a white solid. $^1$H NMR (CD$_3$OD): 7.36 (s, 1H), 7.07 and 7.02 (s, 1H), 4.27-4.21 and 4.16-4.11 (m, 1H), 3.88-3.35 (overlapping m, 6H), 2.70 (q, 2H), 1.48-1.42 (m, 6H), 1.26 (t, 3H). LRMS (ESI): 293.3/295.3 (M+H)+.

Example 65

(3aR,9bS)-6-Chloro-2,8-diethyl-2,3,3a,4-tetrahydro-1H-pyrrolo[3,4-c]isoquinolin-5(9bH)-one hydrochloride

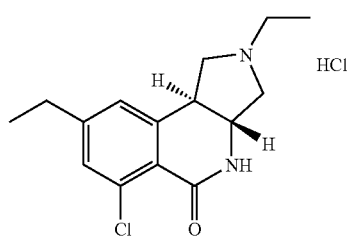

To a solution of (3aR,9bS)-6-chloro-8-ethyl-2,3,3a,4-tetrahydro-1H-pyrrolo[3,4-c]isoquinolin-5(9bH)-one hydrochloride (Example 29) (10 mg, 0.035 mmol) in 2 mL of methanol was added acetaldehyde (0.006 mL, 0.10 mmol) followed by sodium borohydride (7 mg, 0.17 mmol). The reaction mixture was stirred at ambient temperature for 18 h. The reaction was concentrated and the residue was purified (ISCO, elution with 0-15% methanol/methylene chloride) to afford the free base. To the free base in 1 mL of ether was added 4N HCl in dioxane (0.05 mL). The mixture was concentrated in vacuo, triturated with ether, and dried in vacuo to afford 7 mg (64%) of the title compound of Example 65 as an off-white solid. $^1$H NMR (CD$_3$OD): 7.27 (s, 1H), 6.95 and 6.91 (s, 1H), 4.30-4.25 and 3.93-3.85 (m, 2H), 3.70-52 (overlapping m, 3H), 3.42-3.27 (overlapping m, 3H), 2.61 (q, 2H), 1.33 (q, 3H), 1.16 (t, 3H). LRMS (ESI): 279.2/281.2 (M+H)+.

Example 66

(3aR,9bS)-8-Ethyl-6-hydroxy-2,3,3a,4-tetrahydro-1H-pyrrolo[3,4-c]isoquinolin-5(9bH)-one hydrochloride

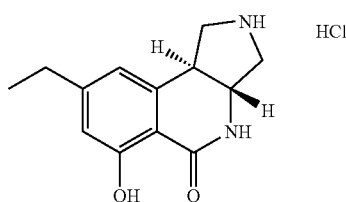

Part A. (3aR,9bS)-tert-Butyl 8-ethyl-6-hydroxy-5-oxo-3,3a,4,5-tetrahydro-1H-pyrrolo[3,4-c]isoquinoline-2(9bH)-carboxylate To a solution of (3aR,9bS)-tert-butyl 8-ethyl-6-methoxy-5-oxo-3,3a,4,5-tetrahydro-1H-pyrrolo[3,4-c]isoquinoline-2(9bH)-carboxylate, the first eluting compound from Example 51, Part B (686 mg, 1.98 mmol) in 100 mL of methylene chloride was added boron tribromide (2.38 mL of a 1 M solution in methylene chloride, 2.38 mmol) dropwise at ambient temperature. The solution was allowed to stir for 8 h and then there was added 100 mL of 1 N sodium hydroxide followed by followed by di-tert-butyl dicarbonate (648 mg, 2.97 mmol). The reaction mixture was stirred at ambient temperature for 18 h. The reaction was diluted with 1 N HCl to give a pH of ~5-6. The layers were separated and the organic layer was washed with water and brine, dried (MgSO$_4$) and concentrated. The residue was purified (ISCO, elution with 0-50% EtOAc/hexane) to afford 413 mg (63%) of the title compound as a white solid. LRMS (ESI): 333.2 (M+H)+.

Part B. (3aR,9bS)-8-Ethyl-6-hydroxy-2,3,3a,4-tetrahydro-1H-pyrrolo[3,4-c]isoquinolin-5(9bH)-one hydrochloride Following the procedure described in Example 45, Part I, (3aR,9bS)-tert-butyl 8-ethyl-6-hydroxy-5-oxo-3,3a,4,5-tetrahydro-1H-pyrrolo[3,4-c]isoquinoline-2(9bH)-carboxylate (32 mg, 0.1 mmol) was converted into 20 mg (74%) of the title compound of Example 66 as a white solid. $^1$H NMR (DMSO-D$_6$): δ 12.33 (s, 1H), 9.73 (broad s, 1H), 9.61 (broad s, 1H), 8.92 (s, 1H), 6.61 (s, 1H), 6.49 (s, 1H), 3.80-3.73 (m, 1H), 3.63-3.57 (m, 1H), 3.44-3.38 (m, 1H), 3.21-3.14 (m, 1H), 3.12-3.06 (m, 1H), 3.03-2.97 (m, 1H), 2.48 (q, 2H, J=7.5 Hz), 1.08 (t, 3H, J=7.5 Hz). LRMS (ESI): 233.1 (M+H)+.

Example 67

(3aR,9bS)-6,7-Dichloro-2-methyl-2,3,3a,4-tetrahydro-1H-pyrrolo[3,4-c]isoquinolin-5(9bH)-one hydrochloride

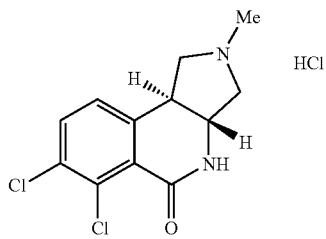

Following the procedure described in Example 62, (3aR,9bS)-6,7-dichloro-2,3,3a,4-tetrahydro-1H-pyrrolo[3,4-c]isoquinolin-5(9bH)-one hydrochloride (Example 59) was converted into the title compound of Example 67 as a white solid. $^1$H NMR (CD$_3$OD): 7.96 (d, 1H, J=8.2 Hz), 7.66 (dd, 1H, J=8.2, 1.1 Hz), 4.19-4.14 (m, 1H), 3.97-3.91 (m, 1H), 3.65-3.60 (m, 1H), 3.55-3.49 (m, 1H), 3.45-3.40 (m, 1H), 3.18-3.11 (m, 1H), 2.84 (s, 3H). LRMS (ESI): 271.0/273.0 (M+H)+.

Example 68

(3aR,9bS)-6-Chloro-7-methyl-2,3,3a,4-tetrahydro-1H-pyrrolo[3,4-c]isoquinolin-5(9bH)-one hydrochloride

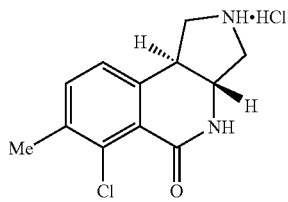

Part A. (±)-trans-tert-Butyl 6-chloro-7-methyl-5-oxo-3,3a,4,5-tetrahydro-1H-pyrrolo[3,4-c]isoquinoline-2(9bH)-carboxylate Following the procedures described in Example 45, Parts D-G, 2-chloro-3-methyl-N,N-diethylbenzamide was converted into the title compound as a racemic mixture.

Part B. Chiral separation of (3aR,9bS)-tert-Butyl 6-chloro-7-methyl-5-oxo-3,3a,4,5-tetrahydro-1H-pyrrolo[3,4-c]isoquinoline-2(9bH)-carboxylate and (3aS,9bR)-tert-Butyl 6-chloro-7-methyl-5-oxo-3,3a,4,5-tetrahydro-1H-pyrrolo[3,4-c]isoquinoline-2(9bH)-carboxylate A 900 mg sample of racemic (±)-trans-tert-butyl 6-chloro-7-methyl-5-oxo-3,3a,4,5-tetrahydro-1H-pyrrolo[3,4-c]isoquinoline-2(9bH)-carboxylate was separated into the two enantiomers by chiral HPLC (Chiralcel OD column, elution with 20% isopropanol/heptane) to afford 250 mg of (3aR,9bS)-tert-butyl 6-chloro-7-methyl-5-oxo-3,3a,4,5-tetrahydro-1H-pyrrolo[3,4-c]isoquinoline-2(9bH)-carboxylate as the first eluting compound (>99% ee on chiralcel OD, 4.6×250, 50% isopropanol/heptane) and 240 mg of (3aS,9bR)-tert-butyl 6-chloro-7-methyl-5-oxo-3,3a,4,5-tetrahydro-1H-pyrrolo[3,4-c]isoquinoline-2(9bH)-carboxylate as the second eluting compound (>99% ee on chiralcel OD, 4.6×250, 50% isopropanol/heptane).

Part C. (3aR,9bS)-6-Chloro-7-methyl-2,3,3a,4-tetrahydro-1H-pyrrolo[3,4-c]isoquinolin-5(9bH)-one hydrochloride Following the procedure described in Example 45, Part I, (3aR,9bS)-tert-butyl 6-chloro-7-methyl-5-oxo-3,3a,4,5-tetrahydro-1H-pyrrolo[3,4-c]isoquinoline-2(9bH)-carboxylate, the first eluting compound from Part B above, was converted into the title compound of Example 68 as a white solid. LRMS (ESI): 237.0/239.0 (M+H)+.

Example 69

(3aS,9bR)-6-Chloro-7-methyl-2,3,3a,4-tetrahydro-1H-pyrrolo[3,4-c]isoquinolin-5(9bH)-one hydrochloride

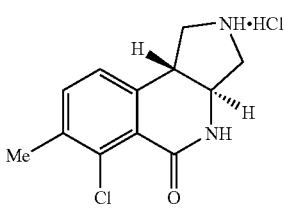

Following the procedure described in Example 45, Part I, (3aS,9bR)-tert-butyl 6-chloro-7-methyl-5-oxo-3,3a,4,5-tetrahydro-1H-pyrrolo[3,4-c]isoquinoline-2(9bH)-carboxylate, the second eluting compound from Example 68, Part B, was converted into the title compound of Example 69 as a white solid. LRMS (ESI): 237.0/239.0 (M+H)+.

Example 70

(3aR,9bS)-6-Methyl-2,3,3a,4-tetrahydro-1H-pyrrolo[3,4-c]isoquinolin-5(9bH)-one hydrochloride

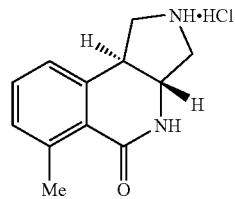

Part A. (E)-Ethyl 2-(3-(benzyloxy)-3-oxoprop-1-enyl)-6-methylbenzoate

To a solution of 6-methylsalicyclic acid ethyl ester (10.0 g, 55.56 mmol) in 250 mL of methylene chloride at −40° C. was added triethylamine (9.3 mL, 66.67 mmol). Then trifluoromethanesulfonic anhydride (9.8 mL, 58.33 mL) was added slowly over 20 min and the reaction was allowed to stir while warming to ambient temperature. The reaction mixture was washed with water and brine, dried (MgSO$_4$) and was concentrated in vacuo to afford a trifluoromethanesulfonate as an oil (18.7 g) which was used without purification. The trifluoromethanesulfonate was taken up in 150 mL of DMF and then there was added benzyl acrylate (14.5 g, 82.5 mmol) and triethylamine (15.3 mL, 110 mmol). The reaction mixture was degassed with a stream of argon and then there was added bis(diphenylphosphino)ferrocene]-dichloropalladium (II) complex with dichloromethane (1:1) (450 mg, 0.55 mmol). The reaction mixture was allowed to stir at 110° C. for 3 days. The reaction mixture was allowed to cool and was diluted with ethyl acetate. The organics were washed with 1 N HCl, water and brine, dried (MgSO$_4$) and concentrated. The residue was purified (ISCO, elution with 0-10% EtOAc/hexane) to afford 5.82 g (33%) of the title compound as an oil. LRMS (ESI): 325.1 (M+H)+.

Part B. (±)-trans-tert-Butyl 6-methyl-5-oxo-3,3a,4,5-tetrahydro-1H-pyrrolo[3,4-c]isoquinoline-2(9bH)-carboxylate Following the procedures described in Example 10, Parts C-E, (E)-ethyl 2-(3-(benzyloxy)-3-oxoprop-1-enyl)-6-methylbenzoate was converted into the title compound as a racemic mixture.

Part C. Chiral separation of (3aR,9bS)-tert-Butyl 6-methyl-5-oxo-3,3a,4,5-tetrahydro-1H-pyrrolo[3,4-c]isoquinoline-2(9bH)-carboxylate and (3 as,9bR)-tert-Butyl 6-methyl-5-oxo-3,3a,4,5-tetrahydro-1H-pyrrolo[3,4-c]isoquinoline-2(9bH)-carboxylate A 900 mg sample of racemic (±)-trans-tert-butyl 6-methyl-5-oxo-3,3a,4,5-tetrahydro-1H-pyrrolo[3,4-c]isoquinoline-2 (9bH)-carboxylate was separated into the two enantiomers by chiral HPLC (Chiralcel OD column, elution with 20% isopropanol/heptane) to afford 250 mg of (3aR,9bS)-tert-butyl 6-methyl-5-oxo-3,3a,4,5-tetrahydro-1H-pyrrolo[3,4-c]isoquinoline-2(9bH)-carboxylate as the first eluting compound (>99% ee on chiralcel OD, 4.6×250, 50% isopropanol/heptane) and 240 mg of (3aS,9bR)-tert-butyl 6-methyl-5-oxo-3, 3a,4,5-tetrahydro-1H-pyrrolo[3,4-c]isoquinoline-2(9bH)-carboxylate as the second eluting compound (>99% ee on chiralcel OD, 4.6×250, 50% isopropanol/heptane).

Part D. (3aR,9bS)-6-methyl-2,3,3a,4-tetrahydro-1H-pyrrolo[3,4-c]isoquinolin-5(9bH)-one hydrochloride Following the procedure described in Example 45, Part I, (3aR,9bS)-tert-butyl 6-methyl-5-oxo-3,3a,4,5-tetrahydro-1H-pyrrolo[3,4-c]isoquinoline-2(9bH)-carboxylate, the first eluting compound from Part C above, was converted into the title compound of Example 70 as a white solid. LRMS (ESI): 203.1 (M+H)+.

Example 71

(3aS,9bR)-6-Methyl-2,3,3a,4-tetrahydro-1H-pyrrolo[3,4-c]isoquinolin-5(9bH)-one hydrochloride

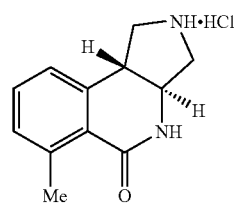

Following the procedure described in Example 45, Part I, (3aS,9bR)-tert-butyl 6-methyl-5-oxo-3,3a,4,5-tetrahydro-1H-pyrrolo[3,4-c]isoquinoline-2(9bH)-carboxylate, the second eluting compound from Example 70, Part C, was converted into the title compound of Example 71 as a white solid. LRMS (ESI): 203.1 (M+H)+.

Example 72

(±)-trans-8-Methoxy-6-methyl-2,3,3a,4-tetrahydro-1H-pyrrolo[3,4-c]isoquinolin-5(9bH)-one hydrochloride

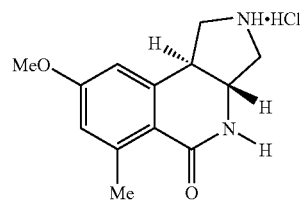

Part A. Ethyl 2-hydroxy-4-methoxy-6-methylbenzoate

To a solution of ethyl 2,4-dimethoxy-6-methylbenzoate (5.73 g, 25.6 mmol) in 200 mL of methylene chloride at −78° C. was added boron trichloride (28.1 mL of a 1.0 M solution in methylene chloride, 28.1 mmol) via an addition funnel over 15 min. The solution was allowed to stir at −78° C. for 2 h. The cooling bath was removed, the reaction was allowed to warm for 15 min. and then was carefully quenched with 1N HCl. Most of the methylene chloride was removed by rotary evaporator and the reaction was diluted with ethyl acetate. The organics were washed with 1N HCl and brine, dried (MgSO$_4$) and concentrated. The residue was purified by flash chromatography (elution with 8:1 hexane/ethyl acetate) to afford 3.8 g (70%) of the title compound as a tan solid. $^1$H NMR (CDCl$_3$): δ 11.85 (s, 1H), 6.31 (d, 1H, J=2.2 Hz), 6.25 (d, 1H, J=2.6 Hz), 4.37 (q, 2H, J=7.2 Hz), 3.77 (s, 3H), 2.49 (s, 3H), 1.39 (t, 3H, J=7.4 Hz).

Part B. (E)-Ethyl 2-(3-(benzyloxy)-3-oxoprop-1-enyl)-4-methoxy-6-methylbenzoate

To a solution of ethyl 2-hydroxy-4-methoxy-6-methylbenzoate (3.8 g, 18.1 mmol) in 40 mL of pyridine at 0° C. was added trifluoromethanesulfonic anhydride (3.65 mL, 21.7 mmol) over 5 min. The reaction was allowed to stir for 10 min at 0° C. and then for 1 h at ambient temperature. The reaction mixture was diluted with ethyl acetate, washed sequentially with 1N HCl, sat'd aq. NaHCO$_3$, and brine, dried (MgSO$_4$), filtered through a pad of silica gel and concentrated to afford 6.1 g (98%) of a triflate as a yellow oil that was sufficiently pure to be used without purification. The triflate was taken up in 60 mL of DMF and the solution was degassed with a stream of argon at 60° C. Then there was added benzyl acrylate (7.22 g, 44.55 mmol), triethylamine (4.96 mL, 35.6 mmol), and bis(diphenylphosphino)ferrocene]-dichloropalladium (II) complex with dichloromethane (1:1) (363 mg, 0.45 mmol). The reaction mixture was allowed to stir at 100° C. for 18 h. Starting material remained and so additional benzyl acrylate (2.4 g, 14.85 mmol), triethylamine (1.65 mL, 11.9 mmol), and bis(diphenylphosphino)ferrocene]-dichloropalladium (II) complex with dichloromethane (1:1) (120 mg, 0.15 mmol) were added and heating was continued at 100° C. for 4 h. The reaction was allowed to cool and was diluted with ethyl acetate. The organics were washed sequentially with water, 1N HCl, sat'd aq. NaHCO$_3$, and brine, dried (MgSO$_4$), filtered through a pad of silica gel and concentrated. The residue was purified by flash chromatography (elution with 9:1 hexane/EtOAc) to afford 5.1 g (80%) of the title compound as a yellow oil that solidified upon standing. $^1$H NMR (CDCl$_3$): δ 7.84 (d, 1H, J=15.9 Hz), 7.43-7.32 (m, 5H), 6.92 (d, 1H, J=2.2 Hz), 6.77 (d, 1H, J=2.2 Hz), 6.38 (d, 1H, J=15.4 Hz), 5.23 (s, 2H), 4.37 (q, 2H, J=7.2 Hz), 3.81 (s, 3H), 2.36 (s, 3H), 1.34 (t, 3H, J=7.2 Hz). LRMS (ESI): 355.3 (M+H)+.

Part C. (±)-trans-tert-Butyl 8-methoxy-6-methyl-5-oxo-3,3a,4,5-tetrahydro-1H-pyrrolo[3,4-c]isoquinoline-2(9bH)-carboxylate Following the procedures described in Example 10, Parts C-E, (E)-ethyl 2-(3-(benzyloxy)-3-oxoprop-1-enyl)-4-methoxy-6-methylbenzoate was converted into the title compound as a white solid. LRMS (ESI): 333.3 (M+H)+.

Part D. (±)-trans-8-Methoxy-6-methyl-2,3,3a,4-tetrahydro-1H-pyrrolo[3,4-c]isoquinolin-5(9bH)-one hydrochloride Following the procedure described in Example 45, Part I, (±)-trans-tert-butyl 8-methoxy-6-methyl-5-oxo-3,3a,4,5-tetrahydro-1H-pyrrolo[3,4-c]isoquinoline-2(9bH)-carboxylate was converted into the title compound of Example 72 as an off-white solid. $^1$H NMR (DMSO-d$_6$): δ 9.66 (broad s, 1H), 9.50 (broad s, 1H), 8.34 (s, 1H), 6.77 (d, 1H, J=2.6 Hz), 6.62 (d, 1H, J=2.2 Hz), 3.90-3.84 (m, 1H), 3.79 (s, 3H), 3.52-3.40 (m, 2H), 3.19-3.12 (m, 2H), 3.09-3.03 (m, 1H), 2.54 (s, 3H). LRMS (ESI): 233.3 (M+H)+.

Example 73

(±)-trans-8-Hydroxy-6-methyl-2,3,3a,4-tetrahydro-1H-pyrrolo[3,4-c]isoquinolin-5(9bH)-one hydrochloride

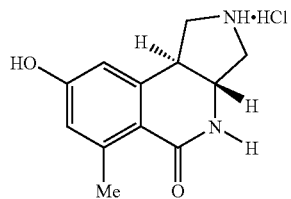

Part A. (±)-trans-tert-Butyl 8-hydroxy-6-methyl-5-oxo-3,3a,4,5-tetrahydro-1H-pyrrolo[3,4-c]isoquinoline-2(9bH)-carboxylate To a solution of (±)-trans-tert-butyl 8-methoxy-6-methyl-5-oxo-3,3a,4,5-tetrahydro-1H-pyrrolo[3,4-c]isoquinoline-2(9bH)-carboxylate from Example 72, Part C (0.43 g, 1.29 mmol) in 8 mL of N-methylpyrrolidinone was added thiophenol (0.15 mL, 1.42 mmol) and potassium carbonate (27 mg, 0.19 mmol). The resulting mixture was stirred in a sealed vial at 160° C. for 4 h. The solution was allowed to cool and was partitioned between ether and 1N NaOH. The aqueous layer was washed with ether. The combined organic layers were discarded. The aqueous layer was acidified with 12 N HCl, whereby a solid precipitated out of solution. The mixture was filtered and the solid washed with water and dried in vacuo to afford 0.26 g (65%) of the title compound as an off-white solid. LRMS (ESI): 319.3 (M+H)+.

Part B. (±)-trans-8-Hydroxy-6-methyl-2,3,3a,4-tetrahydro-1H-pyrrolo[3,4-c]isoquinolin-5(9bH)-one hydrochloride Following the procedure described in Example 45, Part I, (±)-trans-tert-butyl 8-hydroxy-6-methyl-5-oxo-3,3a,4,5-tetrahydro-1H-pyrrolo[3,4-c]isoquinoline-2(9bH)-carboxylate was converted into the title compound of Example 73 as an off-white solid. $^1$H NMR (DMSO-d$_6$): δ 9.62 (broad s, 1H), 9.42 (broad s, 1H), 8.23 (s, 1H), 6.58 (d, 1H, J=2.2 Hz), 6.39 (d, 1H, J=2.2 Hz), 3.83-3.78 (m, 1H), 3.52-3.40 (m, 2H), 3.13-2.98 (m, 3H), 2.48 (s, 3H). LRMS (ESI): 219.3 (M+H)+.

Example 74

(3aR,9bS)-8-Ethyl-6-methyl-2,3,3a,4-tetrahydro-1H-pyrrolo[3,4-c]isoquinolin-5(9bH)-one hydrochloride

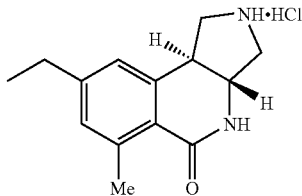

Part A. (±)-tert-Butyl 8-ethyl-6-methyl-5-oxo-3,3a,4,5-tetrahydro-1H-pyrrolo[3,4-c]isoquinoline-2(9bH)-carboxylate To a solution of (±)-trans-tert-butyl 8-hydroxy-6-methyl-5-oxo-3,3a,4,5-tetrahydro-1H-pyrrolo[3,4-c]isoquinoline-2

(9bH)-carboxylate from Example 73, Part A (0.35 g, 1.11 mmol) in 10 mL of pyridine at 0° C. was added trifluoromethanesulfonic anhydride (0.23 mL, 1.39 mmol). The reaction mixture was stirred with warming to ambient temperature for 2 h. Additional trifluoromethanesulfonic anhydride (0.10 mL, 0.6 mmol) was added to drive the reaction to completion and stirring was continued for 1 h at ambient temperature. The reaction was diluted with ethyl acetate, washed sequentially with 1N HCl, sat'd aq. NaHCO$_3$, and brine, dried (MgSO$_4$), filtered through a pad of silica gel and concentrated. The residue was triturated with hexanes and the solid was dried in vacuo to afford 0.44 g (88%) of a triflate as a tan solid.

This triflate was dissolved in 20 mL THF and the solution was degassed with a stream of argon. Then there was added diethylzinc (2.7 mL of a 1.1 M solution in toluene, 2.94 mmol) and bis(diphenylphosphino)ferrocene]-dichloropalladium (II) complex with dichloromethane (1:1) (40 mg, 0.05 mmol). The resulting mixture was stirred in a sealed flask at 65° C. for 18 h. The reaction mixture was allowed to cool and was diluted with ethyl acetate. The organics were washed with brine, dried (MgSO$_4$), filtered through a pad of silica gel and concentrated. The residue was purified by flash chromatography (elution with 25-50% EtOAc in hexane) to afford 275 mg (84%) of the title compound as an off-white solid. $^1$H NMR (DMSO-d$_6$) (some signals doubled due to rotamers): δ 8.39 and 8.34 (s, 1H), 7.02 (s, 1H), 6.83 and 6.80 (s, 1H), 3.95-3.90 (m, 1H), 3.63-3.58 (m, 1H), 3.49-3.41 (m, 1H), 3.25-3.05 (overlapping m, 3H), 2.57 (q, 2H, J=7.5 Hz), 2.54 (s, 3H), 1.43 and 1.42 (s, 9H), 1.16 (t, 3H). LRMS (ESI): 331.3 (M+H)+.

Part B. Chiral separation of (3aR,9bS)-tert-Butyl 8-ethyl-6-methyl-5-oxo-3,3a,4,5-tetrahydro-1H-pyrrolo[3,4-c]isoquinoline-2(9bH)-carboxylate and (3aS,9bR)-tert-Butyl 8-ethyl-6-methyl-5-oxo-3,3a,4,5-tetrahydro-1H-pyrrolo[3,4-c]isoquinoline-2(9bH)-carboxylate A 270 mg sample of racemic (±)-trans-tert-butyl 8-ethyl-6-methyl-5-oxo-3,3a,4,5-tetrahydro-1H-pyrrolo[3,4-c]isoquinoline-2(9bH)-carboxylate was separated into the two enantiomers by chiral HPLC (Chiralcel OD column, elution with 20% MeOH-EtOH (1:1)/heptane) to afford 110 mg of (3aR,9bS)-tert-butyl 8-ethyl-6-methyl-5-oxo-3,3a,4,5-tetrahydro-1H-pyrrolo[3,4-c]isoquinoline-2(9bH)-carboxylate as the first eluting compound (>99% ee on chiralcel OD, 4.6×250, 30% MeOH-EtOH (1:1)/heptane, retention time 5.7 min) and 100 mg of (3aS,9bR)-tert-butyl 8-ethyl-6-methyl-5-oxo-3,3a,4,5-tetrahydro-1H-pyrrolo[3,4-c]isoquinoline-2 (9bH)-carboxylate as the second eluting compound (>99% ee on chiralcel OD, 4.6×250, 30% MeOH-EtOH (1:1)/heptane, retention time 10.6 min).

Part C. (3aR,9bS)-8-Ethyl-6-methyl-2,3,3a,4-tetrahydro-1H-pyrrolo[3,4-c]isoquinolin-5(9bH)-one hydrochloride To a solution of (3aR,9bS)-tert-butyl 8-ethyl-6-methyl-5-oxo-3,3a,4,5-tetrahydro-1H-pyrrolo[3,4-c]isoquinoline-2 (9bH)-carboxylate, the first eluting compound from Part B above, (48 mg, 0.15 mmol) in 2 mL of diethyl ether was added 1 mL of 12 N HCl. The resulting mixture was stirred vigorously for 5 min at ambient temperature and then was concentrated and dried in vacuo. The resulting white solid was triturated twice with diethyl ether and dried in vacuo. The residue was dissolved in 1 mL distilled water, filtered, and lyophilized to afford 30 mg (79%) of the title compound of Example 74 as a white powder. $^1$H NMR (DMSO-d$_6$): δ 9.40 (broad s, 2H), 8.47 (s, 1H), 7.07 (s, 1H), 6.89 (s, 1H), 3.87-3.82 (m, 1H), 3.52-3.46 (m, 1H), 3.45-3.40 (m, 1H), 3.21-3.10 (overlapping m, 2H), 3.07-3.01 (m, 1H), 2.58 (q, 2H, J=7.5 Hz), 2.54 (s, 3H), 1.18 (t, 3H, J=7.7 Hz). LRMS (ESI): 231.2 (M+H)+.

Example 75

(3aS,9bR)-8-Ethyl-6-methyl-2,3,3a,4-tetrahydro-1H-pyrrolo[3,4-c]isoquinolin-5(9bH)-one hydrochloride

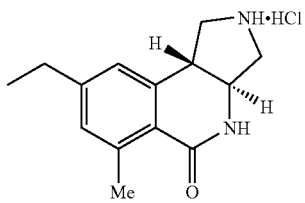

Following the procedure described in Example 74, Part C, (3aS,9bR)-tert-butyl 8-ethyl-6-methyl-5-oxo-3,3a,4,5-tetrahydro-1H-pyrrolo[3,4-c]isoquinoline-2(9bH)-carboxylate, the second eluting compound from Example 74, Part B, was converted into the title compound of Example 75 as a white solid. $^1$H NMR (DMSO-d$_6$): δ 9.40 (broad s, 2H), 8.47 (s, 1H), 7.07 (s, 1H), 6.89 (s, 1H), 3.87-3.82 (m, 1H), 3.52-3.46 (m, 1H), 3.45-3.40 (m, 1H), 3.21-3.10 (overlapping m, 2H), 3.07-3.01 (m, 1H), 2.58 (q, 2H, J=7.5 Hz), 2.54 (s, 3H), 1.18 (t, 3H, J=7.7 Hz). LRMS (ESI): 231.2 (M+H)+.

Example 76

(3aR,9bS)-8-Ethyl-4,6-dimethyl-2,3,3a,4-tetrahydro-1H-pyrrolo[3,4-c]isoquinolin-5(9bH)-one hydrochloride

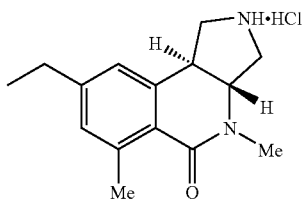

Following the procedures described in Example 15, Part A and Example 74, Part C, (3aR,9bS)-tert-butyl 8-ethyl-6-methyl-5-oxo-3,3a,4,5-tetrahydro-1H-pyrrolo[3,4-c]isoquinoline-2(9bH)-carboxylate, the first eluting compound from Example 74, Part B, was converted into the title compound of Example 76 as a pale yellow powder. $^1$H NMR (DMSO-D$_6$): δ 9.80-9.40 (very broad s, 2H), 7.07 (s, 1H), 6.89 (s, 1H), 3.92-3.86 (m, 1H), 3.70-3.62 (overlapping m, 2H), 3.45-3.20 (overlapping m, 3H), 2.97 (s, 3H), 2.59 (q, 2H, J=7.5 Hz), 2.55 (s, 3H), 1.18 (t, 3H, J=7.7 Hz). LRMS (ESI): 245.2 (M+H)+.

Example 77

(3aR,9bS)-8-Ethyl-2,6-dimethyl-2,3,3a,4-tetrahydro-1H-pyrrolo[3,4-c]isoquinolin-5(9bH)-one hydrochloride

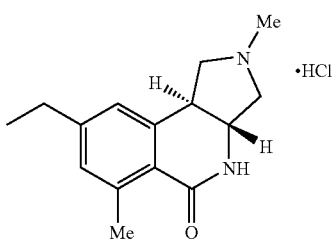

Following the procedure described in Example 62, (3aR, 9bS)-8-ethyl-6-methyl-2,3,3a,4-tetrahydro-1H-pyrrolo[3,4-c]isoquinolin-5(9bH)-one hydrochloride (Example 74) was converted into the title compound of Example 77 as an off-white powder. $^1$H NMR (DMSO-D$_6$): δ 8.51 (s, 1H), 7.09 (s, 1H), 6.85 (broad s, 1H), 4.20-3.10 (very broad overlapping m, 6H), 2.94 (broad s, 3H), 2.59 (q, 2H, J=7.5 Hz), 2.55 (s, 3H), 1.19 (t, 3H, J=7.5 Hz). LRMS (ESI): 245.1 (M+H)+.

Example 78

(±)-trans-4-Benzyl-8-ethyl-6-methyl-2,3,3a,4-tetrahydro-1H-pyrrolo[3,4-c]isoquinolin-5(9bH)-one hydrochloride

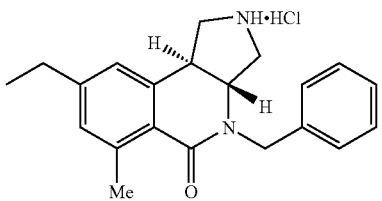

Part A. (±)-trans-tert-Butyl 4-benzyl-8-ethyl-6-methyl-5-oxo-3,3a,4,5-tetrahydro-1H-pyrrolo[3,4-c]isoquinoline-2(9bH)-carboxylate To a suspension of hexane-washed sodium hydride (6 mg of 60% dispersion in mineral oil, 0.15 mmol) in 1 mL THF was added (±)-trans-tert-butyl 8-ethyl-6-methyl-5-oxo-3,3a,4,5-tetrahydro-1H-pyrrolo[3,4-c]isoquinoline-2(9bH)-carboxylate from Example 74, Part A (25 mg, 0.076 mmol) in 2 mL of THF. The mixture was stirred at ambient temperature for 30 min, at which time gas evolution had ceased. Then there was added benzyl bromide (0.027 mL, 0.23 mmol) and the resulting mixture was allowed to stir at ambient temperature for 18 h. The reaction was quenched with 1N HCl and diluted with ethyl acetate. The organics were washed sequentially with sat'd aq. NaHCO$_3$, and brine, dried (MgSO$_4$), and concentrated. The residue was purified by flash chromatography (elution with 4:1 hexane/EtOAc) to afford 28 mg (88%) of the title compound as an oil. LRMS (ESI): 421.1 (M+H)+.

Part B. (±)-trans-4-Benzyl-8-ethyl-6-methyl-2,3,3a,4-tetrahydro-1H-pyrrolo[3,4-c]isoquinolin-5(9bH)-one hydrochloride Following the procedure described in Example 45, Part I, (±)-trans-tert-butyl 4-benzyl-8-ethyl-6-methyl-5-oxo-3,3a,4,5-tetrahydro-1H-pyrrolo[3,4-c]isoquinoline-2(9bH)-carboxylate was converted into the title compound of Example 78 as an off-white powder. $^1$H NMR (DMSO-D$_6$): δ 9.65 (broad s, 1H), 9.45 (broad s, 1H), 7.36-7.22 (m, 5H), 7.12 (s, 1H), 6.91 (s, 1H), 5.00 and 4.51 (ABq, 2H, J$_{AB}$=16.0 Hz), 3.89 (dd, 1H, J=7.7, 10.4 Hz), 3.71-3.63 (m, 1H), 3.50-3.42 (m, 2H), 3.24-3.13 (m, 2H), 2.60 (q, 2H, J=7.5 Hz), 2.59 (s, 3H), 1.19 (t, 3H, J=7.5 Hz). LRMS (ESI): 321.1 (M+H)+.

Example 79

(±)-trans 2-((8-Ethyl-6-methyl-5-oxo-1,2,3,3a-tetrahydro-5H-pyrrolo[3,4-c]isoquinolin-4(9bH)-yl)methyl)benzonitrile hydrochloride

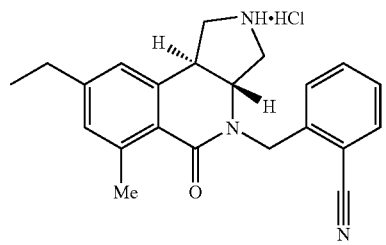

Following the procedures described in Example 78, Parts A and B, except that 2-(bromomethyl)benzonitrile was used instead of benzyl bromide, (±)-trans-tert-butyl 8-ethyl-6-methyl-5-oxo-3,3a,4,5-tetrahydro-1H-pyrrolo[3,4-c]isoquinoline-2(9bH)-carboxylate from Example 74, Part A, was converted into the title compound of Example 79 as an off-white powder. $^1$H NMR (DMSO-D$_6$): δ 9.52 (broad s, 1H), 9.39 (broad s, 1H), 7.86 (dd, 1H, J=1.4, 7.9 Hz), 7.69-7.64 (m, 1H), 7.50-7.45 (m, 2H), 7.12 (s, 1H), 6.94 (s, 1H), 4.97 and 4.82 (ABq, 2H, J$_{AB}$=17.0 Hz), 3.96-3.86 (overlapping m, 2H), 3.64-3.58 (m, 1H), 3.55-3.50 (m, 1H), 3.26-3.15 (m, 2H), 2.61 (q, 2H, J=7.7 Hz), 2.54 (s, 3H), 1.19 (t, 3H, J=7.7 Hz). LRMS (ESI): 346.1 (M+H)+.

Example 80

(±)-trans 3-((8-Ethyl-6-methyl-5-oxo-1,2,3,3a-tetrahydro-5H-pyrrolo[3,4-c]isoquinolin-4(9bH)-yl)methyl)benzonitrile hydrochloride

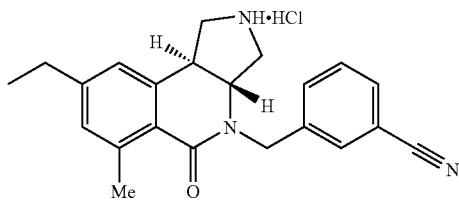

Following the procedures described in Example 78, Parts A and B, except that 3-(bromomethyl)benzonitrile was used instead of benzyl bromide, (±)-trans-tert-butyl 8-ethyl-6-methyl-5-oxo-3,3a,4,5-tetrahydro-1H-pyrrolo[3,4-c]isoquinoline-2(9bH)-carboxylate from Example 74, Part A, was converted into the title compound of Example 80 as an off-white powder. ¹H NMR (DMSO-D₆): δ 9.45 (broad s, 1H), 9.36 (broad s, 1H), 7.78-7.72 (m, 2H), 7.63 (d, 1H, J=7.7 Hz), 7.56 (t, 1H, J=7.7 Hz), 7.13 (s, 1H), 6.92 (s, 1H), 4.84 and 4.69 (ABq, 2H, $J_{AB}$=16.2 Hz), 3.93-3.88 (m, 1H), 3.83-3.77 (m, 1H), 3.60-3.52 (m, 2H), 3.25-3.18 (m, 1H), 3.12-3.05 (m, 1H), 2.61 (q, 2H, J=7.5 Hz), 2.58 (s, 3H), 1.19 (t, 3H, J=7.5 Hz). LRMS (ESI): 346.1 (M+H)+.

Example 81

(±)-trans 4-((8-Ethyl-6-methyl-5-oxo-1,2,3,3a-tetrahydro-5H-pyrrolo[3,4-c]isoquinolin-4(9bH)-yl)methyl)benzonitrile hydrochloride

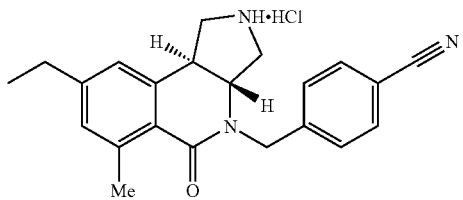

Following the procedures described in Example 78, Parts A and B, except that 4-(bromomethyl)benzonitrile was used instead of benzyl bromide, (±)-trans-tert-butyl 8-ethyl-6-methyl-5-oxo-3,3a,4,5-tetrahydro-1H-pyrrolo[3,4-c]isoquinoline-2(9bH)-carboxylate from Example 74, Part A, was converted into the title compound of Example 81 as an off-white powder. ¹H NMR (DMSO-D₆): δ 9.54 (broad s, 1H), 9.42 (broad s, 1H), 7.82 (d, 2H, J=8.2 Hz), 7.48 (d, 2H, J=8.2 Hz), 7.13 (s, 1H), 6.92 (s, 1H), 4.91 and 4.71 (ABq, 2H, $J_{AB}$=16.5 Hz), 3.93-3.88 (m, 1H), 3.80-3.73 (m, 1H), 3.56-3.48 (m, 2H), 3.25-3.18 (m, 1H), 3.11-3.04 (m, 1H), 2.61 (q, 2H, J=7.5 Hz), 2.57 (s, 3H), 1.19 (t, 3H, J=7.5 Hz). LRMS (ESI): 346.1 (M+H)+.

Example 82

(±)-trans 4-(3-Methoxybenzyl)-8-ethyl-6-methyl-2,3,3a,4-tetrahydro-1H-pyrrolo[3,4-c]isoquinolin-5(9bH)-one hydrochloride

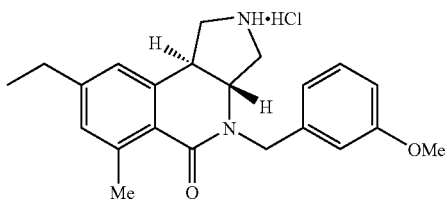

Following the procedures described in Example 78, Parts A and B, except that 3-methoxybenzyl bromide was used instead of benzyl bromide, (±)-trans-tert-butyl 8-ethyl-6-methyl-5-oxo-3,3a,4,5-tetrahydro-1H-pyrrolo[3,4-c]isoquinoline-2(9bH)-carboxylate from Example 74, Part A, was converted into the title compound of Example 82 as an off-white powder. ¹H NMR (DMSO-D₆): δ 9.65-9.35 (very broad overlapping s, 2H), 7.27-7.22 (m, 1H), 7.12 (s, 1H), 6.90 (s, 1H), 6.85-6.80 (m, 3H), 4.97 and 4.47 (ABq, 2H, $J_{AB}$=16.0 Hz), 3.88 (dd, 1H, J=7.7, 11.0 Hz), 3.71 (s, 3H), 3.68-3.62 (m, 1H), 3.50-3.42 (m, 2H), 3.22-3.12 (m, 2H), 2.60 (q, 2H, J=7.5 Hz), 2.59 (s, 3H), 1.18 (t, 3H, J=7.5 Hz). LRMS (ESI): 351.1 (M+H)+.

Example 83

(3aR,9bS)-4-Benzyl-8-ethyl-6-methyl-2,3,3a,4-tetrahydro-1H-pyrrolo[3,4-c]isoquinolin-5(9bH)-one hydrochloride

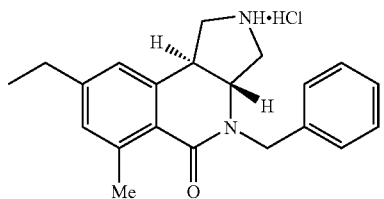

Following the procedures described in Example 78, Part A and Example 74, Part C, (3aR,9bS)-tert-butyl 8-ethyl-6-methyl-5-oxo-3,3a,4,5-tetrahydro-1H-pyrrolo[3,4-c]isoquinoline-2(9bH)-carboxylate, the first eluting peak from Example 74, Part B, was converted into the title compound of Example 83 as an off-white powder. ¹H NMR (DMSO-D₆): δ 9.48 (broad s, 2H), 7.36-7.22 (m, 5H), 7.13 (s, 1H), 6.91 (s, 1H), 5.00 and 4.51 (ABq, 2H, $J_{AB}$=16.0 Hz), 3.89 (dd, 1H, J=7.7, 10.4 Hz), 3.71-3.63 (m, 1H), 3.50-3.42 (m, 2H), 3.24-3.13 (m, 2H), 2.60 (q, 2H, J=7.5 Hz), 2.59 (s, 3H), 1.19 (t, 3H, J=7.5 Hz). LRMS (ESI): 321.1 (M+H)+.

Example 84

(3aS,9bR)-4-Benzyl-8-ethyl-6-methyl-2,3,3a,4-tetrahydro-1H-pyrrolo[3,4-c]isoquinolin-5(9bH)-one hydrochloride

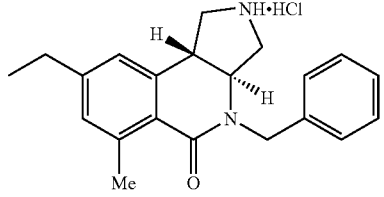

Following the procedures described in Example 78, Part A and Example 74, Part C, (3aS,9bR)-tert-butyl 8-ethyl-6-methyl-5-oxo-3,3a,4,5-tetrahydro-1H-pyrrolo[3,4-c]isoquinoline-2(9bH)-carboxylate, the second eluting peak from Example 74, Part B, was converted into the title compound of Example 84 as an off-white powder. ¹H NMR (DMSO-D₆): δ 9.70 (broad s, 1H), 9.51 (broad s, 1H), 7.36-7.22 (m, 5H), 7.13 (s, 1H), 6.92 (s, 1H), 5.01 and 4.52 (ABq, 2H, $J_{AB}$=16.0 Hz), 3.89 (dd, 1H, J=7.7, 10.4 Hz), 3.71-3.63 (m, 1H), 3.50-3.42 (m, 2H), 3.24-3.13 (m, 2H), 2.61 (q, 2H, J=7.5 Hz), 2.60 (s, 3H), 1.20 (t, 3H, J=7.5 Hz). LRMS (ESI): 321.1 (M+H)+.

Example 85

(3aR,9bS)-4-(3-Methoxybenzyl)-8-ethyl-6-methyl-2,3,3a,4-tetrahydro-1H-pyrrolo[3,4-c]isoquinolin-5(9bH)-one hydrochloride

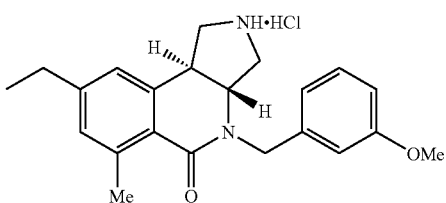

Following the procedures described in Example 82, (3aR,9bS)-tert-butyl 8-ethyl-6-methyl-5-oxo-3,3a,4,5-tetrahydro-1H-pyrrolo[3,4-c]isoquinoline-2(9bH)-carboxylate, the first eluting peak from Example 74, Part B, was converted into the title compound of Example 85 as an off-white powder. $^1$H NMR (DMSO-D$_6$): δ 9.65-9.35 (very broad overlapping s, 2H), 7.27-7.22 (m, 1H), 7.12 (s, 1H), 6.91 (s, 1H), 6.85-6.80 (m, 3H), 4.98 and 4.48 (ABq, 2H, $J_{AB}$=16.0 Hz), 3.88 (dd, 1H, J=7.7, 11.0 Hz), 3.71 (s, 3H), 3.68-3.62 (m, 1H), 3.50-3.42 (m, 2H), 3.22-3.12 (m, 2H), 2.60 (q, 2H, J=7.5 Hz), 2.59 (s, 3H), 1.19 (t, 3H, J=7.5 Hz). LRMS (ESI): 351.3 (M+H)+.

Example 86

(±)-trans 8-Ethyl-4-(2-hydroxyethyl)-6-methyl-2,3,3a,4-tetrahydro-1H-pyrrolo[3,4-c]isoquinolin-5(9bH)-one hydrochloride

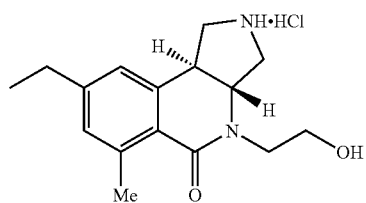

Part A. (±)-trans tert-Butyl 8-ethyl-4-(2-methoxy-2-oxoethyl)-6-methyl-5-oxo-3,3a,4,5-tetrahydro-1H-pyrrolo[3,4-c]isoquinoline-2(9bH)-carboxylate To a suspension of sodium hydride (33 mg of 60% dispersion in mineral oil, hexane-washed, 0.87 mmol) in 4 mL of THF was added (±)-trans-tert-butyl 8-ethyl-6-methyl-5-oxo-3,3a,4,5-tetrahydro-1H-pyrrolo[3,4-c]isoquinoline-2(9bH)-carboxylate from Example 74, Part A (191 mg, 0.58 mmol) in 10 mL of THF. The resulting mixture was stirred at ambient temperature for 30 min, at which time gas evolution has ceased. Then there was added methyl bromoacetate (0.082 mL, 0.87 mmol) and the resulting mixture was stirred at ambient temperature for 18 h. The reaction was quenched with 10 mL of 1 N HCl and extracted with ethyl acetate. The organics were washed with sat'd aq NaHCO$_3$ and brine, dried (MgSO$_4$), and concentrated. The residue was purified by flash chromatography (elution with 15-25% EtOAc/hexane) to afford 180 mg (77%) of the title compound. LRMS (ESI): 403.1 (M+H)+.

Part B. (±)-trans tert-Butyl 8-ethyl-4-(2-hydroxyethyl)-6-methyl-5-oxo-3,3a,4,5-tetrahydro-1H-pyrrolo[3,4-c]isoquinoline-2(9bH)-carboxylate To a solution of (±)-trans tert-butyl 8-ethyl-4-(2-methoxy-2-oxoethyl)-6-methyl-5-oxo-3,3a,4,5-tetrahydro-1H-pyrrolo[3,4-c]isoquinoline-2(9bH)-carboxylate (180 mg, 0.45 mmol) in 6 mL of THF and 3 mL of water was added lithium hydroxide (22 mg, 0.90 mmol). The resulting mixture was allowed to stir at ambient temperature for 2 h. The reaction was quenched with 10 mL of 1N HCl and extracted with ethyl acetate. The organics were washed with brine, dried (MgSO$_4$) and concentrated in vacuo to afford 165 mg of a carboxylic acid which was used without purification.

To a solution of carboxylic acid (165 mg, 0.42 mmol) in 4 mL of THF at 0° C. was added triethylamine (0.071 mL, 0.51 mmol) and ethyl chloroformate (0.049 mL, 0.51 mmol). The reaction was allowed to stir for 30 min at 0° C. and then there was added sodium borohydride (48 mg, 1.26 mmol) in a minimal amount of water. The resulting mixture was stirred for 1 h at 0° C. and then was quenched with 10 mL of 1N HCl. The mixture was extracted with ethyl acetate and the organics were washed with sat'd aq NaHCO$_3$ and brine, dried (MgSO$_4$), filtered through a pad of silica gel and concentrated in vacuo. The residue was purified by flash chromatography (elution with 1:1 hexane/ethyl acetate) to afford 120 mg (76%) of the title compound. LRMS (ESI): 375.1 (M+H)+.

Part C. (±)-trans 8-Ethyl-4-(2-hydroxyethyl)-6-methyl-2,3,3a,4-tetrahydro-1H-pyrrolo[3,4-c]isoquinolin-5(9bH)-one hydrochloride Following the procedure described in Example 45, Part I, (±)-trans tert-butyl 8-ethyl-4-(2-hydroxyethyl)-6-methyl-5-oxo-3,3a,4,5-tetrahydro-1H-pyrrolo[3,4-c]isoquinoline-2(9bH)-carboxylate was converted into the title compound of Example 86 as a white powder. $^1$H NMR (DMSO-D$_6$): δ 9.55 (broad s, 1H), 9.42 (broad s, 1H), 7.08 (s, 1H), 6.88 (s, 1H), 4.90 (t, 1H, J=5.2 Hz), 3.95-3.90 (m, 1H), 3.82-3.75 (m, 1H), 3.72-3.63 (m, 2H), 3.56-3.49 (m, 2H), 3.42-3.32 (m, 2H), 3.27-3.18 (m, 2H), 2.59 (q, 2H, J=7.5 Hz), 2.55 (s, 3H), 1.18 (t, 3H, J=7.7 Hz). LRMS (ESI): 275.0 (M+H)+.

Example 87

(±)-trans 8-Ethyl-4-(2-methoxyethyl)-6-methyl-2,3,3a,4-tetrahydro-1H-pyrrolo[3,4-c]isoquinolin-5(9bH)-one hydrochloride

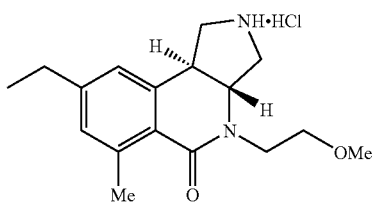

Following the procedures described in Example 21, Part A and Example 45, Part I, (±)-trans tert-butyl 8-ethyl-4-(2-hydroxyethyl)-6-methyl-5-oxo-3,3a,4,5-tetrahydro-1H-pyrrolo[3,4-c]isoquinoline-2(9bH)-carboxylate, from Example 86, Part B, was converted into the title compound of Example 87 as an off-white powder. ¹H NMR (DMSO-D₆): δ 9.65-9.45 (very broad s, 2H), 7.09 (s, 1H), 6.89 (s, 1H), 3.92 (dd, 1H, J=7.2, 10.4 Hz), 3.86-3.80 (m, 1H), 3.77-3.70 (m, 1H), 3.67-3.61 (m, 1H), 3.50-3.40 (m, 2H), 3.38-3.28 (m, 3H), 3.26-3.21 (m, 1H), 3.24 (s, 3H), 2.59 (q, 2H, J=7.5 Hz), 2.55 (s, 3H), 1.18 (t, 3H, J=7.7 Hz). LRMS (ESI): 289.1 (M+H)+.

Example 88

(±)-trans 8-Ethyl-6-methyl-4-(2-phenoxyethyl)-2,3,3a,4-tetrahydro-1H-pyrrolo[3,4-c]isoquinolin-5(9bH)-one hydrochloride

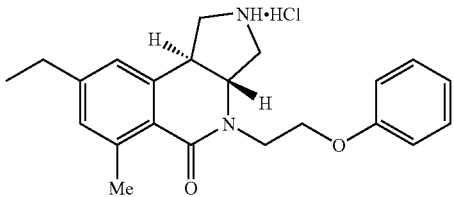

Part A. (±)-trans tert-Butyl 8-ethyl-6-methyl-5-oxo-4-(2-phenoxyethyl)-3,3a,4,5-tetrahydro-1H-pyrrolo[3,4-c]isoquinoline-2(9bH)-carboxylate To a solution of (±)-trans tert-butyl 8-ethyl-4-(2-hydroxyethyl)-6-methyl-5-oxo-3,3a,4,5-tetrahydro-1H-pyrrolo[3,4-c]isoquinoline-2(9bH)-carboxylate, from Example 86, Part B, (24 mg, 0.064 mmol) in 1 mL of toluene was added phenol (9 mg, 0.096 mmol), triphenylphosphine (20 mg, 0.077 mmol) and diethylazodicarboxylate (0.035 mL, 0.077 mmol). The resulting mixture was allowed to stir at ambient temperature for 18 h. The reaction was diluted with 10 mL of 1 N HCl and extracted with ethyl acetate. The organics were washed with sat'd aq NaHCO₃ and brine, dried (MgSO₄), filtered through a pad of silica gel and concentrated in vacuo. The residue was purified by flash chromatography (elution with 3:1 hexane/ethyl acetate) to afford 17 mg (59%) of the title compound as an oil. LRMS (ESI): 451.1 (M+H)+.

Part B. (±)-trans 8-Ethyl-6-methyl-4-(2-phenoxyethyl)-2,3,3a,4-tetrahydro-1H-pyrrolo[3,4-c]isoquinolin-5(9bH)-one hydrochloride Following the procedure described in Example 45, Part I, (±)-trans tert-butyl 8-ethyl-6-methyl-5-oxo-4-(2-phenoxyethyl)-3,3a,4,5-tetrahydro-1H-pyrrolo[3,4-c]isoquinoline-2(9bH)-carboxylate was converted into the title compound of Example 88 as an off-white powder. ¹H NMR (DMSO-D₆): δ 9.62-9.52 (very broad s, 2H), 7.26 (dd, 2H, J=7.5, 8.6 Hz), 7.09 (s, 1H), 6.99 (d, 2H, J=7.7 Hz), 6.92 (t, 1H), 6.90 (s, 1H), 4.16-4.11 (m, 1H), 4.10-4.01 (m, 2H), 3.98-3.92 (m, 1H), 3.86-3.78 (m, 2H), 3.61-3.56 (m, 1H), 3.53-3.47 (m, 1H), 3.40-3.34 (m, 1H), 3.31-3.25 (m, 1H), 2.59 (q, 2H, J=7.5 Hz), 2.55 (s, 3H), 1.18 (t, 3H, J=7.7 Hz). LRMS (ESI): 351.1 (M+H)+.

Example 89

(±)-trans 8-Ethyl-6-methyl-4-(2-(pyridin-3-yloxy)ethyl)-2,3,3a,4-tetrahydro-1H-pyrrolo[3,4-c]isoquinolin-5(9bH)-one dihydrochloride

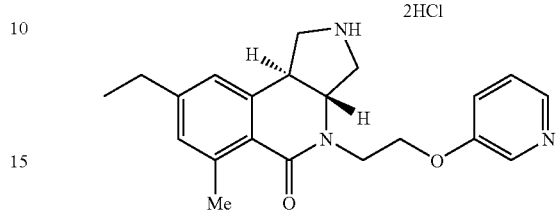

Part A. (±)-trans tert-Butyl 8-ethyl-6-methyl-5-oxo-4-(2-(pyridin-3-yloxy)ethyl)-3,3a,4,5-tetrahydro-1H-pyrrolo[3,4-c]isoquinoline-2(9bH)-carboxylate To a solution of (±)-trans tert-butyl 8-ethyl-4-(2-hydroxyethyl)-6-methyl-5-oxo-3,3a,4,5-tetrahydro-1H-pyrrolo[3,4-c]isoquinoline-2(9bH)-carboxylate, from Example 86, Part B, (24 mg, 0.064 mmol) in 1 mL of toluene was added 3-hydroxypyridine (9 mg, 0.096 mmol), triphenylphosphine (20 mg, 0.077 mmol) and diethylazodicarboxylate (0.035 mL, 0.077 mmol). The resulting mixture was allowed to stir at ambient temperature for 18 h. The reaction was diluted with ethyl acetate. The organics were washed with sat'd aq NaHCO₃ and brine, dried (MgSO₄), filtered through a pad of silica gel and concentrated in vacuo. The residue was purified by flash chromatography (elution with 3:2 to 1:2 hexane/ethyl acetate) to afford 20 mg of the title compound which was contaminated with a small amount of triphenylphosphine oxide. LRMS (ESI): 452.3 (M+H)+.

Part B. (±)-trans 8-Ethyl-6-methyl-4-(2-(pyridin-3-yloxy)ethyl)-2,3,3a,4-tetrahydro-1H-pyrrolo[3,4-c]isoquinolin-5(9bH)-one dihydrochloride To a solution of (±)-trans tert-butyl 8-ethyl-6-methyl-5-oxo-4-(2-(pyridin-3-yloxy)ethyl)-3,3a,4,5-tetrahydro-1H-pyrrolo[3,4-c]isoquinoline-2(9bH)-carboxylate (20 mg, 0.044 mmol) in 4 mL of ether was added 1 mL of 12 N HCl. The reaction was stirred vigorously for 5 min and then was diluted with 5 mL of water. The reaction was washed with ethyl acetate twice to remove the triphenylphosphine impurity. The aqueous layer was concentrated in vacuo, taken up in water, filtered and lyophilized to afford 8 mg (44%) of the title compound of Example 89 as a light tan powder. ¹H NMR (DMSO-D₆): δ 9.96-9.90 (broad m, 3H), 8.71 (s, 1H), 8.31-8.26 (m, 1H), 8.03-7.98 (m, 1H), 7.69-7.63 (m, 1H), 6.99 (s, 1H), 6.83 (s, 1H), 4.28-4.23 (m, 1H), 4.20-4.15 (m, 1H), 4.07-4.00 (m, 1H), 3.90-3.84 3.82-3.70 (overlapping m, 2H), 3.55-3.49 (m, 1H), 3.46-3.39 (m, 1H), 3.33-3.26 (m, 1H), 3.21-3.14 (m, 1H), 2.50 (q, 2H, J=7.5 Hz), 2.46 (s, 3H), 1.08 (t, 3H, J=7.7 Hz). LRMS (ESI): 352.1 (M+H)+.

Example 90

(3aR,9bS)-8-Ethyl-4-(2-hydroxyethyl)-6-methyl-2,3,
3a,4-tetrahydro-1H-pyrrolo[3,4-c]isoquinolin-5
(9bH)-one hydrochloride

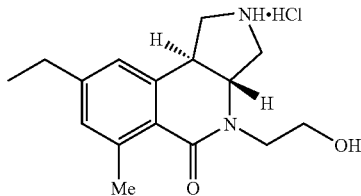

Following the procedures described in Example 86, Parts A-B and Example 74, Part C, (3aR,9bS)-tert-butyl 8-ethyl-6-methyl-5-oxo-3,3a,4,5-tetrahydro-1H-pyrrolo[3,4-c]isoquinoline-2(9bH)-carboxylate, the first eluting peak from Example 74, Part B, was converted into the title compound of Example 90 as an off-white powder. $^1$H NMR (DMSO-D$_6$): δ 9.78-9.68 (broad s, 2H), 7.08 (s, 1H), 6.89 (s, 1H), 4.92 (t, 1H, J=5.5 Hz), 3.95-3.90 (m, 1H), 3.82-3.75 (m, 1H), 3.72-3.63 (m, 2H), 3.56-3.49 (m, 2H), 3.42-3.32 (m, 2H), 3.27-3.18 (m, 2H), 2.59 (q, 2H, J=7.5 Hz), 2.55 (s, 3H), 1.18 (t, 3H, J=7.7 Hz). LRMS (ESI): 275.1 (M+H)+.

Example 91

(3aR,9bS)-8-Cyclopropyl-6-methyl-2,3,3a,4-tetrahydro-1H-pyrrolo[3,4-c]isoquinolin-5(9bH)-one hydrochloride

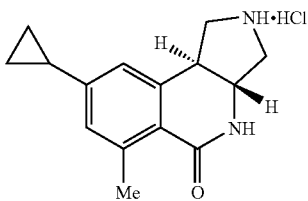

Part A. (±)-trans tert-Butyl 6-methyl-5-oxo-8-(trifluoromethylsulfonyloxy)-3,3a,4,5-tetrahydro-1H-pyrrolo[3,4-c]isoquinoline-2(9bH)-carboxylate To a solution of (±)-trans-tert-butyl 8-hydroxy-6-methyl-5-oxo-3,3a,4,5-tetrahydro-1H-pyrrolo[3,4-c]isoquinoline-2 (9bH)-carboxylate from Example 73, Part A (0.80 g, 2.5 mmol) in 15 mL of pyridine at 0° C. was added trifluoromethanesulfonic anhydride (0.63 mL, 3.75 mmol). The reaction was allowed to warm to ambient temperature and was stirred for 18 h. The reaction mixture was diluted with ethyl acetate, washed with water, 1 N HCl (2×), sat'd aq NaHCO$_3$ and brine, dried (MgSO$_4$), filtered through a pad of silica gel and concentrated in vacuo. The residue was purified by flash chromatography (elution with 1:1 hexane/ethyl acetate) to afford 0.73 g (65%) of the title compound as an orange-yellow solid. $^1$H NMR (CDCl$_3$) (some signals doubled due to rotamers): δ 7.05 (s, 1H), 6.75 (s, 1H), 6.29 and 6.20 (s, 1H), 4.07-4.01 and 3.98-3.92 (m, 1H), 3.89-3.84 and 3.81-3.76 (m, 1H), 3.63-3.55 (m, 1H), 3.32-3.16 (overlapping m, 3H), 2.67 (s, 3H), 1.45 and 1.42 (s, 9H). LRMS (ESI): 451.0 (M+H)+.

Part B. (±)-trans tert-Butyl 8-cyclopropyl-6-methyl-5-oxo-3,3a,4,5-tetrahydro-1H-pyrrolo[3,4-c]isoquinoline-2(9bH)-carboxylate Zinc (II) chloride (412 mg, 3.03 mmol) was placed in a flask and dried at 100° C. under vacuum for 2 h. The flask was allowed to cool to ambient temperature and then there was added 2 Ml of THF followed by cyclopropylmagnesium bromide (12.1 mL of a 0.5 M solution in THF, 6.1 mmol) dropwise. The reaction was allowed to stir at ambient temperature for 2 h, at which time the solution was homogeneous. This solution was added to a solution of (±)-trans tert-butyl 6-methyl-5-oxo-8-(trifluoromethylsulfonyloxy)-3,3a,4,5-tetrahydro-1H-pyrrolo[3,4-c]isoquinoline-2(9bH)-carboxylate (455 mg, 1.01 mmol). The reaction mixture was degassed with a stream of argon and then there was added bis(diphenylphosphino)ferrocene]-dichloropalladium (II) complex with dichloromethane (1:1) (41 mg, 0.05 mmol). The reaction mixture was allowed to stir at 65° C. for 18 h. The reaction was allowed to cool to ambient temperature and was quenched with 1N HCl. The mixture was diluted with ethyl acetate and the organics were washed with brine, dried (MgSO$_4$), filtered through a pad of silica gel and concentrated in vacuo to afford 0.28 g (80%) of the title compound as an off-white solid, which was sufficiently pure to be employed directly in Part C. LRMS (ESI): 343.2 (M+H)+.

Part C. Chiral separation of (3aR,9bS)-tert-Butyl 8-cyclopropyl-6-methyl-5-oxo-3,3a,4,5-tetrahydro-1H-pyrrolo[3,4-c]isoquinoline-2(9bH)-carboxylate and (3aS,9bR)-tert-Butyl 8-cyclopropyl-6-methyl-5-oxo-3,3a,4,5-tetrahydro-1H-pyrrolo[3,4-c]isoquinoline-2(9bH)-carboxylate A 280 mg sample of racemic (±)-trans tert-butyl 8-cyclopropyl-6-methyl-5-oxo-3,3a,4,5-tetrahydro-1H-pyrrolo[3,4-c]isoquinoline-2(9bH)-carboxylate was separated into the two enantiomers by chiral HPLC (Chiralcel OD column, elution with 20% MeOH-EtOH (1:1)/heptane) to afford 120 mg of (3aR,9bS)-tert-butyl 8-cyclopropyl-6-methyl-5-oxo-3, 3a,4,5-tetrahydro-1H-pyrrolo[3,4-c]isoquinoline-2(9bH)-carboxylate as the first eluting compound (>99% ee on chiralcel OD, 4.6×250, 30% MeOH-EtOH (1:1)/heptane) and 110 mg of (3aS,9bR)-tert-butyl 8-cyclopropyl-6-methyl-5-oxo-3, 3a,4,5-tetrahydro-1H-pyrrolo[3,4-c]isoquinoline-2(9bH)-carboxylate as the second eluting compound (>99% ee on chiralcel OD, 4.6×250, 30% MeOH-EtOH (1:1)/heptane). Data for first eluting compound, (3aR,9bS)-tert-butyl 8-cyclopropyl-6-methyl-5-oxo-3,3a,4,5-tetrahydro-1H-pyrrolo [3,4-c]isoquinoline-2(9bH)-carboxylate. $^1$H NMR (CDCl$_3$) (some signals doubled due to rotamers): δ 6.84 and 6.83 (s, 1H), 6.53 (s, 1H), 6.32 and 6.30 (s, 1H), 4.07-4.01 and 3.99-3.93 (m, 1H), 3.89-3.84 and 3.82-3.77 (m, 1H), 3.61-3.52 (m, 1H), 3.38-3.30 (m, 1H), 3.28-3.13 (overlapping m, 2H), 2.63 (s, 3H), 1.90-1.82 (m, 1H), 1.49 and 1.47 (s, 9H), 1.06-0.98 (m, 2H), 0.76-0.68 (m, 2H). LRMS (ESI): 343.3 (M+H)+.

Part D. (3aR,9bS)-8-Cyclopropyl-6-methyl-2,3,3a,4-tetrahydro-1H-pyrrolo[3,4-c]isoquinolin-5(9bH)-one hydrochloride Following the procedure described in Example 45, Part I, (3aR,9bS)-tert-butyl 8-cyclopropyl-6-methyl-5-oxo-3,3a,4, 5-tetrahydro-1H-pyrrolo[3,4-c]isoquinoline-2(9bH)-carboxylate, the first eluting compound from Part C above, was converted into the title compound of Example 91 as an off-white solid. $^1$H NMR (DMSO-D$_6$): δ 9.61 (broad s, 1H), 9.45 (broad s, 1H), 8.43 (s, 1H), 6.93 (s, 1H), 6.71 (s, 1H), 3.89-3.82 (m, 1H), 3.53-3.42 (m, 2H), 3.19-3.11 (m, 2H), 3.08-3.00 (m, 1H), 2.52 (s, 3H), 1.93-1.87 (m, 1H), 1.00-0.93 (m, 2H), 0.79-0.72 (m, 2H). LRMS (ESI): 243.1 (M+H)+.

Example 92

(3aR,9bS)-6,8-Dimethyl-2,3,3a,4-tetrahydro-1H-pyrrolo[3,4-c]isoquinolin-5(9bH)-one hydrochloride

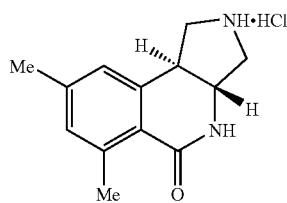

Part A. (±)-trans tert-Butyl 6,8-dimethyl-5-oxo-3,3a,4,5-tetrahydro-1H-pyrrolo[3,4-c]isoquinoline-2(9bH)-carboxylate To a solution of (±)-trans tert-butyl 6-methyl-5-oxo-8-(trifluoromethylsulfonyloxy)-3,3a,4,5-tetrahydro-1H-pyrrolo[3,4-c]isoquinoline-2(9bH)-carboxylate from Example 91, Part A (225 mg, 0.5 mmol) was added dimethylzinc (0.75 mL of a 2.0 M solution in toluene, 1.5 mmol). The reaction mixture was degassed with a stream of argon and then there was added bis(diphenylphosphino)ferrocene]-dichloropalladium (II) (18 mg, 0.025 mmol). The reaction mixture was allowed to stir at 65° C. for 18 h. The reaction was allowed to cool to ambient temperature and was quenched with 1N HCl. The mixture was diluted with ethyl acetate and the organics were washed with brine, dried (MgSO$_4$), filtered through a pad of silica gel and concentrated in vacuo to afford 0.18 g of the title compound as an off-white solid, which was sufficiently pure to be employed directly in Part B. LRMS (ESI): 317.3 (M+H)+.

Part B. Chiral separation of (3aR,9bS)-tert-Butyl 6,8-dimethyl-5-oxo-3,3a,4,5-tetrahydro-1H-pyrrolo[3,4-c]isoquinoline-2(9bH)-carboxylate and (3aS,9bR)-tert-Butyl 6,8-dimethyl-5-oxo-3,3a,4,5-tetrahydro-1H-pyrrolo[3,4-c]isoquinoline-2(9bH)-carboxylate A 180 mg sample of racemic (±)-trans tert-butyl 6,8-dimethyl-5-oxo-3,3a,4,5-tetrahydro-1H-pyrrolo[3,4-c]isoquinoline-2(9bH)-carboxylate was separated into the two enantiomers by chiral HPLC (Chiralcel OD column, elution with 20% MeOH-EtOH (1:1)/heptane) to afford 60 mg of (3aR,9bS)-tert-butyl 6,8-dimethyl-5-oxo-3,3a,4,5-tetrahydro-1H-pyrrolo[3,4-c]isoquinoline-2(9bH)-carboxylate as the first eluting compound (>99% ee on chiralcel OD, 4.6×250, 30% MeOH-EtOH (1:1)/heptane) and 50 mg of (3aS,9bR)-tert-butyl 6,8-dimethyl-5-oxo-3,3a,4,5-tetrahydro-1H-pyrrolo[3,4-c]isoquinoline-2(9bH)-carboxylate as the second eluting compound (>99% ee on chiralcel OD, 4.6×250, 30% MeOH-EtOH (1:1)/heptane). Data for first eluting compound, (3aR,9bS)-tert-butyl 6,8-dimethyl-5-oxo-3,3a,4,5-tetrahydro-1H-pyrrolo[3,4-c]isoquinoline-2(9bH)-carboxylate. $^1$H NMR (CDCl$_3$) (some signals doubled due to rotamers): δ 6.95 (s, 1H), 6.64 (s, 1H), 6.05 (broad s, 1H), 4.05-3.99 and 3.96-3.90 (m, 1H), 3.85-3.76 (m, 1H), 3.61-3.52 (broad m, 1H), 3.33-3.27 (m, 1H), 3.23-3.10 (overlapping m, 2H), 2.61 (s, 3H), 2.29 (s, 3H), 1.44 and 1.43 (s, 9H). LRMS (ESI): 317.3 (M+H)+.

Part C. (3aR,9bS)-6,8-Dimethyl-2,3,3a,4-tetrahydro-1H-pyrrolo[3,4-c]isoquinolin-5(9bH)-one hydrochloride Following the procedure described in Example 45, Part I, (3aR,9bS)-tert-butyl 6,8-dimethyl-5-oxo-3,3a,4,5-tetrahydro-1H-pyrrolo[3,4-c]isoquinoline-2(9bH)-carboxylate, the first eluting compound from Part B above, was converted into the title compound of Example 92 as an off-white solid. $^1$H NMR (DMSO-D$_6$): δ 9.48 (broad s, 1H), 9.32 (broad s, 1H), 8.46 (s, 1H), 7.05 (s, 1H), 6.87 (s, 1H), 3.89-3.82 (m, 1H), 3.54-3.43 (m, 2H), 3.22-3.12 (m, 2H), 3.09-3.02 (m, 1H), 2.53 (s, 3H), 2.29 (s, 3H). LRMS (ESI): 217.2 (M+H)+.

Example 93

(3aS,9bR)-6,8-Dimethyl-2,3,3a,4-tetrahydro-1H-pyrrolo[3,4-c]isoquinolin-5(9bH)-one hydrochloride

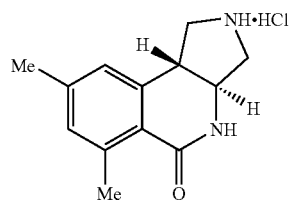

Following the procedure described in Example 45, Part I, (3aS,9bR)-tert-butyl 6,8-dimethyl-5-oxo-3,3a,4,5-tetrahydro-1H-pyrrolo[3,4-c]isoquinoline-2(9bH)-carboxylate, the second eluting compound from Example 92, Part B, was converted into the title compound of Example 93 as an off-white solid. $^1$H NMR (DMSO-D$_6$): δ 9.60 (broad s, 1H), 9.46 (broad s, 1H), 8.46 (s, 1H), 7.04 (s, 1H), 6.87 (s, 1H), 3.89-3.82 (m, 1H), 3.54-3.43 (m, 2H), 3.22-3.12 (m, 2H), 3.09-3.02 (m, 1H), 2.52 (s, 3H), 2.29 (s, 3H). LRMS (ESI): 217.2 (M+H)+.

Example 94

(3aR,9bS)-8-Isopropyl-6-methyl-2,3,3a,4-tetrahydro-1H-pyrrolo[3,4-c]isoquinolin-5(9bH)-one hydrochloride

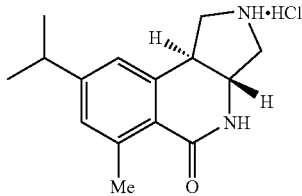

Part A. (±)-trans tert-Butyl 8-isopropyl-6-methyl-5-oxo-3,3a,4,5-tetrahydro-1H-pyrrolo[3,4-c]isoquinoline-2(9bH)-carboxylate To a solution of (±)-trans tert-butyl 6-methyl-5-oxo-8-(trifluoromethylsulfonyloxy)-3,3a,4,5-tetrahydro-1H-pyrrolo[3,4-c]isoquinoline-2(9bH)-carboxylate from Example 91, Part A (265 mg, 0.59 mmol) was added diisopropylzinc (1.76 mL of a 1.0 M solution in toluene, 1.76 mmol). The reaction mixture was degassed with a stream of argon and then there was added bis(diphenylphosphino)ferrocene]-dichloropalladium (II) (22 mg, 0.029 mmol). The reaction mixture was allowed to stir at 65° C. for 18 h. The reaction was allowed to cool to ambient temperature and was quenched with 1N HCl. The mixture was diluted with ethyl acetate and the organics were washed with brine, dried (MgSO₄), filtered through a pad of silica gel and concentrated in vacuo to afford 0.22 g of the title compound as an off-white solid, which was sufficiently pure to be employed directly in Part B. LRMS (ESI): 345.2 (M+H)+.

Part B. Chiral separation of (3aR,9bS)-tert-Butyl 8-isopropyl-6-methyl-5-oxo-3,3a,4,5-tetrahydro-1H-pyrrolo[3,4-c]isoquinoline-2(9bH)-carboxylate and (3aS,9bR)-tert-Butyl 8-isopropyl-6-methyl-5-oxo-3,3a,4,5-tetrahydro-1H-pyrrolo[3,4-c]isoquinoline-2(9bH)-carboxylate A 180 mg sample of racemic (±)-trans tert-butyl 8-isopropyl-6-methyl-5-oxo-3,3a,4,5-tetrahydro-1H-pyrrolo[3,4-c]isoquinoline-2(9bH)-carboxylate was separated into the two enantiomers by chiral HPLC (Chiralcel OD column, elution with 20% MeOH-EtOH (1:1)/heptane) to afford 60 mg of (3aR,9bS)-tert-butyl 8-isopropyl-6-methyl-5-oxo-3,3a,4,5-tetrahydro-1H-pyrrolo[3,4-c]isoquinoline-2(9bH)-carboxylate as the first eluting compound (>99% ee on chiralcel OD, 4.6×250, 30% MeOH-EtOH (1:1)/heptane) and 50 mg of (3aS,9bR)-tert-butyl 8-isopropyl-6-methyl-5-oxo-3,3a,4,5-tetrahydro-1H-pyrrolo[3,4-c]isoquinoline-2(9bH)-carboxylate as the second eluting compound (>99% ee on chiralcel OD, 4.6×250, 30% MeOH-EtOH (1:1)/heptane). Data for first eluting compound, (3aR,9bS)-tert-butyl 8-isopropyl-6-methyl-5-oxo-3,3a,4,5-tetrahydro-1H-pyrrolo[3,4-c]isoquinoline-2(9bH)-carboxylate. ¹H NMR (CDCl₃) (some signals doubled due to rotamers): δ 7.03 (s, 1H), 6.72 and 6.70 (s, 1H), 6.10 (broad s, 1H), 4.08-4.03 and 4.02-3.97 (m, 1H), 3.88-3.80 (m, 1H), 3.66-3.58 (broad m, 1H), 3.41-3.33 (m, 1H), 3.29-3.16 (overlapping m, 2H), 2.90-2.83 (m, 1H), 2.67 (s, 3H), 1.50 and 1.47 (s, 9H), 1.24 and 1.22 (overlapping d, 6H). LRMS (ESI): 345.2 (M+H)+.

Part C. (3aR,9bS)-8-Isopropyl-6-methyl-2,3,3a,4-tetrahydro-1H-pyrrolo[3,4-c]isoquinolin-5(9bH)-one hydrochloride Following the procedure described in Example 45, Part I, (3aR,9bS)-tert-butyl 8-isopropyl-6-methyl-5-oxo-3,3a,4,5-tetrahydro-1H-pyrrolo[3,4-c]isoquinoline-2(9bH)-carboxylate, the first eluting compound from Part B above, was converted into the title compound of Example 94 as a pale yellow solid. ¹H NMR (DMSO-D₆): δ 9.72 (broad s, 1H), 9.58 (broad s, 1H), 8.48 (s, 1H), 7.10 (s, 1H), 6.92 (s, 1H), 3.92-3.85 (m, 1H), 3.56-3.42 (m, 2H), 3.24-3.12 (m, 2H), 3.11-3.03 (m, 1H), 2.90-2.82 (m, 1H), 2.55 (s, 3H), 1.20 (overlapping d, 6H). LRMS (ESI): 245.2 (M+H)+.

Example 95

(3aS,9bR)-8-Isopropyl-6-methyl-2,3,3a,4-tetrahydro-1H-pyrrolo[3,4-c]isoquinolin-5(9bH)-one hydrochloride

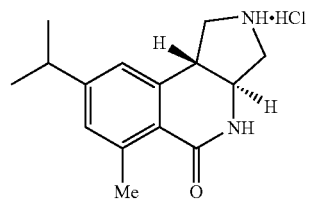

Following the procedure described in Example 45, Part I, (3aS,9bR)-tert-butyl 8-isopropyl-6-methyl-5-oxo-3,3a,4,5-tetrahydro-1H-pyrrolo[3,4-c]isoquinoline-2(9bH)-carboxylate, the second eluting compound from Example 94, Part B, was converted into the title compound of Example 95 as a pale yellow solid. ¹H NMR (DMSO-D₆): δ 9.65 (broad s, 1H), 9.52 (broad s, 1H), 8.47 (s, 1H), 7.10 (s, 1H), 6.92 (s, 1H), 3.92-3.85 (m, 1H), 3.56-3.42 (m, 2H), 3.24-3.12 (m, 2H), 3.11-3.03 (m, 1H), 2.90-2.82 (m, 1H), 2.55 (s, 3H), 1.20 (overlapping d, 6H). LRMS (ESI): 245.2 (M+H)+.

Example 96

(±)-trans-8-Ethyl-6-methyl-4-phenyl-2,3,3a,4-tetrahydro-1H-pyrrolo[3,4-c]isoquinolin-5(9bH)-one hydrochloride

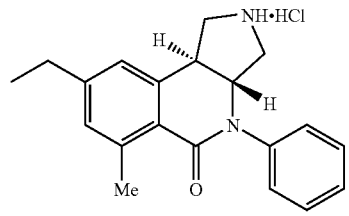

Part A. (±)-trans-tert-Butyl 8-ethyl-6-methyl-4-phenyl-5-oxo-3,3a,4,5-tetrahydro-1H-pyrrolo[3,4-c]isoquinoline-2(9bH)-carboxylate To a solution of (±)-trans-tert-butyl 8-ethyl-6-methyl-5-oxo-3,3a,4,5-tetrahydro-1H-pyrrolo[3,4-c]isoquinoline-2(9bH)-carboxylate from Example 74, Part A (50 mg, 0.15 mmol) in 2 mL of degassed toluene was added copper (I) iodide (2.1 mg, 0.011 mmol), potassium phosphate (70 mg, 0.33 mmol), iodobenzene (0.020 mL, 0.18 mmol) and N,N'-dimethylethylenediamine (0.0025 mL, 0.022 mmol). The mixture was stirred at 110° C. for 2 days. The reaction was cooled and quenched with 1N HCl and diluted with ethyl acetate. The organics were washed sequentially with sat'd aq. NaHCO₃, and brine, dried (MgSO₄), and concentrated. The residue was purified by flash chromatography (elution with 6:1 hexane/EtOAc) to afford 25 mg (41%) of the title compound as an oil. LRMS (ESI): 407.3 (M+H)+.

Part B. (±)-trans-8-Ethyl-6-methyl-4-phenyl-2,3,3a,
4-tetrahydro-1H-pyrrolo[3,4-c]isoquinolin-5(9bH)-
one hydrochloride Following the procedure described in Example 45, Part I, (±)-trans-tert-butyl 8-ethyl-6-methyl-4-phenyl-5-oxo-3,3a, 4,5-tetrahydro-1H-pyrrolo[3,4-c]isoquinoline-2(9bH)-carboxylate was converted into the title compound of Example 96 as an off-white powder. ¹H NMR (DMSO-D₆): δ 9.70 (broad s, 1H), 9.54 (broad s, 1H), 7.49-7.41 (m, 2H), 7.39-7.29 (m, 3H), 7.14 (s, 1H), 6.98 (s, 1H), 4.36-4.28 (m, 1H), 4.02-3.95 (m, 1H), 3.68-3.60 (m, 1H), 3.33-3.25 (m, 1H), 3.22-3.15 (m, 1H), 2.87-2.80 (m, 1H), 2.63 (q, 2H, J=7.5 Hz), 2.52 (s, 3H), 1.21 (t, 3H, J=7.7 Hz). LRMS (ESI): 307.2 (M+H)+.

Example 97

(±)-trans-8-Ethyl-4-(2-hydroxyphenyl)-6-methyl-2,3,
3a,4-tetrahydro-1H-pyrrolo[3,4-c]isoquinolin-5
(9bH)-one hydrochloride

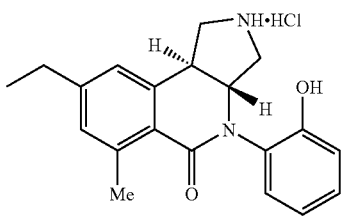

Following the procedures described in Example 96, Parts A and B, except that 2-iodophenol was used instead of iodobenzene, (±)-trans-tert-butyl 8-ethyl-6-methyl-5-oxo-3,3a,4,5-tetrahydro-1H-pyrrolo[3,4-c]isoquinoline-2(9bH)-carboxylate from Example 74, Part A was converted into the title compound of Example 97 as an off-white powder. ¹H NMR (DMSO-D₆): δ 9.93 (s, 1H), 9.52 (broad s, 1H), 9.38 (broad s, 1H), 7.26-7.15 (m, 2H), 7.13 (s, 1H), 6.99-6.92 (m, 2H), 6.84 (t, 1H, J=7.5 Hz), 4.23-4.13 (m, 1H), 4.02-3.93 (m, 1H), 3.70-3.58 (m, 1H), 3.30-3.22 (m, 1H), 3.10-3.00 (m, 1H), 2.94-2.80 (m, 1H), 2.63 (q, 2H, J=7.5 Hz), 2.53 (s, 3H), 1.20 (t, 3H, J=7.5 Hz). LRMS (ESI): 323.2 (M+H)+.

Example 98

(3aR,9bS)-8-Ethyl-6-methyl-4-phenethyl-2,3,3a,4-
tetrahydro-1H-pyrrolo[3,4-c]isoquinolin-5(9bH)-one
hydrochloride

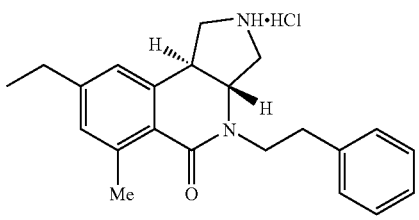

Part A. (3aR,9bS)-tert-Butyl 8-ethyl-6-methyl-5-oxo-
4-phenethyl-3,3a,4,5-tetrahydro-1H-pyrrolo[3,4-c]
isoquinoline-2(9bH)-carboxylate To a solution of (3aR,9bS)-tert-butyl 8-ethyl-6-methyl-5-oxo-3,3a,4,5-tetrahydro-1H-pyrrolo[3,4-c]isoquinoline-2(9bH)-carboxylate, the first eluting peak from Example 74, Part B, (30 mg, 0.09 mmol) in 1 mL of DMF at ambient temperature was added sodium hydride (4 mg of 60% in mineral oil, 0.10 mmol) and phenethyliodide (33 mg, 0.14 mmol). The resulting mixture was allowed to stir at ambient temperature for 18 h. Starting material remained so the reaction was heated at 60° C. for 4 h. The reaction was quenched with water and extracted with ethyl acetate. The organics were washed with brine, dried (MgSO₄) and concentrated. The residue was purified by flash chromatography (elution with 3:1 hexane ethyl acetate) to afford 16 mg (41%) of the title compound as an oil. LRMS (ESI): 435.4 (M+H)+.

Part B. (3aR,9bS)-8-Ethyl-6-methyl-4-phenethyl-2,3,
3a,4-tetrahydro-1H-pyrrolo[3,4-c]isoquinolin-5
(9bH)-one hydrochloride Following the procedure described in Example 45, Part I, (3aR,9bS)-tert-butyl 8-ethyl-6-methyl-5-oxo-4-phenethyl-3, 3a,4,5-tetrahydro-1H-pyrrolo[3,4-c]isoquinoline-2(9bH)-carboxylate was converted into the title compound of Example 98 as an off-white solid. ¹H NMR (CD₃OD): δ 7.21-7.10 (m, 5H), 7.01 (s, 1H), 6.72 (s, 1H), 4.02-3.90 (overlapping m, 2H), 3.54-3.47 (m, 2H), 3.39-3.33 (m, 1H), 3.28-3.20 (m, 2H), 3.08-3.02 (m, 1H), 2.94-2.87 (m, 1H), 2.85-2.78 (m, 1H), 2.55 (q, 2H, J=7.7 Hz), 2.47 (s, 3H), 1.14 (t, 3H, J=7.5 Hz). LRMS (ESI): 335.4 (M+H)+.

Example 99

(±)-trans-8-Methoxy-2,3,3a,4-tetrahydro-1H-pyrrolo
[3,4-c]isoquinolin-5(9bH)-one hydrochloride

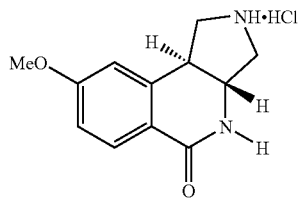

Part A. (±)-trans tert-Butyl 8-methoxy-5-oxo-3,3a,4,
5-tetrahydro-1H-pyrrolo[3,4-c]isoquinoline-2(9bH)-
carboxylate Following the procedures described in Example 72, Part B and in Example 10, Parts C-E, methyl 2-hydroxy-4-methoxybenzoate was converted into the title compound as a white solid. ¹H NMR (CDCl₃) (some signals doubled due to rotamers): δ 8.07 (dd, 1H, J=5.0, 8.3 Hz), 6.91 (dd, 1H, J=2.5, 8.5 Hz), 6.58 (s, 1H), 6.12 (d, 1H, J=5.0 Hz), 4.12-4.07 and 4.03-3.97 (m, 1H), 3.92-3.84 (m, 1H), 3.88 and 3.87 (s, 3H), 3.75-3.67 (m, 1H), 3.44-3.37 (m, 1H), 3.35-3.25 (m, 2H), 1.52 and 1.51 (s, 9H). LRMS (ESI): 319.3 (M+H)+.

Part B. (±)-trans-8-Methoxy-2,3,3a,4-tetrahydro-1H-
pyrrolo[3,4-c]isoquinolin-5(9bH)-one hydrochloride Following the procedure described in Example 45, Part I, (±)-trans tert-butyl 8-methoxy-5-oxo-3,3a,4,5-tetrahydro-1H-pyrrolo[3,4-c]isoquinoline-2(9bH)-carboxylate was converted into the title compound of Example 99 as an off-white solid. ¹H NMR (DMSO-d₆): δ 9.80 (broad s, 1H), 9.67 (broad s, 1H), 8.40 (s, 1H), 7.81 (d, 1H, J=8.8 Hz), 6.96 (dd, 1H, J=2.2, 8.8 Hz), 6.84 (s, 1H), 3.92-3.86 (m, 1H), 3.82 (s, 3H), 3.65-3.55 (m, 1H), 3.49-3.42 (m, 1H), 3.30-3.15 (overlapping m, 2H), 3.10-3.00 (m, 1H). LRMS (ESI): 219.1 (M+H)+.

Example 100

(±)-trans-8-Methoxy-4-methyl-2,3,3a,4-tetrahydro-1H-pyrrolo[3,4-c]isoquinolin-5(9bH)-one hydrochloride

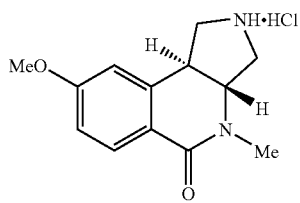

Following the procedures described in Example 15, Part A and in Example 45, Part I, (±)-trans tert-butyl 8-methoxy-5-oxo-3,3a,4,5-tetrahydro-1H-pyrrolo[3,4-c]isoquinoline-2(9bH)-carboxylate from Example 99, Part A was converted into the title compound of Example 100 as an off-white solid. $^1$H NMR (DMSO-$d_6$): δ 9.88 (broad s, 1H), 9.76 (broad s, 1H), 7.82 (d, 1H, J=8.2 Hz), 6.96 (dd, 1H, J=2.2, 8.8 Hz), 6.83 (s, 1H), 3.99-3.91 (m, 1H), 3.82 (s, 3H), 3.76-3.64 (overlapping m, 2H), 3.44-3.39 (m, 1H), 3.34-3.22 (m, 2H), 2.96 (s, 3H). LRMS (ESI): 233.2 (M+H)+.

Example 101

(3aR,9bS)-2-Benzyl-6-methyl-2,3,3a,4-tetrahydro-1H-pyrrolo[3,4-c]isoquinolin-5(9bH)-one

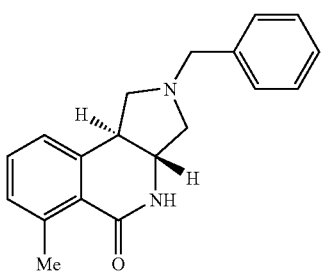

Part A. (±)-trans-2-Benzyl-6-methyl-2,3,3a,4-tetrahydro-1H-pyrrolo[3,4-c]isoquinolin-5(9bH)-one To a solution of (±)-trans-methyl I-benzyl-4-(2-(ethoxycarbonyl)-3-methylphenyl)pyrrolidine-3-carboxylate, which can be prepared from ethyl 2-bromo-6-methylbenzoate and methyl acrylate and following procedures described in Example 70, Part A and Example 10, Part C, (4.82 g, 12.64 mmol) in 100 mL of 1:1 THF/H$_2$O was added lithium hydroxide (365 mg, 15.2 mmol). The mixture was allowed to stir at ambient temperature for 18 h. The reaction was diluted with ethyl acetate and the pH was adjusted to pH 7 with 1N HCl. The organics were washed with water and brine, dried (MgSO$_4$) and concentrated to afford a carboxylic acid as a foam.

To this acid in 50 mL of THF at 0° C. was added triethylamine (2.19 mL, 15.2 mmol) followed by ethyl chloroformate (1.45 mL, 15.2 mmol). The resulting cloudy mixture was stirred for 30 min at 0° C. Then there was added sodium azide (4.11 g, 63.2 mmol) as a solution in ~5 mL of H$_2$O. The resulting solution was stirred at 0° C. for 1 h. The reaction mixture was diluted with EtOAc, washed sequentially with water and brine, dried (MgSO$_4$) and concentrated in vacuo. The residue was dissolved in 50 mL of toluene and stirred at 100° C. for 2 h. The reaction was cooled and concentrated in vacuo to afford an intermediate isocyanate. This isocyanate was dissolved in 50 mL of THF and then there was added 50 mL of 1 N HCl and the resulting mixture was stirred at 50° C. for 2 h. Then there was added potassium hydroxide (6 g, 107 mmol) and the resulting mixture was stirred at 65° C. for 18 h. The reaction was cooled and concentrated in vacuo. The residue was diluted with EtOAc and water, and the organics were washed with brine, dried (MgSO$_4$) and concentrated in vacuo. The residue was purified (ISCO, elution with 0-10% methanol/methylene chloride) to afford 2.56 g (69%) of the title compound as a solid. LRMS (ESI): 293.2 (M+H)+.

Part B. (3aR,9bS)-2-Benzyl-6-methyl-2,3,3a,4-tetrahydro-1H-pyrrolo[3,4-c]isoquinolin-5(9bH)-one A 1.6 g sample of racemic (−)-trans-2-benzyl-6-methyl-2,3,3a,4-tetrahydro-1H-pyrrolo[3,4-c]isoquinolin-5(9bH)-one was separated into the two enantiomers by chiral HPLC (Chiralcel OD column, elution with 30-45% i-PrOH/heptane) to afford (3aS,9bR)-2-benzyl-6-methyl-2,3,3a,4-tetrahydro-1H-pyrrolo[3,4-c]isoquinolin-5(9bH)-one as the first eluting compound (>99% ee on chiralcel OD, 4.6×250, 30% i-PrOH/heptane) and (3aR,9bS)-2-benzyl-6-methyl-2,3,3a,4-tetrahydro-1H-pyrrolo[3,4-c]isoquinolin-5(9bH)-one as the second eluting compound (>99% ee on chiralcel OD, 4.6×250, 30% i-PrOH/heptane). Data for the second eluting compound, (3aR,9bS)-2-benzyl-6-methyl-2,3,3a,4-tetrahydro-1H-pyrrolo[3,4-c]isoquinolin-5(9bH)-one, the title compound of Example 101. $^1$H NMR (CDCl$_3$): δ 7.40-7.25 (m, 6H), 7.16 (d, 1H, J=7.5 Hz), 6.84 (d, 1H, J=7.5 Hz), 6.26 (broad s, 1H), 3.90 (ABq, 2H, J$_{AB}$=13.2 Hz), 3.66-3.59 (m, 1H), 3.38-3.23 (m, 2H), 3.11 (dd, 1H, J=7.1, 8.4 Hz), 2.99-2.86 (m, 2H), 2.69 (s, 3H). LRMS (ESI): 293.3 (M+H)+.

Example 102

(±)-trans-6-Methyl-2-phenethyl-2,3,3a,4-tetrahydro-1H-pyrrolo[3,4-c]isoquinolin-5(9bH)-one

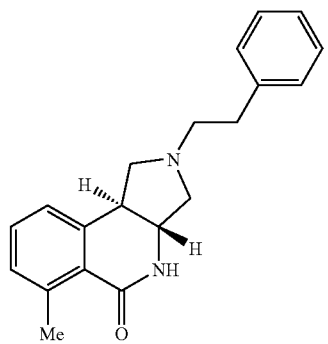

To a solution of (±)-trans-2-benzyl-6-methyl-2,3,3a,4-tetrahydro-1H-pyrrolo[3,4-c]isoquinolin-5(9bH)-one, from Example 101, Part A (57 mg, 0.2 mmol) in 10 mL of methanol was added phenylacetaldehyde (24 mg, 0.2 mmol) and 10% Pd/C catalyst (6 mg). The reaction mixture was purged several times with hydrogen and stirred under 1 atm of hydrogen, maintained by a balloon, for 18 h. The reaction mixture was filtered through a pad of Celite and concentrated in vacuo. The residue was purified (ISCO, elution with 0-8% methanol/methylene chloride) to afford the title compound of Example 102 as a solid. $^1$H NMR (CDCl$_3$): δ 7.36-7.20 (m, 6H), 7.18 (d, 1H, J=7.7 Hz), 6.88 (d, 1H, J=7.7 Hz), 6.22 (broad s, 1H), 3.66-3.58 (m, 1H), 3.41 (app t, 1H, J=8.3 Hz), 3.30-3.22 (m, 1H), 3.14 (app t, 1H, J=7.7 Hz), 3.05-2.93 (m, 4H), 2.88-2.81 (m, 2H), 2.70 (s, 3H). LRMS (ESI): 307.3 (M+H)+.

Example 103

(3aR,9bS)-7-Penta-1,3-dienyl-1,2,3,3a,4,9b-hexahydro-1H-pyrrolo[3,4-c]isoquinolin-5(9bH)-one hydrochloride

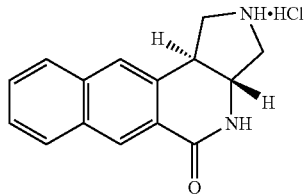

Part A. (E)-Methyl 3-(3-methoxy-3-oxoprop-1-enyl)-2-naphthoate

To a solution of methyl 3-hydroxy-2-naphthoate (2.02 g, 10.0 mmol) in 100 mL of methylene chloride was added triethylamine (1.55 mL, 11.0 mmol) and then trifluoromethanesulfonic anhydride (1.85 mL, 11.0 mmol) was added dropwise. The reaction mixture was allowed to stir at ambient temperature for 18 h. Starting material remained and so additional triethylamine (0.7 mL, 5.0 mmol) and trifluoromethanesulfonic anhydride (0.84 mL, 5.0 mmol) were added and stirring was continued for another 3 h at ambient temperature. The reaction mixture was washed 1 N HCl, water and brine, dried (MgSO$_4$) and concentrated in vacuo. The residue was purified (ISCO, elution with 0-10% hexane/EtOAc) to afford 3.12 g (93%) of a trifluoromethanesulfonate as a solid.

This triflate (3.12 g, 9.34 mmol) was dissolved in 10 mL of DMF and then there was added methyl acrylate (2.6 mL, 28.0 mmol) and triethylamine (2.6 mL, 18.7 mmol). The mixture was degassed with argon and then added bis(diphenylphosphino)ferrocene]-dichloropalladium (II) (66 mg, 0.094 mmol). The reaction mixture was heated in a microwave oven at 150° C. for 6 h. The reaction was allowed to cool to ambient temperature. The mixture was diluted with ethyl acetate and the organics were washed with 1 N HCl, water and brine, dried (MgSO$_4$) and concentrated. The residue was purified by flash chromatography (elution with 5% EtOAc/hexane) to afford 1.65 g of the title compound as a solid.

Part B. (±)-trans-Methyl 1-benzyl-4-(3-(methoxycarbonyl)naphthalen-2-yl)pyrrolidine-3-carboxylate To a solution of (E)-methyl 3-(3-methoxy-3-oxoprop-1-enyl)-2-naphthoate (1.65 g, 6.09 mmol) in 15 mL of methylene chloride was added trifluoroacetic acid (0.07 mL, 0.91 mmol) and N-(methoxymethyl)-N-(trimethylsilylmethyl)benzylamine (2.34 mL, 9.13 mmol). The reaction mixture was allowed to stir at ambient temperature for 18 h. The solution was concentrated in vacuo and purified (ISCO, elution with 0-25% EtOAc/hexane) to afford 2.1 g (86%) of the title compound as an oil. $^1$H NMR (CDCl$_3$): δ 8.34 (s, 1H), 8.15 (s, 1H), 7.87-7.80 (m, 2H), 7.58-7.53 (m, 1H), 7.50-7.41 (m, 3H), 7.39-7.33 (m, 2H), 7.30-7.25 (m, 1H), 4.57-4.51 (m, 1H), 3.94 (s, 3H), 3.74 (ABq, 2H), 3.68 (s, 3H), 3.36-3.31 (m, 1H), 3.27-3.20 (m, 1H), 3.07-3.02 (m, 2H), 2.80-2.75 (m, 1H). LRMS (ESI): 404.0 (M+H)+.

Part C. (±)-trans-1-tert-Butyl 3-methyl 4-(3-(methoxycarbonyl)naphthalen-2-yl)pyrrolidine-1,3-dicarboxylate To a solution of (±)-trans-methyl 1-benzyl-4-(3-(methoxycarbonyl)naphthalen-2-yl)pyrrolidine-3-carboxylate (1.82 g, 4.51 mmol) in 10 mL of methylene chloride was added 1-chloroethyl chloroformate (1.0 mL, 9.02 mmol) and the mixture was heated in a microwave oven at 120° C. for 1 h. The reaction was concentrated in vacuo. The residue was taken up in 20 mL of methanol and stirred at 65° C. for 1 h. The reaction was concentrated in vacuo. The residue was dissolved in 50 mL of methylene chloride and then there was added 1 N sodium hydroxide (50 mL) and di-tert-butyldicarbonate (2.0 g, 9.02 mmol). The reaction was stirred at ambient temperature for 18 h. The organics were washed with brine, dried (MgSO$_4$) and concentrated. The residue was purified (ISCO, elution with 0-40% EtOAc/hexane) to afford 1.53 g (82%) of the title compound as an oil. LRMS (ESI): 414.2 (M+H)+.

Part D. (±)-trans-5-Oxo-7-penta-1,3-dienyl-1,3,3a,4,5,9b-hexahydro-pyrrolo[3,4-c]isoquinoline-2-carboxylic acid tert-butyl ester To a solution of (±)-trans-1-tert-butyl 3-methyl 4-(3-(methoxycarbonyl)naphthalen-2-yl)pyrrolidine-1,3-dicarboxylate (1.53 g, 3.70 mmol) in 40 mL of 1:1 THF/H$_2$O was added lithium hydroxide (98 mg, 4.07 mmol). The mixture was allowed to stir at ambient temperature for 18 h. The reaction was diluted with ethyl acetate and the pH was adjusted to pH 4-5 with 1N HCl. The organics were washed with water and brine, dried (MgSO$_4$) and concentrated to afford a carboxylic acid as a foam.

To this acid in 50 mL of THF at 0° C. was added triethylamine (0.62 mL, 4.44 mmol) followed by ethyl chloroformate (0.42 mL, 4.44 mmol). The resulting cloudy mixture was stirred for 30 min at 0° C. Then there was added sodium azide (0.72 g, 11.1 mmol) as a solution in 2 mL of H$_2$O. The resulting solution was stirred at 0° C. for 1 h. The reaction mixture was diluted with EtOAc, washed sequentially with water and brine, dried (MgSO$_4$) and concentrated in vacuo. The residue was dissolved in 50 mL of toluene and stirred at 100° C. for 2 h. The reaction was cooled and concentrated in vacuo to afford an intermediate isocyanate. This isocyanate was dissolved in 50 mL of THF and then there was added 50 mL of 0.5 N HCl and the resulting mixture was stirred at ambient temperature for 18 h. Then there was added potassium hydroxide (4 g, 71.4 mmol) and the resulting mixture was stirred at ambient temperature for 18 h. The reaction was cooled and concentrated in vacuo. The residue was diluted with EtOAc and water, and the organics were washed with brine, dried (MgSO$_4$) and concentrated in vacuo. The residue was purified (ISCO, elution with 0-10% methanol/methylene chloride) to afford 1.04 g (83%) of the title compound as a solid. LRMS (ESI): 339.3 (M+H)+.

Part E. (3aR,9bS)-5-Oxo-7-penta-1,3-dienyl-1,3,3a,4,5,9b-hexahydro-pyrrolo[3,4-c]isoquinoline-2-carboxylic acid tert-butyl ester A 1.0 g sample of racemic (±)-trans-5-oxo-7-penta-1,3-dienyl-1,3,3a,4,5,9b-hexahydro-pyrrolo[3,4-c]isoquinoline-2-carboxylic acid tert-butyl ester was separated into the two enantiomers by chiral HPLC (Chiralcel AD column, elution with 10-25% i-PrOH/heptane) to afford (3aS,9bR)-5-oxo-7-penta-1,3-dienyl-1,3,3a,4,5,9b-hexahydro-pyrrolo[3,4-c]isoquinoline-2-carboxylic acid tert-butyl ester as the first eluting compound (>99% ee on chiralcel OD, 4.6×250, 20% i-PrOH/heptane, retention time 17.8 min) and (3aR,9bS)-5-oxo-7-penta-1,3-dienyl-1,3,3a,4,5,9b-hexahydro-pyrrolo[3,4-c]isoquinoline-2-carboxylic acid tert-butyl ester as the second eluting compound (>99% ee on chiralcel OD, 4.6×250, 20% i-PrOH/heptane, retention time 16.3 min). Data for the second eluting compound, (3aR,9bS)-5-oxo-7-penta-1,3-dienyl-1,3,3a,4,5,9b-hexahydro-pyrrolo[3,4-c]isoquinoline-2-carboxylic acid tert-butyl ester. $^1$H NMR (CDCl$_3$) (some peaks doubled due to carbamate rotamers): δ 8.66 (app d, 1H), 7.98-7.94 (m, 1H), 7.86-7.81 (m, 1H), 7.59 (app t, 1H), 7.52 (app t, 1H), 7.48 (s, 1H), 7.40 and 7.14 (s, 1H), 4.26-4.12 and 4.17-4.12 (m, 1H), 4.03-3.98 and 3.96-3.91 (m, 1H), 3.80-3.72 (m, 1H), 3.58-3.52 (m, 1H), 3.50-3.41 (m, 1H), 3.40-3.34 (m, 1H), 1.53 and 1.51 (s, 9H).

Part F. (3aR,9bS)-7-Penta-1,3-dienyl-1,2,3,3a,4,9b-hexahydro-1H-pyrrolo[3,4-c]isoquinolin-5(9bH)-one hydrochloride Following the procedure described in Example 45, Part I, (3aR,9bS)-5-oxo-7-penta-1,3-dienyl-1,3,3a,4,5,9b-hexahydro-pyrrolo[3,4-c]isoquinoline-2-carboxylic acid tert-butyl ester was converted into the title compound of Example 103 as a light yellow solid. $^1$H NMR (CD$_3$OD): δ 8.48 (s, 1H), 7.93 (d, 1H, J=8.3 Hz), 7.84 (d, 1H, J=8.3 Hz), 7.60 (s, 1H), 7.55 (t, 1H, J=7.2 Hz), 7.49 (t, 1H, J=7.4 Hz), 4.12-4.07 (m 1H), 3.81-3.75 (m, 1H), 3.70-3.65 (m, 1H), 3.55-3.42 (m, 2H), 3.28-3.22 (m, 1H). LRMS (ESI): 239.2 (M+H)+.

Example 104

(±)-trans-Methyl 6-(trifluoromethyl)-1,2,3,3a-tetrahydro-5H-pyrrolo[3,4-c]isoquinoline-4(9bH)-carboxylate hydrochloride

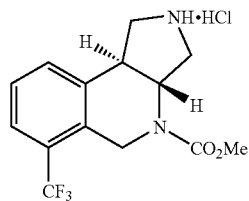

Part A. (±)-trans-2-Benzyl-6-(trifluoromethyl)-2,3,3a,4-tetrahydro-1H-pyrrolo[3,4-c]isoquinolin-5(9bH)-one To a solution of (±)-trans-6-(trifluoromethyl)-2,3,3a,4-tetrahydro-1H-pyrrolo[3,4-c]isoquinolin-5(9bH)-one, the free base of Example 10, (161 mg, 0.63 mmol) in 4 mL of 1,2-dichloroethane was added benzaldehyde (0.076 mL, 0.76 mmol), sodium triacetoxyborohydride (267 mg, 1.26 mmol) and 3 drops of glacial acetic acid. The mixture was allowed to stir at ambient temperature for 3 h. The reaction was diluted with sat'd aq NaHCO$_3$ and extracted with ethyl acetate. The organics were washed with brine, dried (MgSO$_4$) and concentrated in vacuo to afford 180 mg (83%) of the title compound which was sufficiently pure to be used without purification. LRMS (ESI): 347.2 (M+H)+.

Part B. (±)-trans-Methyl 2-benzyl-6-(trifluoromethyl)-1,2,3,3a-tetrahydro-5H-pyrrolo[3,4-c]isoquinoline-4(9bH)-carboxylate To a solution of lithium aluminum hydride (4.24 mL of a 1 M solution in THF, 4.24 mmol) at −78° C. was added sulfuric acid (2.12 mL of a 1 M solution in THF, 2.12 mmol) dropwise. Gas evolution occurred. The solution was stirred at −78° C. for 5 min and then was allowed to stir at ambient temperature for 30 min. The reaction was cooled to at 0° C. and then was added (±)-trans-2-benzyl-6-(trifluoromethyl)-2,3,3a,4-tetrahydro-1H-pyrrolo[3,4-c]isoquinolin-5(9bH)-one (185 mg, 0.53 mmol) as a solution in 4 mL of THF. The reaction was allowed to stir with warming to ambient temperature for 4 h. The reaction was cooled to at 0° C. and then was quenched by dropwise addition of sat'd aq NaHCO$_3$. Then there was added 4 mL of methanol and 30 mL of brine and the mixture was extracted with ethyl acetate. The organics were washed with brine, dried (MgSO$_4$) and concentrated in vacuo to afford an amine.

The amine was dissolved in 6 mL of THF, cooled to 0° C. and then there was added triethylamine (0.15 mL, 1.06 mmol) and methyl chloroformate (0.041 mL, 0.53 mmol). The reaction was stirred with warming to ambient temperature for 1 h and then was quenched with 1 N HCl. The reaction was extracted with ethyl acetate and the organics were washed with sat'd aq NaHCO$_3$ and brine, dried (MgSO$_4$) and concentrated in vacuo to afford 170 mg (82%) of the title compound, which was used without purification. LRMS (ESI): 391.3 (M+H)+.

Part C. (±)-trans-Methyl 6-(trifluoromethyl)-1,2,3,3a-tetrahydro-5H-pyrrolo[3,4-c]isoquinoline-4(9bH)-carboxylate hydrochloride Following the procedures described in Example 10, Part D and Example 45, Part I, (±)-trans-methyl 2-benzyl-6-(trifluoromethyl)-1,2,3,3a-tetrahydro-5H-pyrrolo[3,4-c]isoquinoline-4(9bH)-carboxylate was converted into the title compound of Example 104 as an off-white powder. $^1$H NMR (DMSO-d$_6$): δ 9.80-9.50 (very broad m, 2H), 7.73-7.68 (m, 1H), 7.58-7.51 (m, 2H), 5.20 and 4.50 (very broad ABq, 2H), 3.96-3.90 (m, 1H), 3.75-3.67 (m, 1H), 3.66 (s, 3H), 3.45-3.30 (m, 3H), 3.22-3.15 (m, 1H). LRMS (ESI): 301.1 (M+H)+.

Example 105

(±)-trans-4,6-Dimethyl-2,3,3a,4,5,9b-hexahydro-1H-pyrrolo[3,4-c]isoquinoline dihydrochloride

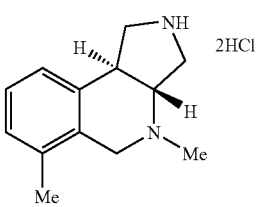

Part A. (±)-trans-2-Benzyl-6-methyl-2,3,3a,4,5,9b-hexahydro-1H-pyrrolo[3,4-c]isoquinoline To a solution of (±)-trans-2-benzyl-6-methyl-2,3,3a,4-tetrahydro-1H-pyrrolo[3,4-c]isoquinolin-5(9bH)-one, from Example 101, Part A, (830 mg, 2.84 mmol) in 20 mL of THF was added lithium aluminum hydride (3.4 mL of a 1 M solution in THF, 3.4 mmol). The reaction was heated in a microwave oven at 100° C. for 1.5 h. The reaction was cooled, filtered through a pad of silica gel with 10% methanol/methylene chloride, and concentrated in vacuo. The residue was purified (ISCO, elution with 0-12% methanol/methylene chloride) to afford 345 mg (44%) of the title compound as a solid. $^1$H NMR (CDCl$_3$): δ 7.40-7.25 (m, 5H), 7.08-6.98 (m, 2H), 6.80 (d, 1H), 4.12 (ABq, 2H), 3.87 (ABq, 2H), 3.42-3.37 (m, 1H), 3.15-3.06 (m, 2H), 2.98-2.90 (m, 1H), 2.80-2.71 (m, 2H), 2.17 (s, 3H). LRMS (ESI): 279.2 (M+H)+.

Part B. (±)-trans-4,6-Dimethyl-2,3,3a,4,5,9b-hexahydro-1H-pyrrolo[3,4-c]isoquinoline dihydrochloride To a solution of (±)-trans-2-benzyl-6-methyl-2,3,3a,4,5,9b-hexahydro-1H-pyrrolo[3,4-c]isoquinoline (65 mg, 0.23 mmol) in 2 mL of acetonitrile was added formaldehyde (0.057 mL of 37% aq solution, 0.7 mmol) and sodium borohydride (27 mg, 0.70 mmol). The reaction was allowed to stir at ambient temperature for 18 h. The solution was concentrated and purified (ISCO, elution with 0-10% methanol/methylene chloride) to afford an oil.

This material was dissolved in methanol and then was added 10% Pd/C catalyst (10 mg) and 1 drop of 12 N HCl. The mixture was hydrogenated on a Parr shaker under 65 psi of hydrogen for 5 h. The mixture was filtered through a pad of Celite, concentrated to a solid which was triturated with ether and dried in vacuo to afford 19 mg (32%) of the title compound of Example 105 as an off-white solid. LRMS (ESI): 203.2 (M+H)+.

Example 106

(±)-trans-6-Methyl-1,2,3,3a-tetrahydro-5H-pyrrolo[3,4-c]isoquinolin-4(9bH)-yl)(phenyl)methanone hydrochloride

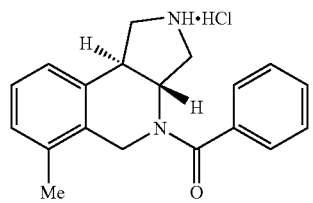

To a solution of (±)-trans-2-benzyl-6-methyl-2,3,3a,4,5,9b-hexahydro-1H-pyrrolo[3,4-c]isoquinoline from Example 105, Part A (65 mg, 0.23 mmol) in 2 mL of methylene chloride was added triethylamine (0.065 mL, 0.47 mmol) and benzoyl chloride (0.054 mL, 0.47 mmol). The reaction was allowed to stir at ambient temperature for 18 h. The solution was concentrated and purified (ISCO, elution with 0-100% EtOAc/hexane) to afford a benzamide as an oil.

This benzamide was dissolved in methanol and then was added 10% Pd/C catalyst (10 mg) and 2 drops of 12 N HCl. The mixture was hydrogenated on a Parr shaker under 65 psi of hydrogen for 18 h. The mixture was filtered through a pad of Celite, concentrated to a solid which was purified (ISCO, elution with 0-10% methanol/methylene chloride) to afford 36 mg (48%) of the title compound of Example 106 as an off-white solid. $^1$H NMR (CD$_3$OD): δ 7.62-7.51 (m, 5H), 7.23 (t, 1H), 7.13 (d, 1H), 7.03 (d, 1H), 4.88-4.80 (broad m, 1H), 4.58-4.52 (m, 1H), 4.32-4.20 (broad m, 1H), 4.05-3.98 (m, 1H), 3.67-3.60 (m, 1H), 3.56-3.45 (m, 2H), 3.39-3.31 (m, 1H), 2.01 (broad s, 3H). LRMS (ESI): 293.4 (M+H)+.

Example 107

(±)-trans-Ethyl 6-methyl-1,2,3,3a-tetrahydro-5H-pyrrolo[3,4-c]isoquinoline-4(9bH)-carboxylate hydrochloride

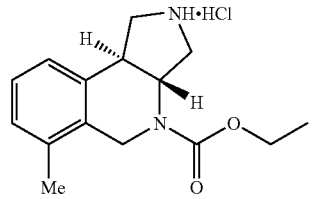

To a solution of (±)-trans-2-benzyl-6-methyl-2,3,3a,4,5,9b-hexahydro-1H-pyrrolo[3,4-c]isoquinoline from Example 105, Part A (71 mg, 0.26 mmol) in 2 mL of methylene chloride was added triethylamine (0.053 mL, 0.38 mmol) and ethyl chloroformate (0.024 mL, 0.26 mmol). The reaction was allowed to stir at ambient temperature for 1 h. The solution was concentrated and purified (ISCO, elution with 0-20% EtOAc/hexane) to afford 35 mg of a carbamate as a solid.

This carbamate was dissolved in methanol and then was added 10% Pd/C catalyst (10 mg) and 2 drops of 12 N HCl. The mixture was hydrogenated on a Parr shaker under 65 psi of hydrogen for 18 h. The mixture was filtered through a pad of Celite, concentrated to a solid which was triturated with ether and dried in vacuo to afford 23 mg (31%) of the title compound of Example 107 as a light yellow solid. LRMS (ESI): 261.3 (M+H)+.

Example 108

(±)-trans-1-(2-Benzyl-6-methyl-1,2,3,3a-tetrahydro-5H-pyrrolo[3,4-c]isoquinolin-4(9bH)-yl)ethanone

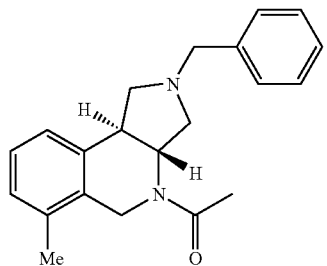

To a solution of (±)-trans-2-benzyl-6-methyl-2,3,3a,4,5,9b-hexahydro-1H-pyrrolo[3,4-c]isoquinoline from Example 105, Part A (28 mg, 0.1 mmol) in 1 mL of methylene chloride was added triethylamine (0.021 mL, 0.15 mmol) and acetyl chloride (0.009 mL, 0.15 mmol). The reaction was allowed to stir at ambient temperature for 2 h. The solution was concentrated and purified (ISCO, elution with 0-5% methanol/methylene chloride) to afford 25 mg of the title compound of Example 108 as an off-white solid. $^1$H NMR (CDCl$_3$): δ 7.74-7.68 (m, 2H), 7.50-7.42 (m, 3H), 7.21-7.13 (m, 2H), 6.80-6.75 (m, 1H), 4.78 and 4.38 (ABq, 2H), 4.31-4.25 (m, 1H), 4.16-4.03 (m, 2H), 3.89-3.80 (m, 1H), 3.71-3.63 (m, 1H), 3.49 (s, 2H), 3.07-2.98 (m, 1H), 2.35 (s, 3H), 2.21 (s, 3H). LRMS (ESI): 321.3 (M+H)+.

Example 109

(±)-trans-2-Benzyl-6-methyl-N-phenyl-1,2,3,3a-tetrahydro-5H-pyrrolo[3,4-c]isoquinoline-4(9bH)-carboxamide

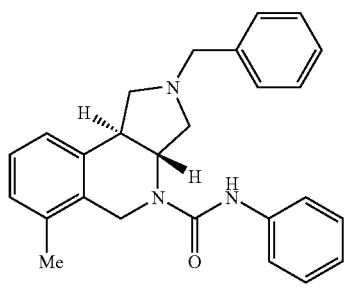

To a solution of (±)-trans-2-benzyl-6-methyl-2,3,3a,4,5,9b-hexahydro-1H-pyrrolo[3,4-c]isoquinoline from Example 105, Part A (28 mg, 0.1 mmol) in 1 mL of methylene chloride was added triethylamine (0.015 mL, 0.11 mmol) and phenylisocyanate (0.012 mL, 0.11 mmol). The reaction was allowed to stir at ambient temperature for 2 h. The solution was concentrated and purified (ISCO, elution with 0-5% methanol/methylene chloride) to afford 23 mg of the title compound of Example 109 as a white solid. $^1$H NMR (CDCl$_3$): δ 7.40-7.22 (m, 9H), 7.19-7.15 (m, 1H), 7.14-7.10 (m, 1H), 7.07-7.02 (m, 1H), 6.92-6.88 (m, 1H), 6.28 (s, 1H), 5.19 and 4.22 (ABq, 2H), 3.92 (ABq, 2H), 3.56-3.50 (m, 1H), 3.48-3.40 (m, 2H), 3.33-3.27 (m, 1H), 3.13 (app t, 1H), 3.02 (app t, 1H), 2.35 (s, 3H). LRMS (ESI): 398.3 (M+H)+.

Example 110

(±)-trans-6-Methyl-N-phenyl-1,2,3,3a-tetrahydro-5H-pyrrolo[3,4-c]isoquinoline-4(9bH)-carboxamide hydrochloride

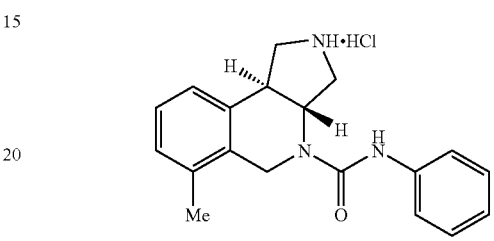

To a solution of (±)-trans-2-benzyl-6-methyl-N-phenyl-1,2,3,3a-tetrahydro-5H-pyrrolo[3,4-c]isoquinoline-4(9bH)-carboxamide from Example 109 (15 mg, 0.04 mmol) in methanol was added 10% Pd/C catalyst (3 mg) and 1 drop of 12 N HCl. The mixture was hydrogenated on a Parr shaker under 65 psi of hydrogen for 18 h. The mixture was filtered through a pad of Celite, concentrated and purified (ISCO, elution with 0-15% methanol/methylene chloride) to afford 3 mg (25%) of the title compound of Example 110 as an off-white solid. $^1$H NMR (CDCl$_3$) (all peaks broad): δ 7.97 (broad s, 1H), 7.41-7.32 (m, 2H), 7.22-7.15 (m, 2H), 7.12-7.04 (m, 2H), 6.97-6.91 (m, 1H), 6.67-6.61 (m, 1H), 4.82 and 4.58 (broad ABq, 2H), 4.20-4.13 (m, 1H), 3.65-3.58 (m, 1H), 3.41-3.32 (m, 2H), 3.20-3.05 (m, 2H), 2.25 (broad s, 3H). LRMS (ESI): 308.3 (M+H)+.

Examples 111 and 112

(4aR,10bR)-8-(Trifluoromethyl)-1,2,3,4,4a,5-hexahydrobenzo[c][1,6]naphthyridin-6(10bH)-one and (4aS,10bS)-8-(Trifluoromethyl)-1,2,3,4,4a,5-hexahydrobenzo[c][1,6]naphthyridin-6(10bH)-one (Enantiomer A and Enantiomer B)

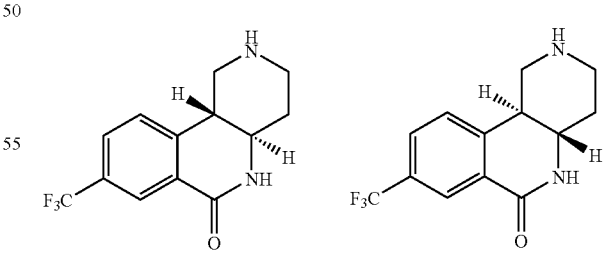

Part A. Methyl 2-chloro-5-(trifluoromethyl)benzoate

To a solution of 2-chloro-5-(trifluoromethyl)benzoic acid (15 g, 66.8 mmol) in methylene chloride (200 mL) was added oxalyl chloride (12.7 g, 100 mmol) drop wise followed by the addition of 5-6 drops of DMF. The reaction mixture was concentrated, the residue partitioned between methylene chloride and 5% aq. sodium carbonate. The organic layer was dried (MgSO$_4$) and concentrated to give the title compound as a pale oil (16 g).

Part B. Methyl 2-(4,4,5,5-tetramethyl-1,3,2-dioxaborolan-2-yl)-5-(trifluoromethyl)benzoate A mixture of the title compound from part A (5.6 g, 23.5 mmol), bis(pinacolato)diboron (6.56 g, 25.8 mmol) and potassium acetate (6.91 g, 70.5 mmol) in DMF (50 mL) was purged with nitrogen for 5 minutes, added palladium acetate (264 mg, 1.18 mmol) and heated with stirring at 80° C. for 10 h. The reaction mixture was filtered, the filtrate was diluted with ethyl acetate, washed with brine, dried (MgSO$_4$) and concentrated. The residue was subjected to flash chromatography (silica gel/hexanes-EtOAc 100:0 to 50:50 gradient) to give the title compound as a white solid (1.5 g).

Part C. Ethyl 1-benzyl-5-(2-(methoxycarbonyl)-4-(trifluoromethyl)phenyl)-1,2,3,6-tetrahydropyridine-4-carboxylate A mixture of the title compound from part B (1.4 g, 4.24 mmol), ethyl 1-benzyl-5-(trifluoromethylsulfonyloxy)-1,2,3,6-tetrahydropyridine-4-carboxylate (1.83 g, 4.7 mmol, for preparation of this compound see WO 03014121) and potassium carbonate (1.46 g, 10.6 mmol) in DMF (30 mL) was purged with nitrogen followed by the addition of Pd(Ph$_3$P)$_4$ (122.5 mg, 0.106 mmol). The mixture was heated at 80° C. for 0.5 h, diluted with EtOAc and washed with brine. The organic layer was dried (MgSO$_4$), concentrated and the residue was subjected to flash chromatography (silica gel/hexanes-EtOAc 100:0 to 50:50 gradient) to give the title compound as a pale oil (0.9 g).

Part D. (±)-cis-Ethyl 3-(2-(methoxycarbonyl)-4-(trifluoromethyl)phenyl)piperidine-4-carboxylate A mixture of the title compound from part C (0.5 g), 10% Pt/C (0.5 g), 1 N HCl (3 mL) in MeOH (50 mL) was shaken under hydrogen (55 psi, Parr shaker) for 24 h. The mixture was then transferred to a steel bomb, filled with 55 psi hydrogen and heated at 100° C. for 5 h (the inside pressure increased to ca. 100 psi during heating). The mixture was allowed to cool to RT, filtered through celite, concentrated and the residue was subjected to reversed phase prep. HPLC (C18 column/methanol-water-TFA 10:90:0.1 to 90:10:0.1 gradient) to give in the order of elution ethyl 5-(2-(methoxycarbonyl)-4-(trifluoromethyl)phenyl)-1,2,3,6-tetrahydropyridine-4-carboxylate (125 mg) and the title compound (160 mg).

Part E. (±)-cis-Ethyl 1-benzyl 3-(2-(methoxycarbonyl)-4-(trifluoromethyl)phenyl)piperidine-1,4-dicarboxylate Benzyl chloroformate (69.4 mg, 4.06 mmol) was added to a mixture of the title compound from part D (160 mg, 0.34 mmol) and sodium bicarbonate (0.45 g) in 1:1 water-THF (6 mL). The reaction mixture was stirred at RT for 10 minutes, diluted with EtOAc, washed with saturated sodium bicarbonate, dried (MgSO$_4$) and concentrated to give the title compound as a colorless gum (140 mg).

Part F. (±)-cis-Ethyl 1-benzyl 3-(2-(tert-butoxycarbonyl)-4-(trifluoromethyl)phenyl)piperidine-1,4-dicarboxylate To a solution of the title compound from step E (140 mg, 0.28 mmol) in 3 mL t-BuOH-water (ca. 99:1) was added potassium t-butoxide (41.6 mg, 0.34 mmol). The mixture was stirred at RT for 5 min., partitioned between 5% aq. potassium carbonate and ether. The aqueous layer was acidified and extracted with ethyl acetate. The ethyl acetate layer was dried (MgSO$_4$) and concentrated to give (±)-Cis-2-(1-(benzyloxycarbonyl)-4-(ethoxycarbonyl)piperidin-3-yl)-5-(trifluoromethyl)benzoic acid as a colorless foamy solid (0.105 g). To a solution of this material in THF (3 mL) was added di-tert-butyldicarbonate (144 mg, 0.66 mmol) and DMAP (10.8 mg, 0.088 mmol). The mixture was stirred at RT for 14 h followed by heating at 60° C. for 6 h. The mixture was diluted with EtOAc, washed successively with 5% aq. potassium hyrogensulfate, sat. NaHCO$_3$ and brine. The organic layer was dried (MgSO$_4$), concentrated and the residue was subjected to flash chromatography (silica gel/hexane-EtOAc 100:0 to 80:20 to give the title compound (55 mg) as a colorless gum.

Part G. (±)-trans-3-(2-(tert-Butoxycarbonyl)-4-(trifluoromethyl)phenyl)-1-(benzyloxycarbonyl)piperidine-4-carboxylic acid A mixture of the title compound from part F (55 mg) and potassium carbonate (200 mg) in EtOH (3 mL) and water (1 mL) was refluxed for 2 h. HPLC/MS analysis showed a gradual conversion to the trans isomer. The mixture was refluxed for additional 2.5 h to effect hydrolysis of the ethyl ester as indicated by HPLC/MS analysis. The mixture was concentrated, diluted with EtOAc and acidified. The organic layer was dried (MgSO$_4$) and concentrated to give the title compound as a colorless gum (50 mg).

Part H. (±)-trans-Benzyl 6-oxo-8-(trifluoromethyl)-1,4,4a,5,6,10b-hexahydrobenzo[c][1,6]naphthyridine-2(3H)-carboxylate Diphenylphosphoryl azide (32.6 mg, 0.12 mmol) and triethylamine (24 mg, 0.24 mmol) were added sequentially to a stirred solution of the title compound from part G (40 mg, 0.079 mmol) in toluene (2 mL). The mixture was stirred at RT for 15 min., then added 2-trimethylsilylethanol (0.5 mL) and stirred at 85° C. for 9 h. The mixture was diluted with EtOAc, washed with sat. NaHCO$_3$, dried (MgSO$_4$) and concentrated to give crude (±)-trans-benzyl 3-(2-(tert-butoxycarbonyl)-4-(trifluoromethyl)phenyl)-4-((2-(trimethylsilyl)ethoxy)carbonyl)piperidine-1-carboxylate. This was dissolved in THF (3 mL), then added a solution of 1 M TBAF in THF (0.15 mL) and stirred at 60° C. for 1 h. The mixture was concentrated and the residue was subjected to flash chromatography (silica gel/hexanes-EtOAc 100:0 to 50:50 gradient) to give the title compound as a colorless foamy solid (12 mg).

Part I. (±)-trans-8-(Trifluoromethyl)-1,2,3,4,4a,5-hexahydrobenzo[c][1,6]naphthyridin-6(10bH)-one A mixture of the title compound from part H (12 mg) and 10% palladium on C (4 mg) in MeOH (10 mL) and 1N HCl (0.25 mL) was stirred for 0.5 h under hydrogen (55 psi). The mixture was filtered, the filtrate was concentrated and the residue was subjected to cation exchange chromatography (sulfonic acid resin/2 N NH$_3$ in MeOH) to isolate the title compound as a free base (7 mg).

Part J. (4aR,10bR)-8-(Trifluoromethyl)-1,2,3,4,4a,5-hexahydrobenzo[c][1,6]naphthyridin-6(10bH)-one and (4aS,10bS)-8-(Trifluoromethyl)-1,2,3,4,4a,5-hexahydrobenzo[c][1,6]naphthyridin-6(10bH)-one. Enantiomer A and Enantiomer B The racemate from Part I was subjected to chiral chromatography (Chiralcel OD column/hexanes-EtOH-MeOH-triethylamine 80:10:10:0.2) to give Enantiomer A (2.5 mg, white solid) and Enantiomer B (2.3 mg, white solid) in the order of elution; $^1$H NMR (CD3OD): δ 8.14 (s, 1H), 7.74 (d, 1H, J=8.2 Hz), 7.40 (d, 1H, J=8.2 Hz), 3.68 (1H, dd, J=3.8, 12.1 Hz), 3.35 (dt, 1H, 3.9, 11.6 Hz), 3.06 (br d, 1H, J=12.7 Hz), 2.81 (br t, 1H, J=8.8 Hz), 2.62 (m, 2H), 1.95 (dd, 1H, J=3.3, 13.1 Hz), 1.61 (ddd, 1H, J=12.1, 7.7, 4.4 Hz); LRMS (ESI): 271 (M+H)$^+$.

Examples 113 and 114

(4aS,10bR)-7-Methyl-1,2,3,4,4a,5-hexahydrobenzo[c][1,6]naphthyridin-6(10bH)-one and (4aR,10bS)-7-Methyl-1,2,3,4,4a,5-hexahydrobenzo[c][1,6]naphthyridin-6(10bH)-one (Enantiomer A and Enantiomer B)

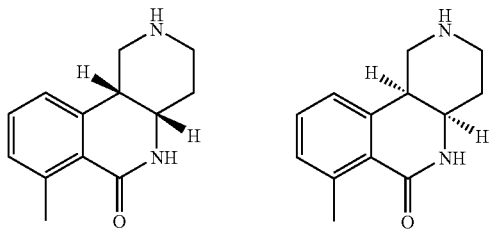

Part A. (±)-Ethyl 1-benzyl 3-(2-(methoxycarbonyl)-3-methylphenyl)piperidine-1,4-dicarboxylate The title compound was prepared from 2-bromo-6-methylbenzoic acid following the procedures described in Example 111 and 112, Parts A-E.

Part B. (±) cis-1-(Benzyloxycarbonyl)-3-(2-(methoxycarbonyl)-3-methylphenyl)piperidine-4-carboxylic acid A mixture of the compound from part A (0.26 g) and potassium carbonate (1.0 g) in 20 mL 1:1 water-EtOH was refluxed for 24 h, concentrated and partitioned between water and ether. The aqueous layer was acidified, extracted with ethyl acetate, dried (MgSO$_4$) and concentrated to give the title compound as a thick colorless oil (75 mg).

Part C. (±)-cis-Benzyl 7-methyl-6-oxo-1,4,4a,5,6,10b-hexahydrobenzo[c][1,6]naphthyridine-2 (3H)-carboxylate The title compound was prepared from (±) cis-1-(benzyloxycarbonyl)-3-(2-(methoxycarbonyl)-3-methylphenyl)piperidine-4-carboxylic acid following the procedure described in Example 111, Part H.

Part D. (±)-cis 7-Methyl-1,2,3,4,4a,5-hexahydrobenzo[c][1,6]naphthyridin-6(10bH)-one The title compound was prepared from (±)-cis-benzyl 7-methyl-6-oxo-1,4,4a,5,6,10b-hexahydrobenzo[c][1,6]naphthyridine-2 (3H)-carboxylate following the procedure described in Example 111, Part I.

Part E: (4aS,10bR)-7-Methyl-1,2,3,4,4a,5-hexahydrobenzo[c][1,6]naphthyridin-6(10bH)-one and (4aR,10bS)-7-Methyl-1,2,3,4,4a,5-hexahydrobenzo[c][1,6]naphthyridin-6(10bH)-one. Enantiomer A and Enantiomer B The racemate from step D was subjected to chiral chromatography (Chiralpak AS column/hexanes-EtOH-MeOH-triethylamine 80:10:10:0.2) to give Enantiomer A (white solid) and Enantiomer B (white solid) in the order of elution; $^1$H NMR (CD$_3$OD): δ 7.26 (t, 1H, J=7.7 Hz), 7.08 (d, 1H, J=7.6 Hz), 6.97 (d, 1H, J=7.7 Hz), 3.60 (1H, dd, J=3.7, 12.2 Hz), 3.14 (dt, 1H, 4.2, 11.7 Hz), 3.04 (br d, 1H, J=12.8 Hz), 2.55 (m, 3H), 2.52 (s, 3H), 1.90 (m, 1H), 1.57 (ddd, 1H, J=12.5, 7.6, 4.2 Hz); LRMS (ESI): 217 (M+H)$^+$.

While it is apparent that the embodiments of the application herein disclosed are well suited to fulfill the objectives stated above, it will be appreciated that numerous modifications and other embodiments may be implemented by those skilled in the art, and it is intended that the appended claims cover all such modifications and embodiments that fall within the true spirit and scope of the present application.

A number of references have been cited and the entire disclosures of which are incorporated herein by reference.

What is claimed is:
1. A compound according to Formula II:

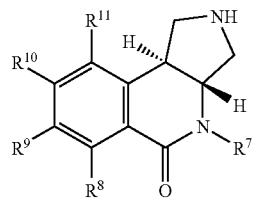

including all stereoisomers, pharmaceutically acceptable salt forms, and prodrug esters thereof, wherein:
$R^7$ is selected from the group consisting of H and alkyl, wherein each alkyl may optionally be substituted with one or more hydroxy, aryl, heteroaryl or oxyheteroaryl; and
$R^8$, $R^9$, $R^{10}$ and $R^{11}$ are each independently selected from the group consisting of H, alkyl, halogen and perfluoroalkyl.
2. The compound according to claim 1, wherein:
$R^8$ is perfluoroalkyl.
3. The compound according to claim 2, wherein the perfluoroalkyl is $CF_3$.
4. The compound according to claim 1, wherein:
$R^8$ is chloro.
5. The compound according to claim 1, wherein:
$R^8$ is methyl.
6. A pharmaceutical composition, comprising:
at least one compound according to claim 1; and
at least one pharmaceutically acceptable adjuvant or carrier.
7. The pharmaceutical composition according to claim 6, further comprising:
at least one additional therapeutic agent.

* * * * *

UNITED STATES PATENT AND TRADEMARK OFFICE
CERTIFICATE OF CORRECTION

PATENT NO. : 7,572,805 B2
APPLICATION NO. : 11/180268
DATED : August 11, 2009
INVENTOR(S) : John M. Fevig, Jianxin Feng and Saleem Ahmad It is certified that error appears in the above-identified patent and that said Letters Patent is hereby corrected as shown below:

First Page, Column 1, under Other Publications
Line 4, "acenapthen" should read -- acenaphthen --.

Column 132
Line 50-51, "periluoroalkyl" should read -- perfluoroalkyl --;
Line 53, "chioro." should read -- chloro. --.

Signed and Sealed this

Ninth Day of November, 2010

David J. Kappos
*Director of the United States Patent and Trademark Office*